US010292983B2

(12) United States Patent
McWherter

(10) Patent No.: US 10,292,983 B2
(45) Date of Patent: May 21, 2019

(54) OXYMETHYLENE ARYL COMPOUNDS FOR TREATING INFLAMMATORY GASTROINTESTINAL DISEASES OR GASTROINTESTINAL CONDITIONS

(71) Applicant: Cymabay Therapeutics, Inc., Newark, CA (US)

(72) Inventor: Charles A. McWherter, Newark, CA (US)

(73) Assignee: CymaBay Therapeutics, Inc., Newark, CA (US)

( * ) Notice: Subject to any disclaimer, the term of this patent is extended or adjusted under 35 U.S.C. 154(b) by 2 days.

(21) Appl. No.: 15/667,004

(22) Filed: Aug. 2, 2017

(65) Prior Publication Data

US 2018/0036307 A1 Feb. 8, 2018

Related U.S. Application Data

(60) Provisional application No. 62/370,404, filed on Aug. 3, 2016.

(51) Int. Cl.
*A61K 31/506* (2006.01)
*A61K 31/155* (2006.01)
*A61K 45/06* (2006.01)

(52) U.S. Cl.
CPC .......... *A61K 31/506* (2013.01); *A61K 31/155* (2013.01); *A61K 45/06* (2013.01)

(58) Field of Classification Search
CPC .......................... A61K 31/454; A61K 31/506
See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,778,443 A | 12/1973 | Arya |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,094,987 A | 6/1978 | Hasspacher et al. |
| 4,673,564 A | 6/1987 | Kawata et al. |
| 4,894,235 A | 1/1990 | Kohne et al. |
| 5,013,556 A | 5/1991 | Woodle et al. |
| 5,187,677 A | 2/1993 | Linz et al. |
| 5,340,591 A | 8/1994 | Nakano et al. |
| 5,420,298 A | 5/1995 | Edwards et al. |
| 5,456,923 A | 10/1995 | Nakamichi et al. |
| 5,707,646 A | 1/1998 | Yajima et al. |
| 5,792,769 A | 8/1998 | Lu et al. |
| 5,817,667 A | 10/1998 | Chu et al. |
| 5,817,677 A | 10/1998 | Linz et al. |
| 5,880,138 A | 3/1999 | Heinz et al. |
| 5,939,099 A | 8/1999 | Grabowski et al. |
| 6,015,712 A | 1/2000 | Monia et al. |
| 6,015,715 A | 1/2000 | Kirschner et al. |
| 6,020,346 A | 2/2000 | Armour et al. |
| 6,051,712 A | 4/2000 | Binggeli et al. |
| 6,150,526 A | 11/2000 | Binggeli et al. |
| 6,221,660 B1 | 4/2001 | Bonini et al. |
| 6,255,305 B1 | 7/2001 | Broughton et al. |
| 6,274,735 B1 | 8/2001 | Lohri et al. |
| 6,468,756 B1 | 10/2002 | Bonini et al. |
| 6,506,757 B1 | 1/2003 | Tajima et al. |
| 6,770,645 B2 | 8/2004 | Denton et al. |
| 6,784,185 B2 | 8/2004 | Allerton et al. |
| 6,969,724 B2 | 11/2005 | Barlocco et al. |
| 7,012,083 B2 | 3/2006 | Gibson et al. |
| 7,108,991 B2 | 9/2006 | Chen et al. |
| 7,319,104 B2 | 1/2008 | Cadilla et al. |
| 7,524,838 B2 | 4/2009 | Genevois-Borella et al. |
| 7,576,074 B2 | 8/2009 | Rice et al. |
| 7,638,541 B2 | 12/2009 | Chen et al. |
| 7,709,481 B2 | 5/2010 | Keil et al. |
| 7,851,473 B2 | 12/2010 | Matsumoto et al. |
| 8,114,865 B2 | 2/2012 | Bandiera et al. |
| 8,119,778 B2 | 2/2012 | Fischer et al. |
| 8,183,381 B2 | 5/2012 | Ma et al. |
| 8,188,098 B2 | 5/2012 | Erickson et al. |
| 8,227,495 B2 | 7/2012 | Chen et al. |
| 8,277,495 B2 | 10/2012 | Demetriou et al. |
| 8,288,384 B2 | 10/2012 | Chen et al. |
| 8,344,001 B2 | 1/2013 | Hohlweg et al. |
| 8,410,127 B2 | 4/2013 | Song et al. |
| 8,455,491 B2 | 6/2013 | Puech et al. |
| 8,513,264 B2 | 8/2013 | Mark et al. |
| 2002/0099214 A1 | 7/2002 | Gibson et al. |
| 2002/0198223 A1 | 12/2002 | Allerton et al. |
| 2003/0064990 A1 | 4/2003 | Denton et al. |
| 2004/0024218 A1 | 2/2004 | Barlocco et al. |
| 2004/0162278 A1 | 8/2004 | Armour et al. |
| 2004/0220170 A1 | 11/2004 | Atkinson et al. |
| 2005/0165005 A1 | 7/2005 | Genevois-Borella et al. |
| 2006/0135501 A1 | 6/2006 | Knox et al. |
| 2006/0142262 A1 | 6/2006 | Jones et al. |
| 2006/0155128 A1 | 7/2006 | Jones et al. |
| 2006/0206074 A1 | 9/2006 | Bernal et al. |
| 2006/0227281 A1 | 10/2006 | Kang et al. |
| 2007/0129341 A1 | 6/2007 | Kallus et al. |
| 2007/0265332 A1 | 11/2007 | Ge et al. |
| 2009/0054475 A1 | 2/2009 | Chen et al. |
| 2009/0137590 A1 | 5/2009 | Ma et al. |
| 2009/0186112 A1 | 7/2009 | Maingueneau |
| 2009/0270404 A1 | 10/2009 | Wilson et al. |
| 2009/0286812 A1 | 11/2009 | Erickson et al. |

(Continued)

FOREIGN PATENT DOCUMENTS

| | | |
|---|---|---|
| CN | 1829718 A | 9/2006 |
| CN | 1898235 A | 1/2007 |

(Continued)

OTHER PUBLICATIONS

Higuchi, et al., "Pro-Drugs as Novels Delivery Systems," American Chemical Society, 1975, vol. 14.

(Continued)

*Primary Examiner* — San Ming R Hui
(74) *Attorney, Agent, or Firm* — Foley & Lardner LLP; Antoinette F. Konski; Yogeeta Jadhav

(57) ABSTRACT

Use of oxymethylene aryl GPR119 agonists, and optionally DPP IV inhibitors and optionally metformin, for the treatment of inflammatory gastrointestinal diseases or gastrointestinal conditions involving malabsorption of nutrients and/or fluids are provided.

22 Claims, No Drawings

(56) References Cited

U.S. PATENT DOCUMENTS

| | | |
|---|---|---|
| 2010/0087465 A1 | 4/2010 | Chen et al. |
| 2010/0130511 A1 | 5/2010 | Chen et al. |
| 2010/0267721 A1 | 10/2010 | Hohlweg et al. |
| 2011/0046137 A1 | 2/2011 | Beswick et al. |
| 2011/0137032 A1 | 6/2011 | Endo et al. |
| 2011/0152270 A1 | 6/2011 | Song et al. |
| 2011/0160222 A1 | 6/2011 | Chen et al. |
| 2011/0263617 A1 | 10/2011 | Mark et al. |
| 2011/0294836 A1 | 12/2011 | Song et al. |
| 2011/0313160 A1 | 12/2011 | Chen et al. |
| 2011/0318418 A1 | 12/2011 | McWherter et al. |
| 2012/0184572 A1 | 7/2012 | Song et al. |
| 2012/0322804 A1 | 12/2012 | Ma et al. |
| 2013/0109703 A1 | 5/2013 | Eickelmann et al. |
| 2013/0131086 A1 | 5/2013 | Chu et al. |
| 2013/0281691 A1 | 10/2013 | Chen et al. |
| 2013/0310398 A1 | 11/2013 | Mark et al. |
| 2014/0024830 A1 | 1/2014 | Chen et al. |

FOREIGN PATENT DOCUMENTS

| | | |
|---|---|---|
| CN | 101616586 A | 12/2009 |
| DE | 27 01 705 A1 | 8/1977 |
| EP | 0 630 887 A1 | 12/1994 |
| EP | 0 755 923 A1 | 1/1997 |
| EP | 0 867 183 A1 | 9/1998 |
| EP | 0 901 786 A2 | 3/1999 |
| EP | 1 092 727 A2 | 4/2001 |
| EP | 1 129 706 A2 | 9/2001 |
| EP | 1 176 147 A1 | 1/2002 |
| EP | 1 422 228 A1 | 5/2004 |
| EP | 1 500 648 A1 | 1/2005 |
| EP | 1 133 559 B1 | 8/2005 |
| EP | 1 707 202 A1 | 10/2006 |
| EP | 1 584 683 B1 | 7/2007 |
| EP | 1 813 606 A1 | 8/2007 |
| EP | 1 829 863 A1 | 9/2007 |
| EP | 1 852 433 A1 | 11/2007 |
| EP | 2 280 704 B1 | 2/2011 |
| GB | 0 882 813 | 11/1961 |
| GB | 1 422 263 A | 1/1976 |
| JP | 11-500447 | 1/1999 |
| JP | 11-513382 | 11/1999 |
| JP | 2002-514169 | 5/2002 |
| JP | 2002-539192 | 11/2002 |
| JP | 2005-532272 | 10/2005 |
| JP | 2005-330266 | 12/2005 |
| JP | 2006-505509 | 2/2006 |
| JP | 2006-506380 | 2/2006 |
| JP | 2006-518763 | 8/2006 |
| JP | 2006-293353 | 10/2006 |
| JP | 2006-525355 | 11/2006 |
| JP | 2007-045752 | 2/2007 |
| JP | 2007-145828 | 6/2007 |
| JP | 2007-533672 | 11/2007 |
| JP | 2008-526235 | 7/2008 |
| JP | 2008-532647 | 8/2008 |
| JP | 2009-509988 | 3/2009 |
| JP | 2009-541512 | 11/2009 |
| JP | 2009-541518 | 11/2009 |
| JP | 2010-512418 | 4/2010 |
| JP | 2010-514795 | 5/2010 |
| JP | 2010-526793 | 8/2010 |
| JP | 2010-530840 | 9/2010 |
| JP | 2011-516428 | 5/2011 |
| JP | 2012-502081 | 1/2012 |
| WO | WO-98/04559 | 2/1998 |
| WO | WO-99/46232 | 9/1999 |
| WO | WO-00/50562 A2 | 8/2000 |
| WO | WO-00/55126 | 9/2000 |
| WO | WO-01/14372 A2 | 3/2001 |
| WO | WO-02/098223 A1 | 5/2002 |
| WO | WO-02/088101 A2 | 11/2002 |
| WO | WO-2003/047568 | 6/2003 |
| WO | WO-03/074495 A1 | 9/2003 |
| WO | WO-03/099795 | 12/2003 |
| WO | WO-2004/006846 A2 | 1/2004 |
| WO | WO-2004/037809 A1 | 5/2004 |
| WO | WO-2004/076413 | 9/2004 |
| WO | WO-2004/078413 A1 | 9/2004 |
| WO | WO-2004/089373 A1 | 10/2004 |
| WO | WO-2004/098518 A2 | 11/2004 |
| WO | WO-2004/099154 | 11/2004 |
| WO | WO-2004/113323 A1 | 12/2004 |
| WO | WO-2005/007658 | 1/2005 |
| WO | WO-2005/011654 A2 | 2/2005 |
| WO | WO-2005/061489 A1 | 7/2005 |
| WO | WO-2005/061547 A2 | 7/2005 |
| WO | WO-2005/082089 A2 | 9/2005 |
| WO | WO-2005/116653 | 12/2005 |
| WO | WO-2005/121088 A1 | 12/2005 |
| WO | WO-2006/054652 A1 | 5/2006 |
| WO | WO-2006/069788 A1 | 7/2006 |
| WO | WO-2006/073167 A1 | 7/2006 |
| WO | WO-2006/074057 A2 | 7/2006 |
| WO | WO-2006/076231 A2 | 7/2006 |
| WO | WO-2006/091428 A2 | 8/2006 |
| WO | WO-2006/094763 A1 | 9/2006 |
| WO | WO-2006/124692 A2 | 11/2006 |
| WO | WO-2006/133216 A2 | 12/2006 |
| WO | WO-2006/134487 A1 | 12/2006 |
| WO | WO-2007/003960 A1 | 1/2007 |
| WO | WO-2007/003961 A2 | 1/2007 |
| WO | WO-2007/014290 A2 | 2/2007 |
| WO | WO-2007/023507 A2 | 3/2007 |
| WO | WO-2007/035355 A2 | 3/2007 |
| WO | WO-2007/039177 A2 | 4/2007 |
| WO | WO-2007/120702 A2 | 10/2007 |
| WO | WO-2008/008887 A2 | 1/2008 |
| WO | WO-2008/025800 A1 | 3/2008 |
| WO | WO-2008/070692 A2 | 6/2008 |
| WO | WO-2008/073929 A1 | 6/2008 |
| WO | WO-2008/073936 A1 | 6/2008 |
| WO | WO-2008/074749 A1 | 6/2008 |
| WO | WO-2008/083238 A2 | 7/2008 |
| WO | WO-2008/109702 A1 | 9/2008 |
| WO | WO-2008/137436 | 11/2008 |
| WO | WO-2008/138876 | 11/2008 |
| WO | WO-2009/010429 | 1/2009 |
| WO | WO-2009/010761 | 1/2009 |
| WO | WO-2009/014637 | 1/2009 |
| WO | WO-2009/016516 | 2/2009 |
| WO | WO-2009/037394 | 3/2009 |
| WO | WO-2009/070869 A1 | 6/2009 |
| WO | WO-2009/123992 A1 | 10/2009 |
| WO | WO-2010/008739 A2 | 1/2010 |
| WO | WO-2010/013849 A1 | 2/2010 |
| WO | WO-2010/048149 A2 | 4/2010 |
| WO | WO-2011/041154 A1 | 4/2011 |
| WO | WO-2010/029089 A2 | 3/2012 |

OTHER PUBLICATIONS

Langer, Robert, "New Methods of Drug Delivery," Science, Sep. 28, 1990, vol. 249, No. 4976, pp. 1527-1533.
Still, et al., "Rapid Chromatographic Technique for Preparative Separations With Moderate Resolution," Journal of Organic Chemistry, 1978, 43, 14, pp. 2923-2925.
U.S. Appl. No. 12/830,911, filed Jul. 6, 2010, Chen et al.
U.S. Appl. No. 13/006,298, filed Jan. 13, 2011, Song,et al.
U.S. Appl. No. 13/032,513, filed Feb. 22, 2011, Chen, et al.
U.S. Appl. No. 13/152,752, filed Jun. 3, 2011, Chen, et al.
U.S. Appl. No. 13/165,651, filed Jun. 21, 2011, McWherter, et al.
U.S. Appl. No. 13/449,238, filed Apr. 17, 2012, Xin, et al.
U.S. Appl. No. 13/463,617, filed May 3, 2012, Jingyuan, et al.
U.S. Appl. No. 13/612,451, filed Sep. 12, 2012, Xin, et al.
"Report of the Expert committee on the diagnosis and classification of diabetes mellitus", Diabetes Care, vol. 26, (Suppl 1): S5-19, (2003).
Annoura, et al., "Synthesis and Biological Evaluation of New 4-Arlypiperidines and 4-Aryl-4-piperidinols: Dual Na+ and Ca2+ Channel Blockers with Reduced Affinity for Dopamine D2 Receptors," Biorganic & Medicinal Chemistry, 10, 2002, pp. 371-383.

(56) References Cited

OTHER PUBLICATIONS

Ashcroft & Gribble. "ATP-sensitive K+ Channels and Insulin Secretion: Their Role in Health and Disease," Diabetologia, (1999) 42: 903-19.
Barrett-Conner. "Epidemiology, Obesity, and Non-insulin-dependent Diabetes Mellitus" Epidemiologic Reviews, (1998) 11: 172-81.
Bell & Polonsky. "Diabetes Mellitus and Genetically Programmed Defects in β-cell Function," Nature, (2001) 414: 788-91.
Bighley et al., "Salt Forms of Drugs and Absorption," in Swarbrick, J. and Boylan, J.C., et al., eds. "Encyclopedia of Pharmaceutical Technology." 13 Ed., Marcel Dekker, NY (1996) pp. 453-499.
Blicklé. "Meglitinide Analogues: a Review of Clinical Data Focused on Recent Trials," Diabetes & Metabolism, (2006) 32(2): 113-20.
Blough, et al., "Synthesis and Transporter Binding Properties of 3.beta.-[4'(Phenylalkyl, -phenylalkenyl, and -phenylalkynl)phenyl]tropane-2.beta.-carboxylic Acid Methyl Esters: Evidence of a Remote Phenyl Binding Domain on the Dopamine Transporter," Journal of Medicinal Chemistry, 45:18, 2002, pp. 4029-4037.
Brubaker. "The Glucagon-Like Peptides Pleiotropic Regulators of Nutrient Homeostatsis," Annals of New York Academy of Sciences, (2006) 1070: 10-26.
Byrn et al., "Solid-State Chemistry of Drugs, 11: Hydrates and Solvates," 2nd ed., SSCI, Inc., (1999) 233-247 & 516.
Cannon, J. G., Chapter Nineteen in Burger's Medicinal Chemistry and Drug Discovery, Fifth Edition, vol. I: Principles and Practice, Wiley-Interscience 1995, pp. 783-802.
Cantin et al., "PDE-10A Inhibitors as Insulin Secretagogues," Bioorganic & Medicinal Chemistry Letters, (2007) 17(10): 2869-73.
Castro, et al., "Enhancement of Oral Absorption in Selective 5-HT1D Receptor Agonists: Fluorinated 3-[3-(Piperidin-1-yl)propyl]indoles," Journal of Medicinal Chemistry (1998) 41(15): 2667-70.
Cavaghan et al., "Interactions Between Insulin Resistance and Insulin Secretion in the Development of Glucose Intolerance," The Journal of Clinical Investigation, (2000) 106(3): 329-33.
Cavalla et al., "Analgetics Based on the Pyrrolidine Ring. V," Journal of Medicinal Chemistry, (1970) 13(5): 794-800.
Chiasson et al., "The Efficacy of Acarbose in the Treatment of Patients with Non-Insulin-dependent Diabetes Mellitus: A Multicenter Controlled Clinical Trial." Annals of Internal Medicine, (1994) 121(12): 928-35.
Chilean Examination Report dated Jun. 15, 2011 for Chilean Application No. 2042-2008.
Choi et al., "Alterations in Regulation of Energy Homeostasis in Cyclic Nucleotide Phosphodiesterase 3B-null Mice." Journal of Clinical Investigation, (2006) 116(12): 3240-51.
Coniff et al., "Acarbose: A Review of US Clinical Experience." Clinical Therapy, (1997) 19(1): 16-26.
Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus." American Journal of Medicine, (1995) 98: 443-51.
Crawley et al., "Methoxytetrahydropyrans. A New Series of Selective and Orally Potent 5-Lioxygenase Inhibitors," Journal of Medicinal Chemistry, (1992) 35(14): 2600-9.
Deacon. "Dipeptidyl Peptidase 4 Inhibition with Sitagliptin: a New Therapy for Type 2 Diabetes." Expert Opinion on Investigational Drugs, 16:4, 2007, pp. 533-545.
Deng et al., "A Novel and Efficient Synthesis of 2,5-Substituted 1,2,4-Triazol-3-Ones," Tetrahedron Letters, (2005) 46(46): 7993-6.
Drucker, "The Role of Gut Hormones in Glucose Homeostasis," Journal of Clinical Investigation, (2007) 117(1): 24-32.
Elahi et al., "The Insulinotropic Actions of Glucose-dependent Insulinotropic Polypeptide (GIP) and Glucagon-like Peptide-1 (7-37) in Normal and Diabetic Subjects," Regulatory Peptides, (1994) 61: 63-74.

Farilla et al., "Glucagon-Like Peptide 1 Inhibits Cell Apoptosis and Improves Glucose Responsiveness of Freshly Isolated Human Islets," Endocrinology, (2003) 144(12) 5149-58.
Farilla et al., "Glucagon-Like Peptide-1 Promotes Islet Cell Growth and Inhibits Apoptosis in Zucker Diabetic Rats," Endocrinology, 143:11, (2002), pp. 4397-4408.
Filipsson et al., "The Neuropeptide Pituitary Adenylate Cyclase-Activating Polypeptide and Islet Function," Diabetes, (2001) 50(9): 1959-69.
Flier, "Insulin receptors and insulin resistance," Annual Reviews of Medicine, 34, (1983), pp. 145-160.
Freudenrich, et al., "Design of Inhibitors from the Three-dimensional Structure of Alcohol Dehydrogenase. Chemical Synthesis and Enzymic Properties," Journal of the American Chemical Society, 106:11, 1984, pp. 3344-3353.
Friedrichsen et al., "Stimulation of Pancreatic ß-cell Replication by Incretins Involves Transcriptional Induction of Cyclin D1 via Multiple Signalling Pathways." Journal of Endocrinology, (2006) 188(3): 481-92.
Furman et al., "Modulation of Cyclic Nucleotides and Cyclic Nucleotide Phosphodiesterases in Pancreatic Islet ß-cells and Intestinal L-cells as Targets for Treating Diabetes Mellitus," Current Opinions in Investigational Drugs, (2006) 7(10): 898-905.
Gavin, et al. "Report of the Expert Committee on the Diagnosis and Classification of Diabetes Mellitus", Diabetes Care, (2003) 26(Supp 1): S5-S20.
Gilon et al., "Mechanisms and Physiological Significance of the Cholinergic Control of Pancreatic ß-Cell Function," Endocrinology Reviews, (2001) 22(5): 565-604.
Gloyn et al., "Insights into the Structure and Regulation of Glucokinase from a Novel Mutation (V62M), Which Causes Maturity-onset Diabetes of the Young." J Biol Chem (2005) 280(14): 14105-14113.
González et al., "Investigational treatments for type 2 diabetes mellitus: exenatide and liraglutide." Expert Opin Investig Drugs (2006) 15(8): 887-895.
Gould et al., "Pyrrolidines. IX. 3-Aryl-3-pyrrolidinols," Journal of Medicinal Chemistry, (1964) 7(1): 60-7.
Gould, P.L., "Salt Selection for Basic Drugs," International Journal Pharmaceutics, 33, 1986, pp. 201-217.
Green et al. "Dipeptidyl peptidase IV (DPP IV) inhibitors: a newly emerging drug class for the treatment of type 2 diabetes." Diabetes Vasc. Dis. Res. (2006), 3:159-165.
Greene, T.W., "Protective Groups in Organic Synthesis," 3rd Edition, John Wiley & Sons, Inc., (1999) 518-23.
Gromada et al., "Glucagon-Like Peptide 1(7-36) Amide Stimulates Exocytosis in Human Pancreatic beta-Cells by Both Proximal and Distal Regulatory Steps in Stimulus-Secretion Coupling." Diabetes (1998) 47(1): 57-65.
Guertin et al., "Small Molecule Glucokinase Activators as Glucose Lowering Agents: A New Paradigm for Diabetes Therapy." Curr Med Chem (2006) 13(15): 1839-1843.
Guillory, J.K., "Generation of Polymorphs, hydrates, Solvates and Amorphous Solids," in "Polymorphism in Pharmaceutical Solids." Brittain, H.G. ed., (1999) 183-220.
Haffner, "Management of Dyslipidemia in Adults With Diabetes." Diabetes Care (1998) 21(1): 160-178.
Han et al., "The Calcium/Calmodulin-dependent Phosphodiesterase PDE1C Down-regulates Glucose-induced Insulin Secretion." J Biol Chem (1999) 274(32): 22337-22344.
Hansen, "Towards Selective Kir6.2/SUR1 Potassium Channel Openers, Medicinal Chemistry and Therapeutic Perspectives." Curr Med Chem (2006) 13(4): 361-376.
Hansotia et al., "Extrapancreatic incretin receptors modulate glucose homeostasis, body weight, and energy expenditure." J Clin Invest (2007) 117(1): 143-152, Epub Dec. 21, 2006.
Härndahl et al., "Important Role of Phosphodiesterase 3B for the Stimulatory Action of cAMP on Pancreatic ß-Cell Exocytosis and Release of Insulin." J Biol Chem (2002) 277(40): 37446-37455.
Hatakeyama et al., "Rapid glucose sensing by protein kinase A for insulin exocytosis in mouse pancreatic islets." J Physiol (2006) 570(Pt 2): 271-282.

(56) References Cited

OTHER PUBLICATIONS

Henquin, "Pathways in ß-Cell Stimulus-Secretion Coupling as Targets from Therapeutic Insulin Secretagogues." Diabetes (2004) 53(Supp 3): S48-S58.
Holz, "Perspectives in Diabetes in Epac: A New cAMP-Binding Protein in Support of Glucagon-Like Peptide-1 Receptor-Mediated Signal Transduction in the Pancreatic ß-Cell." Diabetes (2004) 53(1): 5-13.
Hussain et al., "Increased Pancreatic ß-Cell Proliferation Mediated by CREB Binding Protein Gene Activation." Mol Cell Biol (2006) 26(20): 7747-7759.
International Search Report and Written Opinion dated Feb. 22, 2010 in related PCT Application No. PCT/US2009/047551.
International Search Report and Written Opinion dated Jan. 26, 2009 in related PCT Application No. PCT/US2008/069714.
International Search Report and Written Opinion dated Jun. 19, 2009 in related PCT Application No. PCT/US2009/038847.
International Search Report and Written Opinion dated May 23, 2008 in related PCT Application No. PCT/US2007/088978.
International Search Report and Written Opinion dated Oct. 29, 2010 in related PCT Application No. PCT/US2010/049486.
International Search Report dated Oct. 10, 2011 in related PCT Application No. PCT/US2011/040972.
International Search Report dated Oct. 6, 2011 in related PCT Application No. PCT/US11/39069.
Iwamoto et al., "Effect of Combination Therapy of Troglitazone and Sulphonylureas in Patients with Type 2 Diabetes Who Were Poorly Controlled by Sulphonylurea Therapy Alone." Diabet Med (1996) 13: 365-370.
Kahn, "The Importance of ß-Cell Failure in the Development and Progression of Type 2 Diabetes." J Clin Endicrinol Metab (2001) 86:4047-4058.
Kahn, "The Importance of the ß-Cell in the Pathogenesis of Type 2 Diabetes Mellitus." Am J Med (2000) 108 Suppl 6a, 2S-8S.
Kahn, "Type 2 Diabetes: When Insulin Secretion Fails to Compensate for Insulin Resistance." Cell (1998) 92: 593-596.
Kaplan et al., "Cardiovascular diseases" in Health and Human Behavior, (McGraw-Hill, New York 1993): 206-242.
Kashima et al., "Critical Role of cAMP-GEFII Rim2 Complex in Incretin-potentiated Insulin Secretion." J Biol Chem (2001) 276(49): 46046-46053, Epub Oct. 11, 2001.
Kim et al., "(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine: A potent, orally active dipeptidyl peptidase IV inhibitor for the treatment of type 2 diabetes." J. Med. Chem., 2005, 48(1):141-151.
Kim et al., "Exendin-4 induction of cyclin D1 expression in INS-1 ß-cells: involvement of cAMP-responsive element." J Endocrinol (2006) 188(3): 623-633.
Knowler et al., "Obesity in the Pima Indians: its magnitude and relationship with diabetes," Am. J. Clin. Nutr. (1991) 53:1543S-1551S.
Kwiterovich, "State-of-the-Art Update and Review: Clinical Trials of Lipid-Lowering Agents." Am J Cardiol (1998) 82(12A): 3U-17U.
Langer, "New Methods of Drug Delivery." Science (1990) 249: 1527-1533.
Le Bourdonnec, B., et al., "Discovery of a series of aminopiperidines as novel iNOS inhibitors," Bioorganic and Medicinal Chemistry Letters, vol. 18, Issue 1, pp. 336-343 (2008).
Le Bourdonnec, et al., "Synthesis and Structure-activity Relationships of a New Series of 2α-substitued Trans-4,5-dimethyl-4-(3-hydroxyphenyl)piperidine as µ-selective Opioid Antagonists," Bioorganic and Medicinal Chemistry Letters, (2006) 16(4): 864-8.
Levy et al., "Beta-cell Deterioration Determines the Onset and Rate of Progression of Secondary Dietary Failure in Type 2 Diabetes Mellitus: the 10-year Follow-up of the Belfast Diet Study." Diabetes Med (1998) 15: 290-296.
Li et al., "Glucagon-like Peptide-1 Receptor Signaling Modulates ß Cell Apoptosis." J Biol Chem (2003) 278(1): 471-478.

Mahler et al., "Clinical Review 102 Type 2 Diabetes Mellitus: Update on Diagnosis, Pathophysiology, and Treatment." J Clin Endocrinol Metab (1999) 84(4): 1165-1171.
Matschinsky et al., "Perspectives in Diabetes the Network of Glucokinase-Expressing Cells in Glucose Homeostasis and the Potential of Glucokinase Activators for Diabetes Therapy." Diabetes (2006) 55(1): 1-12.
Matschinsky, "Glucokinase, Glucose Homeostasis, and Diabetes Mellitus." Curr Diab Rep (2005) 5(3): 171-176.
Meneilly et al., "The Effect of Glyburide on ß-Cell Sensitivity to Glucose-Dependent Insulinotropic Polypeptide." Diabetes Care (1993) 16(1): 110-114.
Miura et al., "Glucagon-like peptide-1 induces a cAMP-dependent increase of [Na+]i associated with insulin secretion in pancreatic ß-cells." Am J Physiol Endocrinol Metab (2003) 285, E1001-E1009.
Morissette, et al., "High-throughput Crystallization: Polymorphs, Salt, Co-crystals and Solvates of Pharmaceutical Solids," Advanced Drug Delivery Reviews, 56, 2004, pp. 275-300.
Morissette, et al., "High-throughput crystallization: Polymorphs, salts, co-crystals and solvates of pharmaceutical solids," Adv. Drug Deliv. Rev., (2004), 56(3):275-300.
Morissette, et al.,"High-Throughput Crystallization: Polymorphs, Salts, Co-Crystals and Solvates of Pharmaceutical Solids", Advanced Drug Delivery Reviews, vol. 56, p. 275-300 (2004).
Nauck et al., "Preserved Incretin Activity of Glucagon-like Peptide 1 [7-36 Amide] but Not of Synthetic Human Gastric Inhibitory Polypeptide in Patients with type-2 Diabetes Mellitus." J Clin Invest (1993) 91: 301-307.
Patani et al., "Bioisosterism: A Rational Approach in Drug Design", Chem. Rev., 1996, 96 (8), 3147-3176.
Prentki et al., "Islet ß cell Failure in type 2 dieabetes." J Clin Invest (2006) 116(7): 1802-1812.
Qader et al., "Expression of islet inducible nitric oxide synthase and inhibition of glucose-stimulated insulin release after long-term lipid infusion in the rat is counteracted by PACAP27." Am J Physiol Endocrinol Metab (2007) 292(5): E1447-E1455.
Reaven, "Insulin Resistance and Human Disease: A Short History." J Basic & Clin Phys & Pharm (1998) 9: 387-406.
Reimann et al., "Signaling Mechanisms Underlying the Release of Glucagon-Like Peptide 1." Diabetes (2006) 55(Suppl 2): S78-S85.
Rendell, "The Role of Sulphonylureas in the Management of Type 2 Diabetes Mellitus." Drugs (2004) 64(12): 1339-13.58.
Saltiel, "New Perspectives into the Molecular Pathogenesis and Treatment of Type 2 Diabetes." Cell (2001) 104: 517-529.
Sato, et al., "New µ-Opioid Receptor Agonists with Phenoxyacetic Acid Moiety," Chemical & Pharmaceutical Bulletin, (2002) 50(2): 292-7.
Saxena et al., "Genome-Wide Association Analysis Identifies Loci for Type 2 Diabetes and Triglyceride Levels." Science (2007) 316: 1331-1336.
Seino, "ATP-Sensitive Potassium Channels: A Model of Heteromultimeric Potassium Channel/Receptor Assemblies." Annu Rev Physiol (1999) 61: 337-362.
Shibasaki et al., "Interaction of ATP Sensor, cAMP Sensor, Ca2+ Sensor, and Voltage-dependent Ca2+ Channel in Insulin Granule Exocytosis." J Biol Chem (2004) 279(9): 7956-7961.
Shinki Tonyobyoyaku no Kaihatsu Jokyo (Development of Novel Agent for Diabetes), Medicament News, Feb. 15, 2008, No. 1934 (10).
Shinki Tonyobyoyaku no Kaihatsu Jokyo (Translated as: Development status of novel diabetes drugs), Medicament News, Feb. 15, 2008, No. 1934, (10).
Singer, et al., "Synthesis of SAR of Tolylamine 5-HT6 Antagonists," Bioorganic & Medicinal Chemistry Letters, (2009) 19: 2409-12.
Soga et al., "Lysophosphatidylcholine Enhances Glucose-dependent Insulin Secretion via an Orphan G-protein-coupled Receptor." Biochemical and Biophysical Research Communications (2005) 326(4): 744-751.
Steinthorsdottir et al., "A Variant in CDKAL1 Influences Insulin Response and Risk of Type 2 Diabetes." Nature Genetics (2007) 39(6): 770-775.

(56) References Cited

OTHER PUBLICATIONS

Still et al., "Rapid Chromatographic Technique for Preparative Separations with Moderate Resolution." J. Org. Chem., 1978, 43(14):2923-2925.

Supplementary European Search Report dated Mar. 4, 2011 in related European Application No. 07869989.9.

Supplementary Partial European Search Report dated Jul. 25, 2012 in related European Application No. 09798422.3.

Thomas, et al., "Investigation of the N-Substituent Conformation Governing Potency and .mu. Receptor Subtype-Selectivity in (+)-(3R,4R)-Dimethyl-4-(3-hydroxyphenyl)-piperidine Opioid Antagonists," Journal of Medicinal Chemistry, 41:11, 1998, pp. 1980-1990.

Thorens et al., "Cloning and Functional Expression of the Human Islet GLP-1 Receptor: Demonstration that Exendin-4 is an Agonist and Exendin-(9-39) an Antagonist of the Receptor." Diabetes (1993) 42, 1678-1682.

Thorens, "GLUT2 in pancreatic and extra-pancreatic gluco-detection." Mol Membr Biol (2001) 18(4): 265-273.

Turner et al., "Glycemic Control With Diet, Sulfonylurea, Metformin, or Insulin in Patients With Type 2 Diabetes Mellitus: Progressive Requirement for Multiple Therapies (UKPDS 49)." JAMA (1999) 281(21): 2005-2012.

Turner et al., "Insulin resistance, impaired glucose tolerance and non-insulin-dependent diabetes, pathologic mechanisms and treatment: Current status and therapeutic possibilities." Prog Drug Res (1998) 51: 33-94.

U.K. Prospective Diabetes Study Group: "UKPDS 28: A Randomized Trial of Efficacy of Early Addition of Metformin in Sulfonylurea-Treated Type 2 Diabetes," Diabetes Care (1998) 21(1): 87-92.

Vilsbøll et al., "Reduced Postprandial Concentrations of Intact Biologically Active Glucagon-Like Peptide 1 in Type 2 Diabetic Patients." Diabetes (2001) 50: 609-613.

Vippagunta, et al., "Crystalline Solids," Advanced Drug Delivery Reviews, (2001) 48: 3-26.

Waid, et al., "Constrained Amino Acids, An Approach to the Synthesis of 3-Substituted Prolines," Tetrahedron Letters, (1996) 37(24): 4091-4.

Walz et al., "Early and rapid development of insulin resistance, islet dysfunction and glucose intolerance after high-fat feeding in mice overexpressing phosphodiesterase 3B." J Endocrinol (2006) 189(3): 629-641.

Wu, et al., "Pyrrolidines. VII. 3-Hydroxy-1-Pyrrolidinecarboxylic Acid Esters," Journal of Medicinal Chemistry, 5:4, 1962, pp. 752-762.

Yamada et al., "Cytosolic Ca2+ responses to sub-picomolar and nanomolar PACAP in pancreatic ß-cells are mediated by VPAC2 and PAC1 receptors." Regul Pept (2004) 123(1-3): 147-153.

Zhou et al., "Overexpression of Repressive cAMP Response Element Modulators in High Glucose and Fatty Acid-treated Rat Islets." J Biol Chem (2003) 278(51): 51316-51323.

OXYMETHYLENE ARYL COMPOUNDS FOR TREATING INFLAMMATORY GASTROINTESTINAL DISEASES OR GASTROINTESTINAL CONDITIONS

CROSS-REFERENCE TO RELATED PATENT APPLICATIONS

This application claims priority to U.S. Provisional Application No. 62/370404, filed on Aug. 3, 2016.

FIELD

The present disclosure relates to methods of treating an inflammatory gastrointestinal disease or a gastrointestinal condition involving malabsorption of nutrients and/or fluids in a patient in need thereof.

SUMMARY

In one aspect, provided herein are methods of treating an inflammatory gastrointestinal disease or a gastrointestinal condition in a patient in need thereof. In one embodiment, the inflammatory gastrointestinal disease or the gastrointestinal condition involves malabsorption of nutrients and/or fluids. In another embodiment, the method comprising administering to the patient a therapeutically effective amount of a compound of Formula (I),

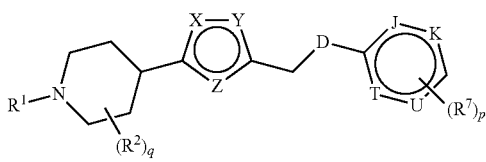

wherein,
- D is selected from the group consisting of O, S, and $NR^8$;
- X, Y, and Z are independently selected from the group consisting of O, N, $NR^8$, S, and $CR^3$ and at least one of X, Y, and Z is O, N, $NR^8$, or S;
- J, K, T, and U are each independently selected from the group consisting of C, CH, and N;
- the subscript p is an integer of from 0 to 4;
- the subscript q is an integer of from 0 to 4;
- $R^1$ is a member selected from the group consisting of H, $C_{1-10}$alkyl, $C_{1-10}$substituted alkyl, $C_{3-7}$cycloalkyl, $C_{2-10}$ alkenyl, $C_{2-10}$ alkynyl, $-X^1-CO_2R^a$, $-X^1CONR^aR^b$, $-SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1-10}$alkyl, $C_{1-10}$substituted alkyl, $C_{3-7}$cycloalkyl, $C_{2-10}$ alkenyl, $C_{2-10}$ alkynyl, aryl, heteroaryl, $-CN$, $-NR^aCOR^b$, $-NR^aCONR^aR^b$, $-NO_2$, $-OR^a$, $-NR^aR^b$, $-COR^a$, $-CO_2R^a$, $-CONR^aR^b$, $-S(O)_mR^a$, $-NR^aS(O)_2R^b$, and $SO_2NR^aR^b$, or optionally $R^a$ and $R^b$ are combined to form a 4-, 5- or 6-membered ring, and $X^1$ is selected from the group consisting of a bond, $C_{2-6}$alkene, $C_{2-6}$alkyne, $-C(O)-$, and $-C(O)-(CH_2)_{1-4}-$, wherein the aliphatic portions of $X^1$ are optionally substituted with one to three members selected from halogen, $C_{1-4}$alkyl, $C_{1-4}$substituted alkyl and $C_{1-4}$haloalkyl;
- each $R^2$ is a member independently selected from the group consisting of halogen, $C_{1-5}$ alkyl, $C_{1-5}$substituted alkyl, $C_{3-7}$cycloalkyl, $-COR^a$, $-CO_2R^a$, $-CONR^aR^b$, $-OR^a$, $-NR^aR^b$, $-NR^aCOR^b$, $-SOR^aR^b$, $-SO_2R^a$ and $-SO_2NR^aR^b$, and wherein when the subscript q is 2 and $R^2$ is alkyl or substituted alkyl, the two $R^2$ members can optionally cyclize to form a ring;
- $R^3$ is a member selected from the group consisting of hydrogen, halogen, $C_{1-4}$alkyl, and $C_{1-4}$haloalkyl;
- each $R^7$ is independently selected from the group consisting of halo, $C_{1-10}$alkyl, $C_{1-10}$ substituted alkyl, $C_{3-7}$cycloalkyl, $C_{2-10}$ alkenyl, $C_{2-10}$ alkynyl, $-CN$, $-NO_2$, $-OR^a$, $-NR^aR^b$, $-COR^a$, $-CO_2R^a$, $-CONR^aR^b$, $-NR^aCOR^b$, $-NR^aCO_2R^b$, $-NR^aCONR^aR^b$, $-S(O)_mR^a$, $-NR^aS(O)_mR^b$, $-SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, $-CN$, $-NO_2$, $-OR^a$, $-NR^aR^b$, $-COR^a$, $-CO_2R^a$, $-CONR^aR^b$, $-NR^aCOR^b$, $-NR^aCO_2R^b$, $-NR^aCONR^aR^b$, $-S(O)_mR^a$, $-NR^aSO_2R^b$, and $-SO_2NR^aR^b$ and wherein the subscript m is an integer of from 0 to 2, or optionally $R^a$ and $R^b$ are combined to form a 4-, 5- or 6-membered ring;
- $R^8$ is a member independently selected from the group consisting of hydrogen, $C_{1-4}$alkyl, and $C_{1-4}$haloalkyl;
- and each $R^a$ and $R^b$ is independently selected from the group consisting of hydrogen, $C_{1-10}$ alkyl, $C_{1-10}$haloalkyl, $C_{3-10}$ cycloalkyl, heterocyclyl, $C_{2-10}$ alkenyl, $C_{2-10}$ alkynyl, aryl, 5- to 6-membered heteroaryl and aryl$C_{1-4}$alkyl; and wherein the aliphatic portions of each of said $R^a$ and $R^b$ is optionally substituted with from one to three members selected from the group consisting of halo, $-OR''$, $-OCOR''$, $-OC(O)N(R'')_2$, $-SR''$, $-S(O)R''$, $-S(O)_2R''$, $-S(O)_2N(R'')_2$, $-NR''S(O)_2R''$, $-C(O)N(R'')_2$, $-C(O)R''$, $-NR''C(O)R''$, $-NR''C(O)N(R'')_2$, $-CO_2R''$, $-NR^1CO_2R''$, $-CN$, $-NO_2$, $-N(R'')_2$ and $-NR''S(O)_2N(R'')_2$, wherein each $R''$ is independently hydrogen or an unsubstituted $C_{1-6}$ alkyl;
- and wherein the aryl and heteroaryl portions are optionally substituted with from one to three members selected from halogen, $-OR'''$, $-OC(O)N(R''')_2$, $-SR'''$, $-S(O)R'''$, $-S(O)_2R'''$, $-S(O)_2N(R''')_2$, $-NR'''S(O)_2R'''$, $-C(O)N(R''')_2$, $-C(O)R'''$, $-NR'''C(O)R'''$, $-NR'''C(O)N(R''')_2$, $-CO_2R'''$, $-NR'''CO_2R'''$, $-CN$, $-NO_2$, $-N(R''')_2$ and $-NR'''S(O)_2N(R''')_2$, wherein each $R'''$ is independently hydrogen or an unsubstituted $C_{1-6}$ alkyl;
- or a pharmaceutically acceptable salt or ester thereof; and
- wherein the molecular weight of said compound is less than 1200.

In some embodiments, the compound of Formula I is selected from the group consisting of the compound of example 52, 76, 77, 95, 148, 162, 170, 171, 182, 184, 185, and 195, or a pharmaceutically acceptable salt thereof. In some embodiments, the compound of Formula (I) is

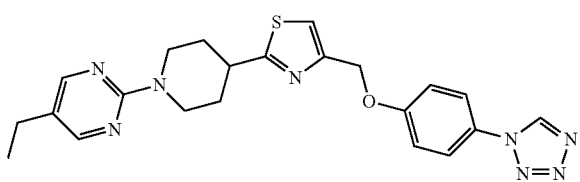 [SMILES: CCc1cnc(N2CCC(c3nc(COc4ccc(-n5cnnn5)cc4)cs3)CC2)nc1]

or a pharmaceutically acceptable salt thereof. In some embodiments, the method further comprises concurrently or sequentially administering a DPP-IV inhibitor to the patient. In some embodiments, the DPP-IV inhibitor is selected from the group consisting of sitagliptin, vildagliptin, denagliptin, saxagliptin, linagliptin, alogliptin, R1438, NVP DPP728, PSN9301, P32/98, NN-7201, ALS2-0426, gemigliptin, anagliptin, teneligliptin, trelagliptin, dutogliptin, and omarigliptin. In some embodiments, the DPP-IV inhibitor is selected from the group consisting of sitagliptin, vildagliptin, saxagliptin, linagliptin, gemigliptin, anagliptin, teneligliptin, trelagliptin, omarigliptin, and alogliptin. In some embodiments, the inflammatory gastrointestinal disease or the gastrointestinal condition involving malabsorption of nutrients and/or fluids is selected from the group consisting of short bowel syndrome (SBS), inflammatory bowel disease, Crohn's disease, ulcerative colitis, *volvulus*, and necrotizing enterocolitis. In some embodiments, the method further comprises concurrently or sequentially administering metformin to the patient.

In another aspect, provided herein are methods of treating short bowel syndrome in a patient in need thereof, the method comprising administering to the patient a therapeutically effective amount of a compound of Formula (I),

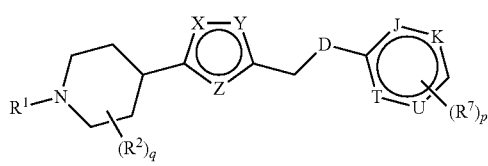

wherein,
D is selected from the group consisting of O, S, and $NR^8$;
X, Y, and Z are independently selected from the group consisting of O, N, $NR^8$, S, and $CR^3$ and at least one of X, Y, and Z is O, N, $NR^8$, or S;
J, K, T, and U are each independently selected from the group consisting of C, CH, and N;
the subscript p is an integer of from 0 to 4;
the subscript q is an integer of from 0 to 4;
$R^1$ is a member selected from the group consisting of H, $C_{1-10}$alkyl, $C_{1-10}$substituted alkyl, $C_{3-7}$cycloalkyl, $C_{2-10}$ alkenyl, $C_{2-10}$ alkynyl, —$X^1$—$CO_2R^a$, —$X^1$—$CONR^aR^b$, —$SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1-10}$alkyl, $C_{1-10}$substituted alkyl, $C_{3-7}$cycloalkyl, $C_{2-10}$ alkenyl, $C_{2-10}$ alkynyl, aryl, heteroaryl, —CN, —$NR^aCOR^b$, —$NR^aCONR^aR^b$, —$NO_2$, —$OR^a$, —$NR^aR^b$, —$COR^a$, —$CO_2R^a$, —$CONR^aR^b$, —$S(O)_mR^a$, —$NR^aS(O)_2R^b$, and $SO_2NR^aR^b$, or optionally $R^a$ and $R^b$ are combined to form a 4-, 5- or 6-membered ring, and $X^1$ is selected from the group consisting of a bond, $C_{2-6}$alkene, $C_{2-6}$alkyne, —C(O)—, and —C(O)—$(CH_2)_{1-4}$-, wherein the aliphatic portions of $X^1$ are optionally substituted with one to three members selected from halogen, $C_{1-4}$alkyl, $C_{1-4}$substituted alkyl and $C_{1-4}$haloalkyl;

each $R^2$ is a member independently selected from the group consisting of halogen, $C_{1-5}$ alkyl, $C_{1-5}$substituted alkyl, $C_{3-7}$cycloalkyl, —$COR^a$, —$CO_2R^a$, —$CONR^aR^b$, —$OR^a$, —$NR^aR^b$, —$NR^aCOR^b$, —$SOR^aR^b$, —$SO_2R^a$ and —$SO_2NR^aR^b$, and wherein when the subscript q is 2 and $R^2$ is alkyl or substituted alkyl, the two $R^2$ members can optionally cyclize to form a ring;

$R^3$ is a member selected from the group consisting of hydrogen, halogen, $C_{1-4}$alkyl, and $C_{1-4}$haloalkyl;

each $R^7$ is independently selected from the group consisting of halo, $C_{1-10}$alkyl, $C_{1-10}$ substituted alkyl, $C_{3-7}$cycloalkyl, $C_{2-10}$alkenyl, $C_{2-10}$ alkynyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aSO_2R^b$, and —$SO_2NR^aR^b$ and wherein the subscript m is an integer of from 0 to 2, or optionally $R^a$ and $R^b$ are combined to form a 4-, 5- or 6-membered ring;

$R^8$ is a member independently selected from the group consisting of hydrogen, $C_{1-4}$alkyl, and $C_{1-4}$haloalkyl;
and each $R^a$ and $R^b$ is independently selected from the group consisting of hydrogen, $C_{1-10}$ alkyl, $C_{1-10}$haloalkyl, $C_{3-10}$ cycloalkyl, heterocyclyl, $C_{2-10}$alkenyl, $C_{2-10}$ alkynyl, aryl, 5- to 6-membered heteroaryl and aryl$C_{1-4}$alkyl; and wherein the aliphatic portions of each of said $R^a$ and $R^b$ is optionally substituted with from one to three members selected from the group consisting of halo, —$OR''$, —$OCOR''$, —$OC(O)N(R'')_2$, —$S(O)R''$, —$S(O)_2R''$, —$S(O)_2N(R'')_2$, —$NR''S(O)_2R''$, —$C(O)N(R'')_2$, —$C(O)R''$, —$NR''C(O)R''$, —$NR''C(O)N(R'')_2$, —$CO_2R''$, —$NR''CO_2R''$, —CN, —$NO_2$, —$N(R'')_2$ and —$NR''S(O)_2N(R'')_2$, wherein each $R''$ is independently hydrogen or an unsubstituted $C_{1-6}$ alkyl;

and wherein the aryl and heteroaryl portions are optionally substituted with from one to three members selected from halogen, —$OR'''$, —$OC(O)N(R''')_2$, —$S(O)R'''$, —$S(O)_2R'''$, —$S(O)_2N(R''')_2$, —$NR'''S(O)_2R'''$, —$C(O)N(R''')_2$, —$C(O)R'''$, —$NR'''C(O)R'''$, —$NR'''C(O)N(R''')_2$, —$CO_2R'''$, —$NR'''CO_2R'''$, —CN, —$NO_2$, —$N(R''')_2$ and —$NR'''S(O)_2N(R''')_2$, wherein each $R'''$ is independently hydrogen or an unsubstituted $C_{1-6}$ alkyl;

or a pharmaceutically acceptable salt or ester thereof; and wherein the molecular weight of said compound is less than 1200.

In some embodiments, the compound of Formula I is selected from the group consisting of the compound of example 52, 76, 77, 95, 148, 162, 170, 171, 182, 184, 185, and 195, or a pharmaceutically acceptable salt thereof. In some embodiments, the compound of Formula (I) is

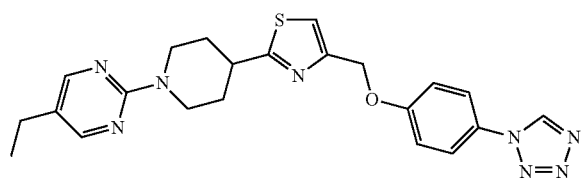 [SMILES: CCc1cnc(N2CCC(c3nc(COc4ccc(-n5cnnn5)cc4)cs3)CC2)nc1]

or a pharmaceutically acceptable salt thereof. In some embodiments, the method further comprises concurrently or sequentially administering a DPP-IV inhibitor to the patient. In some embodiments, the DPP-IV inhibitor is selected from the group consisting of sitagliptin, vildagliptin, denagliptin, saxagliptin, linagliptin, alogliptin, R1438, NVP DPP728, PSN9301, P32/98, NN-7201, ALS2-0426, gemigliptin, anagliptin, teneligliptin, trelagliptin, dutogliptin, and omarigliptin. In some embodiments, the DPP-IV inhibitor is selected from the group consisting of sitagliptin, vildagliptin, saxagliptin, linagliptin, gemigliptin, anagliptin, teneligliptin, trelagliptin, omarigliptin, and alogliptin. In some embodiments, the method further comprises concurrently or sequentially administering metformin to the patient.

In another aspect, provided herein are methods of treating inflammatory bowel disease in a patient in need thereof, the method comprising administering to the patient a therapeutically effective amount of a compound of Formula (I),

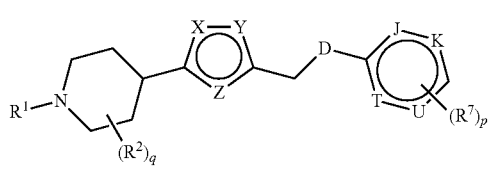

wherein,
D is selected from the group consisting of O, S, and $NR^8$,
X, Y, and Z are independently selected from the group consisting of O, N, $NR^8$, S, and $CR^3$ and at least one of X, Y, and Z is O, N, $NR^8$, or S;
J, K, T, and U are each independently selected from the group consisting of C, CH, and N;
the subscript p is an integer of from 0 to 4;
the subscript q is an integer of from 0 to 4;
$R^1$ is a member selected from the group consisting of H, $C_{1-10}$alkyl, $C_{1-10}$substituted alkyl, $C_{3-7}$cycloalkyl, $C_{2-10}$ alkenyl, $C_{2-10}$ alkynyl, —$X^1$—$CO_2R^a$, —$X^1$—$CONR^aR^b$, —$SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1-10}$alkyl, $C_{1-10}$substituted alkyl, $C_{3-7}$cycloalkyl, $C_{2-10}$ alkenyl, $C_{2-10}$ alkynyl, aryl, heteroaryl, —CN, —$NR^aCOR^b$, —$NR^aCONR^aR^b$, —$NO_2$, —$OR^a$, —$NR^aR^b$, —$COR^a$, —$CO_2R^a$, —$CONR^aR^b$, —$S(O)_mR^a$, —$NR^aS(O)_2R^b$, and $SO_2NR^aR^b$, or optionally $R^a$ and $R^b$ are combined to form a 4-, 5- or 6-membered ring, and $X^1$ is selected from the group consisting of a bond, $C_{2-6}$alkene, $C_{2-6}$alkyne, —C(O)—, and —C(O)—$(CH_2)_{1-4}$-, wherein the aliphatic portions of $X^1$ are optionally substituted with one to three members selected from halogen, $C_{1-4}$alkyl, $C_{1-4}$substituted alkyl and $C_{1-4}$haloalkyl;

each $R^2$ is a member independently selected from the group consisting of halogen, $C_{1-5}$ alkyl, $C_{1-5}$substituted alkyl, $C_{3-7}$cycloalkyl, —$COR^a$, —$CO_2R^a$, —$CONR^aR^b$, —$OR^a$, —$NR^aR^b$, —$NR^aCOR^b$, —$SOR^aR^b$, —$SO_2R^a$ and —$SO_2NR^aR^b$, and wherein when the subscript q is 2 and $R^2$ is alkyl or substituted alkyl, the two $R^2$ members can optionally cyclize to form a ring;

$R^3$ is a member selected from the group consisting of hydrogen, halogen, $C_{1-4}$alkyl, and $C_{1-4}$haloalkyl;

each $R^7$ is independently selected from the group consisting of halo, $C_{1-10}$alkyl, $C_{1-10}$ substituted alkyl, $C_{3-7}$cycloalkyl, $C_{2-10}$ alkenyl, $C_{2-10}$ alkynyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aSO_2R^b$, and —$SO_2NR^aR^b$ and wherein the subscript m is an integer of from 0 to 2, or optionally $R^a$ and $R^b$ are combined to form a 4-, 5- or 6-membered ring;

$R^8$ is a member independently selected from the group consisting of hydrogen, $C_{1-4}$alkyl, and $C_{1-4}$haloalkyl;

and each $R^a$ and $R^b$ is independently selected from the group consisting of hydrogen, $C_{1-10}$ alkyl, $C_{1-10}$haloalkyl, $C_{3-10}$ cycloalkyl, heterocyclyl, $C_{2-10}$ alkenyl, $C_{2-10}$ alkynyl, aryl, 5- to 6-membered heteroaryl and aryl$C_{1-4}$alkyl; and wherein the aliphatic portions of each of said $R^a$ and $R^b$ is optionally substituted with from one to three members selected from the group consisting of halo, —$OR''$, —$OCOR''$, —$OC(O)N(R'')_2$, —$S(O)R''$, —$S(O)_2R''$, —$S(O)_2N(R'')_2$, —$NR''S(O)_2R''$, —$C(O)N(R'')_2$, —$C(O)R''$, —$NR''C(O)R''$, —$NR''C(O)N(R'')_2$, —$CO_2R''$, —$NR''CO_2R''$, —CN, —$NO_2$, —$N(R'')_2$ and —$NR''S(O)_2N(R'')_2$, wherein each $R''$ is independently hydrogen or an unsubstituted $C_{1-6}$ alkyl;

and wherein the aryl and heteroaryl portions are optionally substituted with from one to three members selected from halogen, —$OR'''$, —$OC(O)N(R''')_2$, —$SR'''$, —$S(O)R'''$, —$S(O)_2R'''$, —$S(O)_2N(R''')_2$, —$NR'''S(O)_2R'''$, —$C(O)N(R''')_2$, —$C(O)R'''$, —$NR'''C(O)R'''$, —$NR'''C(O)N(R''')_2$, —$CO_2R'''$, —$NR'''CO_2R'''$, —CN, —$NO_2$, —$N(R''')_2$ and —$NR'''S(O)_2N(R''')_2$, wherein each $R'''$ is independently hydrogen or an unsubstituted $C_{1-6}$ alkyl;

or a pharmaceutically acceptable salt or ester thereof; and
wherein the molecular weight of said compound is less than 1200.

In some embodiments, the compound of Formula I is selected from the group consisting of the compound of example 52, 76, 77, 95, 148, 162, 170, 171, 182, 184, 185, and 195, or a pharmaceutically acceptable salt thereof. In some embodiments, the compound of Formula (I) is

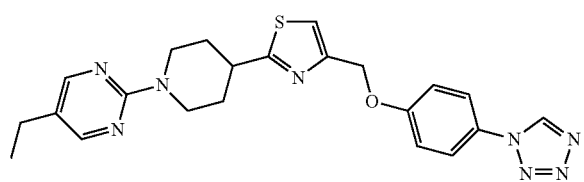 [SMILES: CCc1cnc(N2CCC(c3nc(COc4ccc(-n5cnnn5)cc4)cs3)CC2)nc1]

or a pharmaceutically acceptable salt thereof. In some embodiments, the method further comprises concurrently or sequentially administering a DPP-IV inhibitor to the patient. In some embodiments, the DPP-IV inhibitor is selected from the group consisting of sitagliptin, vildagliptin, denagliptin, saxagliptin, linagliptin, alogliptin, R1438, NVP DPP728, PSN9301, P32/98, NN-7201, ALS2-0426, gemigliptin, anagliptin, teneligliptin, trelagliptin, dutogliptin, and omarigliptin. In some embodiments, the DPP-IV inhibitor is selected from the group consisting of sitagliptin, vildagliptin, saxagliptin, linagliptin, gemigliptin, anagliptin, teneligliptin, trelagliptin, omarigliptin, and alogliptin. In some embodiments, the method further comprises concurrently or sequentially administering metformin to the patient. In some embodiments, the inflammatory bowel disease is Crohn's disease or ulcerative colitis.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Unless otherwise stated, the following terms used in the specification and claims have the meanings given below:

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

"Alkyl" refers to monovalent saturated aliphatic hydrocarbyl groups having from 1 to 10 carbon atoms and, in some embodiments, from 1 to 6 carbon atoms. "$C_{u-v}$alkyl" refers to alkyl groups having from u to v carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Substituted alkyl" refers to an alkyl group having from 1 to 5 and, in some embodiments, 1 to 3 or 1 to 2 substituents selected from the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkylidene" or "alkylene" refers to divalent saturated aliphatic hydrocarbyl groups having from 1 to 10 carbon atoms and, in some embodiments, from 1 to 6 carbon atoms. "($C_{u-v}$)alkylene" refers to alkylene groups having from u to v carbon atoms. The alkylidene and alkylene groups include branched and straight chain hydrocarbyl groups. For example "($C_{1-6}$)alkylene" is meant to include methylene, ethylene, propylene, 2-methypropylene, pentylene, and the like.

"Substituted alkylidene" or "substituted alkylene" refers to an alkylidene group having from 1 to 5 and, in some embodiments, 1 to 3 or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_{u-v}$)alkenyl refers to alkenyl groups having from u to v carbon atoms and is meant to include for example, ethenyl, propenyl, 1,3-butadienyl, and the like.

"Substituted alkenyl" refers to alkenyl groups having from 1 to 3 substituents and, in some embodiments, 1 to 2 substituents, selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined as herein and with the proviso that any hydroxy or thiol substitution is not attached to an acetylenic carbon atom.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Substituted alkynyl" refers to alkynyl groups having from 1 to 3 substituents and, in some embodiments, from 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, substituted hydrazino, heteroaryl, substituted heteroaryl, heterocyclic and substituted heterocyclic are as defined herein. Acyl includes the "acetyl" group $CH_3C(O)$—.

"Acylamino" refers to the groups —NR²⁰C(O)H, —NR²⁰C(O)alkyl, —NR²⁰C(O)substituted alkyl, —NR²⁰C(O)cycloalkyl, —NR²⁰C(O)substituted cycloalkyl, —NR²⁰C(O)alkenyl, —NR²⁰C(O)substituted alkenyl, —NR²⁰C(O)alkynyl, —NR²⁰C(O)substituted alkynyl, —NR²⁰C(O)aryl, —NR²⁰C(O)substituted aryl, —NR²⁰C(O)heteroaryl, —NR²⁰C(O)substituted heteroaryl, —NR²⁰C(O)heterocyclic, and —NR²⁰C(O)substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH₂.

"Substituted amino" refers to the group —NR²¹R²² where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclyl, and —SO₂-substituted heterocyclyl and wherein $R^{21}$ and $R^{22}$ are optionally joined together with the nitrogen bound thereto to form a heterocyclyl or substituted heterocyclyl group, provided that $R^{21}$ and $R^{22}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{21}$ is hydrogen and $R^{22}$ is alkyl, the substituted amino group is sometimes referred to herein as alkylamino. When $R^{21}$ and $R^{22}$ are alkyl, the substituted amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR²³R²⁴ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, hydroxy, alkoxy, substituted alkoxy, amino, substituted amino, and acylamino, and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{23}$R$^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{20}$C(O)NR$^{23}$R$^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{20}$C(s)NR$^{23}$R$^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{23}$R$^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{23}$R$^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{23}$R$^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{20}$—SO$_2$NR$^{23}$R$^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{25}$)NR$^{23}$R$^{24}$ where $R^{25}$, $R^{23}$, and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Substituted aryl" refers to aryl groups which are substituted with 1 to 8 and, in some embodiments, 1 to 5, 1 to 3 or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Arylalkyl" or "Aryl($C_1$-$C_z$)alkyl" refers to the radical —R"R" where R" is an alkylene group (having eight or fewer main chain carbon atoms) and R" is an aryl group as defined herein. Thus, "arylalkyl" refers to groups such as, for example, benzyl, and phenylethyl, and the like. Similarly, "Arylalkenyl" means a radical —R"R" where R" is an alkenylene group (an alkylene group having one or two double bonds) and R" is an aryl group as defined herein, e.g., styrenyl, 3-phenyl-2-propenyl, and the like.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azido" refers to the group —$N_3$.

"Hydrazino" refers to the group —$NHNH_2$.

"Substituted hydrazino" refers to the group —$NR^{26}NR^{27}R^{28}$ where $R^{26}$, $R^{27}$, and $R^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{27}$ and $R^{28}$ are optionally joined, together with the nitrogen bound thereto to form a heterocyclic or substituted heterocyclic group, provided that $R^{27}$ and $R^{28}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "carbonitrile" refers to the group —CN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —$NR^{20}$—C(O)O-alkyl, —$NR^{20}$—C(O)O-substituted alkyl, —$NR^{20}$—C(O)O-alkenyl, —$NR^{20}$—C(O)O-substituted alkenyl, —$NR^{20}$—C(O)O-alkynyl, —$NR^{20}$—C(O)O-substituted alkynyl, —$NR^{20}$—C(O)O-aryl, —$NR^{20}$—C(O)O-substituted aryl, —$NR^{20}$—C(O)O-cycloalkyl, —$NR^{20}$—C(O)O-substituted cycloalkyl, —$NR^{20}$—C(O)O-heteroaryl, —$NR^{20}$—C(O)O-substituted heteroaryl, —$NR^{20}$—C(O)O-heterocyclic, and —$NR^{20}$—C(O)O-substituted heterocyclic wherein $R^{20}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl. "$C_{u-v}$cycloalkyl" refers to cycloalkyl groups having u to v carbon atoms as ring members. "$C_{u-v}$cycloalkenyl" refers to cycloalkenyl groups having u to v carbon atoms as ring members.

"Cycloalkenyl" refers to a partially saturated cycloalkyl ring having at least one site of >C=C<ring unsaturation.

"Substituted cycloalkyl" refers to a cycloalkyl group, as defined herein, having from 1 to 8, or 1 to 5, or in some embodiments 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiocyanate, thiol, alkylthio, and substituted alkylthio, wherein said substituents are as defined herein. The term "substituted cycloalkyl" includes substituted cycloalkenyl groups.

"Cycloalkyloxy" refers to —O-cycloalkyl wherein cycloalkyl is as defined herein.

"Substituted cycloalkyloxy" refers to —O-(substituted cycloalkyl) wherein substituted cycloalkyl is as defined herein.

"Cycloalkylthio" refers to —S-cycloalkyl wherein substituted cycloalkyl is as defined herein.

"Substituted cycloalkylthio" refers to —S-(substituted cycloalkyl) wherein substituted cycloalkyl is as defined herein.

"Guanidino" refers to the group —NHC(=NH)NH₂.

"Substituted guanidino" refers to —NR²⁹C(=NR²⁹)N(R²⁹)₂ where each R²⁹ is independently selected from the group consisting of hydrogen, alkyl, substituted alkyl, aryl, substituted aryl, heteroaryl, substituted heteroaryl, heterocyclyl, and substituted heterocyclyl and two R²⁹ groups attached to a common guanidino nitrogen atom are optionally joined together with the nitrogen bound thereto to form a heterocyclic or substituted heterocyclic group, provided that at least one R²⁹ is not hydrogen, and wherein said substituents are as defined herein.

"Halo" or "halogen" refers to fluoro, chloro, bromo and iodo.

"Haloalkyl" refers to substitution of alkyl groups with 1 to 5 or in some embodiments 1 to 3 halo groups, e.g., —CH₂Cl, —CH₂F, —CH₂Br, —CFClBr, —CH₂CH₂Cl, —CH₂CH₂F, —CF₃, —CH₂CF₃, —CH₂CCl₃, and the like, and further includes those alkyl groups such as perfluoroalkyl in which all hydrogen atoms are replaced by fluorine atoms.

"Haloalkoxy" refers to substitution of alkoxy groups with 1 to 5 or in some embodiments 1 to 3 halo groups, e.g., —OCH₂Cl, —OCH₂F, —OCH₂CH₂Br, —OCH₂CH₂Cl, —OCF₃, and the like.

"Hydroxy" or "hydroxyl" refers to the group —OH.

"Heteroalkyl" means an alkyl radical as defined herein with one, two or three substituents independently selected from cyano, —OR$^w$, —NR$^x$R$^y$, and —S(O)R$^z$ (where n is an integer from 0 to 2), with the understanding that the point of attachment of the heteroalkyl radical is through a carbon atom of the heteroalkyl radical. R$^w$ is hydrogen, alkyl, cycloalkyl, cycloalkyl-alkyl, aryl, arylalkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or arylalkyl. R$^y$ is hydrogen, alkyl, cycloalkyl, cycloalkyl-alkyl, aryl, arylalkyl, alkoxycarbonyl, aryloxycarbonyl, carboxamido, mono- or di-alkylcarbamoyl or alkylsulfonyl. R$^z$ is hydrogen (provided that n is 0), alkyl, cycloalkyl, cycloalkyl-alkyl, aryl, arylalkyl, amino, monoalkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^w$, R$^x$, R$^y$, and R$^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —OR$^w$, —NR$^x$R$^y$, or —S(O)$_n$R$^z$ portions.

"Heteroaryl" refers to an aromatic group of from 1 to 14 carbon atoms and 1 to 6 heteroatoms selected from the group consisting of oxygen, nitrogen, and sulfur and includes a 5 to 18 member ring or ring system that includes a single ring (e.g., imidazolyl) or multiple rings (e.g., benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g., 1,2,3,4-tetrahydroquinolin-6-yl and 5,6,7,8-tetrahydroquinolin-3-yl). In some embodiments the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

"Substituted heteroaryl" refers to heteroaryl groups that are substituted with from 1 to 8, or in some embodiments 1 to 5, or 1 to 3, or 1 to 2 substituents selected from the group consisting of the substituents defined for substituted aryl.

"Heteroaryloxy" refers to —O-heteroaryl wherein heteroaryl is as defined herein.

"Substituted heteroaryloxy" refers to the group —O-(substituted heteroaryl) wherein heteroaryl is as defined herein.

"Heteroarylthio" refers to the group —S-heteroaryl wherein heteroaryl is as defined herein.

"Substituted heteroarylthio" refers to the group —S-(substituted heteroaryl) wherein heteroaryl is as defined herein.

"Heterocycle" or "heterocyclic" or "heterocyclo" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the term "heterocyclic", "heterocycle", "heterocyclo", "heterocycloalkyl" or "heterocyclyl" applies when there is at least one ring heteroatom and the point of attachment is at an atom of a non-aromatic ring (e.g., 1,2,3,4-tetrahydroquinoline-3-yl, 5,6,7,8-tetrahydroquinoline-6-yl, and decahydroquinolin-6-yl). In some embodiments, the nitrogen and/or sulfur atom(s) of the heterocyclic group are optionally oxidized to provide for the N-oxide, sulfinyl, and sulfonyl moieties. More specifically the heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

"Substituted heterocycle" or "substituted heterocyclic" or "substituted heterocyclo" or "substituted heterocycloalkyl" or "substituted heterocyclyl" refers to heterocyclic groups, as defined herein, that are substituted with from 1 to 5 or in some embodiments 1 to 3 of the substituents as defined for substituted cycloalkyl.

"Heterocyclyloxy" refers to the group —O-heterocyclyl wherein heterocyclyl is as defined herein.

"Substituted heterocyclyloxy" refers to the group —O-(substituted heterocyclyl) wherein heterocyclyl is as defined herein.

"Heterocyclylthio" refers to the group —S-heterocycyl wherein heterocyclyl is as defined herein.

"Substituted heterocyclylthio" refers to the group —S-(substituted heterocycyl) wherein heterocyclyl is as defined herein.

Examples of heterocycle and heteroaryl groups include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

"Oxide" refers to products resulting from the oxidation of one or more heteroatoms. Examples include N-oxides, sulfoxides, and sulfones.

"Spirocycloalkyl" refers to a 3 to 10 member cyclic substituent formed by replacement of two hydrogen atoms at a common carbon atom with an alkylene group having 2 to 9 carbon atoms, as exemplified by the following structure wherein the methylene group shown below attached to bonds marked with wavy lines is substituted with a spirocycloalkyl group:

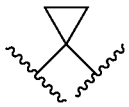 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Compound" and "compounds" as used herein refers to a compound encompassed by the generic formulae disclosed herein, any subgenus of those generic formulae, and any forms of the compounds within the generic and subgeneric formulae, such as an oxide, ester, prodrug, pharmaceutically acceptable salt, or solvate. Unless specified otherwise, the term further includes the racemates, stereoisomers, and tautomers of the compound or compounds.

"Racemates" refers to a mixture of enantiomers.

"Solvate" or "solvates" of a compound refer to those compounds, where compounds are as defined above, that are bound to a stoichiometric or non-stoichiometric amount of a solvent. Solvates of a compound includes solvates of all forms of the compound such as the oxide, ester, prodrug, or pharmaceutically acceptable salt of the disclosed generic and subgeneric formulae. Preferred solvents are volatile, non-toxic, and/or acceptable for administration to humans.

"Stereoisomer" or "stereoisomers" refer to compounds that differ in the chirality of one or more stereocenters. Stereoisomers include enantiomers and diastereomers. The compounds disclosed herein may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of Advanced Organic Chemistry, 4th edition J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a patient. Prodrugs of a compound disclosed herein are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound I is bonded to any group that may be cleaved in vivo to regenerate the free hydroxyl, amino, or sulfhydryl group, respectively. Particularly favored derivatives and prodrugs are those that increase the bioavailability of the compounds of the embodiments when such compounds are administered to a patient (e.g., by allowing an orally administered compound to be more readily absorbed into the blood) or which enhance delivery of the parent compound to a biological compartment (e.g., the brain or lymphatic system) relative to the parent species. Prodrugs include ester, amide, and carbamate (e.g., N,N-dimethylaminocarbonyl) forms of hydroxy functional groups of compounds disclosed herein. Examples of ester prodrugs include formate, acetate, propionate, butyrate, acrylate, and ethylsuccinate derivatives. An general overview of prodrugs is provided in T Higuchi and V Stella, Pro-drugs as Novel Delivery Systems, Vol. 14 of the A.C.S. Symposium Series, and in Edward B Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and includes, by way of example only, sodium, potassium, calcium, magnesium, ammonium, and tetraalkylammonium. When the molecule contains a basic functionality, acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like. Pharmaceutically acceptable salts are suitable for administration in a patient and possess desirable pharmacological properties. Suitable salts further include those described in P. Heinrich Stahl, Camille G. Wermuth (Eds.), Handbook of Pharmaceutical Salts Properties, Selection, and Use; 2002.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Turning next to the compositions disclosed herein, the term "pharmaceutically acceptable carrier or excipient" means a carrier or excipient that is useful in preparing a pharmaceutical composition that is generally safe, possesses acceptable toxicities. Acceptable carriers or excipients include those that are acceptable for veterinary use as well as human pharmaceutical use. A "pharmaceutically acceptable carrier or excipient" as used in the specification and claims includes both one and more than one such carrier or excipient.

With reference to the methods disclosed herein, the following terms are used with the noted meanings:

The terms "treating" or "treatment" of a disease or condition includes:

(1) preventing or reducing the risk of developing the disease or condition, i.e., causing the clinical symptoms of the disease or condition not to develop in a mammal that may be exposed to or predisposed to the disease or condition but does not yet experience or display symptoms of the disease or condition, (2) inhibiting the disease or condition, i.e., arresting or reducing the development of the disease or condition, or its clinical symptoms, or (3) relieving the disease or condition, i.e., causing regression of the disease or condition, or its clinical symptoms, or any combination of two or more thereof.

A preferred embodiment is treatment of a disease or condition that consists of relieving the disease or condition.

The term "diagnosing" refers to determining the presence or absence of a particular disease or condition. Additionally, the term refers to determining the level or severity of a particular disease or condition, as well as monitoring of the disease or condition to determine its response to a particular therapeutic regimen.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease or condition, is sufficient to effect such treatment for the disease or condition. The "therapeutically effective amount" will vary depending on the compound, the disease or condition, and its severity, and the age, weight, etc., of the mammal to be treated.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, the term "subject" is used interchangeably with "patient".

The term "mammal" includes, without limitation, humans, domestic animals (e.g., dogs or cats), farm animals (cows, horses, or pigs), and laboratory animals (mice, rats, hamsters, guinea pigs, pigs, rabbits, dogs, or monkeys).

The term "agonist" refers to a compound that binds to a receptor and triggers a response in a cell. An agonist mimics the effect of an endogenous ligand, a hormone for example, and produces a physiological response similar to that produced by the endogenous ligand.

The term "partial agonist" refers to a compound that binds to a receptor and triggers a partial response in a cell. A partial agonist produces only a partial physiological response of the endogenous ligand.

Glucagon-like peptide-2 (GLP-2) is a 33-amino acid peptide, co-secreted with GLP-1 from intestinal endocrine cells in the small and large intestine.

GPR119 is a G protein-coupled receptor mainly found on enteroendocrine K and L cells and on pancreatic islets.

Provided herein, in one aspect, are methods of treating an inflammatory gastrointestinal disease or a gastrointestinal condition involving malabsorption of nutrients and/or fluids in a patient in need thereof, the methods comprising administering to the patient a therapeutically effective amount of a GPR119 agonist.

In another aspect, provided herein are methods of treating an inflammatory gastrointestinal disease or a gastrointestinal condition involving malabsorption of nutrients and/or fluids in a patient in need thereof, the methods comprising administering to the patient a therapeutically effective amount of a GPR119 agonist and a therapeutically effective amount of a DPP IV inhibitor.

In another aspect, provided herein are methods of treating an inflammatory gastrointestinal disease or a gastrointestinal condition involving malabsorption of nutrients and/or fluids in a patient in need thereof, the methods comprising administering to the patient a therapeutically effective amount of a GPR119 agonist, a therapeutically effective amount of a DPP IV inhibitor, and a therapeutically effective amount of metformin.

Illustrative inflammatory gastrointestinal diseases or gastrointestinal condition s involving malabsorption of nutrients and/or fluids include, but are not limited to, short bowel syndrome (SBS), inflammatory bowel disease (IBD), Crohn's disease, ulcerative colitis, *volvulus*, and necrotizing enterocolitis. In some embodiments, the inflammatory gastrointestinal disease or the gastrointestinal condition involving malabsorption of nutrients and/or fluids is short bowel syndrome. In some embodiments, the inflammatory gastrointestinal disease or the gastrointestinal condition involving malabsorption of nutrients and/or fluids is inflammatory bowel disease. In some embodiments, the inflammatory gastrointestinal disease or the gastrointestinal condition involving malabsorption of nutrients and/or fluids is Crohn's disease or ulcerative colitis. In some embodiments, the inflammatory gastrointestinal disease or the gastrointestinal condition involving malabsorption of nutrients and/or fluids is Crohn's disease. In some embodiments, the inflammatory gastrointestinal disease or the gastrointestinal condition involving malabsorption of nutrients and/or fluids is ulcerative colitis. In some embodiments, the inflammatory gastrointestinal disease or the gastrointestinal condition involving malabsorption of nutrients and/or fluids is *volvulus*. In some embodiments, the inflammatory gastrointestinal disease or the gastrointestinal condition involving malabsorption of nutrients and/or fluids is necrotizing enterocolitis.

In some embodiments, the GPR119 agonists are compounds of Formula (I), represented by the following:

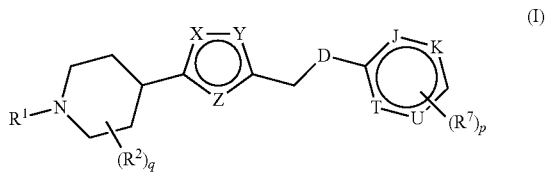

wherein the letters X, Y, and Z are each independently selected from the group consisting of O, N, $NR^8$, S, and $C(R^3)$ and at least one of X, Y, and Z is O, N, $NR^8$, or S; J, K, T, and U are each independently selected from the group consisting of C, CH, and N; the subscript p is an integer of from 0 to 4; and the subscript q is an integer of from 0 to 4.

In Formula (I), $R^1$ is a member selected from the group consisting of H, $C_{1-10}$alkyl, $C_{1-10}$substituted alkyl, $C_{3-7}$cycloalkyl, $C_{2-10}$ alkenyl, $C_{2-10}$ alkynyl, $-X^1-COR^a$, $-X^1-CO_2R^a$, $-X^1-CONR^aR^b$, $-SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1-10}$alkyl, $C_{1-10}$substituted alkyl, $C_{3-7}$cycloalkyl, $C_{2-10}$ alkenyl, $C_{2-10}$ alkynyl, aryl, heteroaryl, $-CN$, $-NR^aCOR^b$, $-NR^aCONR^aR^b$, $-NO_2$, $-OR^a$, $-NR^aR^b$, $-COR^a$, $-CO_2R^a$, $-CONR^aR^b$, $-S(O)_mR^a$, $-NR^aS(O)_2R^b$, and $SO_2NR^aR^b$, or optionally $R^a$ and $R^b$ are combined to form a 4-, 5- or 6-membered ring, and $X^1$ is selected from the group consisting of a bond, $C_{2-6}$alkene, $C_{2-6}$alkyne, $-C(O)-$, and $-C(O)-(CH_2)_{1-4}-$, wherein the aliphatic portions of $X^1$ are optionally substituted with one to three members selected from halogen, $C_{1-4}$alkyl, $C_{1-4}$substituted alkyl and $C_{1-4}$haloalkyl.

Turning next to $R^2$, each $R^2$ is a member independently selected from the group consisting of halogen, $C_{1-5}$ alkyl, $C_{1-5}$substituted alkyl, $C_{3-7}$cycloalkyl, $-COR^a$, $-CO_2R^a$, $-CONR^aR^b$, $-OR^a$, $-NR^aR^b$, $-NR^aCOR^b$, $-SOR^aR^b$, $-SO_2R^a$ and $-SO_2NR^aR^b$, and wherein when the subscript q is 2 and $R^2$ is alkyl or substituted alkyl, the two $R^2$ members can optionally cyclize to form a ring.

$R^3$ is a member selected from the group consisting of hydrogen, halogen, $C_{1-4}$alkyl, and $C_{1-4}$haloalkyl.

Each $R^7$ of Formula (I) is independently selected from the group consisting of halo, $C_{1-10}$alkyl $C_{1-10}$substituted alkyl, $C_{3-7}$cycloalkyl, $C_{2-10}$alkenyl, $C_{2-10}$ alkynyl, $-CN$, $-NO_2$, $-OR^a$, $-NR^aR^b$, $-COR^a$, $-CO_2R^a$, $-CONR^aR^b$, $-NR^aCOR^b$, $-NR^aCO_2R^b$, $-NR^aCONR^aR^b$, $-S(O)_mR^a$, $-NR^aS(O)_mR^b$, $-SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, $-CN$, $-NO_2$, $-OR^a$, $-NR^aR^b$, $-COR^a$, $-CO_2R^a$, $-CONR^aR^b$, $-NR^aCOR^b$, $-NR^aCO_2R^b$, $-NR^aCONR^aR^b$, $-S(O)_mR^a$, $-NR^aSO_2R^b$, and $-SO_2NR^aR^b$ and wherein the subscript m is an integer of from 0 to 2, or optionally $R^a$ and $R^b$ are combined to form a 4-, 5- or 6-membered ring.

$R^8$ is a member independently selected from the group consisting of hydrogen, $C_{1-4}$alkyl, and $C_{1-4}$haloalkyl.

For each of the above groups, each $R^a$ and $R^b$ is independently selected from the group consisting of hydrogen, $C_{1-10}$ alkyl, $C_{1-10}$haloalkyl, $C_{3-10}$ cycloalkyl, heterocyclyl, $C_{2-10}$alkenyl, $C_{2-10}$alkynyl, aryl, 5- to 6-membered heteroaryl and aryl$C_{1-4}$alkyl; and wherein the aliphatic portions of each of said $R^a$ and $R^b$ is optionally substituted with from one to three members selected from the group consisting of halo, —OR″, —OCOR″, —OC(O)N(R″)$_2$, —SR$^a$, —S(O)R″, —S(O)$_2$R″, —S(O)$_2$N(R″)$_2$, —NR″S(O)$_2$R″, —C(O)N(R″)$_2$, —C(O)R″, —NR″C(O)R″, —NR″C(O)N(R″)$_2$, —CO$_2$R″, —NR″CO$_2$R″, —CN, —NO$_2$, —N(R″)$_2$ and —NR″S(O)$_2$N(R″)$_2$, wherein each IV is independently hydrogen or an unsubstituted $C_{1-6}$ alkyl; and wherein the aryl and heteroaryl portions are optionally substituted with from one to three members selected from halogen, —OR‴, —OC(O)N(R‴)$_2$, —SR‴, —S(O)R‴, —S(O)$_2$R‴, —S(O)$_2$N(R‴)$_2$, —NR‴S(O)$_2$R‴, —C(O)N(R‴)$_2$, —C(O)R‴, —NR‴C(O)R‴, —NR‴C(O)N(R‴)$_2$, —CO$_2$R‴, —NR‴CO$_2$R‴, —CN, —NO$_2$, —N(R‴)$_2$ and —NR‴S(O)$_2$N(R‴)$_2$, wherein each R‴ is independently hydrogen or an unsubstituted $C_{1-6}$ alkyl.

The compounds provided herein also include any pharmaceutically acceptable salts of the compounds as well as any isotopically labeled isomers thereof. In general, the compounds useful in the methods described herein are those compound of the formula above, wherein the molecular weight of the compound is less than 1200, more preferably less than about 1000, still more preferably less than about 800 and still more preferably from about 200 to about 600.

In some embodiments, a $R^1$ group is selected from the group consisting of —$X^1$—COR$^a$, —$X^1$—CO$_2$R$^a$, —$X^1$—CONR$^a$R$^b$, —SO$_2$R$^a$, aryl, heteroaryl, substituted aryl and substituted heteroaryl. In some embodiments, when $R^1$ is an aromatic substituent, $R^1$ is selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl.

In some embodiments, when $R^1$ is an aromatic substituent, e.g., aryl or heteroaryl, $R^1$ is substituted with from one to three substituents selected from the group consisting of $C_{1-10}$alkyl, $C_{1-10}$haloalkyl, $C_{3-7}$cycloalkyl, aryl, heteroaryl, —NO$_2$, —OR$^a$, —NR$^a$R$^b$, —CO$_2$R$^a$, —CONR$^a$R$^b$, —S(O)$_m$ R$^a$, —NR$^a$S(O)$_2$R$^b$, and SO$_2$NR$^a$R$^b$.

In some embodiments, $R^2$ is a member independently selected from the group consisting of halo, $C_{1-5}$alkyl, $C_{1-5}$haloalkyl, and the subscript q is an integer of from 0 to 2.

In some embodiments, D is O. In compounds of Formula (I), when D is O, a $R^1$ group is selected from the group consisting of —$X^1$—COR$^a$, —$X^1$—CO$_2$R$^a$, —$X^1$—CONR$^a$R$^b$, —SO$_2$R$^a$, aryl, heteroaryl, substituted aryl and substituted heteroaryl. In some embodiments, when $R^1$ is an aromatic substituent, $R^1$ is selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl.

Additionally, in some embodiments, when D is O, and $R^1$ is an aromatic substituent, e.g., aryl or heteroaryl, $R^1$ is substituted with from one to three substituents selected from the group consisting of $C_{1-10}$alkyl, $C_{1-10}$haloalkyl, $C_{3-7}$cycloalkyl, aryl, heteroaryl, —NO$_2$, —OR$^a$, —NR$^a$R$^b$, —CO$_2$R$^a$, —CONR$^a$R$^b$, —S(O)$_m$R$^a$, —NR$^a$S(O)$_2$R$^b$, and SO$_2$NR$^a$R$^b$.

In some embodiments, J, K, T, and U are all C or CH. In further embodiments, a $R^1$ group is selected from the group consisting of —$X^1$—COR$^a$, —$X^1$—CO$_2$R$^a$, —$X^1$—CONR$^a$R$^b$, —SO$_2$R$^a$, aryl, heteroaryl, substituted aryl and substituted heteroaryl. In some embodiments, when $R^1$ is an aromatic substituent, $R^1$ is selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl. In further embodiments, when J, K, T, and U are all C or CH, and $R^1$ is an aromatic substituent, e.g., aryl or heteroaryl, $R^1$ is substituted with from one to three substituents selected from the group consisting of $C_{1-10}$alkyl, $C_{1-10}$haloalkyl, $C_{3-7}$cycloalkyl, aryl, heteroaryl, —NO$_2$, —OR$^a$, —NR$^a$R$^b$, —CO$_2$R$^a$, —CONR$^a$R$^b$, —S(O)$_m$ R$^a$, —NR$^a$S(O)$_2$R$^b$, and SO$_2$NR$^a$R$^b$.

In some embodiments, the subscript p is an integer of from 1 to 3 and each $R^7$ is independently selected from the group consisting of halo, $C_{1-10}$alkyl, $C_{1-10}$haloalkyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —S(O)$_m$R$^a$, —NR$^a$S(O)$_m$R$^b$, —SO$_2$NR$^a$R$^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, —CN, —NO$_2$, —OR$^a$, —NR$^a$R$^b$, —CO$_2$R$^a$, —CONR$^a$R$^b$, —NR$^a$COR$^b$, —NR$^a$CO$_2$R$^b$, —S(O)$_m$R$^a$, —NR$^a$SO$_2$R$^b$, and —SO$_2$NR$^a$R$^b$ and wherein the subscript m is an integer of from 0 to 2.

In some embodiments, J, K, T, and U are all C or CH. In further embodiments, a $R^1$ group is selected from the group consisting of —$X^1$—COR$^a$, —$X^1$—CO$_2$R$^a$, —$X^1$—CONR$^a$R$^b$, —SO$_2$R$^a$, aryl, heteroaryl, substituted aryl and substituted heteroaryl. In some embodiments, when $R^1$ is an aromatic substituent, $R^1$ is selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl; and the subscript p is an integer of from 1 to 3 and each $R^7$ is independently selected from the group consisting of halo, $C_{1-10}$alkyl, $C_{1-10}$haloalkyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —S(O)$_m$R$^a$, —NR$^a$S(O)$_m$R$^b$, —SO$_2$NR$^a$R$^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, —CN, —NO$_2$, —OR$^a$, —NR$^a$R$^b$, —CO$_2$R$^a$, —CONR$^a$R$^b$, —NR$^a$COR$^b$, —NR$^a$CO$_2$R$^b$, —S(O)$_m$R$^a$, —NR$^a$SO$_2$R$^b$, and —SO$_2$NR$^a$R$^b$ and wherein the subscript m is an integer of from 0 to 2. Optionally, $R^1$ is substituted with from one to three substituents selected from the group consisting of $C_{1-10}$alkyl, $C_{1-10}$haloalkyl, $C_{3-7}$cycloalkyl, aryl, heteroaryl, —NO₂, —ORᵃ, —NRᵃRᵇ, —CO₂Rᵃ, —CONRᵃRᵇ, —S(O)ₘ Rᵃ, —NRᵃS(O)₂Rᵇ, and SO₂NRᵃRᵇ.

In some embodiments, at least one of J, K, T, and U is N. In further embodiments, D is O, S, or NR⁸.

In some embodiments, at least one of J, K, T, and U is N and D is O.

In some embodiments, when at least one of J, K, T, and U is N and D is O, a R¹ group is selected from the group consisting of —X¹—CORᵃ, —X¹—CO₂Rᵃ, —X¹—CONRᵃRᵇ, —SO₂Rᵃ, aryl, heteroaryl, substituted aryl and substituted heteroaryl. In some embodiments, when R¹ is an aromatic substituent, R¹ is selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, substituted imidazolyl, triazolyl, substituted triazolyl, oxazolyl, substituted oxazolyl, thiazolyl, substituted thiazolyl, oxadiazolyl, substituted oxadiazolyl, tetrazolyl, and substituted tetrazolyl; and the subscript p is an integer of from 1 to 3 and each R⁷ is independently selected from the group consisting of halo, $C_{1-10}$alkyl, $C_{1-10}$haloalkyl, —CN, —NO₂, —ORᵃ, —NRᵃRᵇ, —CORᵃ, —CO₂Rᵃ, —CONRᵃRᵇ, —NRᵃCORᵇ, —NRᵃCO₂Rᵇ, —S(O)ₘRᵃ, —NRᵃS(O)ₘRᵇ, —SO₂NRᵃRᵇ, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, —CN, —NO₂, —ORᵃ, —NRᵃRᵇ, —CO₂Rᵃ, —CONRᵃRᵇ, —NRᵃCORᵇ, —NRᵃCO₂Rᵇ, —S(O)ₘRᵃ, —NRᵃSO₂Rᵇ, and —SO₂NRᵃRᵇ and wherein the subscript m is an integer of from 0 to 2. Optionally, R¹ is substituted with from one to three substituents selected from the group consisting of $C_{1-10}$alkyl, $C_{1-10}$haloalkyl, $C_{3-7}$cycloalkyl, aryl, heteroaryl, —NO₂, —ORᵃ, —NRᵃRᵇ, —CO₂Rᵃ, —CONRᵃRᵇ, —S(O)ₘRᵃ, —NRᵃS(O)₂Rᵇ, and —SO₂NRᵃRᵇ.

In some embodiments, when at least one of J, K, T, and U is N and D is O, and R¹ is as described in the above paragraph, the subscript p is an integer of from 1 to 3 and each R⁷ is independently selected from the group consisting of halo, $C_{1-10}$alkyl, $C_{1-10}$haloalkyl, —CN, —NO₂, —ORᵃ, —NRᵃRᵇ, —CORᵃ, —CO₂Rᵃ, —CONRᵃRᵇ, —NRᵃCORᵇ, —NRᵃCO₂Rᵇ, —S(O)ₘRᵃ, —NRᵃS(O)ₘRᵇ, —SO₂NRᵃRᵇ, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, —CN, —NO₂, —ORᵃ, —NRᵃRᵇ, —CO₂Rᵃ, —CONRᵃRᵇ, —NRᵃCORᵇ, —NRᵃCO₂Rᵇ, —S(O)ₘRᵃ, —NRᵃSO₂Rᵇ, and —SO₂NRᵃRᵇ and wherein the subscript m is an integer of from 0 to 2.

In some embodiments, J, T, and U are all C or CH, and D is O, S, or NR⁸.

In some embodiments, J, T, and U are all C or CH, and D is O.

In some embodiments, when J, T, and U are all C or CH, and D is O, the R⁷ group is a member independently selected from the group consisting of halo, $C_{1-10}$ alkyl, $C_{1-10}$ haloalkyl, —CN, —NO₂, —ORᵃ, —NRᵃRᵇ, —CORᵃ, —CO₂Rᵃ, —CONRᵃRᵇ, —NRᵃCORᵇ, —NRᵃCO₂Rᵇ, —S(O)ₘRᵃ, —NR"S(O)ₘRᵇ, —SO₂NRᵃRᵇ, a 4- to 5-membered heterocyclo group, and a 5- to 6-membered heteroaryl group and wherein the subscript m is an integer of from 0 to 2. In some embodiments, R⁷ groups are independently selected from the group consisting of halo, $C_{1-5}$alkyl, $C_{1-5}$haloalkyl, —SORᵃ, —SO₂Rᵃ, and 5-membered heteroaryl group. In further embodiments, R⁷ groups are independently selected from the group consisting of fluoro, chloro, methyl, ethyl, —CF₃, —SO₂CH₃, imidazolyl, triazolyl, and tetrazolyl and wherein the subscript p is integer of from 1 to 2.

In some embodiments, when J, T, and U are all C or CH, and D is O, the R⁷ group is a member independently selected from the group consisting of halo, $C_{1-10}$ alkyl, $C_{1-10}$ haloalkyl, —CN, —NO₂, —ORᵃ, —NRᵃRᵇ, —CORᵃ, —CO₂Rᵃ, —CONRᵃRᵇ, —NRᵃCORᵇ, —NRᵃCO₂Rᵇ, —S(O)ₘRᵃ, —NRᵃS(O)ₘRᵇ, —SO₂NRᵃRᵇ, a 4- to 5-membered heterocyclo group, and a 5- to 6-membered heteroaryl group and wherein the subscript m is an integer of from 0 to 2, and each R² is a member independently selected from the group consisting of halo, $C_{1-5}$alkyl, $C_{1-5}$haloalkyl, and the subscript q is an integer of from 0 to 2. In some embodiments, R⁷ groups are independently selected from the group consisting of halo, $C_{1-5}$alkyl, $C_{1-5}$haloalkyl, —SORᵃ, —SO₂Rᵃ, and 5-membered heteroaryl group. In further embodiments, R⁷ groups are independently selected from the group consisting of fluoro, chloro, methyl, ethyl, —CF₃, —SO₂$C_{1-3}$ alkyl, imidazolyl, triazolyl, and tetrazolyl and wherein the subscript p is integer of from 1 to 2.

In some embodiments, when J, T, and U are all C or CH, and D is O, the R⁷ group is a member as described above, and R¹ is selected from the group consisting of —X¹—CORᵃ, —X¹CO₂Rᵃ, —X¹—CONRᵃRᵇ, —SO₂Rᵃ, aryl, heteroaryl, substituted aryl and substituted heteroaryl. In some embodiments, R¹ group is selected from the group consisting of is aryl, heteroaryl, substituted aryl and substituted heteroaryl. In further embodiments, leis selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl. In still further embodiments, leis selected from the group consisting of pyrimidinyl, substituted pyrimidinyl, oxadiazolyl, substituted oxadiazolyl, and —X¹—CO₂Rᵃ and wherein X¹ is a bond.

In some embodiments, J, T, and U are all C or CH; and D is O, X is S, Y is C, Z is N; R¹ is selected from the group consisting of pyrimidinyl, substituted pyrimidinyl, pyridyl, and substituted pyridyl, each R⁷ is independently selected from the group consisting of fluoro and tetrazolyl.

Compounds of Formula (I) are shown in the example section herein. Preferred compounds of Formula (I) are the compounds of examples 1-210. Even more preferred compounds of Formula (I) are the compounds of examples 52, 76, 77, 95, 148, 162, 170, 171, 182, 184, 185, and 195.

In particular, a preferred compound of Formula (I) is

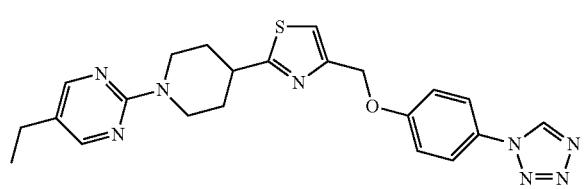 [SMILES: CCc1cnc(N2CCC(c3nc(COc4ccc(-n5cnnn5)cc4)cs3)CC2)nc1]

or a pharmaceutically acceptable salt thereof.

The compounds of Formula (I) are synthesized according to the procedures set forth in co-owned and co-pending applications U.S. Ser. No. 11/964,461 and PCT/US2007/

088978. One of skill in the art can readily synthesize compounds of Formula (I) as taught in these patent applications.

In another aspect, provided herein are methods of treating an inflammatory gastrointestinal disease or a gastrointestinal condition involving malabsorption of nutrients and/or fluids in a patient in need thereof, the methods comprising administering to the patient a therapeutically effective amount of a compound of Formula (I):

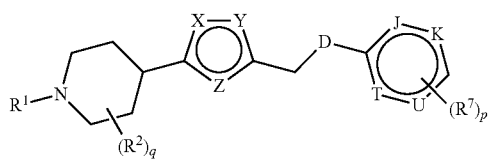

wherein,
D is selected from the group consisting of O, S, and $NR^8$;
X, Y, and Z are independently selected from the group consisting of O, N, $NR^8$, S, and $CR^3$ and at least one of X, Y, and Z is O, N, $NR^8$, or S;
J, K, T, and U are each independently selected from the group consisting of C, CH, and N;
the subscript p is an integer of from 0 to 4;
the subscript q is an integer of from 0 to 4;
$R^1$ is a member selected from the group consisting of H, $C_{1-10}$alkyl, $C_{1-10}$substituted alkyl, $C_{3-7}$cycloalkyl, $C_{2-10}$alkenyl, $C_{2-10}$ alkynyl, —$X^1$—$COR^a$, —$X^1$—$CO_2R^a$, —$X^1$—$CONR^aR^b$, —$SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1-10}$alkyl, $C_{1-10}$substituted alkyl, $C_{3-7}$cycloalkyl, $C_{2-10}$ alkenyl, $C_{2-10}$ alkynyl, aryl, heteroaryl, —CN, —$NR^aCOR^b$, —$NR^aCONR^aR^b$, —$NO_2$, —$OR^a$, —$NR^aR^b$, —$COR^a$, —$CO_2R^a$, —$CONR^aR^b$, —$S(O)_mR^a$, —$NR^aS(O)_2R^b$, and —$SO_2NR^aR^b$, or optionally $R^a$ and $R^b$ are combined to form a 4-, 5- or 6-membered ring, and $X^1$ is selected from the group consisting of a bond, $C_{2-6}$alkene, $C_{2-6}$alkyne, —C(O)—, and —C(O)—$(CH_2)_{1-4}$—, wherein the aliphatic portions of $X^1$ are optionally substituted with one to three members selected from halogen, $C_{1-4}$alkyl, $C_{1-4}$substituted alkyl and $C_{1-4}$haloalkyl;
each $R^2$ is a member independently selected from the group consisting of halogen, $C_{1-5}$ alkyl, $C_{1-5}$substituted alkyl, $C_{3-7}$cycloalkyl, —$COR^a$, —$CO_2R^a$, —$CONR^aR^b$, —$OR^a$, —$NR^aR^b$, —$NR^aCOR^b$, —$SOR^aR^b$, —$SO_2R^a$ and —$SO_2NR^aR^b$, and wherein when the subscript q is 2 and $R^2$ is alkyl or substituted alkyl, the two $R^2$ members can optionally cyclize to form a ring;
$R^3$ is a member selected from the group consisting of hydrogen, halogen, $C_{1-4}$alkyl, and $C_{1-4}$haloalkyl;
each $R^7$ is independently selected from the group consisting of halo, $C_{1-10}$alkyl, $C_{1-10}$ substituted alkyl, $C_{3-7}$cycloalkyl, $C_{2-10}$alkenyl, $C_{2-10}$ alkynyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aSO_2R^b$, and —$SO_2NR^aR^b$ and wherein the subscript m is an integer of from 0 to 2, or optionally $R^a$ and $R^b$ are combined to form a 4-, 5- or 6-membered ring;
$R^8$ is a member independently selected from the group consisting of hydrogen, $C_{1-4}$alkyl, and $C_{1-4}$haloalkyl;
and each $R^a$ and $R^b$ is independently selected from the group consisting of hydrogen, $C_{1-10}$ alkyl, $C_{1-10}$haloalkyl, $C_{3-10}$ cycloalkyl, heterocyclyl, $C_{2-10}$ alkenyl, $C_{2-10}$ alkynyl, aryl, 5- to 6-membered heteroaryl and aryl$C_{1-4}$alkyl; and wherein the aliphatic portions of each of said $R^a$ and $R^b$ is optionally substituted with from one to three members selected from the group consisting of halo, —$OR''$, —$OCOR''$, —$OC(O)N(R'')_2$, —$SR''$, —$S(O)R''$, —$S(O)_2R''$, —$S(O)_2N(R'')_2$, —$NR''S(O)_2R''$, —$C(O)N(R'')_2$, —$C(O)R''$, —$NR''C(O)R''$, —$NR''C(O)N(R'')_2$, —$CO_2R''$, —$NR''CO_2R''$, —CN, —$NO_2$, —$N(R'')_2$ and —$NR''S(O)_2N(R'')_2$, wherein each $R''$ is independently hydrogen or an unsubstituted $C_{1-6}$ alkyl;
and wherein the aryl and heteroaryl portions are optionally substituted with from one to three members selected from halogen, —$OR'''$, —$OC(O)N(R''')_2$, —$S(O)R'''$, —$S(O)_2R'''$, —$S(O)_2N(R''')_2$, —$NR'''S(O)_2R'''$, —$C(O)N(R''')_2$, —$C(O)R'''$, —$NR'''C(O)R'''$, —$NR'''C(O)N(R''')_2$, —$CO_2R'''$, —$NR'''CO_2R'''$, —CN, —$NO_2$, —$N(R''')_2$ and —$NR'''S(O)_2N(R''')_2$, wherein each $R'''$ is independently hydrogen or an unsubstituted $C_{1-6}$ alkyl; or a pharmaceutically acceptable salt or ester thereof; and wherein the molecular weight of said compound is less than 1200.

In some embodiments, the compound of Formula (I) is selected from the group consisting of the compounds of examples 1-210. In further embodiments, the compound of Formula (I) is selected from the group consisting of the compounds of examples 52, 76, 77, 95, 148, 162, 170, 171, 182, 184, 185, and 195. In still further embodiments, the compound of Formula (I) is 5-Ethyl-2-{4-[4-(4-tetrazol-1-yl-phenoxymethyl)-thiazol-2-yl]-piperidin-1-yl}-pyrimidine or a pharmaceutically acceptable salt thereof. The structure of the compound is shown below.

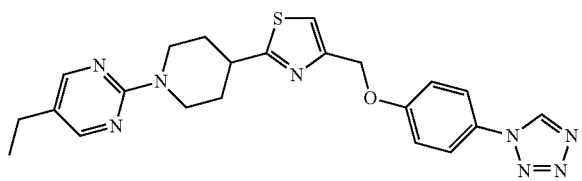 [SMILES: CCc1cnc(N2CCC(c3nc(COc4ccc(-n5cnnn5)cc4)cs3)CC2)nc1]

In another aspect, provided herein are methods of treating an inflammatory gastrointestinal disease or a gastrointestinal condition involving malabsorption of nutrients and/or fluids in a patient in need thereof, the methods comprising administering to the patient a therapeutically effective amount of a DPP IV inhibitor and a therapeutically effective amount of a compound of Formula (I):

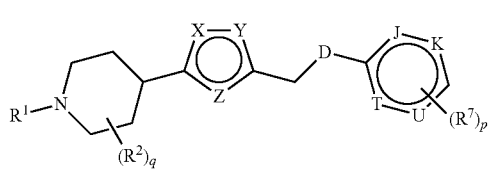

wherein,
D is selected from the group consisting of O, S, and NR$^8$,
X, Y, and Z are independently selected from the group consisting of O, N, NR$^8$, S, and CR$^3$ and at least one of X, Y, and Z is O, N, NR$^8$, or S;
J, K, T, and U are each independently selected from the group consisting of C, CH, and N;
the subscript p is an integer of from 0 to 4;
the subscript q is an integer of from 0 to 4;
R$^1$ is a member selected from the group consisting of H, C$_{1-10}$alkyl, C$_{1-10}$substituted alkyl, C$_{3-7}$cycloalkyl, C$_{2-10}$ alkenyl, C$_{2-10}$ alkynyl, —X$^1$—CO$_2$R$^a$, —X$^1$—CONR$^a$R$^b$, —SO$_2$R$^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, C$_{1-10}$alkyl, C$_{1-10}$substituted alkyl, C$_{3-7}$cycloalkyl, C$_{2-10}$ alkenyl, C$_{2-10}$ alkynyl, aryl, heteroaryl, —CN, —NR$^a$COR$^b$, —NR$^a$CONR$^a$R$^b$, —NO$_2$, —OR$^a$, —NR$^a$R$^b$, —COR$^a$, —CO$_2$R$^a$, —CONR$^a$R$^b$, —S(O)$_m$R$^a$, —NR$^a$S(O)$_2$R$^b$, and SO$_2$NR$^a$R$^b$, or optionally R$^a$ and R$^b$ are combined to form a 4-, 5- or 6-membered ring, and X' is selected from the group consisting of a bond, C$_{2-6}$alkene, C$_{2-6}$alkyne, —C(O)—, and —C(O)—(CH$_2$)$_{1-4}$-, wherein the aliphatic portions of X$^1$ are optionally substituted with one to three members selected from halogen, C$_{1-4}$alkyl, C$_{1-4}$substituted alkyl and C$_{1-4}$haloalkyl;
each R$^2$ is a member independently selected from the group consisting of halogen, C$_{1-5}$ alkyl, C$_{1-5}$substituted alkyl, C$_{3-7}$cycloalkyl, —COR$^a$, —CO$_2$R$^a$, —CONR$^a$R$^b$, —OR$^a$, —NR$^a$R$^b$, —NR$^a$COR$^b$, —SOR$^a$R$^b$, —SO$_2$R$^a$ and —SO$_2$NR$^a$R$^b$, and wherein when the subscript q is 2 and R$^2$ is alkyl or substituted alkyl, the two R$^2$ members can optionally cyclize to form a ring;
R$^3$ is a member selected from the group consisting of hydrogen, halogen, C$_{1-4}$alkyl, and C$_{1-4}$haloalkyl;
each R$^7$ is independently selected from the group consisting of halo, C$_{1-10}$alkyl, C$_{1-10}$ substituted alkyl, C$_{3-7}$cycloalkyl, C$_{2-10}$ alkenyl, C$_{2-10}$ alkynyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —S(O)$_m$R$^a$, —NR$^a$S(O)$_m$R$^b$, —SO$_2$NR$^a$R$^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, C$_{1-4}$ alkyl, C$_{1-4}$ haloalkyl, C$_{3-7}$ cycloalkyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —NR$^a$SO$_2$R$^b$, and —SO$_2$NR$^a$R$^b$ and wherein the subscript m is an integer of from 0 to 2, or optionally R$^a$ and R$^b$ are combined to form a 4-, 5- or 6-membered ring;

R$^8$ is a member independently selected from the group consisting of hydrogen, C$_{1-4}$alkyl, and C$_{1-4}$haloalkyl;
and each R$^a$ and R$^b$ is independently selected from the group consisting of hydrogen, C$_{1-10}$ alkyl, C$_{1-10}$haloalkyl, C$_{3-10}$ cycloalkyl, heterocyclyl, C$_{2-10}$ alkenyl, C$_{2-10}$ alkynyl, aryl, 5- to 6-membered heteroaryl and arylC$_{1-4}$alkyl; and wherein the aliphatic portions of each of said R$^a$ and R$^b$ is optionally substituted with from one to three members selected from the group consisting of halo, —OR", —OCOR", —OC(O)N(R")$_2$, —S(O)R", —S(O)$_2$R", —S(O)$_2$N(R")$_2$, —NR"S(O)$_2$R", —C(O)N(R")$_2$, —C(O)R", —NR"C(O)R", —NR"C(O)N(R")$_2$, —CO$_2$R", —NR"CO$_2$R", —CN, —NO$_2$, —N(R")$_2$ and —NR"S(O)$_2$N(R")$_2$, wherein each R" is independently hydrogen or an unsubstituted C$_{1-6}$ alkyl;
and wherein the aryl and heteroaryl portions are optionally substituted with from one to three members selected from halogen, —OR'", —OC(O)N(R'")$_2$, —S(O)R'", —S(O)$_2$R'", —S(O)$_2$N(R'")$_2$, —NR'"S(O)$_2$R'", —C(O)N(R'")$_2$, —C(O)R'", —NR'"C(O)R'", —NR'"C(O)N(R'")$_2$, —CO$_2$R'", —NR'"CO$_2$R'", —CN, —NO$_2$, —N(R'")$_2$ and —NR'"S(O)$_2$N(R'")$_2$, wherein each R'" is independently hydrogen or an unsubstituted C$_{1-6}$ alkyl; or a pharmaceutically acceptable salt or ester thereof; and wherein the molecular weight of said compound is less than 1200.

In some embodiments, the compound of Formula (I) is selected from the group consisting of the compounds of examples 1-210. In further embodiments, the compound of Formula (I) is selected from the group consisting of the compounds of examples 52, 76, 77, 95, 148, 162, 170, 171, 182, 184, 185, and 195. In still further embodiments, the compound of Formula (I) is 5-Ethyl-2-{4-[4-(4-tetrazol-1-yl-phenoxymethyl)-thiazol-2-yl]-piperidin-1-yl}-pyrimidine or a pharmaceutically acceptable salt thereof. The structure of the compound is shown below.

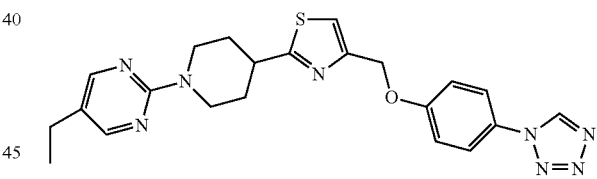

Illustrative DPP IV inhibitors include, but are not limited to, sitagliptin (Merck), vildagliptin (Novartis), BMS-477118 (saxagliptin) (Bristol-Myers Squibb), BI-1356 (linagliptin) (Boehringer Ingelheim), R1438 (aminomethylpyridine) (Roche), NVP DPP728 (Novartis), PSN9301 (Prosidion), P32/98 (isoleucine thiozolidide) (Probiodrug), GSK823093C (denagliptin) (Glaxo Smithkline), SYR-322 (Alogliptin) (Takeda), NN-7201 (NovoNordisk), ALS2-0426 (Alantos), LC15-0444 (gemigliptin) (LG Life Sciences), SK-0403 (anagliptin) (Kowa), teneligliptin (Mitsubishi Tanabe), trelagliptin (Takeda), dutogliptin (Phenomix), and omarigliptin (Merck). (see, e.g., Green B D, Flatt P R, Bailey C J, Dipeptidyl peptidase IB (DPP IV) inhibitors: a newly emerging drug class for the treatment of Type II diabetes, *Diabetes Vasc Dis Res* 2006, 3:159-165) In some embodiments, the DPP IV inhibitor is selected from the group consisting of sitagliptin, vildagliptin, saxagliptin, linagliptin, gemigliptin, anagliptin, teneligliptin, trelagliptin, omarigliptin, and alogliptin. In still further embodiments, the DPP IV inhibitor is sitagliptin or vildagliptin.

The compound of Formula (I) and DPP IV inhibitor are administered in a single dosage or in separate dosages. The single dosage is administered once a day or multiple times a day. When the compound of Formula (I) and DPP IV inhibitor are administered in separate dosages, the dosages are administered once a day or multiple times a day.

In some embodiments, when the compound of Formula (I) and the DPP IV inhibitor are administered in a single dosage, the compound of Formula (I) and DPP IV inhibitor are formulated as a medicament into a single pill, single tablet, or a single capsule. When the compound of Formula (I) and DPP IV inhibitor are administered in separate dosages, the compound of Formula (I) is formulated as a medicament into a pill, tablet or capsule and the DPP IV inhibitor is formulated into a separate pill or capsule.

When the compound of Formula (I) and DPP IV inhibitor are administered in separate dosages, the compound of Formula (I) can be administered first and the DPP IV inhibitor can be administered next, following administration of the compound of Formula (I). Alternatively, the DPP IV inhibitor can be administered first and the compound of Formula (I) can be administered next, following administration of the DPP IV inhibitor. The time between the sequential first administration and the second administration can be varied by a skilled practitioner. In some embodiments, the first administration (a compound of Formula (I) or DPP IV inhibitor), is followed immediately by the second administration (a compound of Formula (I) or DPP IV inhibitor). In some embodiments, the second administration is within 2 minutes, 5 minutes, 10 minutes, 15 minutes, 30 minutes, or 60 minutes, 1 hour, 2 hours, 3 hours, 4 hours, 5 hours, 6 hours, 7 hours, 8 hours, 9 hours, 10 hours, 11 hours, or 12 hours following the first administration. Yet other embodiment provide for the administration to a patient a compound for Formula (I) and/or DPP IV inhibitor in the morning followed by administration to the previously treated patient a compound of Formula (I) and/or DPP IV inhibitor in the evening.

In some embodiments, the method further comprises administering a therapeutically effective amount of metformin. Administration of metformin may be sequentially or concurrently performed with the administration of the GPR119 agonist (e.g., the compound of Formula (I)) or the combination of GPR119 agonist and DPP IV inhibitor.

The compound of Formula (I), DPP IV inhibitor, and metformin are administered in a single dosage or in separate dosages. The single dosage is administered once a day or multiple times a day. When the compound of Formula (I), DPP IV inhibitor, and metformin are administered in separate dosages, the dosages are administered once a day or multiple times a day.

In some embodiments, when the compound of Formula (I), DPP IV inhibitor, and metformin are administered in a single dosage, the compound of Formula (I), DPP IV inhibitor, and metformin are formulated as a medicament into a single pill, single tablet, or a single capsule. In some embodiments, when the compound of Formula ((I), DPP IV inhibitor, and metformin are administered in separate dosages, the compound of Formula (I) is formulated as a medicament into a pill, tablet or capsule, the DPP IV inhibitor is formulated into a separate pill or capsule, and metformin is formulated into a separate pill or capsule.

The time between the sequential first administration of the compound of Formula (I) and the second administration of the compound of Formula (I), and the timing of the administration of the DPP IV inhibitor and metformin, can be varied by a skilled practitioner. In some embodiments, the first administration (a compound of Formula (I), DPP IV inhibitor, or metformin, or any combination thereof), is followed immediately by the second administration (a compound of Formula (I), DPP IV inhibitor, or metformin, or any combination thereof). In another embodiment, the second administration is within 2 minutes, 5 minutes, 10 minutes, 15 minutes, 30 minutes, or 60 minutes, 1 hour, 2 hours, 3 hours, 4 hours, 5 hours, 6 hours, 7 hours, 8 hours, 9 hours, 10 hours, 11 hours, or 12 hours following the first administration. Yet other embodiments provide for the administration to a patient a compound for Formula (I), DPP IV inhibitor, or metformin, or any combination thereof, in the morning followed by administration to the previously treated patient a compound of Formula (I), DPP IV inhibitor, or metformin, or any combination thereof, in the evening.

In another aspect, provided herein are methods of improving the intestinal wall health and integrity of a patient in need thereof, the method comprising administering to the patient a therapeutically effective amount of a compound of Formula (I).

In another aspect, provided herein are methods of improving the intestinal wall health and integrity of a patient in need thereof, the method comprising administering to the patient a therapeutically effective amount of a compound of Formula (I) and a therapeutically effective amount of a DPP IV inhibitor.

In another aspect, provided herein are methods of improving the intestinal wall health and integrity of a patient in need thereof, the method comprising administering to the patient a therapeutically effective amount of a compound of Formula (I), a therapeutically effective amount of a DPP IV inhibitor, and a therapeutically effective amount of metformin.

In another aspect, provided herein are methods of maintaining the intestinal wall health and integrity of a patient in need thereof, the method comprising administering to the patient a therapeutically effective amount of a compound of Formula (I).

In another aspect, provided herein are methods of maintaining the intestinal wall health and integrity of a patient in need thereof, the method comprising administering to the patient a therapeutically effective amount of a compound of Formula (I) and a therapeutically effective amount of a DPP IV inhibitor.

In another aspect, provided herein are methods of maintaining the intestinal wall health and integrity of a patient in need thereof, the method comprising administering to the patient a therapeutically effective amount of a compound of Formula (I), a therapeutically effective amount of a DPP IV inhibitor, and a therapeutically effective amount of metformin.

In another aspect disclosed herein, a therapeutically effective amount of a compound of Formula (I) and optionally, a therapeutically effective amount of DPP IV inhibitor or a therapeutically effective amount of DPP IV inhibitor and metformin, can be used for the preparation of one or more pharmaceutical compositions useful for treating an inflammatory gastrointestinal disease or a gastrointestinal condition involving malabsorption of nutrients and/or fluids.

The compositions disclosed herein may include compounds of Formula (I), and optionally, DPP IV inhibitors or DPP IV inhibitors and metformin, pharmaceutically acceptable salts thereof, or a hydrolysable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound disclosed herein and a pharmaceutically acceptable carrier will be present in order to achieve a desired result, e.g., alleviating a symptom or complication of a disease or condition.

The compounds of Formula (I), optional DPP IV inhibitors and optional metformin that are used in the methods disclosed herein can be incorporated into a variety of formulations for therapeutic administration. More particularly, the compounds of Formula (I), optional DPP IV inhibitors and optional metformin can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. The compounds of Formula (I), optional DPP IV inhibitors and optional metformin can be formulated into a single composition containing a compound of Formula (I), optional DPP IV inhibitor and optional metformin. Alternatively, the compound of Formula (I), optional DPP IV inhibitor and optional metformin can be formulated into separate pharmaceutical formulations and manufactured into a single pill, tablet or capsule that physically separates the compound of Formula (I), optional DPP IV inhibitor and optional metformin. The administration of the compounds can be achieved in various ways, including oral, buccal, rectal, parenteral, intraperitoneal, intradermal, transdermal, and/or intratracheal administration. Moreover, the compound can be administered in a local rather than systemic manner, in a depot or sustained release formulation. In addition, the compounds can be administered in a liposome.

DPP IV inhibitors are commercially available. In particular, sitagliptin is an approved pharmaceutical marketed as JANUVIA', vildagliptin is an approved pharmaceutical marketed as GALVUS™, and linagliptin is an approved pharmaceutical marketed as TRADJENTA®.

The compounds of Formula (I), optional DPP IV inhibitors and optional metformin can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like.

Suitable formulations for use in the methods and compositions disclosed herein are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compound of Formula (I), optional DPP IV inhibitor and optional metformin can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds disclosed herein can be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds of Formula (I), optional DPP IV inhibitors and optional metformin can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use in the methods and compositions disclosed herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds disclosed herein can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide ("DMSO") also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the methods disclosed herein include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method disclosed herein, a therapeutically effective dose can be estimated initially from cell culture assays, animal models, or microdosing of human subjects.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds that exhibit high therapeutic indices are preferred. The data obtained from these cell culture assays and animal studies can be used in formulating a dosage range that is not toxic for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (see, e.g., Fingl, et al., 1975 In: *The Pharmacological Basis of Therapeutics*, Ch. 1).

The amount of active compound that can be combined with a carrier material to produce a single dosage form will vary depending upon the disease or condition treated, the mammalian species, and the particular mode of administration. However, as a general guide, suitable unit doses for the compounds disclosed herein can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease or condition undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The dosing of a compound of Formula (I), optional DPP IV inhibitor and optional metformin can be dosed at the same time, within several minutes, or separated by hours. By way of example, a compound of Formula (I), optional DPP IV inhibitor and optional metformin can be dosed together in the morning, with no further dosing for the remainder of the day. Alternatively, in the morning, a compound of Formula (I), optional DPP IV inhibitor and optional metformin is dosed followed with a second dose of a compound of Formula (I), a DPP IV inhibitor, or metformin, or any combination thereof, in the evening or after a meal.

It can be necessary to administer dosages of the compound of Formula (I) and optional DPP IV inhibitor and optional metformin once a day or more than once a day, or before or after a meal, as will be apparent to those skilled in the art. Further, it is noted that the clinician or treating physician will know how and when to start, interrupt, adjust, or terminate therapy in conjunction with individual patient response.

In addition, in another aspect, provided herein are kits with unit doses of the compounds of Formula (I), DPP IV inhibitor, or metformin, or any combination thereof, either in oral or injectable doses. In addition to the containers containing the unit doses will be an informational package insert describing the use and attendant benefits of the drugs in treating inflammatory gastrointestinal diseases or gastrointestinal conditions involving malabsorption of nutrients and/or fluids. Preferred compounds and unit doses are those described herein above.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

EXAMPLES

General Methods: All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on E. Merck silica gel 60 (240-400 mesh) according to the protocol of Still, Kahn, and Mitra (J. Org. Chem. (1978) 43, 2923). Thin layer chromatography was performed using precoated plates purchased from E. Merck (silica gel 60 PF$_{254}$, 0.25 mm) and spots were visualized with ultraviolet light followed by an appropriate staining reagent.

Nuclear magnetic resonance ("NMR") spectra were recorded on a Varian Inova-400 resonance spectrometer. $^1$H NMR chemical shifts are given in parts per million (δ) downfield from tetramethylsilane ("TMS") using TMS or the residual solvent signal (CHCl$_3$=δ 7.24, DMSO=δ 2.50) as internal standard. $^1$H NMR information is tabulated in the following format: number of protons, multiplicity (s, singlet; d, doublet; t, triplet; q, quartet; m, multiplet), coupling contant(s) (J) in Hertz, and, in selected cases, position assignment. The prefix app is occasionally applied in cases where the true signal multiplicity was unresolved and br indicates the signal in question was broadened.

Preparation of Intermediate 1

4-(4-Chloromethyl-thiazol-2-yl)-piperidine-1-carboxylic acid tert-butyl ester

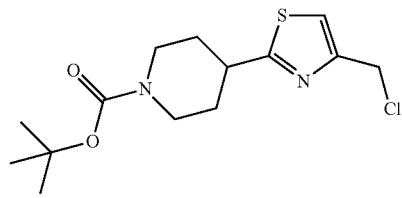 [SMILES: CC(C)(C)OC(=O)N1CCC(c2nc(CCl)cs2)CC1]

To a solution of 4-thiocarbamoyl-piperidine-1-carboxylic acid tert-butyl ester (4.9 g, 20 mmol) in acetone (80 mL) was added 1,3-dichloroacetone (3.3 g, 26 mmol), MgSO$_4$ (3.6 g, 30 mmol) and MgCO$_3$ (1.68 g, 20 mmol). The mixture was heated under reflux overnight, cooled and filtered through celite. The solvent was removed in vacuo and the residue was redissolved with EtOAc (150 mL). The resulting solution was washed successively with 5% NaHSO$_3$, saturated NaHCO$_3$, and brine. After drying (Na$_2$SO$_4$), the solvent was removed to afford the desired product. $^1$H NMR (CDCl$_3$): δ 7.20 (1H, s), 4.67 (2H, s), 4.20 (2H, br), 3.16 (1H, m), 2.87 (2H, m), 2.09 (2H, m), 1.72 (2H, m), 1.47 (9H, s).

Preparation of Intermediate 2

2-[4-(4-Chloromethyl-thiazol-2-yl)-piperidin-1-yl]-5-ethyl-pyrimidine

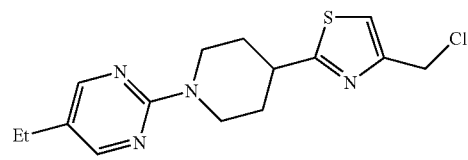 [SMILES: CCc1cnc(N2CCC(c3nc(CCl)cs3)CC2)nc1]

Intermediate 2 was prepared in a manner analogous to Intermediate 1 above.

$^1$H NMR (DMSO-d$_6$): δ 8.45 (2H, d), 7.62 (1H, s), 4.79 (2H, s), 4.61 (2H, m), 3.41 (1H, m), 3.24 (2H, m), 2.52 (2H, q), 2.15 (2H, m), 1.66 (2H, m), 1.17 (3H, m).

Preparation of Intermediate 3

4-[4-(4-Methanesulfonyl-phenoxymethyl)-thiazol-2-yl]-piperidine

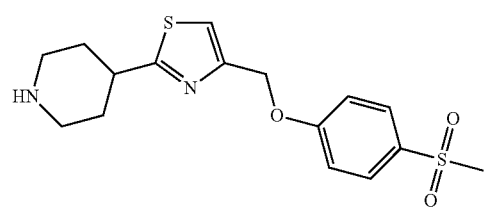 [SMILES: CS(=O)(=O)c1ccc(OCc2csc(C3CCNCC3)n2)cc1]

A solution of 4-[4-(4-Methanesulfonyl-phenoxymethyl)-thiazol-2-yl]-piperidine-1-carboxylic acid tert-butyl ester (615 mg, 1.36 mmol) in methanol (10 mL) was treated with 10 mL of 4 N HCl in dioxane. The resulting solution was stirred at room temperature for 30 minutes. Then all the solvents were removed in vacuo to afford the desired product as a HCl salt.

Preparation of Intermediate 4

4-[4-(4-Tetrazol-1-yl-phenoxymethyl)-thiazol-2-yl]-piperidine

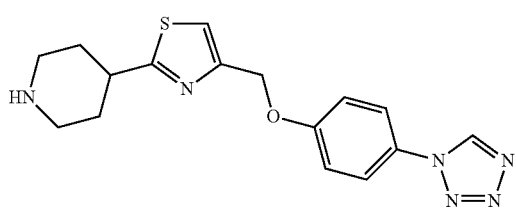 [SMILES: c1cc(-n2cnnn2)ccc1OCc1csc(C2CCNCC2)n1]

Intermediate 4 was prepared in a manner analogous to Intermediate 3 above.
$^1$H NMR (DMSO-d$_6$): δ 9.98 (1H, s), 7.82 (2H, m), 7.63 (1H, s), 7.28 (2H, m), 5.19 (2H, s), 3.01 (3H, m), 2.54 (3H, m), 1.92 (2H, m), 1.54 (2H, m).

Preparation of Intermediate 5

4-[4-(2-Fluoro-4-methanesulfonyl-phenoxymethyl)-thiazol-2-yl]-piperidine

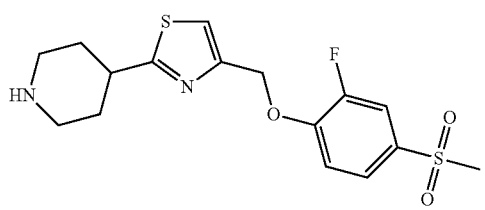 [SMILES: CS(=O)(=O)c1ccc(OCc2csc(C3CCNCC3)n2)c(F)c1]

Intermediate 5 was prepared in a manner analogous to Intermediate 3 above.

Preparation of Intermediate 6

4-[4-(2-Fluoro-4-tetrazol-1-yl-phenoxymethyl)-thiazol-2-yl]-piperidine

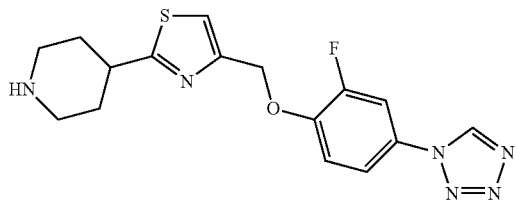 [SMILES: Fc1cc(-n2cnnn2)ccc1OCc1csc(C2CCNCC2)n1]

Intermediate 6 was prepared in a manner analogous to Intermediate 3 above.

Preparation of Intermediate 7

4-[4-(3-Fluoro-4-tetrazol-1-yl-phenoxymethyl)-thiazol-2-yl]-piperidine

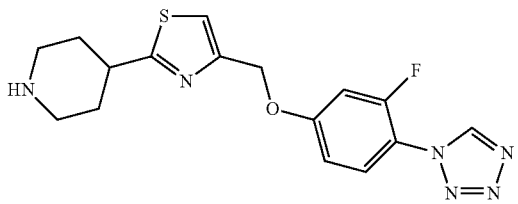 [SMILES: Fc1cc(OCc2csc(C3CCNCC3)n2)ccc1-n1cnnn1]

Intermediate 7 was prepared in a manner analogous to Intermediate 3 above.

Preparation of Intermediate 8

4-[4-(2,6-Difluoro-4-tetrazol-1-yl-phenoxymethyl)-thiazol-2-yl]-piperidine

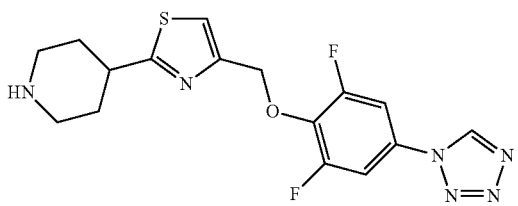 [SMILES: Fc1cc(-n2cnnn2)cc(F)c1OCc1csc(C2CCNCC2)n1]

Intermediate 8 was prepared in a manner analogous to Intermediate 3 above.

Preparation of Intermediate 9

4-[4-(4-Pyrrol-1-yl-phenoxymethyl)-thiazol-2-yl]-piperidine

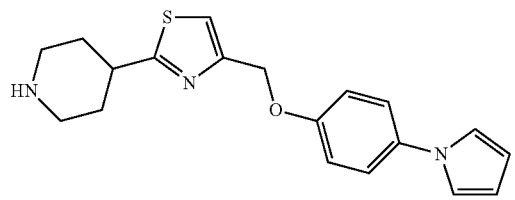 [SMILES: c1ccn(-c2ccc(OCc3csc(C4CCNCC4)n3)cc2)c1]

Intermediate 9 was prepared in a manner analogous to Intermediate 3 above.

Preparation of Intermediate 10: (2-Piperidin-4-yl-thiazol-4-ylmethyl)-(4-tetrazol-1-yl-phenyl)-amine

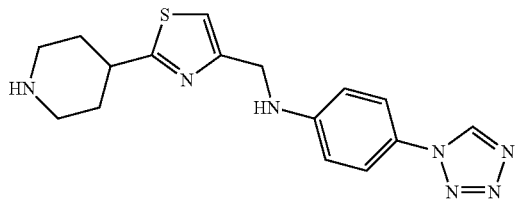 [SMILES: c1cc(-n2cnnn2)ccc1NCc1csc(C2CCNCC2)n1]

Intermediate 10 was prepared in a manner analogous to Intermediate 3 above.

Preparation of Intermediate 11

4-[4-(2-Methyl-4-tetrazol-1-yl-phenoxymethyl)-thiazol-2-yl]-piperidine

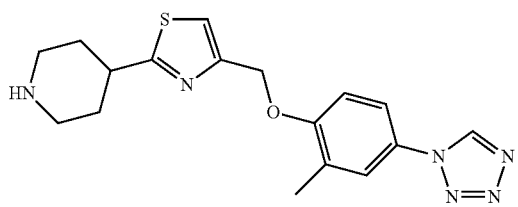 [SMILES: Cc1cc(-n2cnnn2)ccc1OCc1csc(C2CCNCC2)n1]

Intermediate 11 was prepared in a manner analogous to Intermediate 3 above.

Preparation of Intermediate 12

4-[4-(2-Isopropyl-5-methyl-4-tetrazol-1-yl-phenoxymethyl)-thiazol-2-yl]-piperidine

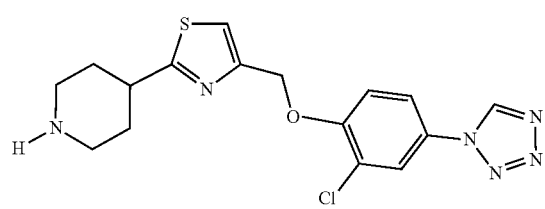 [SMILES: Clc1cc(-n2cnnn2)ccc1OCc1csc(C2CCNCC2)n1]

Intermediate 12 was prepared in a manner analogous to Intermediate 3 above.

Preparation of Intermediate 13

4-[4-(2-Chloro-4-tetrazol-1-yl-phenoxymethyl)-thiazol-2-yl]-piperidine

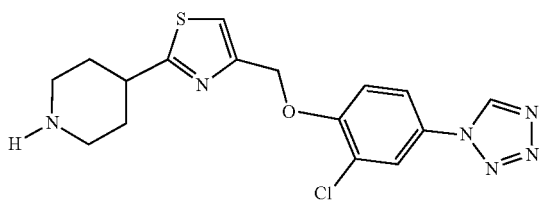 [SMILES: Clc1cc(-n2cnnn2)ccc1OCc1csc(C2CCNCC2)n1]

Intermediate 13 was prepared in a manner analogous to Intermediate 3 above.

Preparation of Intermediate 14

4-(4-Chloromethyl-oxazol-2-yl)-piperidine-1-carboxylic acid tert-butyl ester

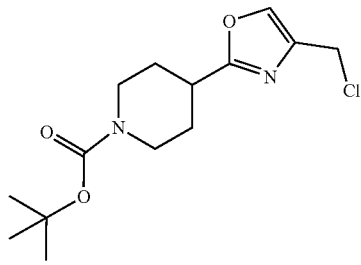 [SMILES: CC(C)(C)OC(=O)N1CCC(c2nc(CCl)co2)CC1]

A mixture of 4-(4-Hydroxymethyl-oxazol-2-yl)-piperidine-1-carboxylic acid tert-butyl ester (800 mg, 2.84 mmol) (obtained by the reduction of 4-(4-ethoxycarbonyl-oxazol-2-yl)-piperidine-1-carboxylic acid tert-butyl ester which was synthesized according to U.S. Patent Publication No. 2006/0135501 A1), TsCl (812 mg, 4.26 mmol) and triethylamine (1 mL, 752 mg, 7.44 mmol) in dichloromethane (20 mL) was stirred at room temperature for 5 hours. The resulting solution was washed successively with 5% NaHSO$_3$, saturated NaHCO$_3$, and brine. After drying (Na$_2$SO$_4$), the solvent was removed to afford the desired product. $^1$H NMR (CDCl$_3$): δ 7.53 (s, 1H), 4.40 (s, 2H), 4.06 (m, 2H), 2.89 (m, 3H), 1.98 (m, 2H), 1.74 (m, 2H), 1.41 (s, 9H).

Preparation of Intermediate 15

4-[4-(4-Tetrazol-1-yl-phenoxymethyl)-oxazol-2-yl]-piperidine

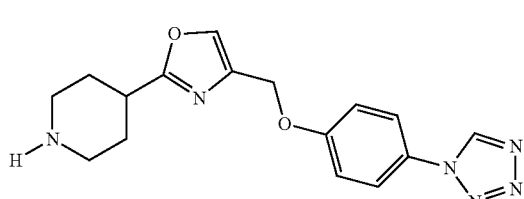

Intermediate 15 was prepared in a manner analogous to Intermediate 3 above.

Preparation of Intermediate 16

4-[4-(2-Fluoro-4-tetrazol-1-yl-phenoxymethyl)-oxazol-2-yl]-piperidine

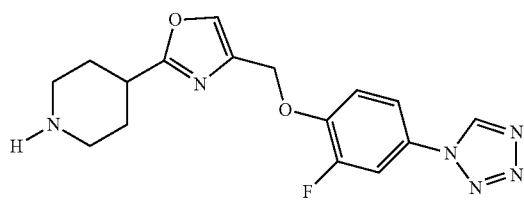 [SMILES: Fc1cc(-n2cnnn2)ccc1OCc1coc(C2CCNCC2)n1]

Intermediate 16 was prepared in a manner analogous to Intermediate 3 above.

Preparation of Intermediate 17

5-(2-Piperidin-4-yl-thiazol-4-ylmethoxy)-2-tetrazol-1-yl-pyridine

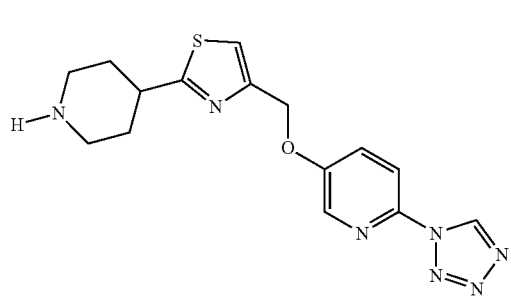 [SMILES: c1cc(-n2cnnn2)ncc1OCc1csc(C2CCNCC2)n1]

Intermediate 17 was prepared in a manner analogous to Intermediate 3 above.

Preparation of Intermediate 18

(6-Fluoro-pyridin-3-yl)-(2-piperidin-4-yl-thiazol-4-ylmethyl)-amine

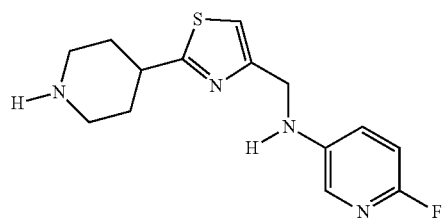 [SMILES: Fc1ccc(NCc2csc(C3CCNCC3)n2)cn1]

Intermediate 18 was prepared in a manner analogous to Intermediate 3 above.

Preparation of Intermediate 19

4-[4-(2, 6-Difluoro-4-methanesulfonyl-phenoxymethyl)-thiazol-2-yl]-piperidine

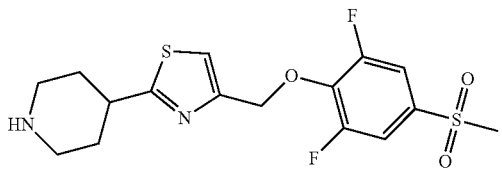 [SMILES: CS(=O)(=O)c1cc(F)c(OCc2csc(C3CCNCC3)n2)c(F)c1]

Intermediate 19 was prepared in a manner analogous to Intermediate 3 above.

Preparation of Intermediate 20

4-[4-(2-Piperidin-4-yl-thiazol-4-ylmethoxy)-phenyl]-morpholine

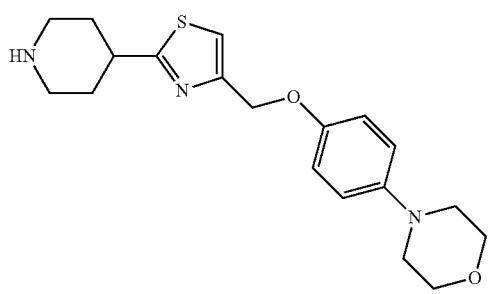 [SMILES: c1cc(N2CCOCC2)ccc1OCc1csc(C2CCNCC2)n1]

Intermediate 20 was prepared in a manner analogous to Intermediate 3 above.

Preparation of Intermediate 21

4-[4-(2-Piperidin-4-yl-thiazol-4-ylmethoxy)-phenyl]-morpholine

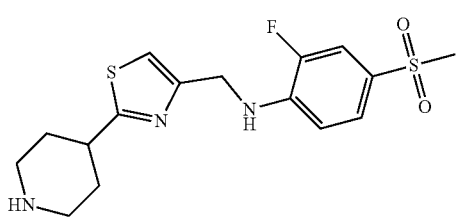 [SMILES: CS(=O)(=O)c1ccc(NCc2csc(C3CCNCC3)n2)c(F)c1]

Intermediate 21 was prepared in a manner analogous to Intermediate 3 above.

Preparation of Intermediate 22

4-(4-Chloromethyl-thiazol-2-yl)-3-methyl-piperidine-1-carboxylic acid tert-butyl ester

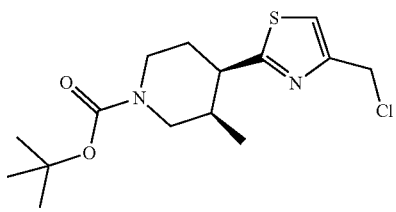 [SMILES: C[C@H]1CN(C(=O)OC(C)(C)C)CC[C@H]1c1nc(CCl)cs1]

Intermediate 22 was prepared in a manner analogous to Intermediate 1 above.

Preparation of Intermediate 23

3-Methyl-4-[4-(4-tetrazol-1-yl-phenoxymethyl)-thiazol-2-yl]-piperidine

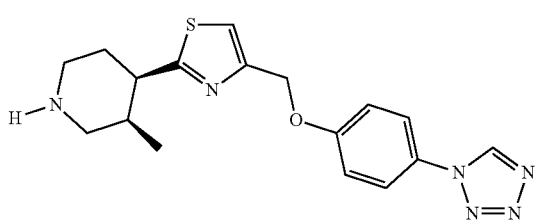 [SMILES: C[C@H]1CNCC[C@H]1c1nc(COc2ccc(-n3cnnn3)cc2)cs1]

Intermediate 23 was prepared in a manner analogous to Intermediate 3 above.

Preparation of Intermediate 24

4-[4-(2-Fluoro-4-tetrazol-1-yl-phenoxymethyl)-thiazol-2-yl]-3-methyl-piperidine

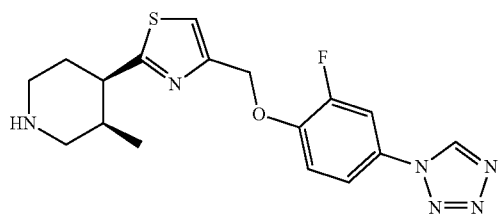 [SMILES: C[C@H]1CNCC[C@H]1c1nc(COc2ccc(-n3cnnn3)cc2F)cs1]

Intermediate 24 was prepared in a manner analogous to Intermediate 3 above.

Preparation of Intermediate 25

4-[4-(4-Methanesulfonyl-benzyloxymethyl)-thiazol-2-yl]-piperidine

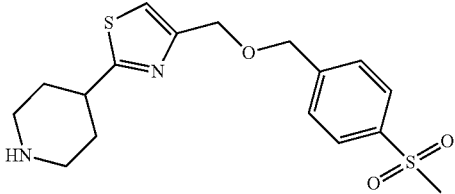 [SMILES: CS(=O)(=O)c1ccc(COCc2csc(C3CCNCC3)n2)cc1]

Intermediate 25 was prepared in a manner analogous to Intermediate 3 above.

Example 1

4-[4-(4-Methanesulfonyl-phenoxymethyl)-thiazol-2-yl]-piperidine-1-carboxylic acid tert-butyl ester

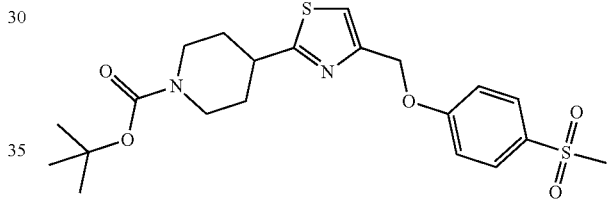

A mixture of 4-(4-Chloromethyl-thiazol-2-yl)-piperidine-1-carboxylic acid tert-butyl ester (Intermediate 1, 463 mg, 1.46 mmol), 4-methanesulfonyl-phenol (252 mg, 1.46 mmol) and $K_2CO_3$ (404 mg, 2.92 mmol) in acetone (25 mL) was heated under reflux overnight. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 7.88 (2H, d, J=8.8 Hz), 7.23 (1H, s), 7.12 (2H, d, J=8.8 Hz), 5.24 (2H, s), 4.21 (2H, br), 3.17 (1H, m), 3.04 (3H, s), 2.88 (2H, m), 2.11 (2H, m), 1.73 (2H, m), 1.47 (9H, s).

The compounds in Examples 2-19 were synthesized from 4-(4-Chloromethyl-thiazol-2-yl)-piperidine-1-carboxylic acid tert-butyl ester (Intermediate 1), 2-[4-(4-Chloromethyl-thiazol-2-yl)-piperidin-1-yl]-5-ethyl-pyrimidine (Intermediate 2), 4-(4-Chloromethyl-oxazol-2-yl)-piperidine-1-carboxylic acid tert-butyl ester (Intermediate 14) or with the corresponding phenol, thiophenol, amine or aniline in a similar manner to that described in Example 1. One skilled in the art of organic synthesis will appreciate that conditions such as solvent (e.g., DMF, CH$_3$CN); temperature, base (e.g., NEt$_3$, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 2

4-[4-(4-Imidazol-1-yl-phenoxymethyl)-thiazol-2-yl]-piperidine-1-carboxylic acid tert-butyl ester

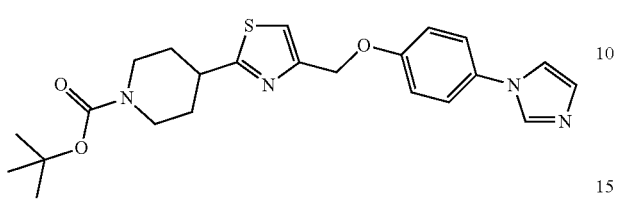

¹H NMR (DMSO-d₆): δ 8.12 (1H, s), 7.63 (2H, m), 7.54 (2H, d, J=9.2 Hz), 7.15 (2H, d, J=9.2 Hz), 7.05 (1H, s), 5.15 (2H, s), 3.98 (2H, m), 3.21 (1H, m), 2.87 (2H, m), 2.01 (2H, m), 1.52 (2H, m), 1.39 (9H, s).

Example 3

4-[4-(4-Acetylamino-phenoxymethyl)-thiazol-2-yl]-piperidine-1-carboxylic acid tert-butyl ester

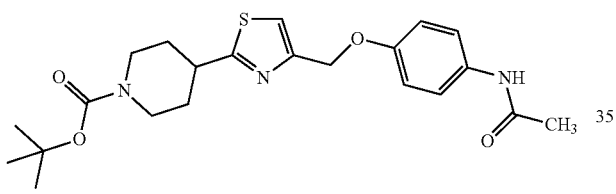

¹H NMR (DMSO-d₆): δ 9.77 (1H, s), 7.57 (1H, s), 7.45 (2H, d, J=9.0 Hz), 6.94 (2H, d, J=9.0 Hz), 5.04 (2H, s), 3.98 (2H, m), 3.18 (1H, m), 2.82 (2H, m), 2.02 (2H, m), 1.99 (3H, s), 1.51 (2H, m), 1.39 (9H, s).

Example 4

4-[4-(4-Methoxy-benzenesulfonyloxymethyl)-thiazol-2-yl]-piperidine-1-carboxylic acid tert-butyl ester

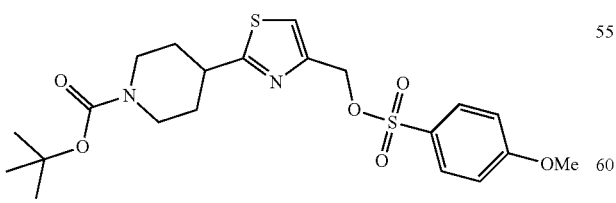

¹H NMR (CDCl₃): δ 7.60 (2H, d, J=9.0 Hz), 7.24 (1H, s), 6.91 (2H, d, J=9.0 Hz), 4.50 (2H, s), 4.10 (2H, m), 3.85 (3H, s), 2.99 (1H, m), 2.82 (2H, m), 1.89~1.92 (2H, m), 1.53~1.57 (2H, m), 1.46 (9H, s).

Example 5

4-[4-(4-[1,2,4]Triazol-1-yl-phenoxymethyl)-thiazol-2-yl]-piperidine-1-carboxylic acid tert-butyl ester

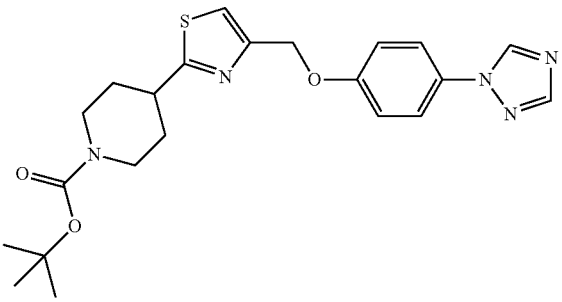 [SMILES: CC(C)(C)OC(=O)N1CCC(c2nc(COc3ccc(-n4cncn4)cc3)cs2)CC1]

¹H NMR (CDCl₃): δ 8.47 (1H, s), 8.08 (1H, s), 7.58 (2H, d, J=9.2 Hz), 7.24 (1H, s), 7.11 (2H, d, J=9.2 Hz), 5.21 (2H, s), 4.2 (2H, m), 3.18 (1H, m), 2.88 (2H, m), 2.11 (2H, m), 1.74 (2H, m), 1.47 (9H, s).

Example 6

4-{4-[4-(2-Oxo-pyrrolidin-1-yl)-phenoxymethyl]-thiazol-2-yl}-piperidine-1-carboxylic acid tert-butyl ester

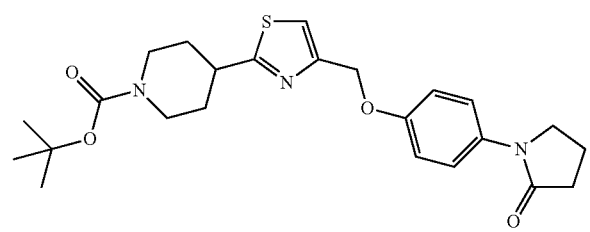 [SMILES: CC(C)(C)OC(=O)N1CCC(c2nc(COc3ccc(N4CCCC4=O)cc3)cs2)CC1]

¹H NMR (CDCl₃): δ 7.50 (2H, d), 7.20 (1H, s), 6.98 (2H, d), 5.17 (2H, s), 4.20 (2H, br), 3.81 (2H, m), 3.18 (1H, m), 2.88 (2H, m), 2.59 (2H, m), 2.16 (4H, m), 1.73 (2H, m), 1.46 (9H, s).

Example 7

4-[4-(4-Tetrazol-1-yl-phenoxymethyl)-thiazol-2-yl]-piperidine-1-carboxylic acid tert-butyl ester

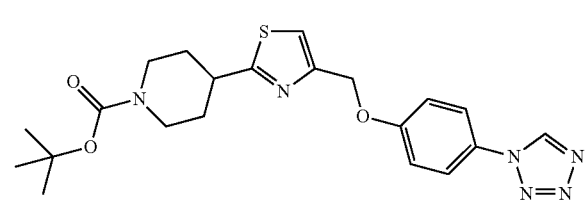 [SMILES: CC(C)(C)OC(=O)N1CCC(c2nc(COc3ccc(-n4cnnn4)cc3)cs2)CC1]

¹H NMR (CDCl₃): δ 8.94 (1H, s), 7.61 (2H, d), 7.25 (1H, s), 7.19 (2H, d), 5.21 (2H, s), 4.20 (2H, br), 3.20 (1H, m), 2.90 (2H, m), 2.16 (2H, m), 1.77 (2H, m), 1.49 (9H, s).

Example 8

4-[4-(4-Methanesulfonyl-phenylsulfanylmethyl)-thiazol-2-yl]-piperidine-1-carboxylic acid tert-butyl ester

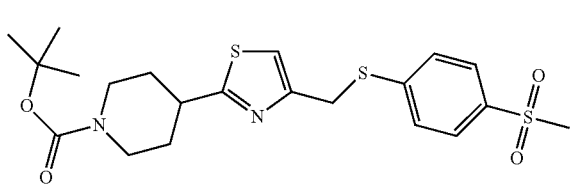 [SMILES: CC(C)(C)OC(=O)N1CCC(c2nc(CSc3ccc(S(C)(=O)=O)cc3)cs2)CC1]

$^1$H NMR (CDCl$_3$): δ 7.7 (2H, d, J=9.0 Hz), 7.36 (2H, d, J=9.0 Hz), 7.00 (1H, s), 4.24 (2H, s), 4.3 (2H, m), 3.05 (1H, m), 2.95 (3H, s), 2.78 (2H, m), 1.99 (2H, m), 1.62 (2H, m), 1.38 (9H, s).

Example 9

4-{2-[1-(5-Ethyl-pyrimidin-2-yl)-piperidin-4-yl]-thiazol-4-ylmethoxy}-benzenesulfonamide

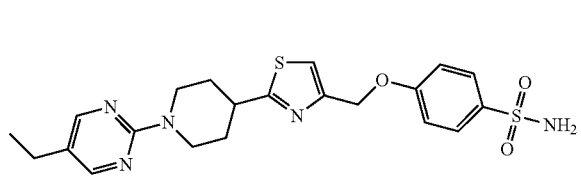 [SMILES: CCc1cnc(N2CCC(c3nc(COc4ccc(S(N)(=O)=O)cc4)cs3)CC2)nc1]

$^1$H NMR (DMSO-d$_6$): δ 8.24 (2H, s), 7.73 (2H, d), 7.64 (1H, s), 7.20 (4H, m), 5.18 (2H, s), 4.67 (2H, m), 3.38 (1H, m), 3.01 (2H, m), 2.47 (2H, m), 2.08 (2H, m), 1.62 (2H, m), 1.53 (3H, m).

Example 10

2-{4-[4-(2,6-Dichloro-4-methanesulfonyl-phenoxymethyl)-thiazol-2-yl]-piperidin-1-yl}-5-ethyl-pyrimidine

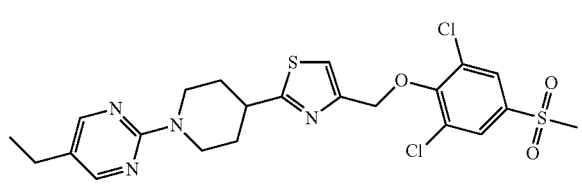 [SMILES: CCc1cnc(N2CCC(c3nc(COc4c(Cl)cc(S(C)(=O)=O)cc4Cl)cs3)CC2)nc1]

$^1$H NMR (DMSO-d$_6$): δ 8.23 (2H, s), 7.99 (2H, s), 7.68 (1H, s), 5.20 (2H, s), 4.64 (2H, m), 3.31 (3H, s), 3.30 (1H, m), 3.0 (2H, m), 2.40 (2H, m), 1.98 (2H, m), 1.54 (2H, m), 1.15 (3H, m).

Example 11

5-Ethyl-2-{4-[4-(3-tetrazol-1-yl-phenoxymethyl)-thiazol-2-yl]-piperidin-1-yl}-pyrimidine

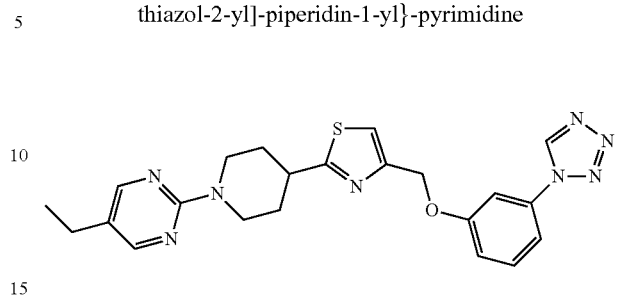

$^1$H NMR (CDCl$_3$): δ 9.05 (1H, s), 8.19 (2H, s), 7.55-7.10 (5H, m), 5.24 (2H, s), 4.83 (2H, m), 3.30 (1H, m), 3.04 (2H, m), 2.47 (2H, q, J=7.6 Hz), 2.21 (2H, m), 1.80 (2H, m), 1.19 (3H, t, J=7.6 Hz).

Example 12

5-Ethyl-2-(4-{4-[4-(5-methyl-tetrazol-1-yl)-phenoxymethyl]-thiazol-2-yl}-piperidin-1-yl)-pyrimidine

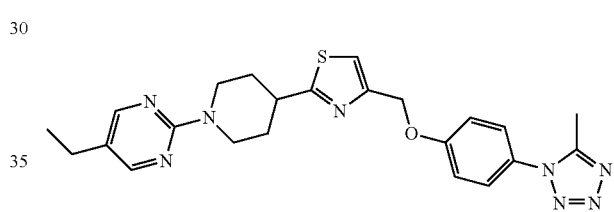

$^1$H NMR (CDCl$_3$): δ 8.19 (2H, s), 7.38 (2H, d, J=9.0 Hz), 7.26 (1H, s), 7.17 (2H, d, J=9.0 Hz), 5.24 (2H, s), 4.84 (2H, m), 3.31 (1H, m), 3.05 (2H, m), 2.58 (3H, s), 2.47 (2H, q, J=7.8 Hz), 2.22 (2H, m), 1.82 (2H, m), 1.20 (3H, t, J=7.8 Hz).

Example 13

5-Ethyl-2-{4-[4-(3-methyl-4-methylsulfanyl-phenoxymethyl)-thiazol-2-yl]-piperidin-1-yl}-pyrimidine

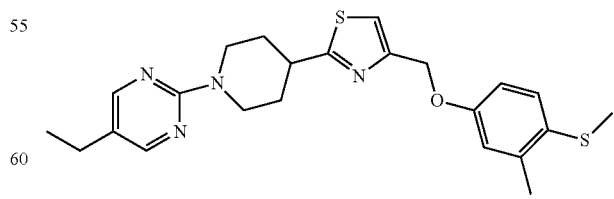

$^1$H NMR (DMSO-d$_6$): δ 8.23 (2H, s), 7.56 (1H, s), 7.16 (1H, m), 6.90 (1H, m), 6.86 (1H, m), 5.06 (2H, s), 4.67 (2H, m), 3.55 (4H, m), 3.01 (2H, m), 2.48 (3H, s), 2.40 (2H, m), 2.09 (2H, m), 1.57 (2H, m), 1.09 (3H, m).

Example 14

5-Ethyl-2-{4-[4-(4-methanesulfonyl-3-methyl-phenoxymethyl)-thiazol-2-yl]-piperidin-1-yl}-pyrimidine

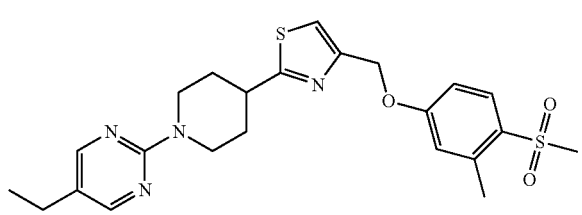 [SMILES: CCc1cnc(N2CCC(c3nc(COc4ccc(S(C)(=O)=O)c(C)c4)cs3)CC2)nc1]

$^1$H NMR (DMSO-d$_6$): δ 8.13 (2H, s), 7.91 (1H, m), 7.20 (1H, s), 6.85 (2H, m), 5.14 (2H, s), 4.76 (2H, m), 3.23 (1H, m), 2.98 (3H, s), 2.60 (3H, s), 2.42 (2H, m), 2.15 (2H, m), 1.97 (2H, m), 1.76 (2H, m), 1.13 (3H, m).

Example 15

6-{2-[1-(5-Ethyl-pyrimidin-2-yl)-piperidin-4-yl]-thiazol-4-ylmethoxy}-benzo[1,3]oxathiol-2-one

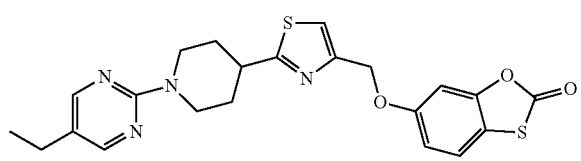 [SMILES: CCc1cnc(N2CCC(c3nc(COc4ccc5sc(=O)oc5c4)cs3)CC2)nc1]

$^1$H NMR (DMSO-d$_6$): δ 8.23 (2H, s), 7.64 (1H, m), 7.62 (1H, s), 7.30 (1H, m), 7.03 (1H, m), 5.14 (2H, s), 4.64 (2H, m), 3.31 (1H, m), 3.02 (2H, m), 2.40 (2H, q), 2.09 (2H, m), 1.58 (2H, m), 1.12 (3H, t).

Example 16

5-Ethyl-2-{4-[4-(4-trifluoromethylsulfanyl-phenoxymethyl)-thiazol-2-yl]-piperidin-1-yl}-pyrimidine

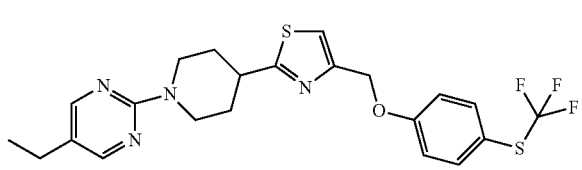 [SMILES: CCc1cnc(N2CCC(c3nc(COc4ccc(SC(F)(F)F)cc4)cs3)CC2)nc1]

$^1$H NMR (DMSO-d$_6$): δ 8.23 (2H, s), 7.63 (3H, m), 7.18 (2H, m), 5.17 (2H, s), 4.67 (2H, m), 3.32 (1H, m), 3.01 (2H, m), 2.40 (2H, q), 2.08 (2H, m), 1.59 (2H, m), 1.13 (3H, t).

Example 17

4-[4-(3-Fluoro-4-tetrazol-1-yl-phenoxymethyl)-thiazol-2-yl]-piperidine-1-carboxylic acid tert-butyl ester

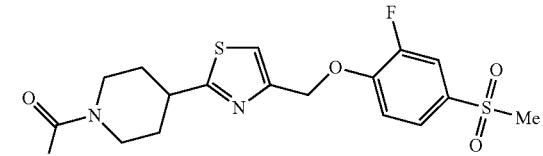

$^1$H NMR (CDCl$_3$): δ 9.04 (1H, s), 7.79 (1H, m), 7.29 (1H, s), 7.01 (2H, m), 5.24 (2H, s), 4.22 (2H, m), 3.19 (1H, m), 2.89 (2H, m), 2.11 (2H, m), 1.74 (2H, m), 1.48 (9H, s).

Example 18

4-[4-(2-Fluoro-4-methanesulfonyl-phenoxymethyl)-thiazol-2-yl]-piperidine-1-carboxylic acid tert-butyl ester

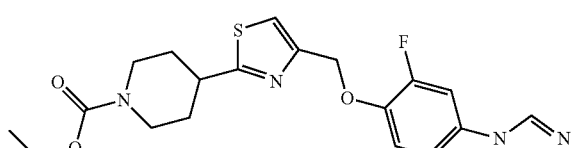

$^1$H NMR (DMSO-d$_6$): δ 7.79 (1H, m), 7.72 (1H, m), 7.70 (1H, s), 7.57 (1H, m), 5.31 (2H, s), 3.99 (2H, m), 3.21 (3H, s), 3.20 (1H, m), 2.85 (2H, m), 2.02 (2H, m), 1.52 (2H, m), 1.39 (9H, s).

Example 19

4-[4-(2-Fluoro-4-tetrazol-1-yl-phenoxymethyl)-thiazol-2-yl]-piperidine-1-carboxylic acid tert-butyl ester $^1$H NMR (CDCl$_3$): δ 8.98 (s, 1H), 7.53 (m, 1H), 7.44 (m, 1H), 7.31 (s, 1H), 7.27 (m, 1H), 5.31 (s, 2H), 4.21 (m, 2H), 3.16 (m, 1H), 2.89 (m, 2H), 2.11 (m, 2H), 1.74 (m, 2H), 1.47 (s, 9H).

Example 20

5-Ethyl-2-{4-[4-(4-trifluoromethanesulfinyl-phenoxymethyl)-thiazol-2-yl]-piperidin-1-yl}-pyrimidine

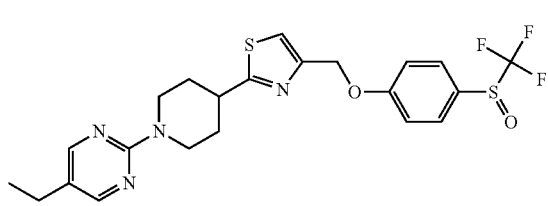 [SMILES: CCc1cnc(N2CCC(c3nc(COc4ccc(S(=O)C(F)(F)F)cc4)cs3)CC2)nc1]

To a solution of 5-Ethyl-2-{4-[4-(4-trifluoromethylsulfanyl-phenoxymethyl)-thiazol-2-yl]-piperidin-1-yl}-pyrimidine (Example 16) in DCM at room temperature was added 3-chloro-benzenecarboperoxoic acid (2 eq.). The reaction was allowed to stir for 1.5 hours and an additional portion of 3-chloro-benzenecarboperoxoic acid (1 eq.) was added to the reaction mixture. The reaction was stirred at room temperature for an additional 4 hours. The organic solution was washed with sodium bicarbonate; the organic layer was isolated, dried over sodium sulfate and filtered. The filtrate was concentrated and the crude product was purified by column chromatography to afford the desired product. $^1$H NMR (DMSO-$d_6$): δ 8.40 (2H, s), 7.58 (2H, d), 7.22 (1H, s), 7.02 (2H, d,), 5.17 (2H, s), 3.74 (2H, m), 3.16 (1H, m), 2.96 (2H, m), 2.57 (2H, m), 2.22 (4H, m), 1.24 (3H, m).

Example 21

4-[4-(4-Methanesulfonyl-benzenesulfonylmethyl)-thiazol-2-yl]-piperidine-1-carboxylic acid tert-butyl ester

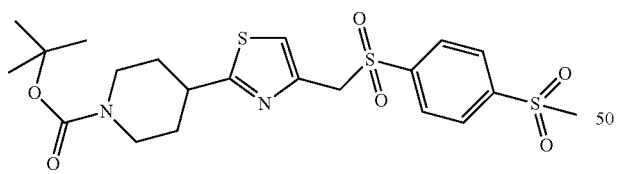

To a solution of 4-[4-(4-Methanesulfonyl-phenylsulfanylmethyl)-thiazol-2-yl]-piperidine-1-carboxylic acid tert-butyl ester (Example 8, 0.1 g, 0.21 mmol) in CH$_2$Cl$_2$ (5 mL) was added mCPBA (0.11 g, 0.42 mmol) at room temperature. The resulting mixture was stirred at room temperature for 2 hours and was washed with 5% NaHSO$_3$, saturated NaHCO$_3$ and brine. The organic layer was dried with Na$_2$SO$_4$ and the solvent was removed in vacuo. The residue was purified by flash chromatography on silica gel to afford the desired product. $^1$H NMR (CDCl$_3$): δ 8.03 (2H, d, J=9.0 Hz), 7.88 (2H, d, J=9.0 Hz), 7.29 (1H, s), 4.57 (2H, s), 4.10 (2H, m), 3.07 (3H, s), 2.92 (1H, m), 2.75 (2H, m), 1.85 (2H, m), 1.46 (2H, m), 1.44 (9H, s).

Example 22

4-[4-(4-Methanesulfonyl-phenoxymethyl)-thiazol-2-yl]-piperidine-1-carboxylic acid isopropyl ester

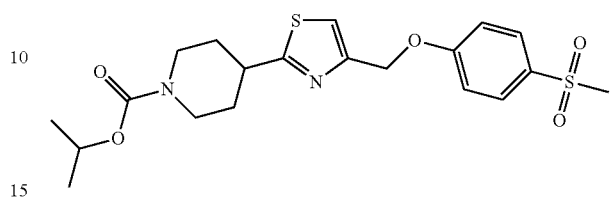

To the HCl salt (Intermediate 3, 43 mg, 0.12 mmol) of 4-[4-(4-Methanesulfonyl-phenoxymethyl)-thiazol-2-yl]-piperidine was added 3 mL of THF, followed by isopropyl chloroformate (1.0 M solution in toluene, 0.15 mL, 0.15 mmol) and Et$_3$N (0.05 mL). The resulting mixture was stirred at room temperature for 2 hours, and then partitioned between EtOAc and H$_2$O. After concentration of the organic layer in vacuo, the residue was purified by silica gel column chromatography with EtOAc/hexanes (40-70%) to give the desired product. $^1$H NMR (CDCl$_3$): δ 7.86 (2H, d, J=9.0 Hz), 7.23 (1H, s), 7.11 (2H, d, J=9.0 Hz), 5.22 (2H, s), 4.92 (1H, m), 4.24 (2H, m), 3.17 (1H, m), 3.03 (3H, s), 2.90 (2H, m), 2.10 (2H, m), 1.72 (2H, m), 1.23 (6H, d, J=6.4 Hz).

The compounds in Examples 23-46 were synthesized from one of Intermediates 3-13 or Intermediates 15-25 with the corresponding sulfonyl chloride, alkyl chloride, alkyl bromide, chloroformate, acid chloride, carbamyl chloride or isocyanate in a manner similar to that described in Example 22. One skilled in the art of organic synthesis will appreciate that conditions such as solvent (e.g., DMF, CH$_3$CN); temperature, base (e.g., NEt$_3$, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 23

4-[4-(4-Methanesulfonyl-phenoxymethyl)-thiazol-2-yl]-piperidine-1-carboxylic acid benzyl ester

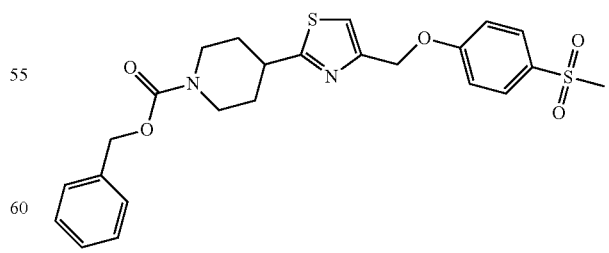

$^1$H NMR (CDCl$_3$): δ 7.87 (2H, d, J=9.2 Hz), 7.31~7.37 (5H, m), 7.23 (1H, s), 7.11 (2H, d, J=9.2 Hz), 5.22 (2H, s), 5.14 (2H, s), 4.29 (2H, m), 3.16~3.22 (1H, m), 3.03 (3H, s), 2.96 (2H, m), 2.12 (2H, m), 1.70~1.80 (2H, m).

Example 24

4-[4-(4-Methanesulfonyl-phenoxymethyl)-thiazol-2-yl]-piperidine-1-carboxylic acid isobutyl ester

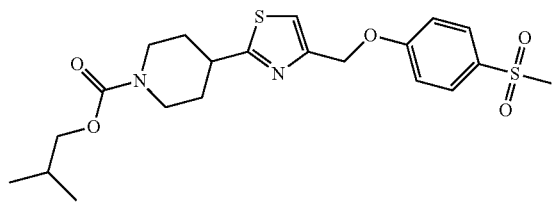 [SMILES: CC(C)COC(=O)N1CCC(c2nc(COc3ccc(S(C)(=O)=O)cc3)cs2)CC1]

$^1$H NMR (CDCl$_3$): δ 7.87 (2H, d, J=9.0 Hz), 7.23 (1H, s), 7.11 (2H, d, J=9.0 Hz), 5.22 (2H, s), 4.25 (2H, m), 3.87 (2H, d, J=6.6 Hz), 3.17 (1H, m), 3.03 (3H, s), 2.94 (2H, m), 2.12 (2H, m), 1.94 (1H, m), 1.75 (2H, m), 0.93 (6H, d, J=6.6 Hz).

Example 25

4-[4-(4-Methanesulfonyl-phenoxymethyl)-thiazol-2-yl]-piperidine-1-carboxylic acid adamantan-1-yl ester

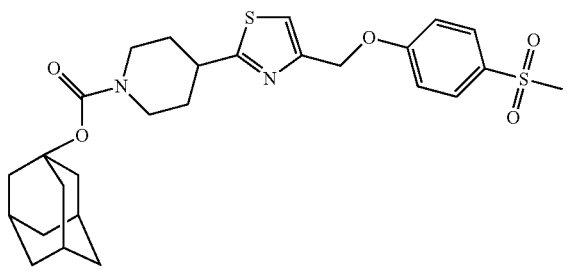 [SMILES: CS(=O)(=O)c1ccc(OCc2csc(C3CCN(C(=O)OC45CC6CC(CC(C6)C4)C5)CC3)n2)cc1]

$^1$H NMR (CDCl$_3$): δ 7.89 (2H, d, J=8.8 Hz), 7.24 (1H, s), 7.12 (2H, d, J=8.8 Hz), 5.23 (2H, s), 4.21 (2H, m), 3.12~3.20 (1H, m), 3.03 (3H, s), 2.87 (2H, m), 2.05~2.17 (11H, m), 1.62~1.79 (8H, m).

Example 26

4-[4-(4-Methanesulfonyl-phenoxymethyl)-thiazol-2-yl]-piperidine-1-carboxylic acid methyl ester

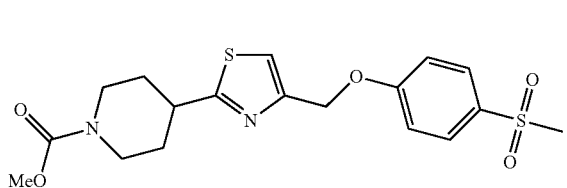 [SMILES: COC(=O)N1CCC(c2nc(COc3ccc(S(C)(=O)=O)cc3)cs2)CC1]

$^1$H NMR (CDCl$_3$): δ 7.87 (2H, d, J=9.0 Hz), 7.23 (1H, s), 7.11 (2H, d, J=9.0 Hz), 5.22 (2H, s), 4.24 (2H, m), 3.71 (3H, s), 3.14~3.17 (1H, m), 3.03 (3H, s), 2.94 (2H, m), 2.12 (2H, m), 1.70~1.80 (2H, m).

Example 27

4-[4-(4-Methanesulfonyl-phenoxymethyl)-thiazol-2-yl]-piperidine-1-carboxylic acid 4-fluoro-phenyl ester

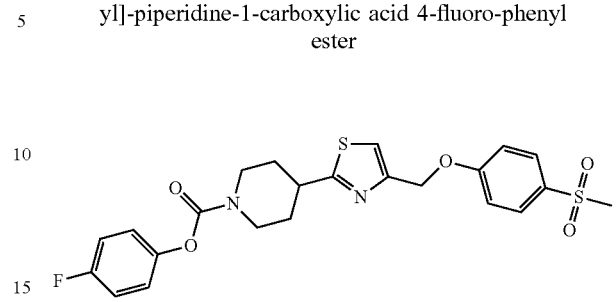

$^1$H NMR (CDCl$_3$): δ 7.88 (2H, d, J=8.8 Hz), 7.12 (2H, d, J=8.8 Hz), 7.01~7.09 (5H, m), 5.24 (2H, s), 4.37 (2H, m), 3.23~3.27 (1H, m), 3.19 (2H, m), 3.04 (3H, s), 2.20 (2H, m), 1.88 (2H, m).

Example 28

4-[4-(4-Methanesulfonyl-phenoxymethyl)-thiazol-2-yl]-piperidine-1-carboxylic acid 4-methoxy-phenyl ester

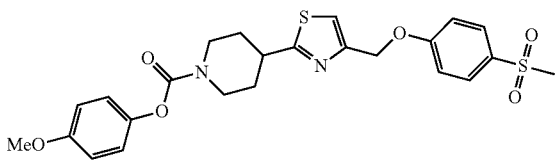 [SMILES: COc1ccc(OC(=O)N2CCC(c3nc(COc4ccc(S(C)(=O)=O)cc4)cs3)CC2)cc1]

$^1$H NMR (CDCl$_3$): δ 7.88 (2H, d, J=8.2 Hz), 7.26 (1H, s), 7.12 (2H, d, J=8.6 Hz), 7.02 (2H, d, J=8.6 Hz), 6.87 (2H, d, J=8.2 Hz), 5.24 (2H, s), 4.38 (2H, m), 3.79 (3H, s), 3.15~3.28 (3H, m), 3.03 (3H, s). 2.19 (2H, m), 1.87 (2H, m).

Example 29

4-[4-(4-Methanesulfonyl-phenoxymethyl)-thiazol-2-yl]-piperidine-1-carboxylic acid naphthalen-1-yl ester

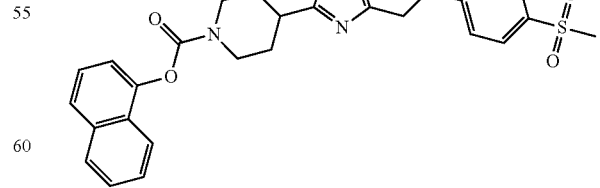

$^1$H NMR (CDCl$_3$): δ 7.88 (4H, m), 7.72 (1H, m), 7.49 (3H, m), 7.29 (2H, m), 7.14 (2H, m), 5.26 (2H, s), 4.64 (1H, m), 4.41 (1H, m), 3.34 (2H, m), 3.12 (1H, m), 3.04 (3H, s), 2.27 (2H, m), 2.00 (2H, m).

Example 30

4-[4-(4-Tetrazol-1-yl-phenoxymethyl)-thiazol-2-yl]-piperidine-1-carboxylic acid isobutyl ester

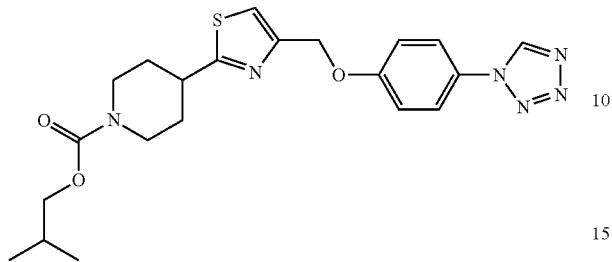

$^1$H NMR (CDCl$_3$): δ 8.94 (1H, s), 7.60 (2H, d), 7.24 (1H, s), 7.14 (2H, d,), 5.20 (2H, s), 4.24 (2H, br), 3.85 (2H, d,), 3.18 (1H, m), 2.92 (2H, m), 2.11 (2H, m), 1.91 (1H, m), 1.75 (2H, m), 0.91 (6H, d,).

Example 31

4-[4-(4-Tetrazol-1-yl-phenoxymethyl)-thiazol-2-yl]-piperidine-1-carboxylic acid pentyl ester

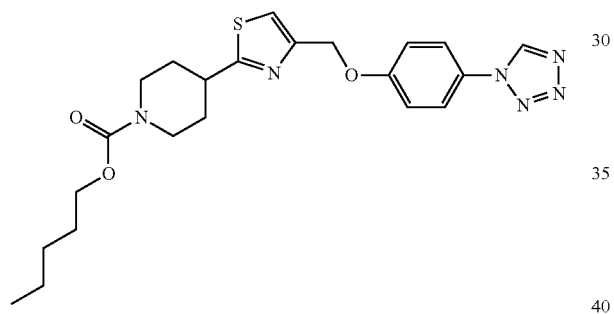

$^1$H NMR (CDCl$_3$): δ 8.94 (1H, s), 7.62 (2H, d, J=9.2 Hz), 7.28 (1H, s), 7.18 (2H, d, J=9.2 Hz), 5.24 (2H, s), 4.27 (2H, br), 4.09 (2H, m), 3.21 (1H, m), 2.94 (2H, m), 2.14 (2H, m), 1.78 (2H, m), 1.65 (2H, m), 1.35 (4H, m), 0.91 (3H, m).

Example 32

4-[4-(4-Tetrazol-1-yl-phenoxymethyl)-thiazol-2-yl]-piperidine-1-carboxylic acid 2-fluoro-ethyl ester

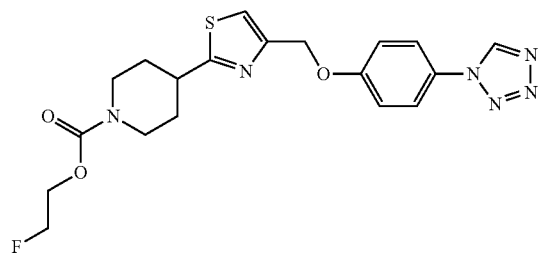 [SMILES: O=C(OCCF)N1CCC(c2nc(COc3ccc(-n4cnnn4)cc3)cs2)CC1]

$^1$H NMR (CDCl$_3$): δ 8.97 (1H, s), 7.62 (2H, d, J=9.0 Hz), 7.28 (1H, s), 7.17 (2H, d, J=9.0 Hz), 5.24 (2H, s), 4.70-4.30 (6H, m), 3.22 (1H, m), 2.99 (2H, m), 2.15 (2H, m), 1.78 (2H, m).

Example 33

4-[4-(4-Tetrazol-1-yl-phenoxymethyl)-thiazol-2-yl]-piperidine-1-carboxylic acid butyl ester

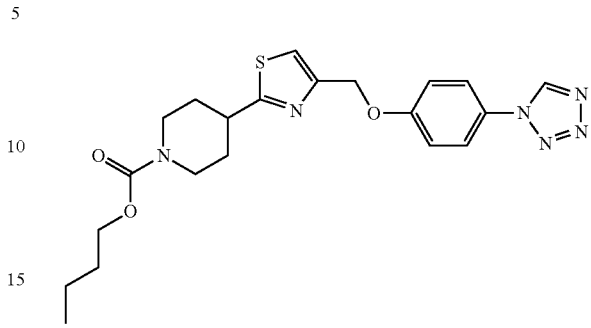

$^1$H NMR (CDCl$_3$): δ 9.01 (1H, s), 7.64 (2H, d, J=8.8 Hz), 7.29 (1H, s), 7.17 (2H, d, J=8.8 Hz), 5.24 (2H, s), 4.26 (2H, m), 4.10 (2H, t), 3.21 (1H, m), 2.95 (2H, m), 2.14 (2H, m), 1.78 (2H, m), 1.63 (2H, m), 1.40 (2H, m), 0.95 (3H, t, J=7.4 Hz).

Example 34

4-[4-(4-Tetrazol-1-yl-phenoxymethyl)-thiazol-2-yl]-piperidine-1-carboxylic acid 2,2-dimethyl-propyl ester

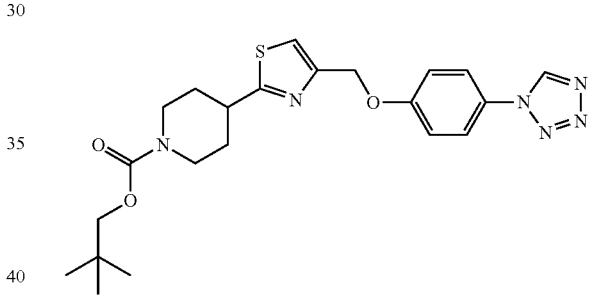

$^1$H NMR (CDCl$_3$): δ 9.00 (1H, s), 7.56 (2H, d, J=8.8 Hz), 7.21 (1H, s), 7.08 (2H, d, J=8.8 Hz), 5.14 (2H, s), 4.17 (2H, br), 3.69 (2H, s), 3.13 (1H, m), 2.88 (2H, m), 2.06 (2H, m), 1.73 (2H, m), 0.86 (9H, s).

Example 35

4-[4-(4-Tetrazol-1-yl-phenoxymethyl)-thiazol-2-yl]-piperidine-1-carboxylic acid hexyl ester

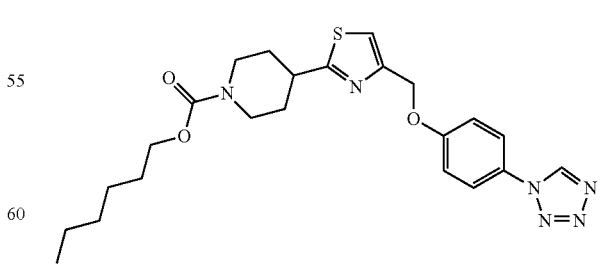

$^1$H NMR (CDCl$_3$): δ 9.06 (1H, s), 7.65 (2H, d, J=8.8 Hz), 7.29 (1H, s), 7.18 (2H, d, J=8.8 Hz), 5.24 (2H, s), 4.27 (2H, br), 4.09 (2H, t), 3.21 (1H, m), 2.95 (2H, m), 2.14 (2H, m), 1.78 (2H, m), 1.64 (2H, m), 1.33 (6H, m), 0.89 (3H, m).

Example 36

4-[4-(4-Tetrazol-1-yl-phenoxymethyl)-thiazol-2-yl]-piperidine-1-carboxylic acid 2-ethyl-hexyl ester

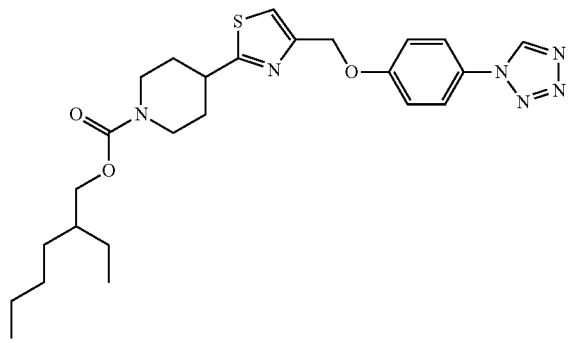 [SMILES: CCCCC(CC)COC(=O)N1CCC(c2nc(COc3ccc(-n4cnnn4)cc3)cs2)CC1]

$^1$H NMR (CDCl$_3$): δ 8.98 (1H, s), 7.58 (2H, d, J=8.8 Hz), 7.23 (1H, s), 7.10 (2H, d, J=8.8 Hz), 5.17 (2H, s), 4.19 (2H, br), 3.95 (2H, m), 3.15 (1H, m), 2.89 (2H, m), 2.07 (2H, m), 1.69 (2H, m), 1.52 (1H, m), 1.35-1.20 (8H, m), 0.90-0.80 (6H, m).

Example 37

4-[4-(4-Tetrazol-1-yl-phenoxymethyl)-thiazol-2-yl]-piperidine-1-carboxylic acid 2-benzyloxy-ethyl ester

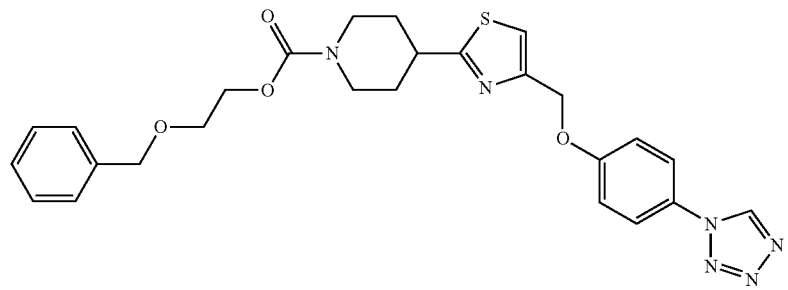 [SMILES: O=C(OCCOCc1ccccc1)N1CCC(c2nc(COc3ccc(-n4cnnn4)cc3)cs2)CC1]

$^1$H NMR (CDCl$_3$): δ 8.98 (1H, s), 7.57 (2H, d, J=8.0 Hz), 7.30-7.20 (6H, m), 7.11 (2H, d, J=8.0 Hz), 5.17 (2H, s), 4.52 (2H, s), 4.25-4.20 (4H, m), 3.65 (2H, m), 3.15 (1H, m), 2.91 (2H, m), 2.08 (2H, m), 1.73 (2H, m).

Example 38

4-[4-(4-Tetrazol-1-yl-phenoxymethyl)-thiazol-2-yl]-piperidine-1-carboxylic acid 2-isopropyl-5-methyl-cyclohexyl ester

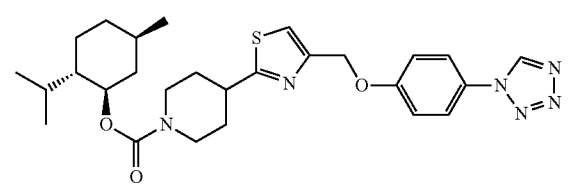 [SMILES: CC(C)[C@@H]1CC[C@@H](C)C[C@H]1OC(=O)N1CCC(c2nc(COc3ccc(-n4cnnn4)cc3)cs2)CC1]

$^1$H NMR (CDCl$_3$): δ 8.97 (1H, s), 7.58 (2H, m), 7.23 (1H, s), 7.11 (2H, m), 5.18 (2H, s), 4.21 (2H, br), 3.13 (1H, m), 2.88 (2H, m), 2.05-0.70 (23H, m).

Example 39

Adamantan-1-yl-{4-[4-(4-methanesulfonyl-phenoxymethyl)-thiazol-2-yl]-piperidin-1-yl}-methanone

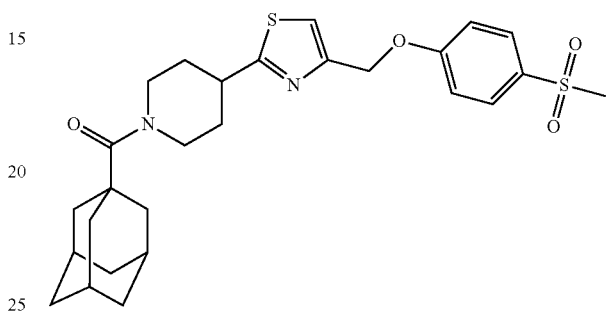

$^1$H NMR (CDCl$_3$): δ 7.88 (2H, d, J=8.8 Hz), 7.24 (1H, s), 7.12 (2H, d, J=8.8 Hz), 5.23 (2H, s), 4.61 (2H, m), 3.24~3.30 (1H, m), 3.03 (3H, s), 2.93~3.00 (2H, m), 2.16 (2H, m), 2.02~2.04 (9H, m), 1.70~1.80 (8H, m).

Example 40

{4-[4-(4-Methanesulfonyl-phenoxymethyl)-thiazol-2-yl]-piperidin-1-yl}-pyridin-3-yl-methanone

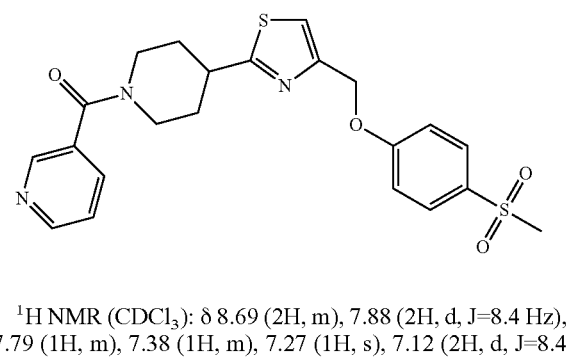

$^1$H NMR (CDCl$_3$): δ 8.69 (2H, m), 7.88 (2H, d, J=8.4 Hz), 7.79 (1H, m), 7.38 (1H, m), 7.27 (1H, s), 7.12 (2H, d, J=8.4

Hz), 5.24 (2H, s), 4.79 (2H, br), 3.86 (2H, br), 3.31 (1H, m), 3.04 (3H, s), 2.20 (2H, m), 1.84 (2H, m).

Example 41

3,3-Dimethyl-1-{4-[4-(4-tetrazol-1-yl-phenoxymethyl)-thiazol-2-yl]-piperidin-1-yl}-butan-1-one

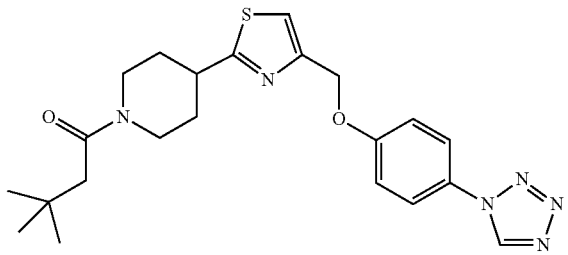 [SMILES: CC(C)(C)CC(=O)N1CCC(c2nc(COc3ccc(-n4cnnn4)cc3)cs2)CC1]

$^1$H NMR (DMSO-d$_6$): δ 9.98 (1H, s), 7.81 (2H, d, J=8.8 Hz), 7.66 (1H, s), 7.29 (2H, d, J=8.8 Hz), 5.20 (2H, s), 4.52 (1H, m), 4.10 (1H, m), 3.26 (1H, m), 3.19 (1H, m), 2.70 (1H, m), 2.25 (2H, m), 2.15 (2H, m), 1.50 (2H, m), 0.96 (9H, s).

Example 42

Oxo-{4-[4-(4-tetrazol-1-yl-phenoxymethyl)-thiazol-2-yl]-piperidin-1-yl}-acetic acid methyl ester

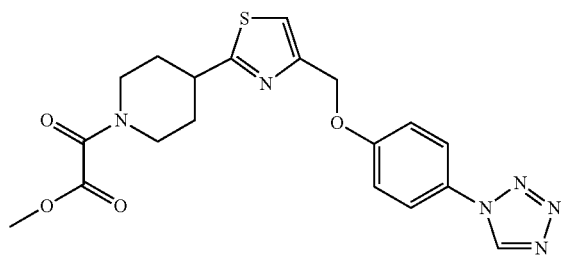 [SMILES: COC(=O)C(=O)N1CCC(c2nc(COc3ccc(-n4cnnn4)cc3)cs2)CC1]

$^1$H NMR (DMSO-d$_6$): δ 9.98 (1H, s), 7.81 (2H, d, J=8.8 Hz), 7.68 (1H, s), 7.29 (2H, d, J=8.8 Hz), 5.21 (2H, s), 4.32 (1H, m), 3.80 (3H, s), 3.60 (1H, m), 3.32 (1H, m), 2.94 (2H, m), 2.13 (2H, m), 1.57 (2H, m).

Example 43

3-Oxo-3-{4-[4-(4-tetrazol-1-yl-phenoxymethyl)-thiazol-2-yl]-piperidin-1-yl}-propionic acid ethyl ester

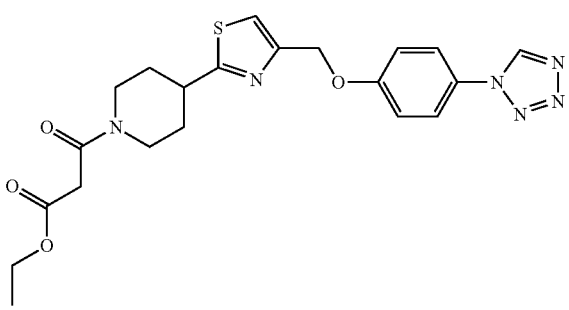 [SMILES: CCOC(=O)CC(=O)N1CCC(c2nc(COc3ccc(-n4cnnn4)cc3)cs2)CC1]

$^1$H NMR (DMSO-d$_6$): δ 8.94 (1H, s), 7.61 (2H, m), 7.26 (1H, s), 7.15 (2H, m), 5.20 (2H, s), 4.65 (1H, m), 4.17 (2H, q), 3.87 (1H, m), 3.48 (2H, s), 3.26 (2H, m), 2.81 (1H, m), 2.18 (2H, m), 1.78 (2H, m), 1.27 (3H, t).

Example 44

(4-Methyl-piperazin-1-yl)-{4-[4-(4-tetrazol-1-yl-phenoxymethyl)-thiazol-2-yl]-piperidin-1-yl}-methanone

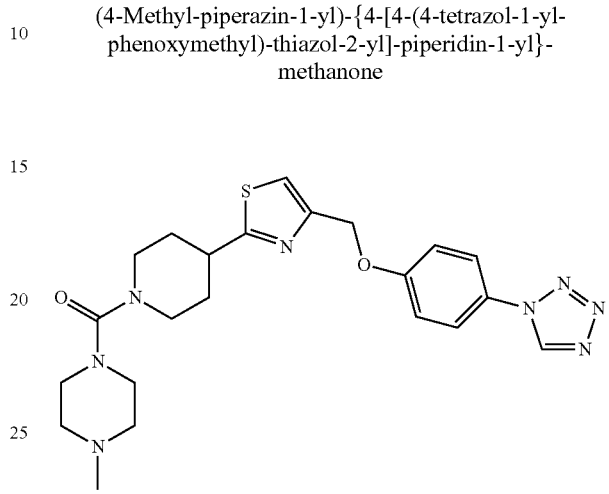

$^1$H NMR (DMSO-d$_6$): δ 9.98 (1H, s), 7.81 (2H, d, J=8.9 Hz), 7.64 (1H, s), 7.29 (2H, d), 5.20 (2H, s), 3.29 (2H, m), 3.18 (5H, m), 2.95 (2H, d), 2.61 (3H, s), 2.38 (2H, m), 2.03 (4H, m), 1.65 (2H, m).

Example 45

4-[4-(4-Tetrazol-1-yl-phenoxymethyl)-thiazol-2-yl]-piperidine-1-carboxylic acid diethylamide

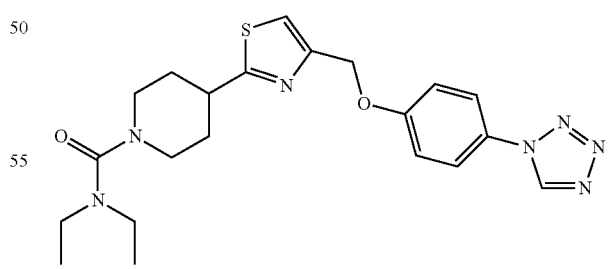

$^1$H NMR (DMSO-d$_6$): δ 9.98 (1H, s), 7.81 (2H, d, J=8.9 Hz), 7.66 (1H, s), 7.29 (2H, d, J=8.9 Hz), 5.20 (2H, s), 3.55 (2H, m), 3.20 (1H, m), 3.14 (4H, q), 2.81 (2H, m), 2.02 (2H, m), 1.64 (2H, m), 1.02 (6H, t, J=6.8 Hz).

Example 46

4-[4-(4-Tetrazol-1-yl-phenoxymethyl)-thiazol-2-yl]-piperidine-1-carboxylic acid ethylamide

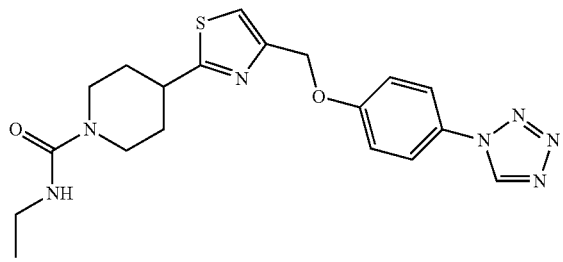 [SMILES: CCNC(=O)N1CCC(c2nc(COc3ccc(-n4cnnn4)cc3)cs2)CC1]

$^1$H NMR (DMSO-d$_6$): δ 9.98 (1H, s), 7.81 (2H, d, J=8.9 Hz), 7.65 (1H, s), 7.29 (2H, d, J=8.9 Hz), 6.47 (1H, m), 5.20 (2H, s), 4.01 (2H, d), 3.17 (1H, m), 3.04 (2H, m), 2.78 (2H, m), 1.97 (2H, m), 1.52 (2H, m), 0.99 (3H, t, J=6.8 Hz).

Example 47

2-{4-[4-(4-Methanesulfonyl-phenoxymethyl)-thiazol-2-yl]-piperidin-1-yl}-pyrimidine

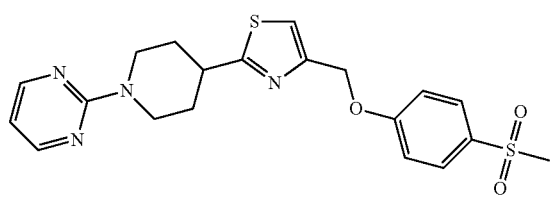 [SMILES: CS(=O)(=O)c1ccc(OCc2csc(C3CCN(c4ncccn4)CC3)n2)cc1]

A mixture of 4-[4-(4-methylsulfonyl-phenoxymethyl)-thiazole-2-yl]-piperidine hydrochloride (100 mg, 0.24 mmol), 2-chloropyrimidine (30 mg, 1.1 eq.) and diisopropylethylamine (122 mg, 4 eq.) in i-PrOH (5 mL) was heated at 90° C. for 1.5 hours. The solvent was removed in vacuo. The residue was purified on silica gel (60% EtOAc in hexanes) to afford the desired product. $^1$H NMR (CDCl$_3$): δ 8.32 (2H, d, J=4.8 Hz), 7.88 (2H, d, J=8.8 Hz), 7.23 (1H, s), 7.12 (2H, d, J=8.8 Hz), 6.49 (1H, t, J=4.8 Hz), 5.24 (2H, s), 4.89 (2H, m), 3.32 (1H, m), 3.06 (2H, m), 3.04 (3H, s), 2.22 (2H, m), 1.81 (2H, m).

The compounds in Examples 48-77 were synthesized from one of Intermediates 3-13 or Intermediates 15-25 with the corresponding substituted 2-chloropyrimidine, 2-iodopyrimidine, 2-chloropyridine, 2-fluoropyridine, 2-methanesulfonyl-pyrimidine, 2-chloropyrazine, 2-chloropyridazine or other suitable heterocycles in a manner similar to that described in Example 47. One skilled in the art of organic synthesis will appreciate that conditions such as solvent (such as DMF, CH$_3$CN); temperature, base (such as NEt$_3$, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 48

2-{4-[4-(4-Methanesulfonyl-phenoxymethyl)-thiazol-2-yl]-piperidin-1-yl}-4-methoxy-pyrimidine

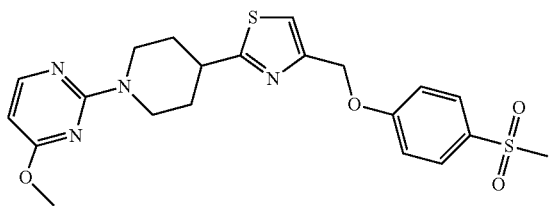 [SMILES: COc1ccnc(N2CCC(c3nc(COc4ccc(S(C)(=O)=O)cc4)cs3)CC2)n1]

$^1$H NMR (CDCl$_3$): δ 8.06 (1H, d, J=6.0 Hz), 7.87 (2H, d, J=8.8 Hz), 7.23 (1H, s), 7.12 (2H, d, J=8.8 Hz), 5.98 (1H, d, J=6.0 Hz), 5.24 (2H, s), 4.88 (2H, m), 3.90 (3H, s), 3.31 (1H, m), 3.04 (5H, m), 2.20 (2H, m), 1.81 (2H, m).

Example 49

2-{4-[4-(4-Methanesulfonyl-phenoxymethyl)-thiazol-2-yl]-piperidin-1-yl}-4-trifluoromethyl-pyrimidine

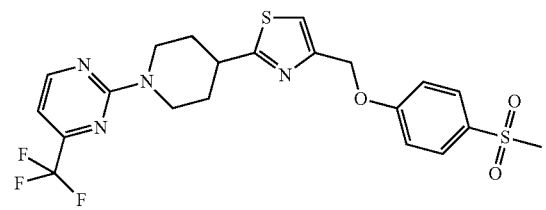 [SMILES: CS(=O)(=O)c1ccc(OCc2csc(C3CCN(c4nccc(C(F)(F)F)n4)CC3)n2)cc1]

$^1$H NMR (CDCl$_3$): δ 8.50 (1H, d, J=4.8 Hz), 7.88 (2H, d, J=8.8 Hz), 7.24 (1H, s), 7.12 (2H, d, J=8.8 Hz), 6.76 (1H, d, J=4.8 Hz), 5.24 (2H, s), 4.92 (2H, m), 3.34 (1H, m), 3.11 (2H, m), 3.04 (3H, s), 2.24 (2H, m), 1.84 (2H, m).

Example 50

2-{4-[4-(4-Methanesulfonyl-phenoxymethyl)-thiazol-2-yl]-piperidin-1-yl}-4,6-dimethyl-pyrimidine

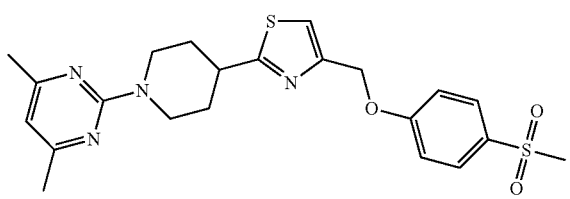

$^1$H NMR (CDCl$_3$): δ 7.88 (2H, d, J=8.4 Hz), 7.22 (1H, s), 7.12 (2H, d, J=8.4 Hz), 6.27 (1H, s), 5.24 (2H, s), 4.96 (2H, m), 3.28 (1H, m), 3.04 (3H, s), 2.99 (2H, m), 2.29 (6H, s), 2.19 (2H, m), 1.80 (2H, m).

Example 51

5-Ethyl-2-{4-[4-(4-methanesulfonyl-phenoxymethyl)-thiazol-2-yl]-piperidin-1-yl}-pyrimidine

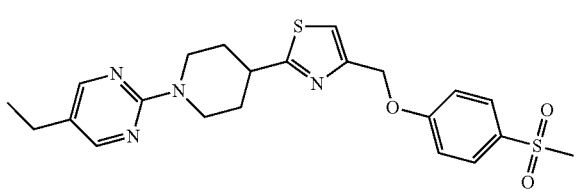 [SMILES: CCc1cnc(N2CCC(c3nc(COc4ccc(S(C)(=O)=O)cc4)cs3)CC2)nc1]

¹H NMR (CDCl₃): δ 8.19 (2H, s), 7.87 (2H, d, J=8.8 Hz), 7.22 (1H, s), 7.12 (2H, d, J=8.8 Hz), 5.24 (2H, s), 4.84 (2H, m), 3.30 (1H, m), 3.04 (2H, m), 3.03 (3H, s), 2.47 (2H, q, J=7.2 Hz), 2.22 (2H, m), 1.81 (2H, m), 1.20 (3H, t, J=7.2 Hz).

Example 52

5-Ethyl-2-{4-[4-(4-tetrazol-1-yl-phenoxymethyl)-thiazol-2-yl]-piperidin-1-yl}-pyrimidine

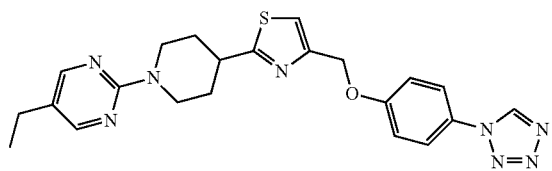 [SMILES: CCc1cnc(N2CCC(c3nc(COc4ccc(-n5cnnn5)cc4)cs3)CC2)nc1]

¹H NMR (DMSO-d₆): δ 9.98 (1H, s), 8.24 (2H, s), 7.80 (2H, d, J=8.8 Hz), 7.66 (1H, s), 7.28 (2H, d, J=8.8 Hz), 5.20 (2H, s), 4.67 (2H, m), 3.32 (1H, m), 3.01 (2H, m), 2.43 (2H, q, J=7.2 Hz), 2.07 (2H, m), 1.59 (2H, m), 1.11 (3H, t, J=7.2 Hz).

Example 53

5-Fluoro-2-{4-[4-(6-tetrazol-1-yl-pyridin-3-yloxymethyl)-thiazol-2-yl]-piperidin-1-yl}-pyrimidine

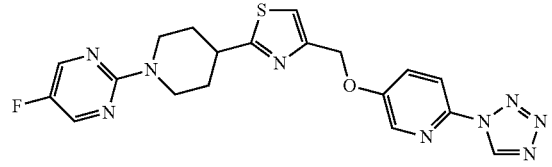 [SMILES: Fc1cnc(N2CCC(c3nc(COc4ccc(-n5cnnn5)nc4)cs3)CC2)nc1]

¹H NMR (DMSO-d₆): δ 10.07 (1H, s), 8.43 (2H, s), 8.41 (1H, d, J=3.2 Hz), 7.98 (1H, d, J=9.2 Hz), 7.86 (1H, dd, J=9.2, 3.2 Hz), 7.71 (1H, s), 5.30 (2H, s), 4.58 (2H, m), 3.31 (1H, m), 3.01 (2H, m), 2.10 (2H, m), 1.59 (2H, m).

Example 54

5-Bromo-2-{4-[4-(4-tetrazol-1-yl-phenoxymethyl)-thiazol-2-yl]-piperidin-1-yl}-pyrimidine

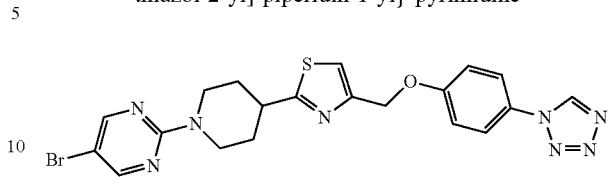

¹H NMR (CDCl₃): δ 8.90 (1H, s), 8.29 (2H, s), 7.60 (2H, d, J=9.0 Hz), 7.25 (1H, s), 7.16 (2H, d, J=9.0 Hz), 5.23 (2H, s), 4.81 (2H, m), 3.31 (1H, m), 3.06 (2H, m), 2.21 (2H, m), 1.79 (2H, m).

Example 55

5-Fluoro-2-{4-[4-(4-tetrazol-1-yl-phenoxymethyl)-thiazol-2-yl]-piperidin-1-yl}-pyrimidine

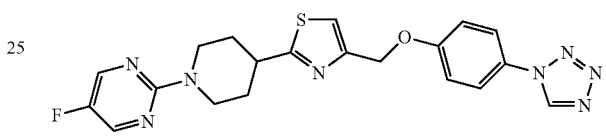

¹H NMR (CDCl₃): δ 8.91 (1H, s), 8.20 (2H, s), 7.60 (2H, d, J=8.6 Hz), 7.25 (1H, s), 7.16 (2H, d, J=8.6 Hz), 5.23 (2H, s), 4.78 (2H, m), 3.31 (1H, m), 3.06 (2H, m), 2.21 (2H, m), 1.83 (2H, m).

Example 56

4,5-Dichloro-2-{4-[4-(4-tetrazol-1-yl-phenoxymethyl)-thiazol-2-yl]-piperidin-1-yl}-pyrimidine

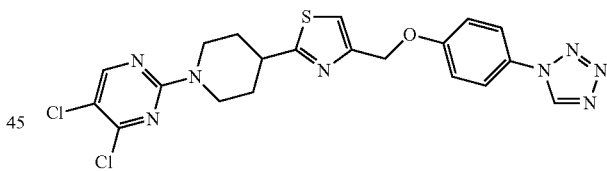

¹H NMR (CDCl₃): δ 8.91 (1H, s), 8.10 (1H, s), 7.61 (2H, d, J=8.8 Hz), 7.27 (1H, s), 7.16 (2H, d, J=8.8 Hz), 5.23 (2H, s), 4.62 (2H, m), 3.34 (1H, m), 3.18 (2H, m), 2.25 (2H, m), 1.98 (2H, m).

Example 57

4-Chloro-5-methyl-2-{4-[4-(4-tetrazol-1-yl-phenoxymethyl)-thiazol-2-yl]-piperidin-1-yl}-pyrimidine

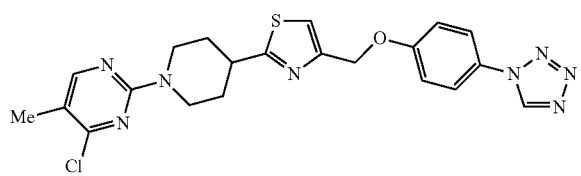 [SMILES: Cc1cnc(N2CCC(c3nc(COc4ccc(-n5cnnn5)cc4)cs3)CC2)nc1Cl]

$^1$H NMR (CDCl$_3$): δ 8.90 (1H, s), 8.08 (1H, s), 7.60 (2H, d, J=8.8 Hz), 7.24 (1H, s), 7.17 (2H, d, J=8.8 Hz), 5.23 (2H, s), 4.80 (2H, m), 3.30 (1H, m), 3.04 (2H, m), 2.19 (2H, m), 2.16 (3H, s), 1.81 (2H, m).

Example 58

2-Chloro-5-methyl-4-{4-[4-(4-tetrazol-1-yl-phenoxymethyl)-thiazol-2-yl]-piperidin-1-yl}-pyrimidine

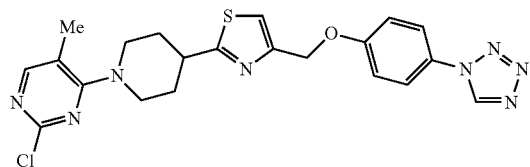 [SMILES: Cc1cnc(Cl)nc1N1CCC(c2nc(COc3ccc(-n4cnnn4)cc3)cs2)CC1]

$^1$H NMR (CDCl$_3$): δ 8.92 (1H, s), 7.96 (1H, s), 7.60 (2H, d, J=8.8 Hz), 7.27 (1H, s), 7.16 (2H, d, J=8.8 Hz), 5.23 (2H, s), 4.17 (2H, m), 3.31 (1H, m), 3.10 (2H, m), 2.26 (2H, m), 2.21 (3H, s), 1.95 (2H, m).

Example 59

5-(4-Chloro-phenyl)-2-{4-[4-(4-tetrazol-1-yl-phenoxymethyl)-thiazol-2-yl]-piperidin-1-yl}-pyrimidine

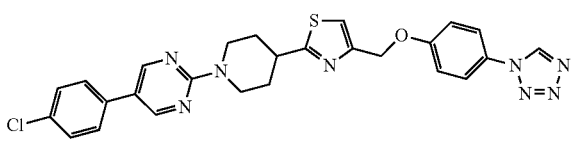 [SMILES: Clc1ccc(-c2cnc(N3CCC(c4nc(COc5ccc(-n6cnnn6)cc5)cs4)CC3)nc2)cc1]

$^1$H NMR (DMSO-d$_6$): δ 9.97 (1H, s), 8.71 (2H, s), 7.80 (2H, d, J=8.8 Hz), 7.67 (2H, d, J=8.4 Hz), 7.66 (1H, s), 7.48 (2H, d, J=8.4 Hz), 7.28 (2H, d, J=8.8 Hz), 5.21 (2H, s), 4.76 (2H, m), 3.37 (1H, m), 3.13 (2H, m), 2.12 (2H, m), 1.66 (2H, m).

Example 60

5-Chloro-2-{4-[4-(4-tetrazol-1-yl-phenoxymethyl)-thiazol-2-yl]-piperidin-1-yl}-pyrimidine

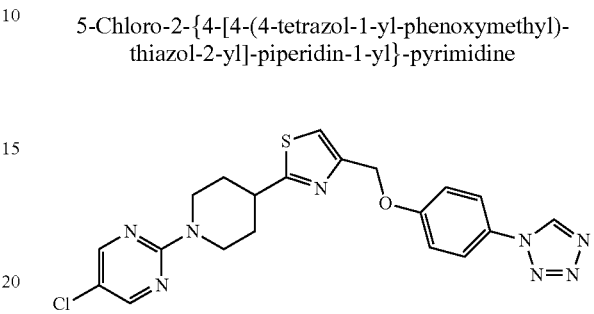

$^1$H NMR (CDCl$_3$): δ 8.91 (1H, s), 8.23 (2H, s), 7.61 (2H, d, J=8.8 Hz), 7.26 (1H, s), 7.17 (2H, d, J=8.8 Hz), 5.24 (2H, s), 4.82 (2H, m), 3.32 (1H, m), 3.07 (2H, m), 2.22 (2H, m), 1.81 (2H, m).

Example 61

5-Heptyl-2-{4-[4-(4-methanesulfonyl-phenoxymethyl)-thiazol-2-yl]-piperidin-1-yl}-pyrimidine

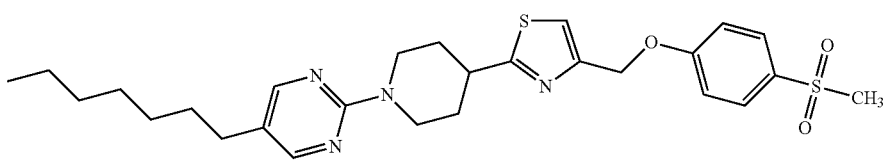 [SMILES: CCCCCCCc1cnc(N2CCC(c3nc(COc4ccc(S(C)(=O)=O)cc4)cs3)CC2)nc1]

$^1$H NMR (CDCl$_3$): δ 8.16 (2H, s), 7.87 (2H, d, J=9.0 Hz), 7.22 (1H, s), 7.12 (2H, d, J=9.0 Hz), 5.24 (2H, s), 4.83 (2H, m), 3.29 (1H, m), 3.04 (2H, m), 3.03 (3H, s), 2.42 (2H, t, J=7.4 Hz), 2.21 (2H, m), 1.80 (2H, m), 1.52 (2H, m), 1.28 (8H, m), 0.89 (3H, t).

Example 62

2-{4-[4-(4-Methanesulfonyl-phenoxymethyl)-thiazol-2-yl]-piperidin-1-yl}-5-pentyl-pyrimidine

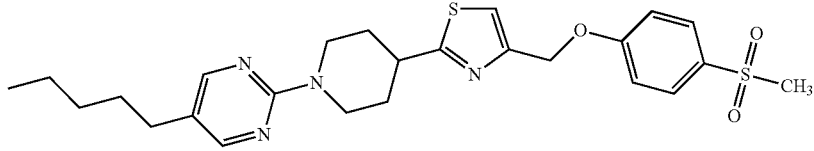 [SMILES: CCCCCc1cnc(N2CCC(c3nc(COc4ccc(S(C)(=O)=O)cc4)cs3)CC2)nc1]

$^1$H NMR (CDCl$_3$): δ 8.16 (2H, s), 7.87 (2H, d, J=8.8 Hz), 7.22 (1H, s), 7.12 (2H, d, J=8.8 Hz), 5.23 (2H, s), 4.83 (2H, m), 3.29 (1H, m), 3.04 (2H, m), 3.03 (3H, s), 2.42 (2H, t, J=7.6 Hz), 2.21 (2H, m), 1.81 (2H, m), 1.56 (2H, m), 1.32 (4H, m), 0.90 (3H, t).

Example 63

5-Heptyl-2-{4-[4-(4-tetrazol-1-yl-phenoxymethyl)-thiazol-2-yl]-piperidin-1-yl}-pyrimidine

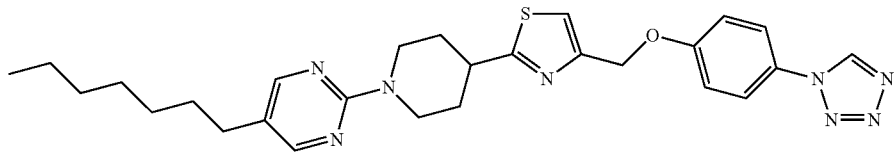 [SMILES: CCCCCCCc1cnc(N2CCC(c3nc(COc4ccc(-n5cnnn5)cc4)cs3)CC2)nc1]

$^1$H NMR (CDCl$_3$): δ 8.90 (1H, s), 8.16 (2H, s), 7.60 (2H, d, J=8.8 Hz), 7.24 (1H, s), 7.17 (2H, d, J=8.8 Hz), 5.23 (2H, s), 4.82 (2H, m), 3.29 (1H, m), 3.04 (2H, m), 2.42 (2H, t), 2.20 (2H, m), 1.80 (2H, m), 1.53 (2H, m), 1.28 (8H, m), 0.87 (3H, t).

Example 64

5-Pentyl-2-{4-[4-(4-tetrazol-1-yl-phenoxymethyl)-thiazol-2-yl]-piperidin-1-yl}-pyrimidine

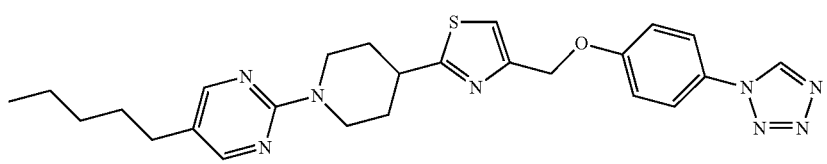 [SMILES: CCCCCc1cnc(N2CCC(c3nc(COc4ccc(-n5cnnn5)cc4)cs3)CC2)nc1]

$^1$H NMR (CDCl$_3$): δ 8.90 (1H, s), 8.16 (2H, s), 7.60 (2H, d, J=8.8 Hz), 7.24 (1H, s), 7.17 (2H, d, J=8.8 Hz), 5.23 (2H, s), 4.83 (2H, m), 3.30 (1H, m), 3.04 (2H, m), 2.42 (2H, t), 2.20 (2H, m), 1.80 (2H, m), 1.54 (2H, m), 1.30 (4H, m), 0.89 (3H, t).

Example 65

5-Methyl-2-{4-[4-(4-tetrazol-1-yl-phenoxymethyl)-thiazol-2-yl]-piperidin-1-yl}-pyrimidine

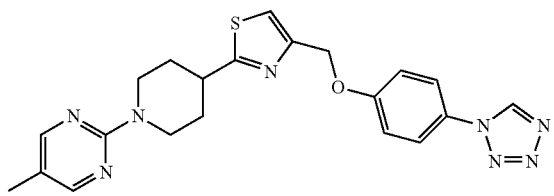 [SMILES: Cc1cnc(N2CCC(c3nc(COc4ccc(-n5cnnn5)cc4)cs3)CC2)nc1]

$^1$H NMR (CDCl$_3$): δ 8.94 (1H, s), 8.17 (2H, s), 7.62 (2H, d, J=8.8 Hz), 7.25 (1H, s), 7.17 (2H, d, J=8.8 Hz), 5.24 (2H, s), 4.82 (2H, d), 3.30 (1H, m), 3.04 (2H, m), 2.22 (2H, m), 2.13 (3H, s), 1.81 (2H, m).

Example 66

5-(4-Methoxy-phenyl)-2-{4-[4-(4-tetrazol-1-yl-phenoxymethyl)-thiazol-2-yl]-piperidin-1-yl}-pyrimidine

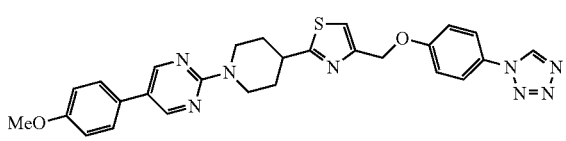 [SMILES: COc1ccc(-c2cnc(N3CCC(c4nc(COc5ccc(-n6cnnn6)cc5)cs4)CC3)nc2)cc1]

$^1$H NMR (CDCl$_3$): δ 8.90 (1H, s), 8.52 (s, 2H), 7.61 (2H, d, J=9.0 Hz), 7.41 (2H, d, J=8.6 Hz), 7.25 (1H, s), 7.17 (2H, d, J=9.0 Hz), 6.99 (2H, d, J=8.6 Hz), 5.24 (2H, s), 4.92 (2H, m), 3.85 (3H, s), 3.34 (1H, m), 3.12 (2H, m), 2.25 (2H, m), 1.85 (2H, m).

Example 67

5-Propyl-2-{4-[4-(4-tetrazol-1-yl-phenoxymethyl)-thiazol-2-yl]-piperidin-1-yl}-pyrimidine

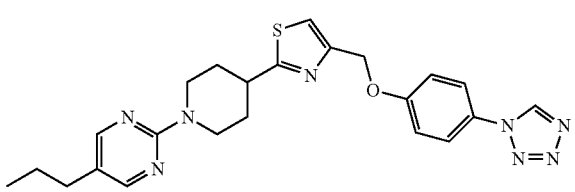 [SMILES: CCCc1cnc(N2CCC(c3nc(COc4ccc(-n5cnnn5)cc4)cs3)CC2)nc1]

$^1$H NMR (CDCl$_3$): δ 8.9 (1H, s), 8.17 (2H, s), 7.61 (2H, d, J=8.8 Hz), 7.24 (1H, s), 7.17 (2H, d, J=8.8 Hz), 5.24 (2H, s), 4.83 (2H, m), 3.31 (1H, m), 3.04 (2H, m), 2.4 (2H, t, J=7.6 Hz), 2.22 (2H, m), 1.81 (2H, m), 1.58 (2H, m), 0.94 (3H, t, J=7.6 Hz).

Example 68

5-Methoxy-2-{4-[4-(4-tetrazol-1-yl-phenoxymethyl)-thiazol-2-yl]-piperidin-1-yl}-pyrimidine

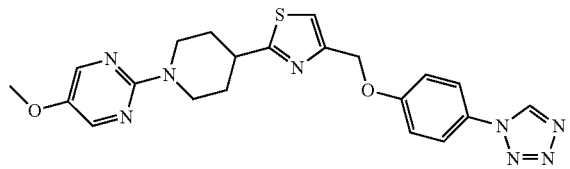 [SMILES: COc1cnc(N2CCC(c3nc(COc4ccc(-n5cnnn5)cc4)cs3)CC2)nc1]

$^1$H NMR (CDCl$_3$): δ 8.93 (1H, s), 8.11 (2H, s), 7.61 (2H, d, J=8.8 Hz), 7.25 (1H, s), 7.17 (2H, d, J=8.8 Hz), 5.24 (2H, s), 4.74 (2H, m), 3.81 (3H, s), 3.31 (1H, m), 3.03 (2H, m), 2.22 (2H, m), 1.82 (2H, m).

Example 69

5'-Methyl-4-[4-(4-tetrazol-1-yl-phenoxymethyl)-thiazol-2-yl]-3,4,5,6-tetrahydro-2H-[1,2']bipyridinyl

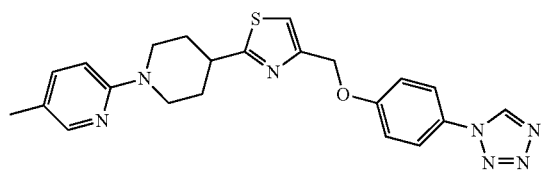 [SMILES: Cc1ccc(N2CCC(c3nc(COc4ccc(-n5cnnn5)cc4)cs3)CC2)nc1]

$^1$H NMR (CDCl$_3$): δ 8.91 (1H, s), 8.03 (1H, m), 7.61 (2H, m), 7.33 (1H, m), 7.26 (1H, s), 7.18 (2H, m), 6.65 (1H, d, J=8.8 Hz), 5.24 (2H, s), 4.33 (2H, m), 3.25 (1H, m), 2.97 (2H, m), 2.22 (2H, m), 2.21 (3H, s), 1.89 (2H, m).

Example 70

4-[4-(4-Tetrazol-1-yl-phenoxymethyl)-thiazol-2-yl]-5',6"-bis-trifluoromethyl-3,4,5,6-tetrahydro-2H-[1,2';6',2"]terpyridine

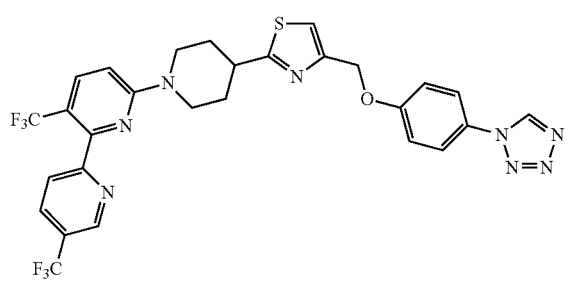 [SMILES: FC(F)(F)c1ccc(-c2nc(N3CCC(c4nc(COc5ccc(-n6cnnn6)cc5)cs4)CC3)ccc2C(F)(F)F)nc1]

$^1$H NMR (DMSO-d$_6$): δ 8.81 (1H, m), 8.39 (1H, m), 8.13 (1H, dd, J=8.8, 2.4 Hz), 7.76 (1H, dd, J=8.8, 2.8 Hz), 7.66 (1H, s), 7.59 (2H, m), 7.25 (2H, m), 6.99 (1H, d, J=9 Hz), 6.8 (1H, d, J=9 Hz), 5.19 (2H, s), 4.48 (2H, m), 3.37 (1H, m), 3.10 (2H, m), 2.11 (2H, m), 1.65 (2H, m).

Example 71

4-[4-(4-Tetrazol-1-yl-phenoxymethyl)-thiazol-2-yl]-5'-trifluoromethyl-3,4,5,6-tetrahydro-2H-[1,2']bipyridinyl

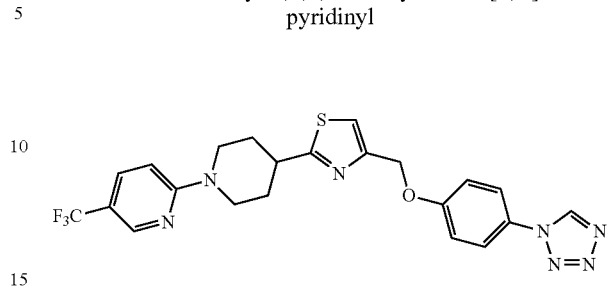

$^1$H NMR (DMSO-d$_6$): δ 9.98 (1H, s), 8.40 (1H, m), 7.81-7.75 (3H, m), 7.66 (1H, s), 7.28 (2H, d), 6.99 (1H, d, J=8.8 Hz), 5.21 (2H, s), 4.48 (2H, d), 3.37 (1H, m), 3.1 (2H, m), 2.12 (2H, m), 1.65 (2H, m).

Example 72

4-[4-(4-Tetrazol-1-yl-phenoxymethyl)-thiazol-2-yl]-3,4,5,6-tetrahydro-2H-[1,2']bipyridinyl-5'-carbaldehyde

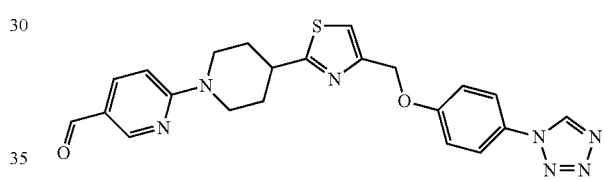

$^1$H NMR (DMSO-d$_6$): δ 9.98 (1H, s), 9.72 (1H, s), 8.58 (1H, d, J=2.4 Hz), 7.86 (1H, dd, J=9.2, 2 Hz), 7.8 (2H, d, J=8.4 Hz), 7.67 (1H, s), 7.28 (2H, d, J=8.4 Hz), 6.99 (1H, d, J=8.8 Hz), 5.2 (2H, s), 4.58 (2H, d), 3.41 (1H, m), 3.17 (2H, m), 2.13 (2H, m), 1.65 (2H, m).

Example 73

1-(3-Isopropyl-[1,2,4]oxadiazol-5-yl)-4-[4-(4-methanesulfonyl-phenoxymethyl)-thiazol-2-yl]-piperidine

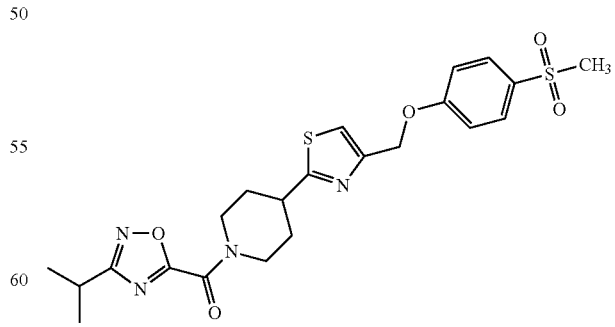

$^1$H NMR (CDCl$_3$): δ 7.87 (2H, m), 7.26 (1H, s), 7.11 (2H, m), 5.23 (2H, s), 4.76-4.68 (1H, m), 4.26-4.18 (1H, m), 3.4~3.3 (2H, m), 3.2~3.04 (2H, m), 3.03 (3H, s), 2.32-2.2 (2H, m), 2.00-1.86 (2H, m), 1.36 (6H, d, J=7.2 Hz).

Example 74

2-{4-[4-(4-Methanesulfonyl-phenoxymethyl)-thiazol-2-yl]-piperidin-1-yl}-benzooxazole

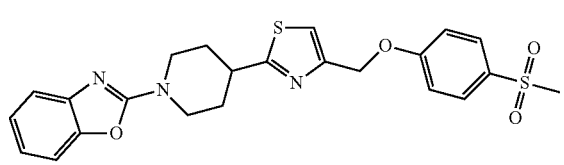 [SMILES: CS(=O)(=O)c1ccc(OCc2csc(C3CCN(c4nc5ccccc5o4)CC3)n2)cc1]

$^1$H NMR (CDCl$_3$): δ 7.87 (2H, d, J=8.4 Hz), 7.36 (1H, d, J=7.6 Hz), 7.01~7.19 (6H, m), 5.24 (2H, s), 4.42 (2H, m), 3.30 (3H, m), 3.03 (3H, s), 2.27 (2H, m), 1.95 (2H, m).

Example 75

4-[4-(4-Methanesulfonyl-phenoxymethyl)-thiazol-2-yl]-5'-trifluoromethyl-3,4,5,6-tetrahydro-2H-[1,2']bipyridinyl

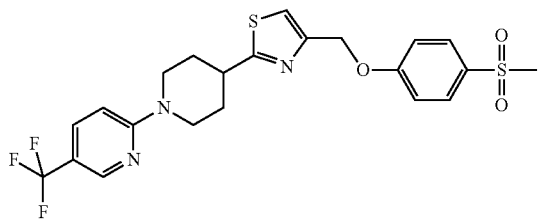 [SMILES: CS(=O)(=O)c1ccc(OCc2csc(C3CCN(c4ccc(C(F)(F)F)cn4)CC3)n2)cc1]

$^1$H NMR (CDCl$_3$): δ 8.4 (1H, s), 7.87 (2H, d), 7.63 (1H, m), 7.26 (1H, s), 7.12 (2H, d), 6.69 (1H, d), 5.23 (2H, s), 4.55-4.50 (2H, m), 3.38-3.28 (1H, m), 3.20-3.10 (2H, m), 3.04 (3H, s), 2.30-2.20 (2H, m), 1.90-1.80 (2H, m).

Example 76

5-Ethyl-2-{4-[4-(2-fluoro-4-methanesulfonyl-phenoxymethyl)-thiazol-2-yl]-piperidin-1-yl}-pyrimidine

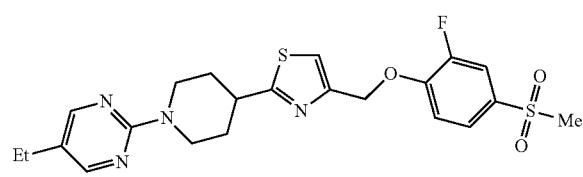 [SMILES: CCc1cnc(N2CCC(c3nc(COc4ccc(S(C)(=O)=O)cc4F)cs3)CC2)nc1]

$^1$H NMR (CDCl$_3$): δ 8.18 (2H, s), 7.65~7.70 (2H, m), 7.21~7.26 (2H, m), 5.30 (2H, s), 4.81~4.84 (2H, m), 3.25~3.28 (1H, m), 3.03 (3H, s), 3.00~3.07 (2H, m), 2.44 (2H, q), 2.21 (2H, m), 1.77~1.81 (2H, m), 1.19 (3H, t).

Example 77

5-Ethyl-2-{4-[4-(2-fluoro-4-tetrazol-1-yl-phenoxymethyl)-thiazol-2-yl]-piperidin-1-yl}-pyrimidine

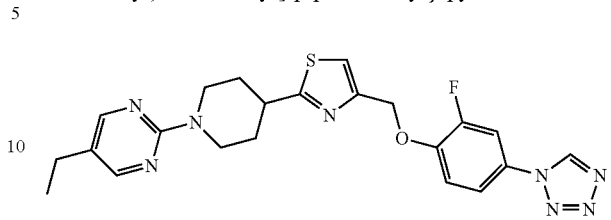

$^1$H NMR (CDCl$_3$): δ 8.96 (1H, s), 8.19 (2H, s), 7.55-7.25 (4H, m), 5.31 (2H, s), 4.82 (2H, m), 3.30 (1H, m), 3.04 (2H, m), 2.47 (2H, q), 2.23 (2H, m), 1.81 (2H, m), 1.20 (3H, t).

Example 78

4-[4-(4-Methanesulfonyl-phenoxymethyl)-thiazol-2-yl]-4-methyl-piperidine-1-carboxylic acid tert-butyl ester

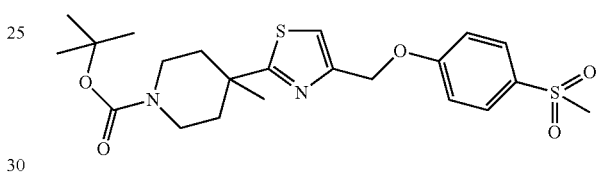

Step 1: 4-Cyano-4-methyl-piperidine-1-carboxylic acid tert-butyl ester

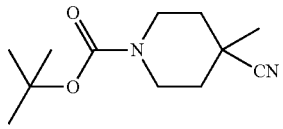 [SMILES: CC1(C#N)CCN(C(=O)OC(C)(C)C)CC1]

To a solution of 4-cyano-piperidine-1-carboxylic acid tert-butyl ester (4.52 g, 20 mmol) in THF (50 mL) was added LHMDS in THF (24 mL, 24 mmol) at 0° C. After stirring at 0° C. for 1 hour, MeI (5.7 g) was added. The reaction mixture was kept at 0° C. for 2 hours, then partitioned between EtOAc and H$_2$O. After concentration in vacuo, the residue was purified by silica column chromatography with EtOAc/hexanes to give the desired product.

Step 2: 4-Carbamoyl-4-methyl-piperidine-1-carboxylic acid tert-butyl ester

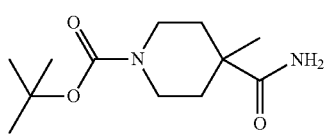

To a solution of 4-cyano-4-methyl-piperidine-1-carboxylic acid tert-butyl ester (2.24 g, 10 mmol) in methanol (25 mL) was added DMSO (1 mL), aqueous 1 N NaOH (12 mL, 12 mmol) and H$_2$O$_2$ (4 mL) at room temperature. The mixture was heated at 50° C. for 3 hours. After cooling to room temperature, the mixture was partitioned between EtOAc and H₂O. The organic layer was washed successively with H₂O and brine. After drying (Na₂SO₄), the solvent was removed to afford the desired product.

Step 3:
4-Methyl-4-thiocarbamoyl-piperidine-1-carboxylic acid tert-butyl ester

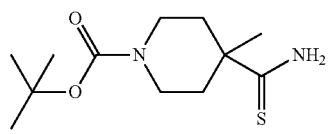 [SMILES: CC(C)(C)OC(=O)N1CCC(C)(C(N)=S)CC1]

To a solution of 4-carbamoyl-4-methyl-piperidine-1-carboxylic acid tert-butyl ester (2.1 g, 8.7 mmol) in THF (30 mL) was added Lawesson's reagent (3.5 g, 8.7 mmol) at room temperature. The mixture was heated at 50° C. for 3 hours. After cooling to room temperature, the solvent was removed in vacuo and the residue was partitioned between EtOAc and H₂O. The organic layer was washed with saturated NaHCO₃, and brine. After drying (Na₂SO₄), the solvent was removed in vacuo, and the residue was purified by silica column chromatography with EtOAc/hexanes to afford the desired product.

Step 4: 4-(4-Ethoxycarbonyl-thiazol-2-yl)-4-methyl-piperidine-1-carboxylic acid tert-butyl ester

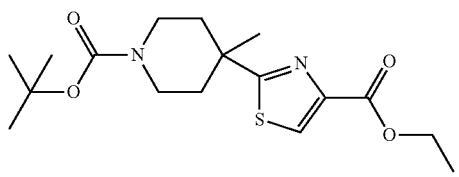 [SMILES: CCOC(=O)c1csc(C2(C)CCN(C(=O)OC(C)(C)C)CC2)n1]

To a solution of 4-methyl-4-thiocarbamoyl-piperidine-1-carboxylic acid tert-butyl ester (1 g, 4 mmol) in EtOH (10 mL) was added ethyl bromopyruvate (0.78 g, 4 mmol) at room temperature. The mixture was heated to refluxing for 3 hours. After cooling to room temperature, the solvent was removed in vacuo. The residue was dissolved in methylene chloride (15 mL), Et₃N (1 mL) and di-tert-butyl dicarbonate (1.3 g) were added to the solution. The mixture was stirred at room temperature overnight. The mixture was washed with H₂O and brine. After drying (Na₂SO₄), the solvent was removed in vacuo, and the residue was purified by silica column chromatography with EtOAc/hexanes to afford the desired product.

Step 5: 4-(4-Hydroxymethyl-thiazol-2-yl)-4-methyl-piperidine-1-carboxylic acid tert-butyl ester

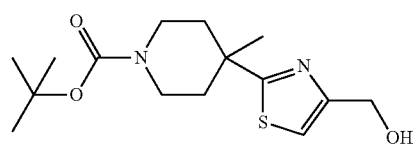 [SMILES: CC(C)(C)OC(=O)N1CCC(C)(c2nc(CO)cs2)CC1]

To a solution of 4-(4-ethoxycarbonyl-thiazol-2-yl)-4-methyl-piperidine-1-carboxylic acid tert-butyl ester (0.6 g, 1.7 mmol) in anhydrous THF (10 mL) was added LiAlH₄ (0.1 g, 2.6 mmol) at 0° C. The mixture was kept at 0° C. for 2 hours and the reaction was quenched with EtOH. The solvent was evaporated and the residue was diluted with EtOAc, washed with 1 N NaOH, brine. After drying (Na₂SO₄), the solvent was removed in vacuo, and the residue was purified by silica column chromatography with EtOAc/hexanes to afford the desired product.

Step 6: 4-(4-Methanesulfonyloxymethyl-thiazol-2-yl)-4-methyl-piperidine-1-carboxylic acid tert-butyl ester

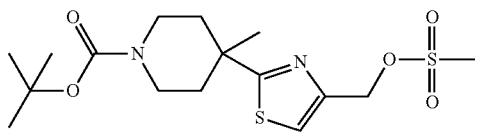 [SMILES: CC(C)(C)OC(=O)N1CCC(C)(c2nc(COS(C)(=O)=O)cs2)CC1]

To a solution of 4-(4-hydroxymethyl-thiazol-2-yl)-4-methyl-piperidine-1-carboxylic acid tert-butyl ester (0.42 g, 1.3 mmol) in methylene chloride (10 mL) was added methanesulfonyl chloride (0.19 g, 1.7 mmol) and triethylamine (0.2 g, 2 mmol) at 0° C. After stirring at 0° C. for 1 hour, the mixture was diluted with EtOAc and washed with H₂O and brine. After drying (Na₂SO₄), the solvent was removed in vacuo, and the residue was purified by silica column chromatography with EtOAc/hexanes to afford the desired product.

Step 7: 4-[4-(4-Methanesulfonyl-phenoxymethyl)-thiazol-2-yl]-4-methyl-piperidine-1-carboxylic acid tert-butyl ester

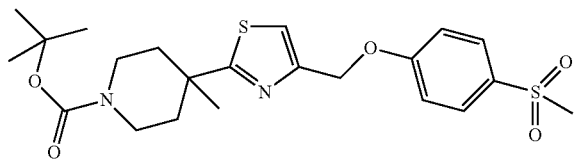 [SMILES: CC(C)(C)OC(=O)N1CCC(C)(c2nc(COc3ccc(S(C)(=O)=O)cc3)cs2)CC1]

A mixture of 4-(4-methanesulfonyloxymethyl-thiazol-2-yl)-4-methyl-piperidine-1-carboxylic acid tert-butyl ester (0.2 g, 0.5 mmol), 4-methanesulfonyl-phenol (86 mg, 0.5 mmol) and Cs₂CO₃ (170 mg, 0.52 mmol) in acetonitrile (4 mL) was heated at 40° C. overnight. After cooling, the solid was filtered through a pad of celite. The filtrate was concentrated in vacuo. The residue was purified on silica gel (EtOAc-hexanes, 1:1) to afford the desired product. ¹H NMR (CDCl₃): δ 7.83 (2H, m), 7.23 (1H, s), 7.09 (2H, m), 5.2 (2H, s), 3.64-3.54 (2H, m), 3.3~3.24 (2H, m), 2.99 (3H, s), 2.2~2.1 (2H, m), 1.72-1.64 (2H, m), 1.41 (9H, s), 1.36 (3H, s).

Example 79

4-[4-(4-Methanesulfonyl-phenoxymethyl)-5-methyl-thiazol-2-yl]-piperidine-1-carboxylic acid tert-butyl ester

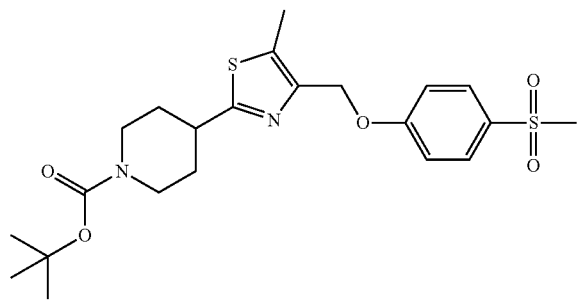 [SMILES: Cc1sc(C2CCN(C(=O)OC(C)(C)C)CC2)nc1COc1ccc(S(C)(=O)=O)cc1]

To a solution of 4-(4-hydroxymethyl-5-methyl-thiazol-2-yl)-piperidine-1-carboxylic acid tert-butyl ester (0.18 g, 0.6 mmol), 4-methanesulfonyl-phenol (0.1 g, 0.6 mmol) and PPh$_3$ (0.19 g, 0.72 mmol) in THF (5 mL) was added diethylazodicarboxylate (DEAD) (0.22 g, 0.72 mmol) at room temperature. The resulting mixture was stirred at room temperature for 30 minutes. The solvent was removed and the residue was purified by flash chromatography on silica gel to afford the desired product. $^1$H NMR (CDCl$_3$): δ 7.9 (2H, d, J=9 Hz), 7.09 (2H, d, J=9 Hz), 5.2 (2H, s), 4.28-4.10 (2H, m), 3.14-3.04 (1H, m), 3.04 (3H, s), 2.9-2.8 (2H, m), 2.44 (3H, s), 2.1-2 (2H, m), 1.76-1.64 (2H, m), 1.47 (9H, s).

Example 80

4-{4-[1-(4-Methanesulfonyl-phenoxy)-ethyl]-5-methyl-thiazol-2-yl}-piperidine-1-carboxylic acid tert-butyl ester

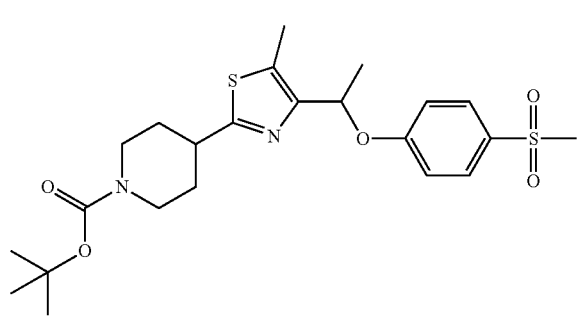 [SMILES: Cc1sc(C2CCN(C(=O)OC(C)(C)C)CC2)nc1C(C)Oc1ccc(S(C)(=O)=O)cc1]

Step 1: 4-[4-(1-Hydroxy-ethyl)-5-methyl-thiazol-2-yl]-piperidine-1-carboxylic acid tert-butyl ester

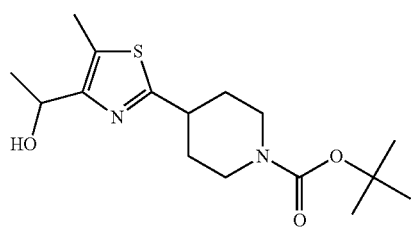 [SMILES: Cc1sc(C2CCN(C(=O)OC(C)(C)C)CC2)nc1C(C)O]

To a solution of 4-(4-formyl-5-methyl-thiazol-2-yl)-piperidine-1-carboxylic acid tert-butyl ester (0.31 g, 1 mmol) in THF (10 mL) was added MeMgI (1 mL, 3 mmol) in Et$_2$O at room temperature. The resulting mixture was stirred at room temperature for 1 hour. The reaction was quenched with saturated aqueous NH$_4$Cl and extracted with EtOAc. The organic layer was washed with H$_2$O and brine. After drying over Na$_2$SO$_4$, the solvent was removed. The residue was purified by flash chromatography on silica gel to afford the desired product.

Step 2: 4-{4-[1-(4-Methanesulfonyl-phenoxy)-ethyl]-5-methyl-thiazol-2-yl}-piperidine-1-carboxylic acid tert-butyl ester

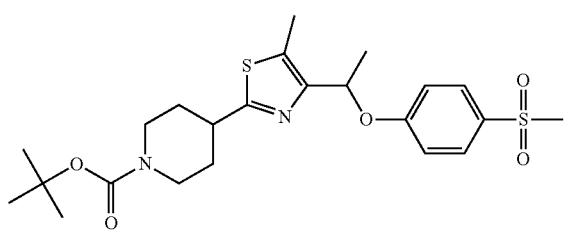 [SMILES: Cc1sc(C2CCN(C(=O)OC(C)(C)C)CC2)nc1C(C)Oc1ccc(S(C)(=O)=O)cc1]

To a solution of 4-[4-(1-Hydroxy-ethyl)-5-methyl-thiazol-2-yl]-piperidine-1-carboxylic acid tert-butyl ester (0.15 g, 0.46 mmol), 4-methanesulfonyl-phenol (0.08 g, 0.46 mmol) and PPh$_3$ (0.14 g, 0.55 mmol) in THF (5 mL) was added DEAD (0.1 g, 0.55 mmol) at room temperature. The resulting mixture was stirred at room temperature for 30 minutes. The solvent was removed. The residue was purified by flash chromatography on silica gel to afford the desired product. $^1$H NMR (CDCl$_3$): δ 7.79 (2H, m), 6.94 (2H, m), 5.59 (1H, q, J=6 Hz),), 4.2-4.04 (2H, m), 3.04-2.94 (1H, m), 2.98 (3H, s), 2.86-2.72 (2H, m), 2.39 (3H, s), 2.04-1.96 (2H, m), 1.67 (3H, d, J=6 Hz), 1.66-1.58 (2H, m), 1.42 (9H, s).

Example 81

4-[3-(4-Methanesulfonyl-phenoxymethyl)-[1,2,4]oxadiazol-5-yl]-piperidine-1-carboxylic acid tert-butyl ester

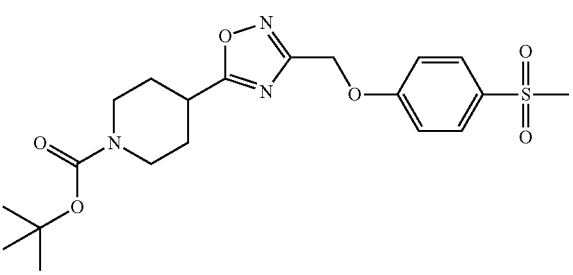 [SMILES: CC(C)(C)OC(=O)N1CCC(c2nc(COc3ccc(S(C)(=O)=O)cc3)no2)CC1]

Step 1: N-Hydroxy-2-(4-methanesulfonyl-phenoxy)-acetamidine

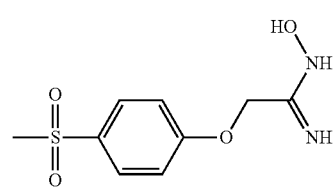 [SMILES: CS(=O)(=O)c1ccc(OCC(=N)NO)cc1]

To a mixture of (4-methanesulfonyl-phenoxy)-acetonitrile (2 g, 9.5 mmol), K$_2$CO$_3$ (1.3 g, 9.5 mmol) in H$_2$O (30 mL) and EtOH (15 mL) was added hydroxylamine hydrogenchloride (1.32 g, 19 mmol). The mixture was heated under reflux overnight, cooled and ethanol was removed in vacuo and the residue was extracted with EtOAc (150 mL). The organic layer was washed successively with H$_2$O and brine. After drying (Na$_2$SO$_4$), the solvent was removed to afford the desired product.

Step 2: 4-[3-(4-Methanesulfonyl-phenoxymethyl)-[1,2,4]oxadiazol-5-yl]-piperidine-1-carboxylic acid tert-butyl ester

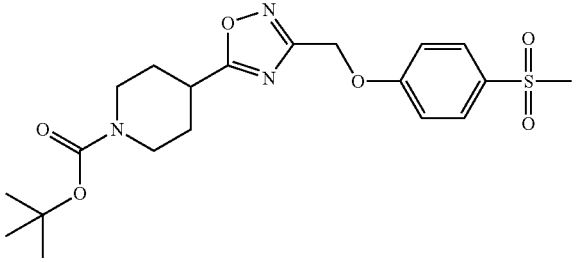 [SMILES: CC(C)(C)OC(=O)N1CCC(c2nc(COc3ccc(S(C)(=O)=O)cc3)no2)CC1]

To a solution of piperidine-1,4-dicarboxylic acid mono-tert-butyl ester (2.06 g, 9 mmol), NEt$_3$ (1.2 g, 12 mmol) in toluene (150 mL) was added isobutylchloroformate (1.23 g, 9 mmol) at 0° C. The mixture was stirred at room temperature for 1.5 hours. N-hydroxy-2-(4-methanesulfonyl-phenoxy)-acetamidine (1.5 g, 6 mmol) was added to the mixture. The mixture was heated under reflux overnight, cooled and the mixture was washed successively with H$_2$O and brine. After drying (Na$_2$SO$_4$), the solvent was removed. The residue was purified by flash chromatography on silica gel to afford the desired product. $^1$H NMR (CDCl$_3$): δ 7.98 (2H, m), 7.14 (2H, m), 5.24 (2H, s), 4.2-4.05 (2H, m), 3.14 (1H, m), 3.03 (3H, s), 2.95 (2H, m), 2.12~2.04 (2H, m), 1.80 (2H, m), 1.46 (9H, s).

Example 82

4-[5-(4-Methanesulfonyl-phenoxymethyl)-[1,2,4]oxadiazol-3-yl]-piperidine-1-carboxylic acid tert-butyl ester

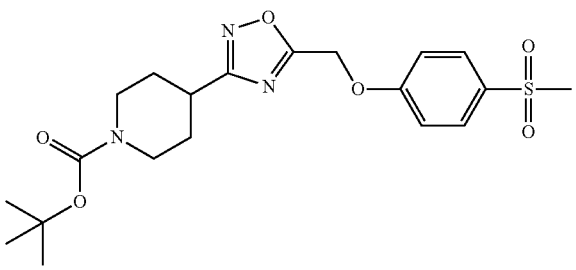 [SMILES: CC(C)(C)OC(=O)N1CCC(c2noc(COc3ccc(S(C)(=O)=O)cc3)n2)CC1]

Step 1: 4-(N-Hydroxycarbamimidoyl)-piperidine-1-carboxylic acid tert-butyl ester

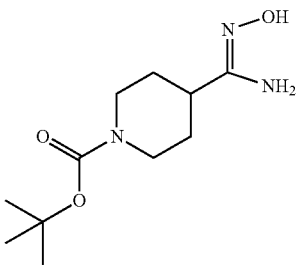 [SMILES: CC(C)(C)OC(=O)N1CCC(/C(N)=N/O)CC1]

To a mixture of 4-cyano-piperidine-1-carboxylic acid tert-butyl ester (6.3 g, 30 mmol), K$_2$CO$_3$ (4.2 g, 30 mmol) in H$_2$O (50 mL) and EtOH (30 mL) was added hydroxylamine hydrogenchloride (4.17 g, 60 mmol). The mixture was heated under reflux overnight, cooled to room temperature and ethanol was removed in vacuo. The residue was extracted with EtOAc (300 mL). The organic layer was washed successively with H$_2$O and brine. After drying (Na$_2$SO$_4$), the solvent was removed to afford the desired product.

Step 2: 4-(5-Hydroxymethyl-[1,2,4]oxadiazol-3-yl)-piperidine-1-carboxylic acid tert-butyl ester

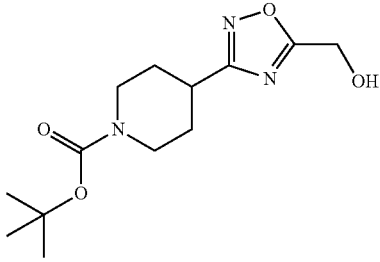 [SMILES: CC(C)(C)OC(=O)N1CCC(c2noc(CO)n2)CC1]

To a solution of hydroxy-acetic acid (1.67 g, 22 mmol), NEt$_3$ (4.4 g, 44 mmol) in toluene (150 mL) was added isobutylchloroformate (6 g, 44 mmol) at 0° C. The mixture was stirred at room temperature for 1.5 hours. 4-(N-Hydroxycarbamimidoyl)-piperidine-1-carboxylic acid tert-butyl ester (5.35 g, 22 mmol) was added to the mixture. The mixture was heated under reflux overnight, and then cooled to room temperature; the mixture was washed successively with H$_2$O and brine. After drying (Na$_2$SO$_4$), the solvent was removed. The residue was dissolved in THF (20 mL), and aqueous NaOH (10 mL, 10 mmol) was added. The mixture was stirred at room temperature for 2 hours and diluted with EtOAc (50 mL). The organic layer was washed with brine, after drying (Na$_2$SO$_4$), the solvent was removed in vacuo, and the residue was purified by silica column chromatography with EtOAc/hexanes to afford the desired product.

Step 3: 4-(5-Methanesulfonyloxymethyl-[1,2,4]oxadiazol-3-yl)-piperidine-1-carboxylic acid tert-butyl ester

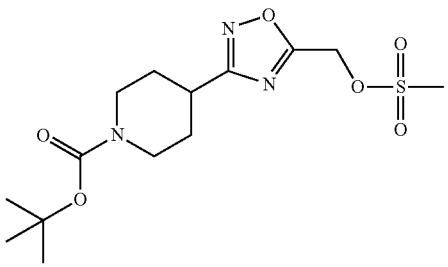 [SMILES: CC(C)(C)OC(=O)N1CCC(c2noc(COS(C)(=O)=O)n2)CC1]

To a solution of 4-(5-hydroxymethyl-[1,2,4]oxadiazol-3-yl)-piperidine-1-carboxylic acid tert-butyl ester (0.2 g, 0.7 mmol) in methylene chloride (5 mL) was added methanesulfonyl chloride (0.1 g, 0.9 mmol) and triethyl amine (0.14 g, 1.4 mmol) at 0° C. After stirred at 0° C. for 1 hour, the mixture was diluted with EtOAc and washed with $H_2O$, brine. After drying ($Na_2SO_4$), the solvent was removed in vacuo, and the residue was purified by silica column chromatography with EtOAc/hexanes to afford the desired product Step 4: 4-[5-(4-Methanesulfonyl-phenoxymethyl)-[1,2,4]oxadiazol-3-yl]-piperidine-1-carboxylic acid tert-butyl ester

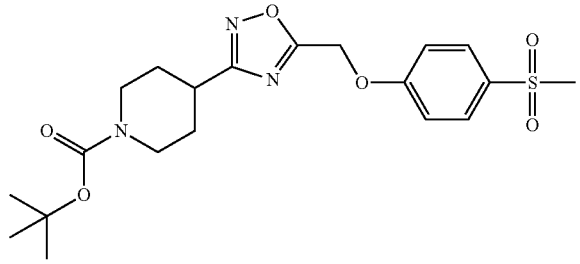 [SMILES: CC(C)(C)OC(=O)N1CCC(c2noc(COc3ccc(S(C)(=O)=O)cc3)n2)CC1]

A mixture of 4-(5-methanesulfonyloxymethyl-[1,2,4]oxadiazol-3-yl)-piperidine-1-carboxylic acid tert-butyl ester (0.12 g, 0.33 mmol), 4-methanesulfonyl-phenol (86 mg, 0.5 mmol) and $Cs_2CO_3$ (0.33 g, 1 mmol) in acetonitrile (5 mL) was heated at 50° C. for 2 hours. After cooling, the solid was filtered through a pad of celite. The filtrate was concentrated in vacuo. The residue was purified on silica gel (EtOAc-hexanes, 1:1) to afford the desired product. $^1H$ NMR ($CDCl_3$): δ 7.9 (2H, d, J=8.8 Hz), 7.12 (2H, d, J=8.8 Hz), 5.34 (2H, s), 4.2~4.05 (2H, m), 3.03 (3H, s), 3.04~2.85 (3H, m), 2.05~1.96 (2H, m), 1.8~1.7 (2H, m), 1.45 (9H, s).

Example 83

4-(5-Benzyloxymethyl-[1,2,4]oxadiazol-3-yl)-piperidine-1-carboxylic acid tert-butyl ester

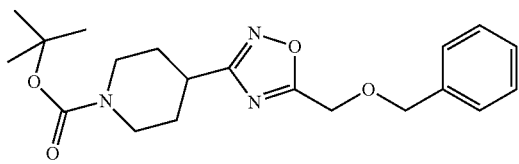 [SMILES: CC(C)(C)OC(=O)N1CCC(c2noc(COCc3ccccc3)n2)CC1]

To a solution of benzyloxy-acetic acid (5 g, 30 mmol), $NEt_3$ (3.6 g, 36 mmol) in toluene (150 mL) was added isobutylchloroformate (4.1 g, 30 mmol) at 0° C. The mixture was stirred at room temperature for 1.5 hours. 4-(N-hydroxycarbamimidoyl)-piperidine-1-carboxylic acid tert-butyl ester (7.3 g, 30 mmol) was added to the mixture. The mixture was heated under reflux overnight, cooled and the mixture was washed successively with $H_2O$ and brine. After drying ($Na_2SO_4$), the solvent was removed. The residue was purified by flash chromatography on silica gel to afford the desired product. $^1H$ NMR ($CDCl_3$): δ 7.4~7.3 (5H, m), 4.7 (2H, s), 4.69 (2H, s), 4.2~4.04 (2H, m), 3.02~2.84 (3H, m), 2.04~1.94 (2H, m), 1.84~1.7 (2H, m), 1.46 (9H, s).

Example 84

5-Ethyl-2-{4-[3-(4-methanesulfonyl-phenoxymethyl)-[1,2,4]oxadiazol-5-yl]-piperidin-1-yl}-pyrimidine

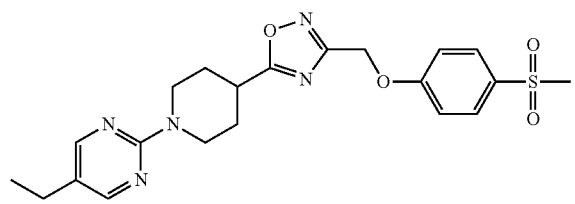 [SMILES: CCc1cnc(N2CCC(c3nc(COc4ccc(S(C)(=O)=O)cc4)no3)CC2)nc1]

To the crude HCl salt (0.18 g, 0.5 mmol) of 4-[3-(4-methanesulfonyl-phenoxymethyl)-[1,2,4]oxadiazol-5-yl]-piperidine, prepared by treatment of 4-[3-(4-methanesulfonyl-phenoxymethyl)-[1,2,4]oxadiazol-5-yl]-piperidine-1-carboxylic acid tert-butyl ester (Example 81) in dixoane with 4N HCl, was added 2-propanol (3 mL), followed by DIPEA (0.13 g, 1 mmol) and 2-Chloro-5-ethyl-pyrimidine (0.14 g, 1 mmol). The resulting mixture was stirred at 70° C. overnight. After concentration in vacuo, the residue was purified by silica column chromatography with EtOAc/hexanes to afford the desired product. $^1H$ NMR ($CDCl_3$): δ 8.18 (2H, s), 7.89 (2H, d, J=8.8 Hz), 7.15 (2H, d, J=8.8 Hz), 5.24 (2H, s), 4.75~4.65 (2H, m), 3.3~3.2 (1H, m), 3.2~3.1 (2H, m), 3.03 (3H, s), 2.47 (2H, q, J=7.6 Hz), 2.22~2.16 (2H, m), 1.96~1.84 (2H, m), 1.19 (3H, t, J=7.6 Hz).

Example 85

4-Hydroxy-4-[4-(4-methylsulfanyl-phenoxymethyl)-thiazol-2-yl]-piperidine-1-carboxylic acid tert-butyl ester

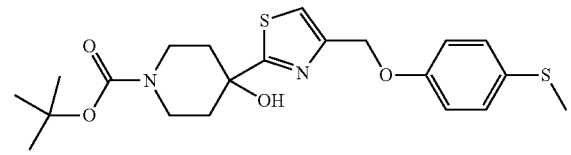 [SMILES: CSc1ccc(OCc2csc(C3(O)CCN(C(=O)OC(C)(C)C)CC3)n2)cc1]

Step 1: 4-(4-Methyl sulfanyl-phenoxymethyl)-thiazole

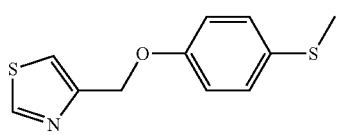

A mixture of 4-chloromethyl thiazole hydrochloride (3.0 g, 17.6 mmol), 4-methylsulfanyl-phenol (2.5 g, 1 eq.) and $K_2CO_3$ (6.1 g, 2.5 eq.) in acetone (60 mL) was heated to reflux for 48 hours. After cooling, the solid was filtered off.

The filtrate was evaporated to dryness in vacuo. The crude product was redissolved in diethyl ether. The solution was washed twice with 2N NaOH solution and then with H$_2$O. After being dried over Na$_2$SO$_4$, removal of the solvent afforded the desired product as an off-white solid.

Step 2: 4-Hydroxy-4-[4-(4-methylsulfanyl-phenoxymethyl)-thiazol-2-yl]-piperidine-1-carboxylic acid tert-butyl ester

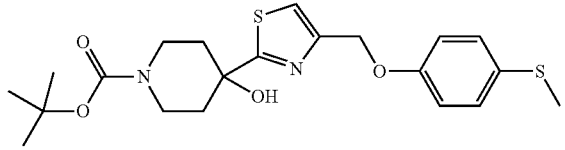 [SMILES: CSc1ccc(OCc2csc(C3(O)CCN(C(=O)OC(C)(C)C)CC3)n2)cc1]

To a stirred solution of 4-(4-methanesulfanyl-phenoxymethyl)-thiazole (3.92 g, 16.5 mmol) in THF (40 mL) at −78° C. was added n-BuLi (1.73 mL, 1.05 eq., 10.0 M in hexanes). The resulting solution was stirred at this temperature for 30 minutes. Then a solution of 1-Boc-4-piperidone (3.30 g, 1 eq.) in THF (20 mL) was added in dropwise. The resulting mixture was stirred for 30 minutes. The reaction was quenched by addition of H$_2$O (5 mL). Most of the THF was removed in vacuo. The mixture was extracted with EtOAc. The organic layer was separated, washed with brine and dried over Na$_2$SO$_4$. After removal of the solvent, the crude product was purified on silica gel (EtOAc:hexanes=2:3) to afford the desired product as a foam. $^1$H NMR (CDCl$_3$): δ 7.27 (2H, d, J=8.8 Hz), 7.26 (1H, s), 6.93 (2H, d, J=8.8 Hz), 5.14 (2H, s), 4.02 (2H, br), 3.27 (2H, br), 2.97 (1H, br), 2.45 (3H, s), 2.11 (2H, m), 1.86 (2H, m), 1.48 (9H, s).

Example 86

4-Hydroxy-4-[4-(4-methanesulfonyl-phenoxymethyl)-thiazol-2-yl]-piperidine-1-carboxylic acid tert-butyl ester

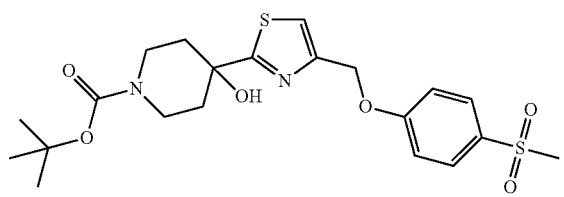 [SMILES: CC(C)(C)OC(=O)N1CCC(O)(c2nc(COc3ccc(S(C)(=O)=O)cc3)cs2)CC1]

To a solution of 4-hydroxy-4-[4-(4-methylsulfanyl-phenoxymethyl)-thiazol-2-yl]-piperidine-1-carboxylic acid tert-butyl ester (Example 85, 6.8 g, 15.6 mmol) in CH$_2$Cl$_2$ (150 mL) at room temperature was added m-CPBA (8.4 g, 2.2 eq.) portionwise. The resulting solution was stirred for 30 minutes, then it was washed with 2 N NaOH solution twice and dried over Na$_2$SO$_4$. After removal of the solvent, the crude product was purified on silica gel (EtOAc:hexanes=3:2) to afford the desired product as a white foam. $^1$H NMR (CDCl$_3$): δ 7.88 (2H, d, J=8.8 Hz), 7.31 (1H, s), 7.12 (2H, d, J=8.8 Hz), 5.24 (2H, s), 4.03 (2H, br), 3.27 (2H, br), 3.04 (3H, s), 2.13 (2H, m), 1.86 (2H, m), 1.48 (9H, s).

Example 87

4-Fluoro-4-[4-(4-methanesulfonyl-phenoxymethyl)-thiazol-2-yl]-piperidine-1-carboxylic acid tert-butyl ester

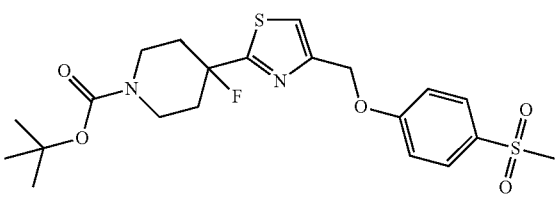

To a solution of 4-hydroxy-4-[4-(4-methanesulfonyl-phenoxymethyl)-thiazol-2-yl]-piperidine-1-carboxylic acid tert-butyl ester (Example 86, 5.29 g, 11.3 mmol) in CH$_2$Cl$_2$ (100 mL) at 0° C. was added DAST (1.8 mL, 1.2 eq.). The reaction mixture was stirred for 30 minutes before it was quenched by addition of saturated NaHCO$_3$ solution (20 mL). The organic phase was separated and dried over Na$_2$SO$_4$. After removal of the solvent, the crude product was purified on silica gel (EtOAc:hexanes=2:3) to afford the desired product as a white solid. $^1$H NMR (CDCl$_3$): δ 7.86 (2H, d, J=9.2 Hz), 7.35 (1H, s), 7.10 (2H, d, J=9.2 Hz), 5.22 (2H, s), 4.08 (2H, br), 3.19 (2H, br), 3.02 (3H, s), 2.05~2.32 (4H, m), 1.46 (9H, s).

Example 88

5-Ethyl-2-{4-fluoro-4-[4-(4-methanesulfonyl-phenoxymethyl)-thiazol-2-yl]-piperidin-1-yl}-pyrimidine

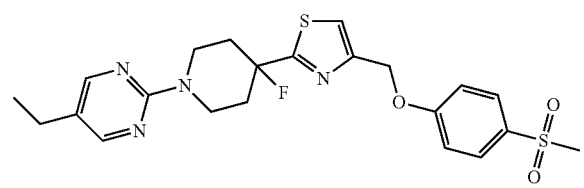 [SMILES: CCc1cnc(N2CCC(F)(c3nc(COc4ccc(S(C)(=O)=O)cc4)cs3)CC2)nc1]

Step 1: 4-Fluoro-4-[4-(4-methanesulfonyl-phenoxymethyl)-thiazol-2-yl]-piperidine hydrochloride

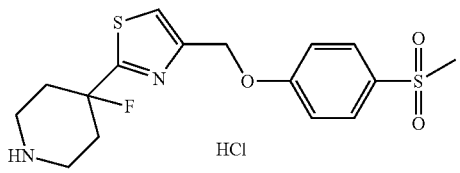 [SMILES: CS(=O)(=O)c1ccc(OCc2csc(C3(F)CCNCC3)n2)cc1 ; Cl]

To a solution of 4-fluoro-4-[4-(4-methanesulfonyl-phenoxymethyl)-thiazol-2-yl]-piperidine-1-carboxylic acid tert-butyl ester (Example 87, 4.24 g, 9.01 mmol) in methanol (50 mL) was added 4 N HCl in dioxane (15 mL). The resulting solution was stirred overnight. The mixture was then evaporated to dryness in vacuo to afford the desired product as a white solid.

Step 2: 5-Ethyl-2-{4-fluoro-4-[4-(4-methanesulfonyl-phenoxymethyl)-thiazol-2-yl]-piperidin-1-yl}-pyrimidine

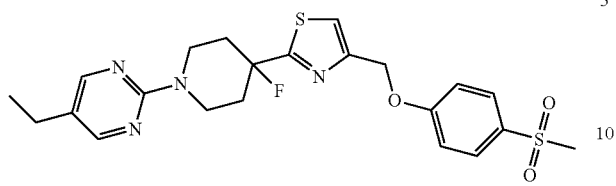

A solution of 4-fluoro-4-[4-(4-methanesulfonyl-phenoxymethyl)-thiazol-2-yl]-piperidine hydrochloride (4.0 g, 9.01 mmol), 2-chloro-5-ethyl-pyrimidine (1.55 g, 1.2 eq.) and DIPEA (4.7 g, 4 eq.) in 2-propanol (30 mL) in a sealed pressure vessel was stirred at 160° C. (oil bath temperature) overnight. After cooling, the solvent was removed in vacuo. The residue was partitioned between water and EtOAc. The organic phase was washed with brine and dried over $Na_2SO_4$. After removal of the solvent, the crude product was purified on silica gel (EtOAc:hexanes=1:1) to afford the desired product as a white solid. $^1$H NMR ($CDCl_3$): δ 8.19 (2H, s), 7.87 (2H, d, J=9.2 Hz), 7.36 (1H, s), 7.10 (2H, d, J=9.2 Hz), 5.23 (2H, s), 4.69 (2H, m), 3.44 (2H, m), 3.03 (3H, s), 2.48 (2H, q, J=7.6 Hz), 2.15~2.39 (4H, m), 1.21 (3H, t, J=7.6 Hz).

Example 89

4-Fluoro-4-[5-(4-methanesulfonyl-phenoxymethyl)-thiazol-2-yl]-piperidine-1-carboxylic acid tert-butyl ester

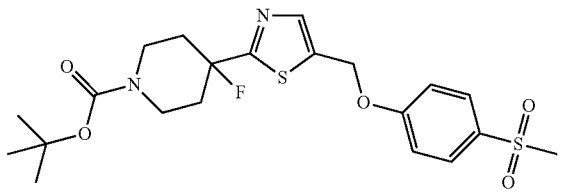 [SMILES: CC(C)(C)OC(=O)N1CCC(F)(c2ncc(COc3ccc(S(C)(=O)=O)cc3)s2)CC1]

Step 1: 4-Hydroxy-4-thiazol-2-yl-piperidine-1-carboxylic acid tert-butyl ester

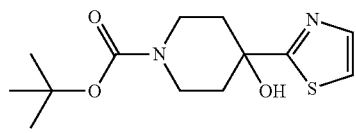 [SMILES: CC(C)(C)OC(=O)N1CCC(O)(c2nccs2)CC1]

To a cooled (−78° C.) and stirred solution of n-BuLi (2.6 mL, 1.05 eq., 10.0 M in hexanes) in dry $Et_2O$ (20 mL) was added dropwise a solution of 2-bromothiazole (4.0 g, 24.4 mmol) in THF (10 mL) over a 10 minute period. After the yellow mixture had been stirred at −78° C. for 30 minutes, a solution of 1-Boc-4-piperidone (4.9 g, 1 eq.) in THF (20 mL) was added slowly. The mixture was then continued to stir for another 30 minutes before the reaction was quenched by addition of water (5 mL). The mixture was warmed to room temperature and extracted with EtOAc. The organic phase was separated, washed with brine and dried over $Na_2SO_4$. After removal of the solvent, the crude product was purified on silica gel (45% EtOAc in hexanes) to afford the desired product as a thick oil.

Step 2: 4-Fluoro-4-thiazol-2-yl-piperidine-1-carboxylic acid tert-butyl ester

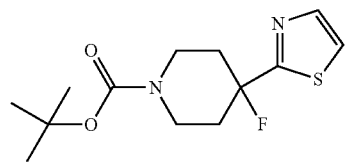 [SMILES: CC(C)(C)OC(=O)N1CCC(F)(c2nccs2)CC1]

To a solution of 4-hydroxy-4-thiazol-2-yl-piperidine-1-carboxylic acid tert-butyl ester (4.36 g, 15.3 mmol) in $CH_2Cl_2$ (50 mL) at 0° C. was added DAST (2.4 mL, 1.2 eq.). The reaction mixture was stirred for 30 minutes before it was quenched by addition of saturated $NaHCO_3$ solution (20 mL). The organic phase was separated and dried over $Na_2SO_4$. After removal of the solvent, the crude product was purified on silica gel (EtOAc:hexanes=1:4) to afford the desired product as a pale yellow oil.

Step 3: 4-Fluoro-4-(5-hydroxymethyl-thiazol-2-yl)-piperidine-1-carboxylic acid tert-butyl ester

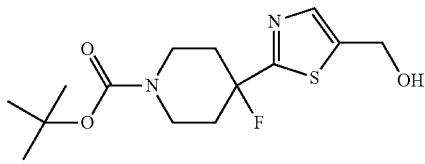 [SMILES: CC(C)(C)OC(=O)N1CCC(F)(c2ncc(CO)s2)CC1]

To a cooled (−78° C.) and stirred solution of 4-fluoro-4-thiazol-2-yl-piperidine-1-carboxylic acid tert-butyl ester (3.65 g, 12.7 mmol) in THF (20 mL) was added n-BuLi (1.33 mL, 1.05 eq., 10.0 M in hexanes). The mixture was stirred at this temperature for 30 minutes. Then a suspension of paraformaldehyde (383 mg, 1 eq.) in THF (10 mL) was added in. The resulting mixture was continued to stir at −78° C. for another 30 minutes and gradually warmed to room temperature overnight. The reaction was quenched by addition of water (10 mL). The mixture was extracted with EtOAc. The organic phase was washed with brine and dried over $Na_2SO_4$. After removal of the solvent, the crude product was purified on silica gel (60% EtOAc in hexanes) to afford the desired product as a pale yellow solid.

Step 4: 4-(5-Chloromethyl-thiazol-2-yl)-4-fluoro-piperidine-1-carboxylic acid tert-butyl ester

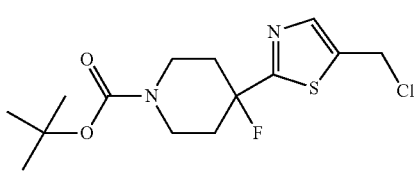 [SMILES: CC(C)(C)OC(=O)N1CCC(F)(c2ncc(CCl)s2)CC1]

To a mixture of 4-fluoro-4-(5-hydroxymethyl-thiazol-2-yl)-piperidine-1-carboxylic acid tert-butyl ester (1.34 g, 4.24 mmol) and pyridine (426 mg, 1.3 eq.) in CH$_2$Cl$_2$ (30 mL) at 0° C. was added MsCl (631 mg, 1.3 eq.). The mixture was warmed to room temperature and stirred overnight. The reaction mixture was washed with saturated NaHCO$_3$ solution and dried over Na$_2$SO$_4$. Removal of the solvent afforded the desired product, which was used directly in the following reaction without further purification.

Step 5: 4-Fluoro-4-[5-(4-methanesulfonyl-phenoxymethyl)-thiazol-2-yl]-piperidine-1-carboxylic acid tert-butyl ester

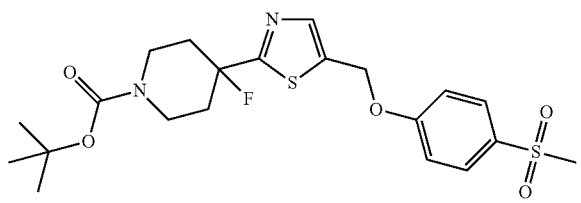 [SMILES: CC(C)(C)OC(=O)N1CCC(F)(c2ncc(COc3ccc(S(C)(=O)=O)cc3)s2)CC1]

A mixture of 4-(5-Chloromethyl-thiazol-2-yl)-4-fluoro-piperidine-1-carboxylic acid tert-butyl ester (1.42 g, 4.24 mmol), 4-methanesulfonyl-phenol (731 mg, 1.0 eq.) and K$_2$CO$_3$ (878 mg, 1.5 eq.) in acetone (30 mL) was heated to reflux overnight. After cooling, the solid was filtered off through a pad of celite. The filtrate was concentrated in vacuo. The crude product was purified on silica gel (EtOAc:hexanes=1:1) to afford the desired product as a white solid. $^1$H NMR (CDCl$_3$): δ 7.86 (2H, d, J=9.2 Hz), 7.35 (1H, s), 7.10 (2H, d, J=9.2 Hz), 5.22 (2H, s), 4.08 (2H, br), 3.19 (2H, br), 3.02 (3H, s), 2.05~2.32 (4H, m), 1.46 (9H, s).

Example 90

5-Ethyl-2-{4-fluoro-4-[5-(4-methanesulfonyl-phenoxymethyl)-thiazol-2-yl]-piperidin-1-yl}-pyrimidine

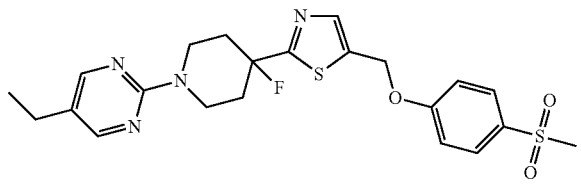 [SMILES: CCc1cnc(N2CCC(F)(c3ncc(COc4ccc(S(C)(=O)=O)cc4)s3)CC2)nc1]

Step 1: 4-Fluoro-4-[5-(4-methanesulfonyl-phenoxymethyl)-thiazol-2-yl]-piperidine hydrochloride

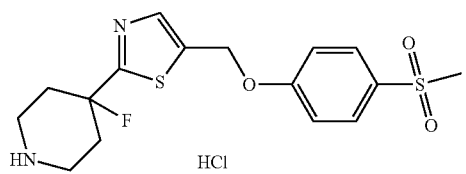 [SMILES: CS(=O)(=O)c1ccc(OCc2cnc(C3(F)CCNCC3)s2)cc1 ; Cl]

To a solution of 4-fluoro-4-[5-(4-methanesulfonyl-phenoxymethyl)-thiazol-2-yl]-piperidine-1-carboxylic acid tert-butyl ester (Example 89, 1.30 g, 2.76 mmol) in methanol (5 mL) was added 4 N HCl in dioxane (10 mL). The resulting solution was stirred overnight. The mixture was then evaporated to dryness in vacuo to afford the desired product as a white solid.

Step 2: 5-Ethyl-2-{4-fluoro-4-[5-(4-methanesulfonyl-phenoxymethyl)-thiazol-2-yl]-piperidin-1-yl}-pyrimidine

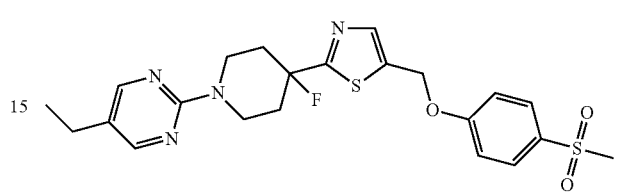

A solution of 4-fluoro-4-[5-(4-methanesulfonyl-phenoxymethyl)-thiazol-2-yl]-piperidine hydrochloride (1.2 g, 2.76 mmol), 2-chloro-5-ethyl-pyrimidine (425 mg, 1.1 eq.) and DIPEA (1.4 g, 4 eq.) in 2-propanol (20 mL) in a sealed pressure vessel was stirred at 160° C. (oil bath temperature) overnight. After cooling, the solvent was removed in vacuo. The residue was partitioned between water and EtOAc. The organic phase was washed with brine and dried over Na$_2$SO$_4$. After removal of the solvent, the crude product was purified on silica gel (EtOAc:hexanes=1:1) to afford the desired product as a white solid. $^1$H NMR (CDCl$_3$): δ 8.19 (2H, s), 7.90 (2H, d, J=8.8 Hz), 7.73 (1H, d), 7.10 (2H, d, J=8.8 Hz), 5.31 (2H, s), 4.67 (2H, m), 3.44 (2H, m), 3.04 (3H, s), 2.48 (2H, q, J=7.6 Hz), 2.13~2.38 (4H, m), 1.20 (3H, t, J=7.6 Hz).

Example 91

4-[4-(4-Methanesulfonyl-phenoxymethyl)-thiazol-2-yl]-piperazine-1-carboxylic acid tert-butyl ester

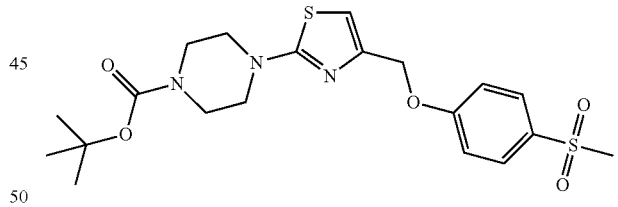

Step 1: 4-(4-Ethoxycarbonyl-thiazol-2-yl)-piperazine-1-carboxylic acid tert-butyl ester

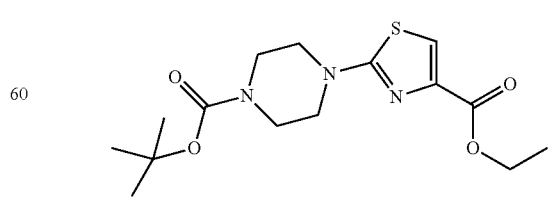

A mixture of 2-bromo-thiazole-4-carboxylic acid ethyl ester (1.4 g, 5.93 mmol), piperazine-1-carboxylic acid tert-butyl ester (1.16 g, 1.05 eq.) and DIPEA (1.15 g, 1.5 eq.) in 1,4-dioxane (20 mL) was heated to reflux overnight. After cooling, the solvent was removed in vacuo. The crude product was purified on silica gel (EtOAc:hexanes=1:4) to afford the desired product as a pale yellow solid.

Step 2: 4-(4-Hydroxymethyl-thiazol-2-yl)-piperazine-1-carboxylic acid tert-butyl ester

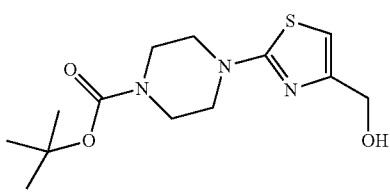 [SMILES: CC(C)(C)OC(=O)N1CCN(c2nc(CO)cs2)CC1]

A solution of 4-(4-ethoxycarbonyl-thiazol-2-yl)-piperazine-1-carboxylic acid tert-butyl ester (1.15 g, 3.37 mmol) in THF (15 mL) at 0° C. was treated with LiAlH$_4$ (128 mg, 1 eq.). The mixture was stirred for 1 hour, then the reaction was quenched with 2 N NaOH solution. The solid was filtered off through a pad of celite and washed with EtOAc (100 mL). The filtrate was washed with water and dried over Na$_2$SO$_4$. Removal of the solvent afforded the desired product as an oil.

Step 3: 4-(4-Chloromethyl-thiazol-2-yl)-piperazine-1-carboxylic acid tert-butyl ester

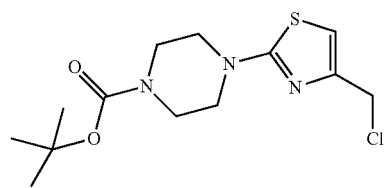 [SMILES: CC(C)(C)OC(=O)N1CCN(c2nc(CCl)cs2)CC1]

To a solution of 4-(4-hydroxymethyl-thiazol-2-yl)-piperazine-1-carboxylic acid tert-butyl ester (848 mg, 2.83 mmol) and DIPEA (550 mg, 1.5 eq.) in CH$_2$Cl$_2$ (10 mL) was added MsCl (285 L, 1.3 eq.) dropwise. The resulting mixture was stirred overnight. The reaction solution was then concentrated in vacuo. The crude product was purified on silica gel (EtOAc:hexanes=1:4) to afford the desired product as an oil.

Step 4: 4-[4-(4-Methanesulfonyl-phenoxymethyl)-thiazol-2-yl]-piperazine-1-carboxylic acid tert-butyl ester

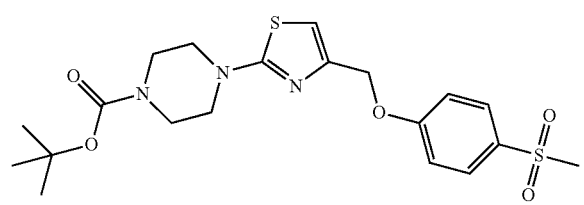 [SMILES: CC(C)(C)OC(=O)N1CCN(c2nc(COc3ccc(S(C)(=O)=O)cc3)cs2)CC1]

A mixture of 4-(4-Chloromethyl-thiazol-2-yl)-piperazine-1-carboxylic acid tert-butyl ester (700 mg, 2.20 mmol), 4-methanesulfonyl-phenol (417 mg, 1.1 eq.) and K$_2$CO$_3$ (609 mg, 2 eq.) in acetone (30 mL) was heated to reflux overnight. After cooling, the solid was filtered off through a pad of celite. The filtrate was concentrated in vacuo. The crude product was purified on silica gel (EtOAc:hexanes=1:1) to afford the desired product as an off-white solid. $^1$H NMR (CDCl$_3$): δ 7.87 (2H, d, J=8.8 Hz), 7.12 (2H, d, J=8.8 Hz), 6.59 (1H, s), 5.05 (2H, s), 3.56 (4H, m), 3.48 (4H, m), 3.04 (3H, s), 1.49 (9H, s).

Example 92

1-[4-(4-Methanesulfonyl-phenoxymethyl)-thiazol-2-yl]-4-(2-methyl-propane-1-sulfonyl)-piperazine

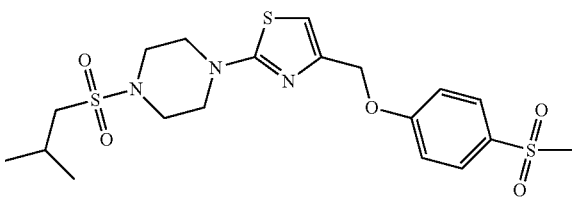 [SMILES: CC(C)CS(=O)(=O)N1CCN(c2nc(COc3ccc(S(C)(=O)=O)cc3)cs2)CC1]

Step 1: 1-[4-(4-Methanesulfonyl-phenoxymethyl)-thiazol-2-yl]-piperazine hydrochloride

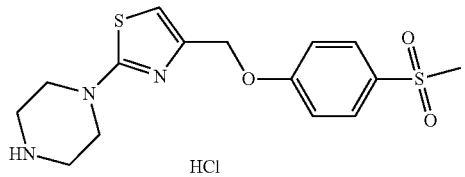 [SMILES: CS(=O)(=O)c1ccc(OCc2csc(N3CCNCC3)n2)cc1 ; Cl]

To a solution of 4-[4-(4-Methanesulfonyl-phenoxymethyl)-thiazol-2-yl]-piperazine-1-carboxylic acid tert-butyl ester (Example 91, 430 mg, 0.95 mmol) in methanol (5 mL) was added 4 N HCl in dioxane (5 mL). The resulting solution was stirred for 30 minutes at room temperature. The mixture was then evaporated to dryness in vacuo to afford the desired product as a pale yellow solid.

Step 2: 1-[4-(4-Methanesulfonyl-phenoxymethyl)-thiazol-2-yl]-4-(2-methyl-propane-1-sulfonyl)-piperazine

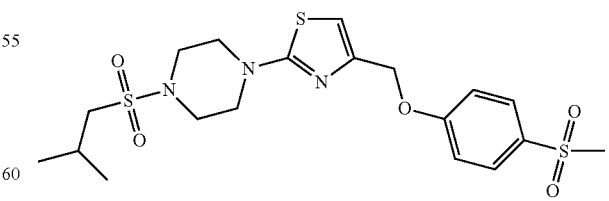

A solution of 1-[4-(4-Methanesulfonyl-phenoxymethyl)-thiazol-2-yl]-piperazine hydrochloride (100 mg, 0.26 mmol) and DIPEA (134 mL, 3 eq.) in CH$_2$Cl$_2$ (5 mL) was added isobutanesulfonyl chloride (41 mL, 1.2 eq.). The mixture was stirred for 1 hour, then the reaction solution was directly purified on silica gel (EtOAc:hexanes=1:1) to afford the desired product as a pale yellow solid. ¹H NMR (CDCl₃): δ 7.87 (2H, d, J=8.8 Hz), 7.12 (2H, d, J=8.8 Hz), 6.62 (1H, s), 5.05 (2H, s), 3.61 (4H, m), 3.39 (4H, m), 3.04 (3H, s), 2.78 (2H, d, J=6.8 Hz), 2.32 (1H, m), 1.12 (6H, d, J=6.8 Hz).

Example 93

4-[4-Methyl-5-(4-tetrazol-1-yl-phenoxymethyl)-thiazol-2-yl]-piperidine-1-carboxylic acid tert-butyl ester

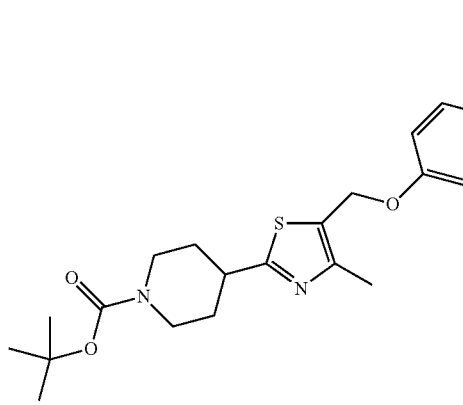

To a solution of 4-(5-Hydroxymethyl-4-methyl-thiazol-2-yl)-piperidine-1-carboxylic acid tert-butyl ester (1.00 g, 3.2 mmol) in THF (6.4 mL) was added, 4-tetrazol-1-yl-phenol (0.52 g, 3.2 mmol), polymer bound triphenylphosphine (3 mmol/g, 1.6 g). To this solution was added ditertierybutylazodicarboxylate (1.1 g, 4.8 mmol), stirred for 4 hours and filtered through a pad of celite. The filtrate was concentrated and purified by silica gel chromatography to provide the desired product. ¹H NMR (CDCl₃): δ 9.01 (1H, s), 7.66 (2H, d), 7.15 (2H, d), 5.21 (2H, s), 4.19 (2H, m), 3.10 (1H, m), 2.86 (2H, m), 2.45 (3H, s), 2.08 (2H, m), 1.72 (2H, m), 1.47 (9H, s).

Example 94

4-{4-[(6-Fluoro-pyridin-3-ylamino)-methyl]-thiazol-2-yl}-piperidine-1-carboxylic acid tert-butyl ester

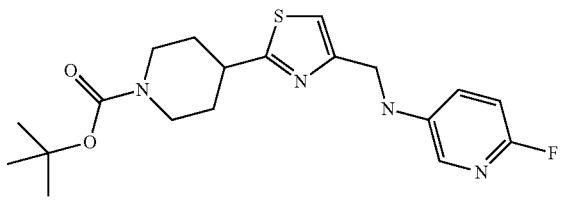 [SMILES: CC(C)(C)OC(=O)N1CCC(c2nc(CNc3ccc(F)nc3)cs2)CC1]

5-amino-2-fluoropyridine (0.476 g, 4.2 mmol) was added to 4-(4-Formyl-thiazol-2-yl)-piperidine-1-carboxylic acid tert-butyl ester (0.84 g, 2.8 mmol) in dry DCM (10 mL). Sodium triacetoxyborohydride (0.9 g, 4.2 mmol) was then added. The reaction was stirred for 3 hours at room temperature under N₂. The organic layer was washed with 2 M NaOH solution, water, brine, dried (MgSO₄), and the solvent was removed in vacuo. The material was purified by silica gel chromatography (DCM/methanol: 10:1 v/v) to give the desired product. ¹H NMR (CDCl₃): δ 7.59-7.60 (1H, m), 7.06-7.10 (1H, m), 7.02 (1H, s), 6.76 (1H, dd, J=8.8, 3.6 Hz), 4.4 (2H, d), 4.20-4.31 (3H, m), 3.09-3.17 (1H, m), 2.8-2.95 (2H, m), 2.07-2.10 (2H, m), 1.77-1.47, (2H, m), 1.47 (9H, s).

Example 95

1-(3-Isopropyl-[1,2,4]oxadiazol-5-yl)-4-[4-(4-tetrazol-1-yl-phenoxymethyl)-thiazol-2-yl]-piperidine Step 1: 4-[4-(4-Tetrazol-1-yl-phenoxymethyl)-thiazol-2-yl]-piperidine-1-carbonitrile

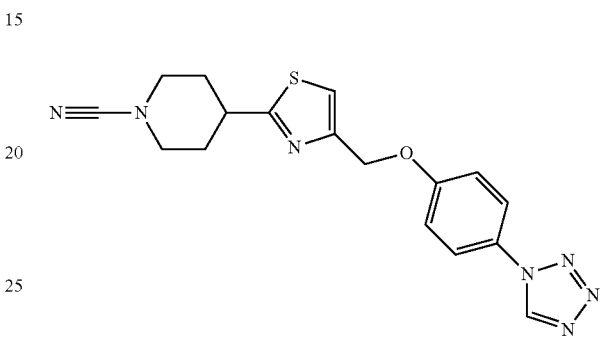

To a mixture of 4-[4-(4-Tetrazol-1-yl-phenoxymethyl)-thiazol-2-yl]-piperidine (1.00 g, 2.92 mmol) and potassium carbonate (1.5 g, 10.9 mmol) in chloroform (25 mL) was added cyanogen bromide (0.371 g, 3.5 mmol). The slurry was refluxed for 48 hours then stirred at room temperature for an additional 48 hours. The reaction was filtered through a pad of celite, concentrated and chromatographed on silica gel (1:1 Hexanes/EtOAc) to afford the desired compound.

Step 2: 1-(3-Isopropyl-[1,2,4]oxadiazol-5-yl)-4-[4-(4-tetrazol-1-yl-phenoxymethyl)-thiazol-2-yl]-piperidine

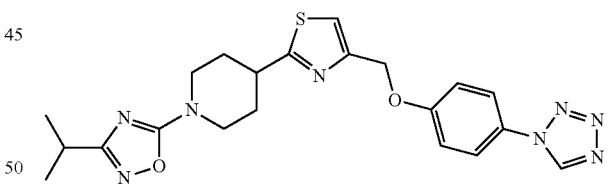

To a solution of 4-[4-(4-Tetrazol-1-yl-phenoxymethyl)-thiazol-2-yl]-piperidine-1-carbonitrile (0.450, 1.22 mmol) and N-hydroxy-isobutyramidine (0.150 g, 1.47 mmol) in dry THF (10 mL) was added a 1 M solution of zinc chloride in THF (1.47 mL, 1.47 mmol) over 15 min. The suspension was left to settle for 15 minutes and the white precipitate was collected by filtration and dissolved in 4 N HCl in ethanol and water (1:1). The solution was refluxed for 1 hour, cooled and the solid precipitate was filtered off. The filtrate was neutralized by the addition of excess sodium carbonate. The excess was filtered off and the filtrate was diluted with EtOAc. The solution was washed with water, separated, dried (Na₂SO₄), filtered and concentrated. The residual oil was chromatographed on silica gel (1:1 Hex/EtOAc) to afford the desired compound. ¹H NMR (CDCl₃): δ 8.92 (1H, s), 7.62 (2H, d), 7.28 (1H, s), 7.19 (2H, d), 5.24 (2H, s), 4.26 (2H, m), 3.20 (3H, m), 2.89 (1H, m), 2.26 (2H, m), 1.92 (2H, m), 1.30 (6H, d).

The following three examples were synthesized in similar manner as Example 95 using the required hydroxy amidine and 4-[4-(4-tetrazol-1-yl-phenoxymethyl)-thiazol-2-yl]-piperidine-1-carbonitrile.

Example 96

1-(3-Ethyl-[1,2,4]oxadiazol-5-yl)-4-[4-(4-tetrazol-1-yl-phenoxymethyl)-thiazol-2-yl]-piperidine

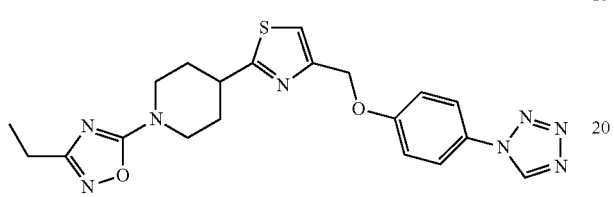

$^1$H NMR (CDCl$_3$): δ 8.85 (1H, s), 7.57 (2H, d), 7.28 (1H, s), 7.19 (2H, d), 5.17 (2H, s), 4.22 (2H, m), 3.22 (3H, m), 2.55 (2H, q), 2.17 (2H, m), 1.89 (2H, m), 1.35 (3H, t).

Example 97

1-(3-Cyclopropyl-[1,2,4]oxadiazol-5-yl)-4-[4-(4-tetrazol-1-yl-phenoxymethyl)-thiazol-2-yl]-piperidine

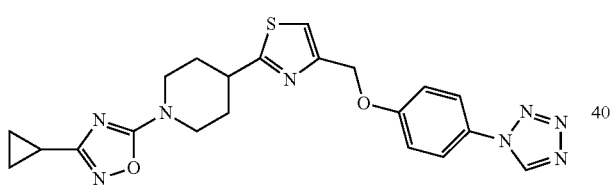

$^1$H NMR (CDCl$_3$): δ 8.90 (1H, s), 7.61 (2H, d), 7.27 (1H, s), 7.17 (2H, d), 5.23 (2H, s), 4.22 (2H, m), 3.22 (3H, m), 2.25 (2H, m), 1.88 (3H, m), 0.96 (4H, m).

Example 98

4-[4-(4-Tetrazol-1-yl-phenoxymethyl)-thiazol-2-yl]-1-(3-trifluoromethyl-[1,2,4]oxadiazol-5-yl)-piperidine

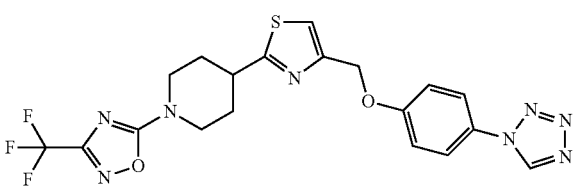 [SMILES: FC(F)(F)c1noc(N2CCC(c3nc(COc4ccc(-n5cnnn5)cc4)cs3)CC2)n1]

$^1$H NMR (CDCl$_3$): δ 8.92 (1H, s), 7.60 (2H, d), 7.23 (1H, s), 7.16 (2H, d), 5.21 (2H, s), 4.25 (2H, m), 4.15 (2H, m), 3.22 (1H, m), 2.90 (2H, m), 2.18 (2H, m).

Example 99

4-[4-(4-Tetrazol-1-yl-phenoxymethyl)-thiazol-2-yl]-piperidine-1-carboxylic acid amide Step 1: 4-[4-(4-Tetrazol-1-yl-phenoxymethyl)-thiazol-2-yl]-piperidine-1-carbonitrile

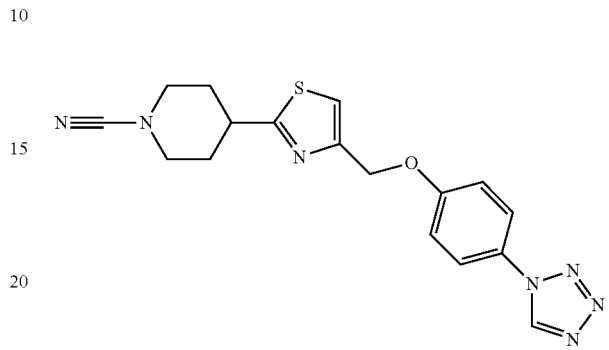

To a mixture of 4-[4-(4-Tetrazol-1-yl-phenoxymethyl)-thiazol-2-yl]-piperidine (1.00 g, 2.92 mmol) and potassium carbonate (1.5 g, 10.9 mmol) in chloroform (25 mL) was added cyanogen bromide (0.371 g, 3.5 mmol). The slurry was refluxed for 48 hours then stirred at room temperature for an additional 48 hours. The reaction was filtered through a pad of celite, concentrated and chromatographed on silica gel (1:1 Hexanes/EtOAc) to afford the desired compound.

Step 2: 4-[4-(4-Tetrazol-1-yl-phenoxymethyl)-thiazol-2-yl]-piperidine-1-carboxylic acid amide

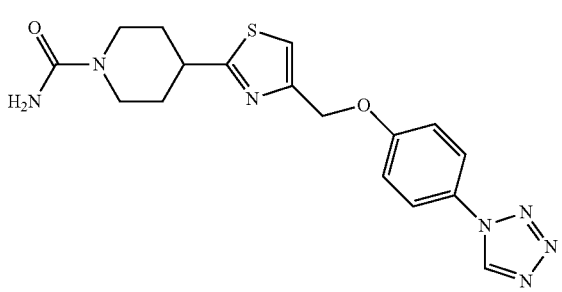 [SMILES: NC(=O)N1CCC(c2nc(COc3ccc(-n4cnnn4)cc3)cs2)CC1]

4-[4-(4-Tetrazol-1-yl-phenoxymethyl)-thiazol-2-yl]-piperidine-1-carbonitrile (1.07 g, 2.92 mmol) was dissolved in 4 N HCl in ethanol/water (1:1). The solution was refluxed for 1 hour, cooled and the solid precipitate was filtered off. The filtrate was neutralized by the addition of excess sodium carbonate. The excess sodium carbonate was filtered off and the filtrate was diluted with EtOAc. The solution was washed with water, separated, dried (Na$_2$SO$_4$), filtered and concentrated. The residual oil was chromatographed on silica gel (1:1 Hexanes/EtOAc) to afford the desired compound. $^1$H NMR (CDCl$_3$): δ 8.92 (1H, s), 7.60 (2H, d), 7.23 (1H, s), 7.167 (2H, d), 5.21 (2H, s), 4.25 (2H, m), 4.15 (2H, m), 3.22 (1H, m), 2.90 (2H, m), 2.18 (2H, m).

Example 100

4-[4-(4-Tetrazol-1-yl-phenoxymethyl)-thiazol-2-yl]-piperidine-1-carboxamidine

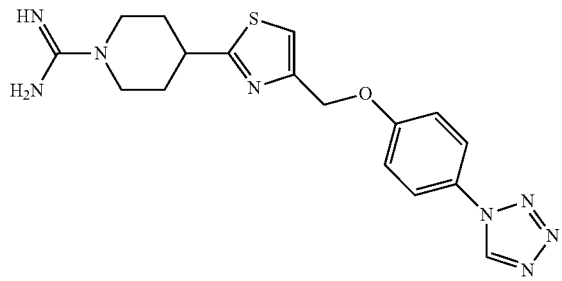 [SMILES: N=C(N)N1CCC(c2nc(COc3ccc(-n4cnnn4)cc3)cs2)CC1]

A mixture of 4-[4-(4-tetrazol-1-yl-phenoxymethyl)-thiazol-2-yl]-piperidine (300 mg, 0.876 mmol), pyrazole-1-carboxamidine hydrochloride (0.128 g, 0.876 mmol.) and triethylamine (0.122 mL, 0.876 mmol) in DMF (2 mL) was stirred at rt for 3 hours. The precipitate was collected by filtration and washed with ether to afford the expected product. $^1$H NMR (DMSO-$d_6$): δ 10.02 (1H, s), 7.93 (1H, s), 7.82 (2H, m), 7.70 (1H, s), 7.60 (2H, br), 7.28 (2H, m), 5.20 (2H, s), 3.95 (2H, m), 3.38 (1H, m), 3.15 (2H, m), 2.09 (2H, m), 1.66 (2H, m).

Example 101

3-[4-(4-tetrazol-1-yl-phenoxymethyl)-thiazol-2-yl]-azetidine-1-carboxylic acid tert-butyl ester

Step 1: 3-(4-chloromethyl-thiazol-2-yl)-azetidine-1-carboxylic acid tert-butyl ester

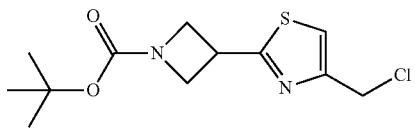 [SMILES: CC(C)(C)OC(=O)N1CC(c2nc(CCl)cs2)C1]

To a solution of 3-Thiocarbamoyl-azetidine-1-carboxylic acid tert-butyl ester (0.800 g, 3.7 mmol) in acetone (15 mL) was added 1,3-dichloroacetone (0.611 g, 4.81 mmol), MgSO$_4$ (0.67 g, 5.6 mmol) and MgCO$_3$ (3.12 g, 3.7 mmol). The mixture was heated under reflux overnight, cooled and filtered through celite. The solvent was removed in vacuo and the residue was redissolved with EtOAc (20 mL). The resulting solution was washed successively with 5% NaHSO$_3$, saturated NaHCO$_3$, and brine. After drying (Na$_2$SO$_4$), the solvent was removed to afford the desired product which was used without further purification.

Step 2: 3-[4-(4-tetrazol-1-yl-phenoxymethyl)-thiazol-2-yl]-azetidine-1-carboxylic acid tert-butyl ester

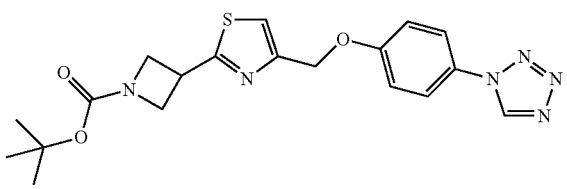 [SMILES: CC(C)(C)OC(=O)N1CC(c2nc(COc3ccc(-n4cnnn4)cc3)cs2)C1]

A mixture of 3-(4-chloromethyl-thiazol-2-yl)-azetidine-1-carboxylic acid tert-butyl ester (From Step 1) (386 mg, 1.34 mmol), 4-tetrazol-1-yl-phenol (217 mg, 1.34 mmol), Cs$_2$CO$_3$ (655 mg, 2.01 mmol) and KI (22 mg, 0.13 mmol) in acetonitrile (5 mL) was heated under reflux for 4 hours. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 8.92 (1H, s), 7.61 (2H, d), 7.32 (1H, s), 7.19 (2H, d), 5.25 (2H, s), 4.39 (2H, m), 4.18 (2H, m), 4.14 (1H, m), 1.46 (9H, s).

Example 102

3-[4-(4-Tetrazol-1-yl-phenoxymethyl)-thiazol-2-yl]-pyrrolidine-1-carboxylic acid tert-butyl ester

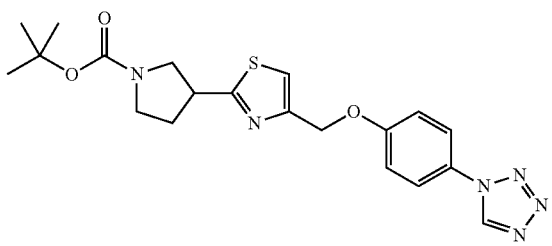 [SMILES: CC(C)(C)OC(=O)N1CCC(c2nc(COc3ccc(-n4cnnn4)cc3)cs2)C1]

Step 1: 3-(4-Chloromethyl-thiazol-2-yl)-pyrrolidine-1-carboxylic acid tert-butyl ester

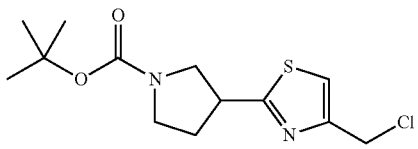 [SMILES: CC(C)(C)OC(=O)N1CCC(c2nc(CCl)cs2)C1]

To a solution of 3-thiocarbamoyl-pyrrolidine-1-carboxylic acid tert-butyl ester (1.06 g, 4.60 mmol) in acetone (25 mL) was added 1,3-dichloroacetone (0.76 g, 5.98 mmol), MgSO$_4$ (0.83 g, 6.1 mmol) and MgCO$_3$ (3.87 g, 4.6 mmol). The mixture was heated under reflux overnight, cooled and filtered through celite. The solvent was removed in vacuo and the residue was redissolved with EtOAc (20 mL). The resulting solution was washed successively with 5% NaHSO$_3$, saturated NaHCO$_3$, and brine. After drying (Na$_2$SO$_4$), the solvent was removed to afford the desired product which was used without further purification.

Step 2: 3-[4-(4-Tetrazol-1-yl-phenoxymethyl)-thiazol-2-yl]-pyrrolidine-1-carboxylic acid tert-butyl ester

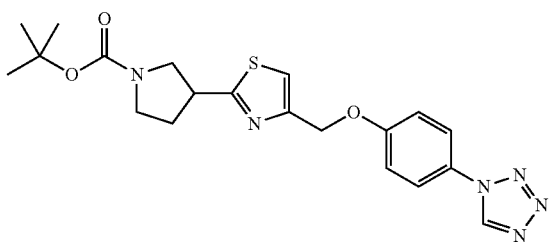 [SMILES: CC(C)(C)OC(=O)N1CCC(c2nc(COc3ccc(-n4cnnn4)cc3)cs2)C1]

A mixture of 3-(4-Chloromethyl-thiazol-2-yl)-pyrrolidine-1-carboxylic acid tert-butyl ester (From Step 1) (775 mg, 2.56 mmol), 4-tetrazol-1-yl-phenol (415 mg, 2.56 mmol), $Cs_2CO_3$ (1.25 mg, 3.84 mmol) and KI (44 mg, 0.26 mmol) in acetonitrile (20 mL) was heated under reflux overnight. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 8.92 (1H, s), 7.63 (2H, d), 7.27 (1H, s), 7.17 (2H, d), 5.24 (2H, s), 3.87 (1H, m), 3.79 (1H, m), 3.65 (2H, m), 3.45 (1H, m), 2.40 (1H, m), 2.23 (1H, m), 1.47 (9H, s).

Example 103

5-Ethyl-2-{3-[4-(4-tetrazol-1-yl-phenoxymethyl)-thiazol-2-yl]-pyrrolidin-1-yl}-pyrimidine Step 1: 1-[4-(2-Pyrrolidin-3-yl-thiazol-4-yl-methoxy)-phenyl]-1H-tetrazole

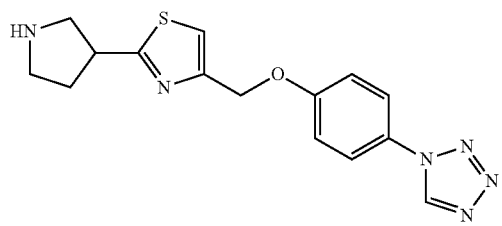 [SMILES: c1cc(-n2cnnn2)ccc1OCc1csc(C2CCNC2)n1]

A solution of 3-[4-(4-Tetrazol-1-yl-phenoxymethyl)-thiazol-2-yl]-pyrrolidine-1-carboxylic acid tert-butyl ester (from Example 102) (411 mg, 0.959 mmol) in dichloromethane (10 mL) and methanol (2 mL) were treated with 1 mL of 4 N HCl in dioxane. The resulting solution was stirred at room temperature for 30 minutes. The solvents were removed in vacuo to afford the desired product as an HCl salt.

Step 2: 5-Ethyl-2-{3-[4-(4-tetrazol-1-yl-phenoxymethyl)-thiazol-2-yl]-pyrrolidin-1-yl}-pyrimidine

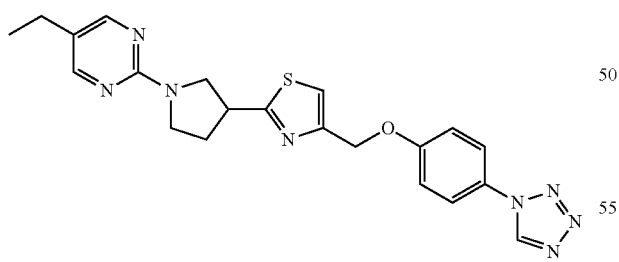

A mixture of 1-[4-(2-Pyrrolidin-3-yl-thiazol-4-yl-methoxy)-phenyl]-1H-tetrazole hydrochloride (From Step 1) (350 mg, 0.959 mmol), 2-chloropyrimidine (0.23 mL, 2.0 eq.) and $K_2CO_3$ (398 mg, 2.88 mmol) in DMF (5 mL) was heated at 90° C. for 4 hours. Water was added and the solution was extracted with ethyl acetate, separated, dried over sodium sulfate, filtered and concentrated. The residue was purified on silica gel (50:50 EtOAc/hexanes) to afford the desired product. $^1$H NMR (CDCl$_3$): δ 8.91 (1H, s), 8.21 (2H, s), 7.62 (2H, d), 7.27 (1H, s), 7.17 (2H, d), 5.24 (2H, s), 4.12 (1H, m), 3.98 (1H, m), 3.87 (2H, m), 3.69 (1H, m), 2.56 (1H, m), 2.47 (2H, m), 2.37 (1H, m), 1.21 (3H, t).

Example 104

3-[4-(4-Tetrazol-1-yl-phenoxymethyl)-thiazol-2-yl]-piperidine-1-carboxylic acid tert-butyl ester

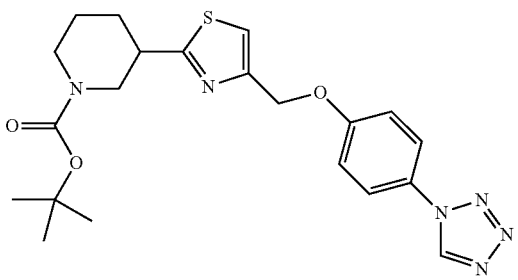 [SMILES: CC(C)(C)OC(=O)N1CCCC(c2nc(COc3ccc(-n4cnnn4)cc3)cs2)C1]

Step 1: 3-(4-Chloromethyl-thiazol-2-yl)-piperidine-1-carboxylic acid tert-butyl ester

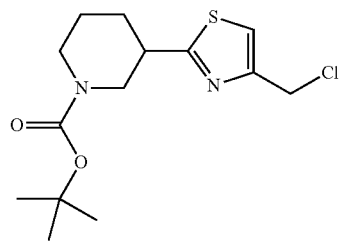 [SMILES: CC(C)(C)OC(=O)N1CCCC(c2nc(CCl)cs2)C1]

To a solution of 3-Thiocarbamoyl-piperidine-1-carboxylic acid tert-butyl ester (2.2 g, 9.02 mmol) in acetone (45 mL) was added 1,3-dichloroacetone (1.49 g, 11.7 mmol), $MgSO_4$ (1.63 g, 13.5 mmol) and $MgCO_3$ (0.76 g, 9.02 mmol). The mixture was heated under reflux overnight, cooled and filtered through celite. The solvent was removed in vacuo and the residue was redissolved with EtOAc (20 mL). The resulting solution was washed successively with 5% $NaHSO_3$, saturated $NaHCO_3$, and brine. After drying ($Na_2SO_4$), the solvent was removed to afford the desired product which was used without further purification.

Step 2: 3-[4-(4-Tetrazol-1-yl-phenoxymethyl)-thiazol-2-yl]-piperidine-1-carboxylic acid tert-butyl ester

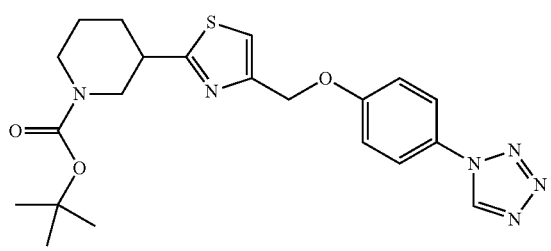 [SMILES: CC(C)(C)OC(=O)N1CCCC(c2nc(COc3ccc(-n4cnnn4)cc3)cs2)C1]

A mixture of 3-(4-Chloromethyl-thiazol-2-yl)-piperidine-1-carboxylic acid tert-butyl ester (From Step 1) (300 mg, 0.946 mmol), 4-tetrazol-1-yl-phenol (155 mg, 0.946 mmol), Cs$_2$CO$_3$ (467 mg, 1.42 mmol) and KI (16 mg, 0.095 mmol) in acetonitrile (10 mL) was heated under reflux for 4 hours. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 8.91 (1H, s), 7.63 (2H, d), 7.26 (1H, s), 7.17 (2H, d), 5.24 (2H, s), 4.30 (1H, br), 4.02 (1H, m), 3.20 (1H, m), 3.10 (1H, br), 2.88 (1H, t), 2.21(1H, m), 1.77 (2H, m), 1.61 (1H, m), 1.47 (9H, s).

Example 105

5-Ethyl-2-{3-[4-(4-tetrazol-1-yl-phenoxymethyl)-thiazol-2-yl]-piperidin-1-yl}-pyrimidine Step 1: 3-[4-(4-Tetrazol-1-yl-phenoxymethyl)-thiazol-2-yl]-piperidine

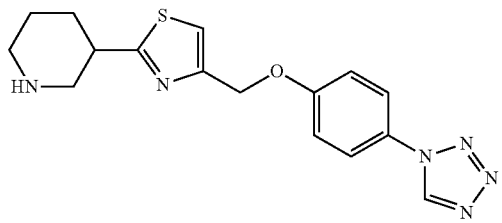 [SMILES: c1cc(-n2cnnn2)ccc1OCc1csc(C2CCCNC2)n1]

A solution of 3-[4-(4-Tetrazol-1-yl-phenoxymethyl)-thiazol-2-yl]-piperidine-1-carboxylic acid tert-butyl ester (500 mg, 1.13 mmol) in dichloromethane (10 mL) and methanol (2 mL) were treated with 2 mL of 4 N HCl in dioxane. The resulting solution was stirred at room temperature for 30 minutes. The solvents were removed in vacuo to afford the desired product as an HCl salt.

Step 2: 5-Ethyl-2-{3-[4-(4-tetrazol-1-yl-phenoxymethyl)-thiazol-2-yl]-piperidin-1-yl}-pyrimidine

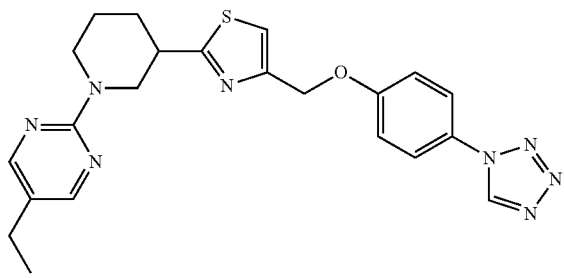 [SMILES: CCc1cnc(N2CCCC(c3nc(COc4ccc(-n5cnnn5)cc4)cs3)C2)nc1]

A mixture of 3-[4-(4-Tetrazol-1-yl-phenoxymethyl)-thiazol-2-yl]-piperidine hydrochloride (150 mg, 0.407 mmol), 2-chloropyrimidine (0.074 mL, 2.0 eq.) and NaHCO$_3$ (171 mg, 2.03 mmol) in DMF (5 mL) was heated at 90° C. for 4 hours. Water was added and the solution was extracted with ethyl acetate, separated, dried over sodium sulfate, filtered and concentrated. The residue was purified on silica gel (50:50 EtOAc/hexanes) to afford the desired product. $^1$H NMR (CDCl$_3$): δ 8.91 (1H, s), 8.19 (2H, s), 7.63 (2H, m), 7.26(1H, s), 7.17 (2H, m), 5.25 (2H, s), 4.97 (1H, m), 4.62 (1H, m), 3.25 (2H, m), 3.07 (1H, m), 2.46 (2H, q), 2.28(1H, m), 1.88 (2H, m), 1.68 (1H, m), 1.20 (3H, t).

Example 106

4-[4-(4-Methanesulfonyl-benzyloxymethyl)-thiazol-2-yl]-piperidine-1-carboxylic acid tert-butyl ester

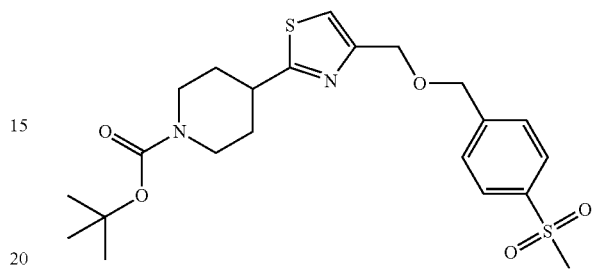

Hydroxybenzyl-4-methylsulfone (1.7 eq.) was dissolved in anhydrous DMF (10 mL), cooled to 0° C. and NaH (2 eq.) was added in one portion. The reaction was allowed to stir at 0° C. for 30 minutes and at room temperature for an additional 30 minutes. 4-(4-Chloromethyl-thiazol-2-yl)-piperidine-1-carboxylic acid tert-butyl ester (Intermediate 1) (0.632 mmol) was added and the reaction was stirred overnight. The reaction was quenched with water and extracted with EtOAc, dried over sodium sulfate, filtered and concentrated under reduced pressure. The residue was purified by silica gel chromatography (EtOAc/hexanes 1:1) to afford the desired product. $^1$H NMR (CDCl$_3$): δ 7.92 (2H, d, J=8.8 Hz), 7.57 (2H, d, J=8.8 Hz), 7.14 (1H, s), 4.71 (2H, s), 4.66 (2H, s), 4.19 (2H, m), 3.13 (1H, m), 3.05 (3H, s), 2.86 (2H, m), 2.09 (2H, m), 1.72 (2H, m), 1.45 (9H, s).

Example 107

2-{4-[4-(4-Tetrazol-1-yl-phenoxymethyl)-thiazol-2-yl]-piperidin-1-yl}-pyrimidin-5-ylamine

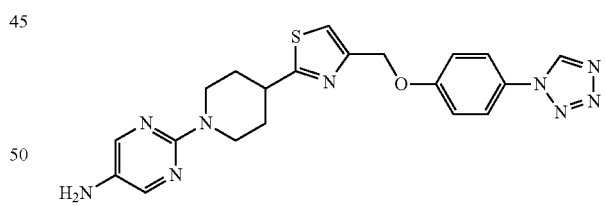

5-Nitro-2-{4-[4-(4-tetrazol-1-yl-phenoxymethyl)-thiazol-2-yl]-piperidin-1-yl}-pyrimidine (Example 192) (1.07 mmol), ammonium chloride (3 eq.) and iron powder (3 eq.) were suspended in EtOH:THF:H$_2$O (40:20:10) and heated at 100° C. for 5 hours. The hot reaction mixture was filtered through a pad of celite and the filtrate was concentrated. The resulting oil was dissolved in DMF and water and extracted with ethylacetate. The organic layer was washed with water, brine and dried over sodium sulfate. The resulting filtrate was concentrated under reduced pressure. Purification using silica gel chromatography (DCM/MeOH 98:2) provided the expected product. $^1$H NMR (DMSO-d$_6$): δ 9.96 (1H, s), 7.97 (2H, m), 7.90 (2H, m), 7.63 (1H, s), 5.19 (2H, s), 4.44 (2H, m), 3.73 (1H, m), 2.97 (2H, m), 2.20 (2H, m), 1.95 (2H, m).

Example 108

N-(2-{4-[4-(4-Tetrazol-1-yl-phenoxymethyl)-thiazol-2-yl]-piperidin-1-yl}-pyrimidin-5-yl)-acetamide

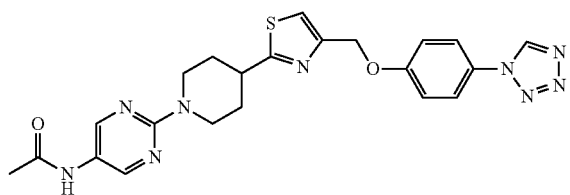 [SMILES: CC(=O)Nc1cnc(N2CCC(c3nc(COc4ccc(-n5cnnn5)cc4)cs3)CC2)nc1]

2-{4-[4-(4-Tetrazol-1-yl-phenoxymethyl)-thiazol-2-yl]-piperidin-1-yl}-pyrimidin-5-ylamine (Example 107) (0.321 mmol) was dissolved in DCM and triethylamine (2 eq.) was added. The reaction was cooled to 0° C., acetylchloride (1 eq.) was added dropwise and the reaction was stirred at room temperature overnight. Water was added and the mixture was extracted with ethyl acetate, dried over sodium sulfate, filtered and concentrated under reduced pressure. Silica gel chromatography of the resulting oil (DCM/MeOH) provided the expected product. $^1$H NMR (CDCl$_3$): δ 8.84 (1H, s), 8.36 (2H, s), 7.55 (2H, m), 7.19 (1H, s), 7.11 (2H, m), 6.94 (1H, s), 5.16 (2H, s), 4.77 (2H, m), 3.25 (1H, m), 3.01 (2H, m), 2.16 (2H, m), 2.15 (3H, s), 1.75 (2H, m).

Example 109

4-[4-(4-Tetrazol-1-yl-phenylcarbamoyl)-thiazol-2-yl]-piperidine-1-carboxylic acid tert-butyl ester

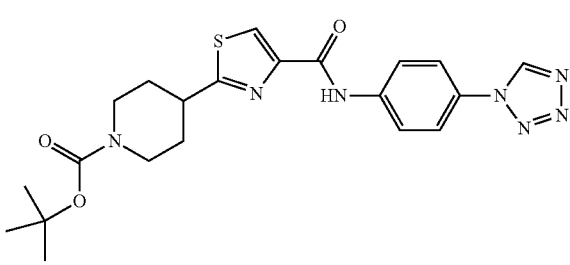 [SMILES: CC(C)(C)OC(=O)N1CCC(c2nc(C(=O)Nc3ccc(-n4cnnn4)cc3)cs2)CC1]

4-(4-Carboxy-thiazol-2-yl)-piperidine-1-carboxylic acid tert-butyl ester (1.28 mmol) was dissolved in anhydrous DMF (20 mL). To the solution was added triethylamine (4 eq.) and O-(Benzotriazol-1-yl)-N,N,N',N'-tetramethyluronium tetrafluoroborate (TBTU) (1.5 eq.). The reaction was allowed to stir at room temperature for 5 minutes before 4-tetrazol-1-yl-phenylamine (1.2 eq.) was added. The reaction was stirred overnight, quenched with water, extracted with ethylacetate, washed with brine, dried over sodium sulfate and filtered. The organic filtrate was concentrated in vacuo and the residual oil was purified by column chromatography (EtOAC/Hex) furnishing the expected product. $^1$H NMR (CDCl$_3$): δ 9.37 (1H, s), 9.02 (1H, s), 8.14 (1H, s), 7.96 (2H, d), 7.72 (2H, d), 4.23 (2H, m), 3.20 (1H, m), 2.91 (2H, m), 2.14 (2H, m), 1.79 (2H, m), 1.45 (9H, s).

Example 110

4-[4-(4-Trifluoromethanesulfonyl-phenoxymethyl)-thiazol-2-yl]-piperidine-1-carboxylic acid tert-butyl ester

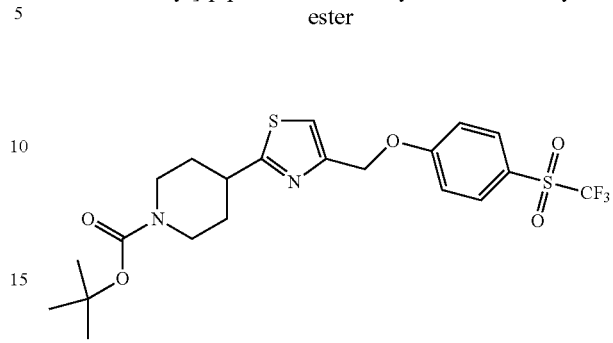

To a solution of [4-(4-Trifluoromethanesulfanyl-phenoxymethyl)-thiazol-2-yl]-piperidine-1-carboxylic acid tert-butyl ester (Example 134) (1.12 mmol) in DCM (20 mL) at room temperature was added 3-chloro-benzenecarboperoxoic acid (2 eq.). The reaction was allowed to stir for 1.5 hours and an additional portion of 3-chloro-benzenecarboperoxoic acid (1 eq.) was added to the reaction mixture. The reaction was stirred at room temperature for an additional 4 hours. The organic solution was washed with sodium bicarbonate, the organic layer was isolated, dried over sodium sulfate and filtered. The filtrate was concentrated and the crude product was purified by column chromatography to afford both the expected sulfone and sulfoxide products. Sulfone: $^1$H NMR (DMSO-d$_6$): δ 8.05 (2H, d, J=8.6 Hz), 7.70 (1H, s), 7.44 (2H, d, J=8.6 Hz), 5.32 (2H, s), 3.98 (2H, m), 3.19 (1H, m), 2.86 (2H, m), 2.02 (2H, m), 1.56 (2H, m), 1.38 (9H, s).

Example 111

4-[4-(4-Trifluoromethanesulfinyl-phenoxymethyl)-thiazol-2-yl]-piperidine-1-carboxylic acid tert-butyl ester

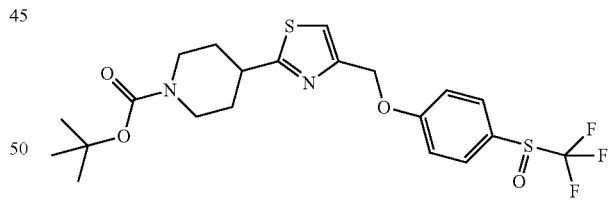

This compound was isolated from the reaction mixture of the previous example. $^1$H NMR (DMSO-d$_6$): δ 8.02 (2H, d, J=8.6 Hz), 7.75 (1H, s), 7.32 (2H, d, J=8.6 Hz), 5.31 (2H, s), 3.96 (2H, m), 3.20 (1H, m), 2.85 (2H, m), 2.02 (2H, m), 1.50 (2H, m), 1.38 (9H, s).

Example 112-145 were synthesized from 4-(4-Chloromethyl-thiazol-2-yl)-piperidine-1-carboxylic acid tert-butyl ester (Intermediate 1), 2-[4-(4-Chloromethyl-thiazol-2-yl)-piperidin-1-yl]-5-ethyl-pyrimidine (Intermediate 2) or 4-(4-Chloromethyl-oxazol-2-yl)-piperidine-1-carboxylic acid tert-butyl ester (Intermediate 14) with the corresponding phenol, thiophenol, amine or aniline in a similar manner to that described in Example 1. One skilled in the art of organic synthesis will appreciate that conditions such as solvent

Example 112

4-[4-(2,6-Difluoro-4-tetrazol-1-yl-phenoxymethyl)-thiazol-2-yl]-piperidine-1-carboxylic acid tert-butyl ester

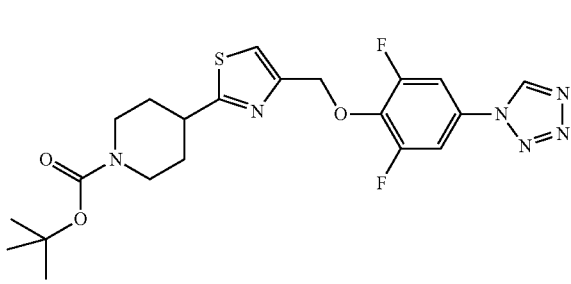 [SMILES: CC(C)(C)OC(=O)N1CCC(c2nc(COc3c(F)cc(-n4cnnn4)cc3F)cs2)CC1]

$^1$H NMR (CDCl$_3$): δ 8.98 (1H, s), 7.34 (2H, m), 7.30 (1H, s), 5.36 (2H, s), 4.19 (2H, m), 3.15 (1H, m), 2.87 (2H, m), 2.07 (2H, m), 1.70 (2H, m), 1.47 (9H, s).

Example 113

4-[4-(4-Pyrrol-1-yl-phenoxymethyl)-thiazol-2-yl]-piperidine-1-carboxylic acid tert-butyl ester

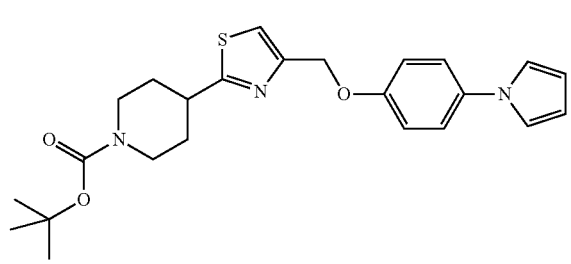 [SMILES: CC(C)(C)OC(=O)N1CCC(c2nc(COc3ccc(-n4cccc4)cc3)cs2)CC1]

$^1$H NMR (CDCl$_3$): δ 7.24 (3H, m), 7.01 (4H, m), 6.31 (2H, m), 5.17 (2H, s), 4.21 (2H, m), 3.14 (1H, m), 2.87 (2H, m), 2.01 (2H, m), 1.74 (2H, m), 1.47 (9H, s).

Example 114

4-{4-[(4-Tetrazol-1-yl-phenylamino)-methyl]-thiazol-2-yl}-piperidine-1-carboxylic acid tert-butyl ester

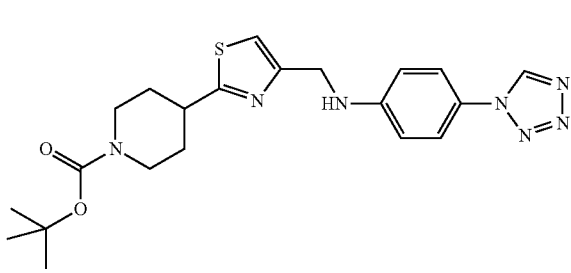 [SMILES: CC(C)(C)OC(=O)N1CCC(c2nc(CNc3ccc(-n4cnnn4)cc3)cs2)CC1]

$^1$H NMR (CDCl$_3$): δ 8.85 (1H, s), 7.40 (2H, m), 7.01 (1H, s), 6.72 (2H, m), 4.76 (1H, s), 4.44 (2H, s), 4.15 (2H, m), 3.08 (1H, m), 2.83 (2H, m), 2.04 (2H, m), 1.66 (2H, m), 1.43 (9H, s).

Example 115

2-{4-[4-(3-Chloro-4-tetrazol-1-yl-phenoxymethyl)-thiazol-2-yl]-piperidin-1-yl}-5-ethyl-pyrimidine

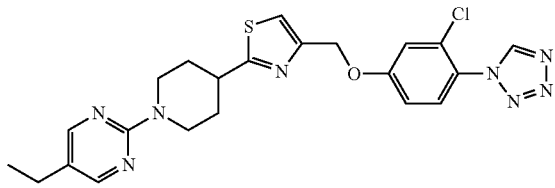 [SMILES: CCc1cnc(N2CCC(c3nc(COc4ccc(-n5cnnn5)c(Cl)c4)cs3)CC2)nc1]

$^1$H NMR (CDCl$_3$): δ 8.93 (1H, s), 8.18 (2H, s), 7.48 (1H, m), 7.25 (1H, s), 7.08 (2H, m), 5.22 (2H, s), 4.82 (2H, m), 3.29 (1H, m), 3.04 (2H, m), 2.46 (2H, q), 2.21 (2H, m), 1.80 (2H, m), 1.18 (3H, t).

Example 116

N-(4-{2-[1-(5-Ethyl-pyrimidin-2-yl)-piperidin-4-yl]-thiazol-4-ylmethoxy}-phenyl)-formamide

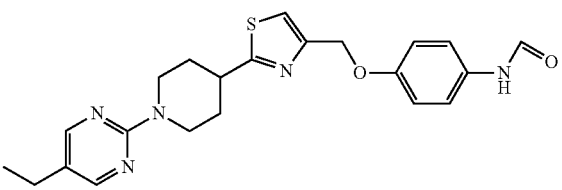 [SMILES: CCc1cnc(N2CCC(c3nc(COc4ccc(NC=O)cc4)cs3)CC2)nc1]

$^1$H NMR (CDCl$_3$): δ 8.55-8.30 (1H, m), 8.18 (2H, s), 7.50-6.90 (6H, m), 5.14 (2H, s), 4.83 (2H, m), 3.29 (1H, m), 3.03 (2H, m), 2.46 (2H, q), 2.20 (2H, m), 1.80 (2H, m), 1.19 (3H, t).

Example 117

N-(4-{2-[1-(5-Ethyl-pyrimidin-2-yl)-piperidin-4-yl]-thiazol-4-ylmethoxy}-phenyl)-methanesulfonamide

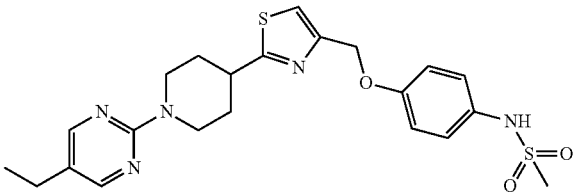 [SMILES: CCc1cnc(N2CCC(c3nc(COc4ccc(NS(C)(=O)=O)cc4)cs3)CC2)nc1]

$^1$H NMR (CDCl$_3$): δ 8.20 (s, 2H), 7.21 (m, 3H), 6.95 (m, 2H), 5.13 (s, 2H), 4.81 (m, 2H), 3.29 (m, 1H), 3.06 (m, 2H), 2.94 (s, 3H), 2.47 (q, 2H), 2.20 (m, 2H), 1.81 (m, 2H), 1.19 (t, 3H).

Example 118

4-[4-(2-Methyl-4-tetrazol-1-yl-phenoxymethyl)-thiazol-2-yl]-piperidine-1-carboxylic acid tert-butyl ester

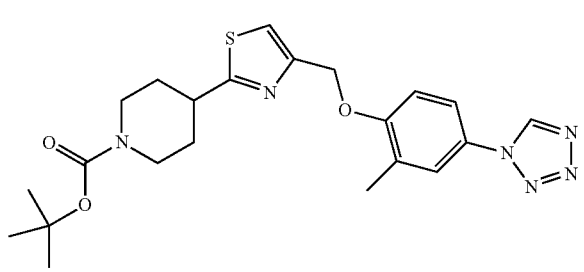 [SMILES: Cc1cc(-n2cnnn2)ccc1OCc1csc(C2CCN(C(=O)OC(C)(C)C)CC2)n1]

¹H NMR (CDCl₃): δ 8.89 (1H, s), 7.48 (1H, s), 7.43 (1H, m), 7.25 (1H, m), 7.05 (1H, m), 5.27 (2H, s), 4.27 (2H, m), 3.18 (1H, m), 2.89 (2H, m), 2.37 (3H, s), 2.21 (2H, m), 1.74 (2H, m), 1.47 (9H, s).

Example 119

5-Ethyl-2-{4-[4-(4-tetrazol-1-yl-2-trifluoromethyl-phenoxymethyl)-thiazol-2-yl]-piperidin-1-yl}-pyrimidine

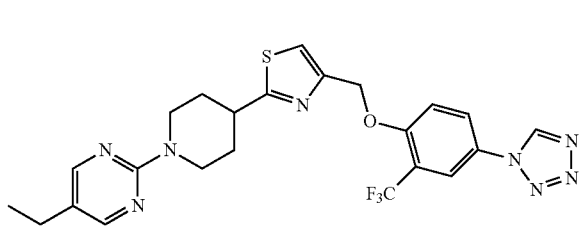 [SMILES: CCc1cnc(N2CCC(c3nc(COc4ccc(-n5cnnn5)cc4C(F)(F)F)cs3)CC2)nc1]

¹H NMR (CDCl₃): δ 8.97 (1H, s), 8.18 (2H, s), 7.92 (1H, m), 7.84 (1H, m), 7.33 (1H, m), 7.26 (1H, s), 5.38 (2H, s), 4.81 (2H, m), 3.27 (1H, m), 3.05 (2H, m), 2.46 (2H, q), 2.19 (2H, m), 1.79 (2H, m), 1.19 (3H, t).

Example 120

2-{4-[4-(2-Chloro-4-tetrazol-1-yl-phenoxymethyl)-thiazol-2-yl]-piperidin-1-yl}-5-ethyl-pyrimidine

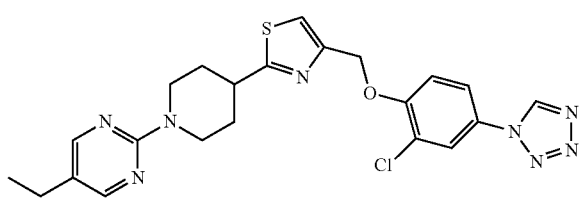 [SMILES: CCc1cnc(N2CCC(c3nc(COc4ccc(-n5cnnn5)cc4Cl)cs3)CC2)nc1]

¹H NMR (acetone-d₆), δ 9.68 (1H, s), 8.24 (2H, s), 8.01 (1H, s), 7.86 (1H, m), 7.60 (1H, m), 7.59 (1H, m), 5.40 (2H, s), 4.82 (2H, m), 3.36 (1H, m), 3.08 (2H, m), 2.48 (2H, q), 2.17 (2H, m), 1.75 (2H, m), 1.18 (3H, t).

Example 121

4-[4-(4-Tetrazol-1-yl-phenoxymethyl)-oxazol-2-yl]-piperidine-1-carboxylic acid tert-butyl ester

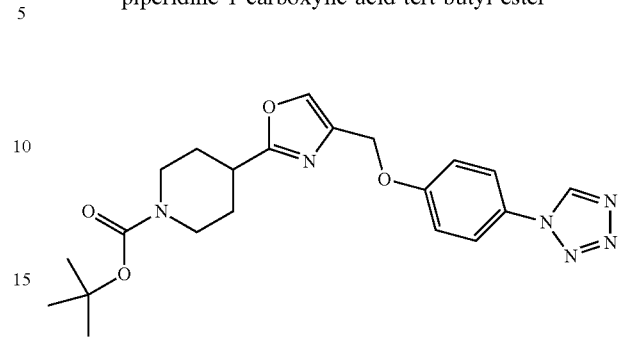

¹H NMR (CDCl₃): δ 8.94 (1H, s), 7.65 (1H, s), 7.60 (2H, m), 7.13 (2H, m), 5.01 (2H, s), 4.08 (2H, m), 2.94 (3H, m), 2.03 (2H, m), 1.75 (2H, m), 1.43 (9H, s).

Example 122

4-[4-(2-Fluoro-4-tetrazol-1-yl-phenoxymethyl)-oxazol-2-yl]-piperidine-1-carboxylic acid tert-butyl ester

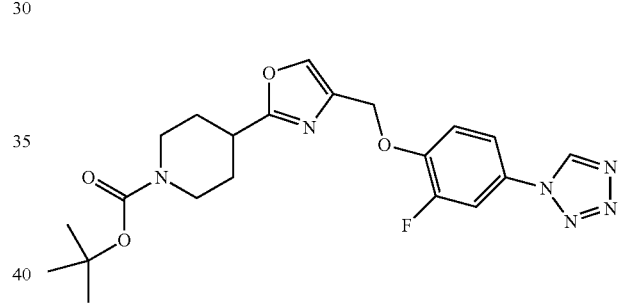

¹H NMR (CDCl₃): δ 8.88 (1H, s), 7.62 (1H, s), 7.45 (1H, m), 7.36 (1H, m), 7.23 (1H, m), 5.05 (2H, s), 4.04 (2H, m), 2.85 (3H, m), 1.97 (2H, m), 1.71 (2H, m), 1.40 (9H, s).

Example 123

5-Ethyl-2-{4-[4-(4-methanesulfonyl-phenoxymethyl)-oxazol-2-yl]-piperidin-1-yl}-pyrimidine

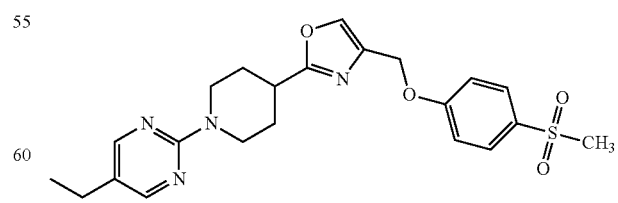

¹H NMR (CDCl₃): δ 8.16 (2H, s), 7.84 (2H, m), 7.63 (1H, s), 7.08 (2H, m), 5.02 (2H, s), 4.67 (2H, m), 3.08 (3H, m), 3.01 (3H, s), 2.44 (2H, q), 2.12 (2H, m), 1.84 (2H, m), 1.17 (3H, t).

Example 124

4-[4-(2,6-Difluoro-4-propionyl-phenoxymethyl)-thiazol-2-yl]-piperidine-1-carboxylic acid tert-butyl ester

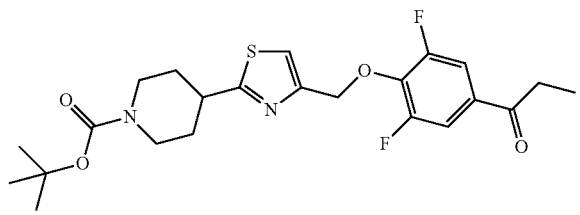 [SMILES: CCC(=O)c1cc(F)c(OCc2csc(C3CCN(C(=O)OC(C)(C)C)CC3)n2)c(F)c1]

¹H NMR (CDCl₃): δ 7.51 (2H, d), 7.27 (1H, s), 5.37 (2H, s), 4.18 (2H, m), 3.14 (1H, m), 2.92 (2H, q, J=7.4 Hz), 2.88 (2H, m), 2.07 (2H, m), 1.71 (2H, m), 1.47 (9H, s), 1.21 (3H, t, J=7.4 Hz).

Example 125

4-[4-(4-Acetyl-2-fluoro-phenoxymethyl)-thiazol-2-yl]-piperidine-1-carboxylic acid tert-butyl ester

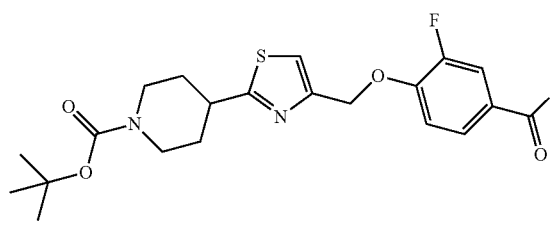

¹H NMR (CDCl₃): δ 7.70~7.72 (2H, m), 7.28 (1H, s), 7.09~7.13 (1H, m), 5.30 (2H, s), 4.20 (2H, m), 3.17 (1H, m), 2.88 (2H, m), 2.55 (3H, s), 2.10 (2H, m), 1.72 (2H, m), 1.47 (9H, s).

Example 126

4-[4-(4-Cyano-2-fluoro-phenoxymethyl)-thiazol-2-yl]-piperidine-1-carboxylic acid tert-butyl ester

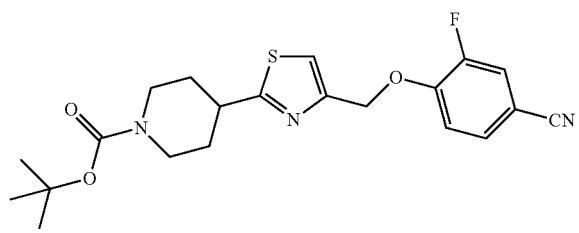 [SMILES: CC(C)(C)OC(=O)N1CCC(c2nc(COc3ccc(C#N)cc3F)cs2)CC1]

¹H NMR (CDCl₃): δ 7.37~7.42 (2H, m), 7.27 (1H, s), 7.13~7.17 (1H, m), 5.28 (2H, s), 4.20 (2H, m), 3.15 (1H, m), 2.89 (2H, m), 2.09 (2H, m), 1.72 (2H, m), 1.47 (9H, s).

Example 127

4-[4-(6-Tetrazol-1-yl-pyridin-3-yloxymethyl)-thiazol-2-yl]-piperidine-1-carboxylic acid tert-butyl ester

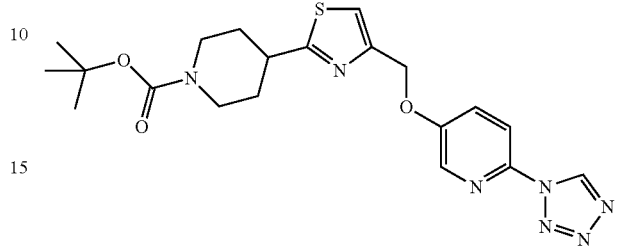

¹H NMR (CDCl₃): δ 9.41 (1H, s), 8.27 (1H, d), 8.01 (1H, d,), 7.58 (1H, dd,), 7.28 (1H, s), 5.27 (2H, s), 4.20 (2H, m), 3.14-3.20 (1H, m), 2.87 (2H, m), 2.09-2.12 (2H, m), 1.68-1.78 (2H, m), 1.46 (9H, s)

Example 128

4-[4-(4-[1,2,3]Triazol-1-yl-phenoxymethyl)-thiazol-2-yl]-piperidine-1-carboxylic acid tert-butyl ester

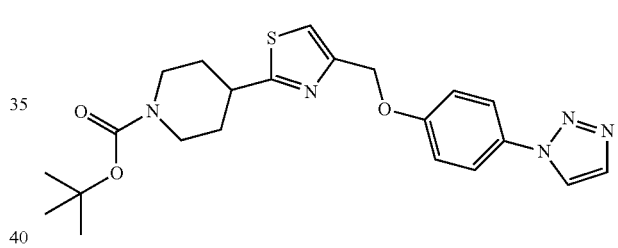

¹H NMR (CDCl₃): δ 7.92 (1H, s), 7.84 (1H, s), 7.65 (2H, d), 7.25 (1H, s), 7.11 (2H, d), 5.22 (2H, s), 4.21 (2H, br), 3.18 (1H, m), 2.88 (2H, br), 2.12 (2H, m), 1.75 (2H, m), 1.47 (9H, s).

Example 129

4-[4-(4-Ethoxycarbonyl-phenoxymethyl)-thiazol-2-yl]-piperidine-1-carboxylic acid tert-butyl ester

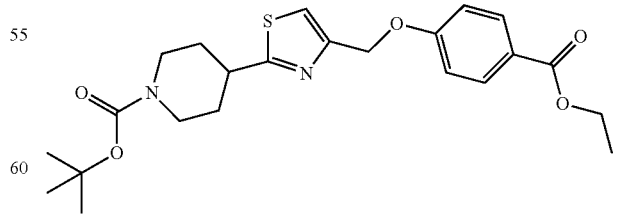

¹H NMR (CDCl₃): δ 8.01 (2H, d), 7.23 (1H, s), 7.01 (2H, d), 5.22 (2H, s), 4.36 (2H, q), 4.22 (2H, br), 3.17 (1H, m), 2.87 (2H, br), 2.12 (2H, m), 1.75 (2H, m), 1.47 (9H, s), 1.39 (2H, t).

Example 130

4-[4-(4-tert-Butoxycarbonylamino-phenoxymethyl)-thiazol-2-yl]-piperidine-1-carboxylic acid tert-butyl ester

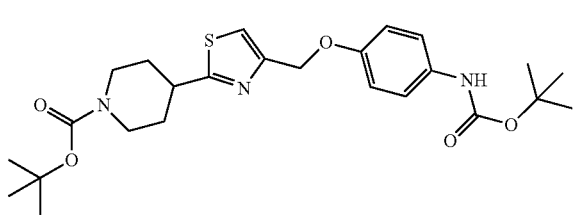 [SMILES: CC(C)(C)OC(=O)Nc1ccc(OCc2csc(C3CCN(C(=O)OC(C)(C)C)CC3)n2)cc1]

¹H NMR (CDCl₃): δ 7.28 (2H, d), 7.19 (1H, s), 6.92 (2H, d), 6.40 (1H, s), 5.12 (2H, s), 4.22 (2H, br), 3.17 (1H, m), 2.87 (2H, br), 2.12 (2H, m), 1.75 (2H, m), 1.50 (9H, s), 1.47 (9H, s).

Example 131

4-[4-(4-Carboxy-phenoxymethyl)-thiazol-2-yl]-piperidine-1-carboxylic acid tert-butyl ester

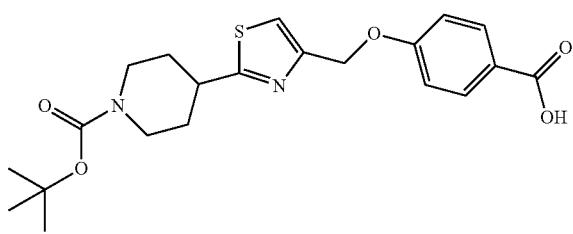 [SMILES: CC(C)(C)OC(=O)N1CCC(c2nc(COc3ccc(C(=O)O)cc3)cs2)CC1]

¹H NMR (DMSO-d₆): δ 7.86 (2H, d), 7.64 (1H, s), 7.10 (2H, d), 5.17 (2H, s), 3.96 (2H, m), 3.18 (1H, m), 2.87 (2H, br), 1.96 (2H, m), 1.49 (2H, m), 1.38 (9H, s).

Example 132

4-[4-(2,6-Difluoro-4-methanesulfonyl-phenoxymethyl)-thiazol-2-yl]-piperidine-1-carboxylic acid tert-butyl ester

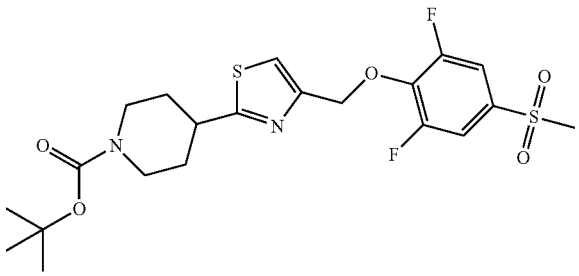 [SMILES: CC(C)(C)OC(=O)N1CCC(c2nc(COc3c(F)cc(S(C)(=O)=O)cc3F)cs2)CC1]

¹H NMR (CDCl₃): δ 7.42 (2H, d), 7.21 (1H, s), 5.25 (2H, s), 4.12 (2H, br), 3.17 (1H, m), 3.00 (3H, s), 2.87 (2H, br), 1.98 (2H, m), 1.71 (2H, m).

Example 133

4-[4-(4-Morpholin-4-yl-phenoxymethyl)-thiazol-2-yl]-piperidine-1-carboxylic acid tert-butyl ester

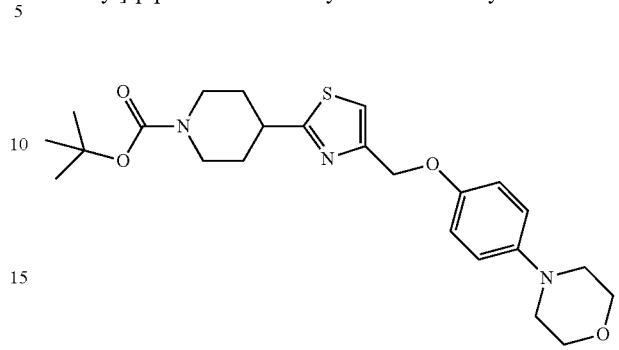

¹H NMR (CDCl₃): δ 7.19 (1H, s), 6.92 (4H, m), 5.12 (2H, s), 4.20 (2H, br), 3.85 (4H, br), 3.16 (1H, m), 3.07 (4H, m), 2.86 (2H, m), 2.10 (2H, m), 1.72 (2H, m), 1.47 (9H, s).

Example 134

4-[4-(4-Trifluoromethylsulfanyl-phenoxymethyl)-thiazol-2-yl]-piperidine-1-carboxylic acid tert-butyl ester

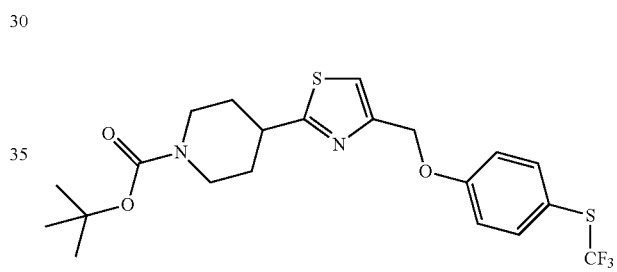

¹H NMR (DMSO-d₆): δ 7.64 (1H, s), 7.63 (2H, d, J=8.6 Hz), 7.17 (2H, d, J=8.6 Hz), 5.17 (2H, s), 3.99 (2H, m), 3.18 (1H, m), 2.83 (2H, m), 2.01 (2H, m), 1.52 (2H, m), 1.38 (9H, s).

Example 135

4-[4-(4-Benzyloxy-phenoxymethyl)-thiazol-2-yl]-piperidine-1-carboxylic acid tert-butyl ester

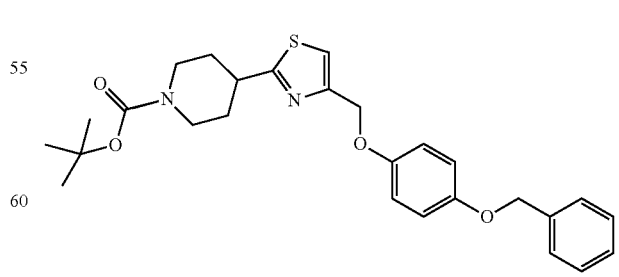

¹H NMR (DMSO-d₆): δ 7.55 (1H, s), 7.41 (5H, m), 6.92 (4H, m), 5.12 (4H, s), 3.98 (2H, m), 3.20 (1H, m), 2.84 (2H, m), 2.01 (2H, m), 1.52 (2H, m), 1.38 (9H, s).

Example 136

4-[4-(2-Acetylamino-4-methanesulfonyl-phenoxymethyl)-thiazol-2-yl]-piperidine-1-carboxylic acid tert-butyl ester

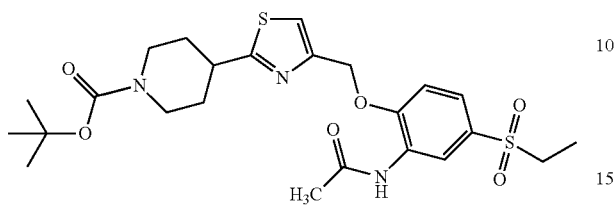

$^{1}$H NMR (CDCl$_{3}$): δ 8.81 (1H, s), 7.97 (1H, s), 7.53 (1H, d), 7.25 (1H, s), 7.09 (1H, d), 5.24 (2H, s), 4.16 (2H, m), 3.10 (3H, m), 2.83 (2H, m), 2.16 (3H, s), 2.04 (2H, d), 1.66 (2H, m), 1.40 (9H, s), 1.19(3H, t).

Example 137

4-(4-Phenoxymethyl-thiazol-2-yl)-piperidine-1-carboxylic acid tert-butyl ester

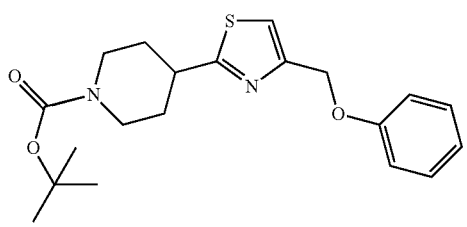

$^{1}$H NMR (CDCl$_{3}$): δ 7.28 (2H, m), 7.19 (1H, s), 6.93 (3H, m), 5.14 (2H, s), 4.19 (2H, s), 3.15 (1H, m), 2.85 (2H, m), 2.07 (2H, d), 1.67 (2H, m), 1.45 (9H, s).

Example 138

4-{4-[(4-Methanesulfonyl-phenylamino)-methyl]-thiazol-2-yl}-piperidine-1-carboxylic acid tert-butyl ester

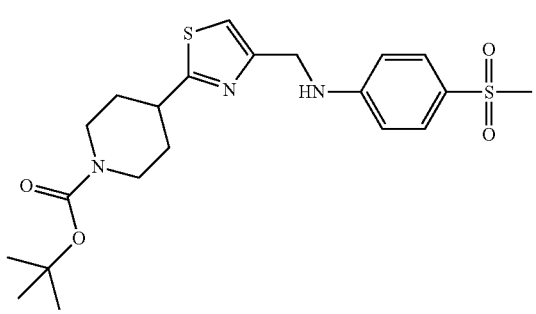 [SMILES: CC(C)(C)OC(=O)N1CCC(c2nc(CNc3ccc(S(C)(=O)=O)cc3)cs2)CC1]

$^{1}$H NMR (CDCl$_{3}$): δ 7.67 (2H, d, J=8.8 Hz), 6.99 (1H, s), 6.67 (2H, d, J=8.8 Hz), 5.07 (1H, m), 4.45 (2H, d), 4.18 (2H, s), 3.13 (1H, m), 2.97 (3H, s), 2.85 (2H, m), 2.04 (2H, d), 1.68 (2H, m), 1.44 (9H, s).

Example 139

4-{4-[(2-Fluoro-4-methanesulfonyl-phenylamino)-methyl]-thiazol-2-yl}-piperidine-1-carboxylic acid isopropyl ester

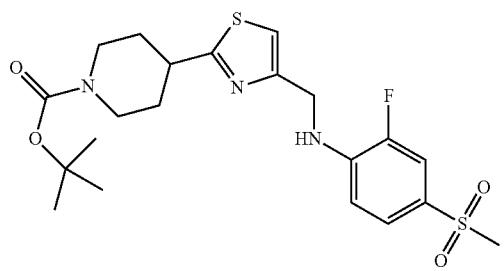 [SMILES: CC(C)(C)OC(=O)N1CCC(c2nc(CNc3ccc(S(C)(=O)=O)cc3F)cs2)CC1]

$^{1}$H NMR (CDCl$_{3}$): δ 7.55 (2H, m), 7.05 (1H, s), 6.76 (1H, m), 5.12 (1H, m), 4.52 (2H, d), 4.19 (2H, m), 3.13 (1H, m), 3.05 (3H, s), 2.86 (2H, m), 2.10 (2H, m), 1.76 (2H, m), 1.46 (9H, s).

Example 140

4-[4-(4-Bromo-phenoxymethyl)-thiazol-2-yl]-piperidine-1-carboxylic acid tert-butyl ester

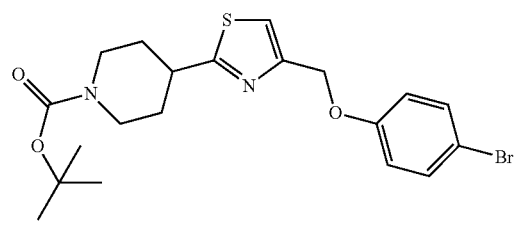 [SMILES: CC(C)(C)OC(=O)N1CCC(c2nc(COc3ccc(Br)cc3)cs2)CC1]

$^{1}$H NMR (CDCl$_{3}$): δ 7.36 (2H, m), 7.17 (1H, s), 6.82 (2H, m), 5.10 (2H, s), 4.18 (2H, s), 3.13 (1H, m), 2.85 (2H, m), 2.09 (2H, d), 1.75 (2H, m), 1.43 (9H, s).

Example 141

{2-[1-(5-Ethyl-pyrimidin-2-yl)-piperidin-4-yl]-thiazol-4-ylmethyl}-(2-fluoro-4-methanesulfonyl-phenyl)-amine

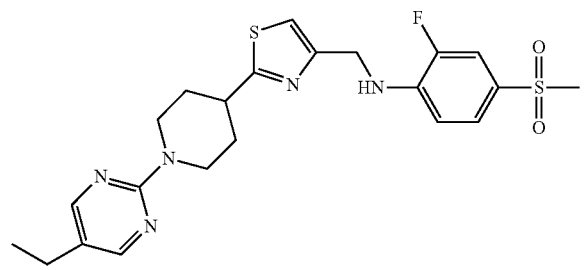 [SMILES: CCc1cnc(N2CCC(c3nc(CNc4ccc(S(C)(=O)=O)cc4F)cs3)CC2)nc1]

¹H NMR (CDCl₃): δ 8.16 (2H, s), 7.52 (2H, m), 7.01 (1H, s), 6.74 (1H, m), 5.15 (1H, m), 4.83 (2H, m), 4.51 (2H, d), 3.26 (1H, m), 3.02 (5H, m), 2.46 (2H, m), 2.19 (2H, m), 1.78 (2H, m), 1.19 (3H, t).

Example 142

4-{4-[(4-Methanesulfonyl-benzylamino)-methyl]-thiazol-2-yl}-piperidine-1-carboxylic acid tert-butyl ester

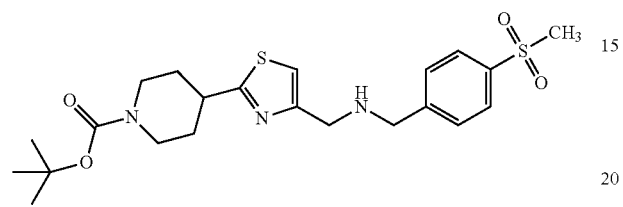

¹H NMR (CDCl₃): δ 7.85 (2H, d, J=8.8 Hz), 7.53 (2H, d, J=8.8 Hz), 6.95 (1H, s), 4.14 (2H, s), 3.87 (2H, s), 3.83 (2H, s), 3.11 (1H, m), 3.04 (3H, s), 2.86 (2H, m), 2.07 (3H, m), 1.67 (2H, m), 1.42 (9H, s).

Example 143

4-(4-{[1-(4-Methanesulfonyl-phenyl)-ethylamino]-methyl}-thiazol-2-yl)-piperidine-1-carboxylic acid tert-butyl ester

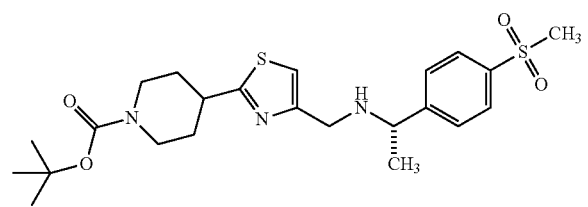 [SMILES: C[C@H](NCc1csc(C2CCN(C(=O)OC(C)(C)C)CC2)n1)c1ccc(S(C)(=O)=O)cc1]

¹H NMR (CDCl₃): δ 7.87 (2H, d, J=8.8 Hz), 7.56 (2H, d, J=8.8 Hz), 6.87 (1H, s), 4.22 (2H, m), 3.90 (1H, s), 3.66 (2H, m), 3.09 (1H, m), 3.04 (3H, s), 2.82 (3H, m), 2.02 (2H, m), 1.71 (2H, m), 1.40 (9H, s), 1.29 (3H, d).

Example 144

3-Methyl-4-[4-(4-tetrazol-1-yl-phenoxymethyl)-thiazol-2-yl]-piperidine-1-carboxylic acid tert-butyl ester

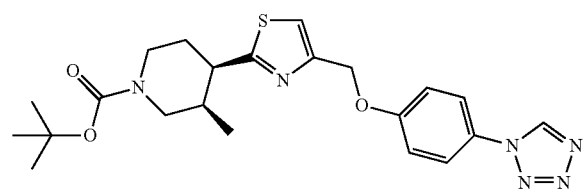 [SMILES: C[C@H]1CN(C(=O)OC(C)(C)C)CC[C@H]1c1nc(COc2ccc(-n3cnnn3)cc2)cs1]

¹H NMR (CDCl₃): δ 8.93 (1H, s), 7.61 (2H, m), 7.25 (1H, m), 7.12 (2H, m), 5.22 (2H, m), 4.2 (1H, m), 3.95 (1H, m), 3.33 (1H, m), 3.13 (1H, m), 2.8 (1H, m), 2.34 (1H, m), 2.04 (1H, m), 1.89 (1H, m), 1.45 (9H, s), 0.85 (3H, m).

Example 145

4-[4-(2-Fluoro-4-tetrazol-1-yl-phenoxymethyl)-thiazol-2-yl]-3-methyl-piperidine-1-carboxylic acid tert-butyl ester

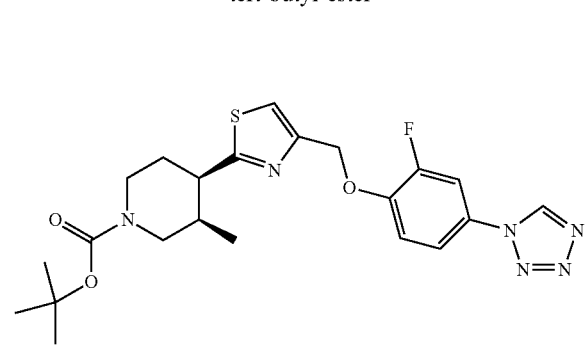

¹H NMR (CDCl₃): δ 9.07 (1H, s), 7.51 (1H, m), 7.41 (1H, m), 7.23 (2H, m), 5.25 (2H, s), 4.16 (1H, m), 3.88 (1H, m), 3.34 (1H, m), 3.09 (1H, m), 2.8 (1H, m), 2.26 (1H, m), 1.96 (1H, m), 1.83 (1H, m), 1.39 (9H, s), 0.76 (3H, m).

Examples 146-157 were synthesized from one of Intermediates 3-13 or Intermediates 15-25 with the corresponding sulfonyl chloride, alkyl chloride, alkyl bromide, chloroformate, acid chloride, carbamyl chloride or isocyanate in a manner similar to that described in Example 22. One skilled in the art of organic synthesis will appreciate that conditions such as solvent (e.g., DMF, CH₃CN); temperature, base (e.g., NEt₃, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 146

4-[4-(2-Fluoro-4-tetrazol-1-yl-phenoxymethyl)-thiazol-2-yl]-piperidine-1-carboxylic acid allyl ester

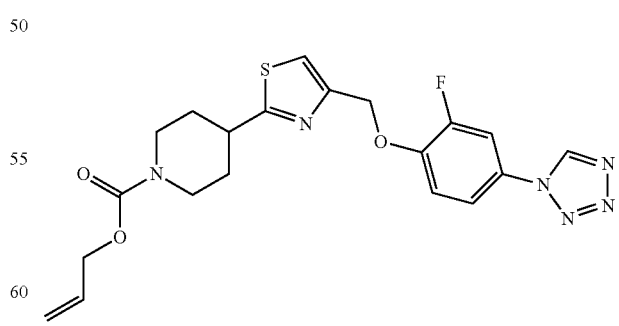

¹H NMR (CDCl₃), δ 9.00 (1H, s), 7.54 (1H, m), 7.45 (1H, m), 7.29 (2H, m), 5.95 (1H, m), 5.30 (3H, m), 5.22 (1H, m), 4.61 (2H, m), 4.28 (2H, m), 3.20 (1H, m), 2.98 (2H, m), 2.14 (2H, m), 1.78 (2H, m).

Example 147

4-[4-(4-Tetrazol-1-yl-phenoxymethyl)-thiazol-2-yl]-piperidine-1-carboxylic acid cyclohexyl ester

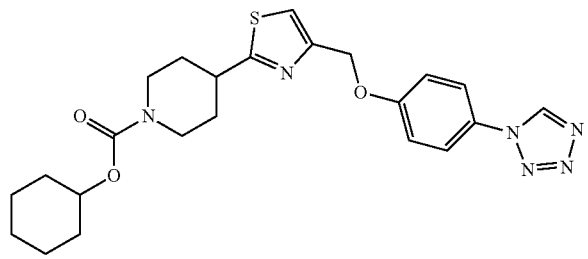 [SMILES: O=C(OC1CCCCC1)N1CCC(c2nc(COc3ccc(-n4cnnn4)cc3)cs2)CC1]

$^1$H NMR (CDCl$_3$): δ 8.91 (1H, s), 7.60 (2H, m), 7.25 (1H, s), 7.16 (2H, m), 5.22 (2H, s), 4.68 (1H, m), 4.36 (2H, m), 3.19 (1H, m), 2.91 (2H, m), 2.12 (2H, m), 1.88 (6H, m), 1.40 (6H, m).

Example 148

4-[4-(2-Fluoro-4-methanesulfonyl-phenoxymethyl)-thiazol-2-yl]-piperidine-1-carboxylic acid isopropyl ester

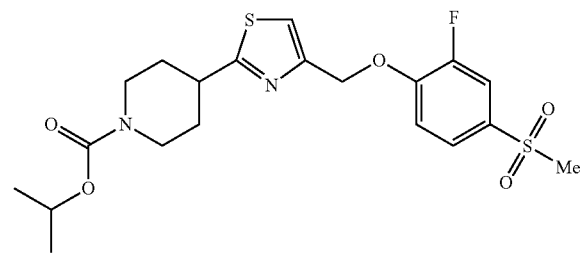 [SMILES: CC(C)OC(=O)N1CCC(c2nc(COc3ccc(S(C)(=O)=O)cc3F)cs2)CC1]

$^1$H NMR (CDCl$_3$): δ 7.64~7.70 (2H, m), 7.20~7.26 (2H, m), 5.29 (2H, s), 4.89~4.95 (1H, m), 4.24 (2H, m), 3.13~3.19 (1H, m), 3.03 (3H, s), 2.86~2.93 (2H, m), 2.11 (2H, m), 1.69~1.78 (2H, m), 1.23 (6H, d, J=6.4 Hz).

Example 149

1-Isopropyl-4-[4-(4-tetrazol-1-yl-phenoxymethyl)-thiazol-2-yl]-piperidine

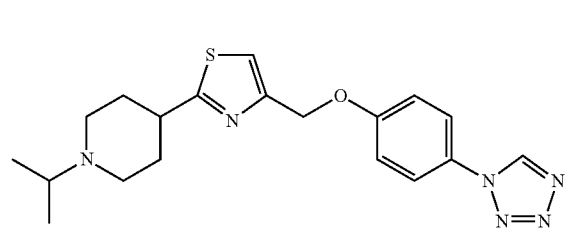 [SMILES: CC(C)N1CCC(c2nc(COc3ccc(-n4cnnn4)cc3)cs2)CC1]

$^1$H NMR (DMSO-d$_6$): δ 9.98 (1H, s), 7.79 (2H, d, J=8.8 Hz), 7.63 (1H, s), 7.28 (2H, d, J=8.8 Hz), 5.19 (2H, s), 2.91 (1H, m), 2.82 (2H, m), 2.68 (1H, m), 2.20 (2H, m), 2.01 (2H, m), 1.63 (2H, m), 0.94 (6H, d, J=6.4 Hz).

Example 150

1-Propyl-4-[4-(4-tetrazol-1-yl-phenoxymethyl)-thiazol-2-yl]-piperidine

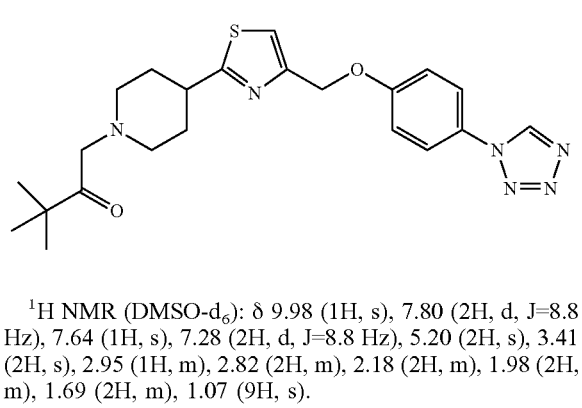

$^1$H NMR (DMSO-d$_6$): δ 9.97 (1H, s), 7.80 (2H, d, J=8.8 Hz), 7.64 (1H, s), 7.28 (2H, d, J=8.8 Hz), 5.20 (2H, s), 2.94 (1H, m), 2.88 (2H, m), 2.22 (2H, t, J=7.2 Hz), 1.99 (4H, m), 1.64 (2H, m), 1.41 (2H, m), 0.83 (3H, t, J=7.2 Hz).

Example 151

3,3-Dimethyl-1-{4-[4-(4-tetrazol-1-yl-phenoxymethyl)-thiazol-2-yl]-piperidin-1-yl}-butan-2-one

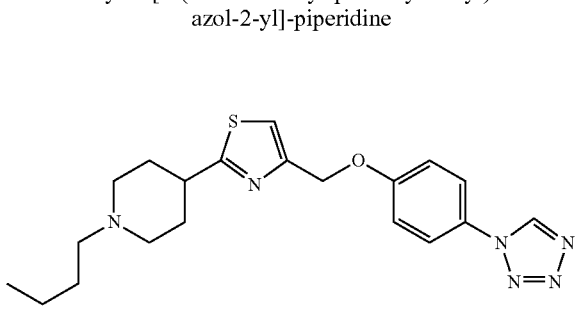

$^1$H NMR (DMSO-d$_6$): δ 9.98 (1H, s), 7.80 (2H, d, J=8.8 Hz), 7.64 (1H, s), 7.28 (2H, d, J=8.8 Hz), 5.20 (2H, s), 3.41 (2H, s), 2.95 (1H, m), 2.82 (2H, m), 2.18 (2H, m), 1.98 (2H, m), 1.69 (2H, m), 1.07 (9H, s).

Example 152

1-Butyl-4-[4-(4-tetrazol-1-yl-phenoxymethyl)-thiazol-2-yl]-piperidine $^1$H NMR (DMSO-d$_6$): δ 9.97 (1H, s), 7.80 (2H, d, J=8.8 Hz), 7.64 (1H, s), 7.28 (2H, d, J=8.8 Hz), 5.20 (2H, s), 2.94 (1H, m), 2.88 (2H, m), 2.26 (2H, t, J=6.8 Hz), 1.98 (4H, m), 1.66 (2H, m), 1.39 (2H, m), 1.26 (2H, m), 0.86 (3H, t, J=7.2 Hz).

Example 153

2-{4-[4-(4-Tetrazol-1-yl-phenoxymethyl)-thiazol-2-yl]-piperidin-1-yl}-1-(4-trifluoromethoxy-phenyl)-ethanone

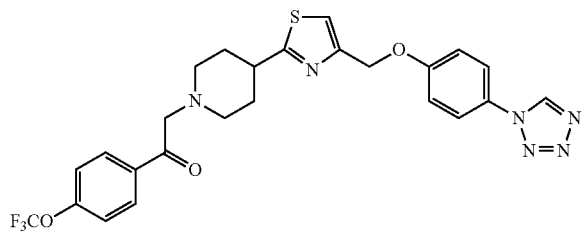 [SMILES: O=C(CN1CCC(c2nc(COc3ccc(-n4cnnn4)cc3)cs2)CC1)c1ccc(OC(F)(F)F)cc1]

$^1$H NMR (DMSO-d$_6$): δ 9.97 (1H, s), 8.14 (2H, d, J=6.4 Hz), 8.02 (2H, d, J=6.4 Hz), 7.80 (2H, d, J=8.8 Hz), 7.64 (1H, s), 7.28 (2H, d, J=8.8 Hz), 5.20 (2H, s), 3.84 (2H, s), 2.98 (1H, m), 2.93 (2H, m), 2.38 (2H, m), 2.00 (2H, m), 1.68 (2H, m).

Example 154

1-Methanesulfonyl-4-[4-(4-tetrazol-1-yl-phenoxymethyl)-thiazol-2-yl]-piperidine

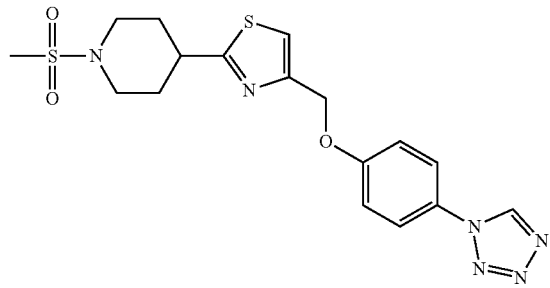 [SMILES: CS(=O)(=O)N1CCC(c2nc(COc3ccc(-n4cnnn4)cc3)cs2)CC1]

$^1$H NMR (DMSO-d$_6$): δ 9.98 (1H, s), 7.81 (2H, d, J=8.8 Hz), 7.69 (1H, s), 7.29 (2H, d, J=8.8 Hz), 5.21 (2H, s), 3.60-3.63 (2H, m), 3.32 (3H, s), 3.12-3.18 (1H, m), 2.83-2.90 (2H, m), 2.14-2.17 (2H, m), 1.71 (2H, m).

Example 155

4-[4-(4-Tetrazol-1-yl-phenoxymethyl)-thiazol-2-yl]-piperidine-1-carboxylic acid heptyl ester

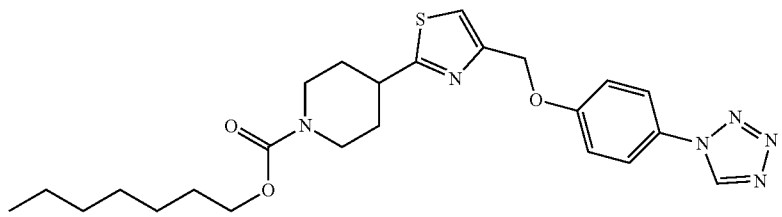 [SMILES: CCCCCCCOC(=O)N1CCC(c2nc(COc3ccc(-n4cnnn4)cc3)cs2)CC1]

$^1$H NMR (CDCl$_3$): δ 8.91 (1H, s), 7.60 (2H, d), 7.25 (1H, s), 7.19 (2H, d), 5.24 (2H, s), 4.26 (2H, br), 4.09 (2H, t), 3.20 (1H, m), 2.94 (2H, m), 2.16 (2H, m), 1.77 (2H, m), 1.60 (2H, m), 1.32 (8H, m), 0.90 (3H, t).

Example 156

4-[4-(4-Tetrazol-1-yl-phenoxymethyl)-thiazol-2-yl]-1-(toluene-4-sulfonyl)-piperidine

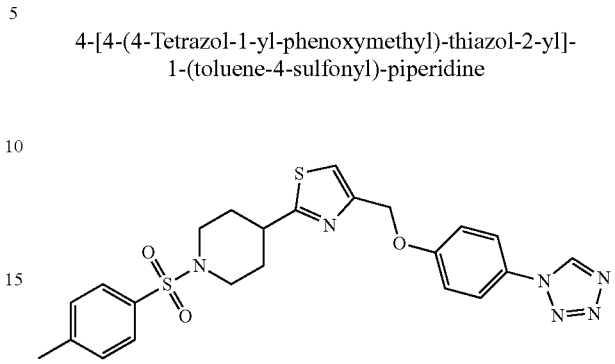

$^1$H NMR (CDCl$_3$): δ 8.91 (1H, s), 7.67 (2H, d, J=8.8 Hz), 7.59 (2H, d, J=8.8 Hz), 7.35 (2H, d, J=8.8 Hz), 7.25 (1H, s), 7.15 (2H, m), 5.19 (2H, s), 3.91 (2H, d), 2.95 (1H, m), 2.44 (3H, s), 2.37 (2H, m), 2.17 (2H, d), 1.94 (2H, m).

Example 157

2-tert-Butoxy-1-{4-[4-(4-tetrazol-1-yl-phenoxymethyl)-thiazol-2-yl]-piperidin-1-yl}-ethanone

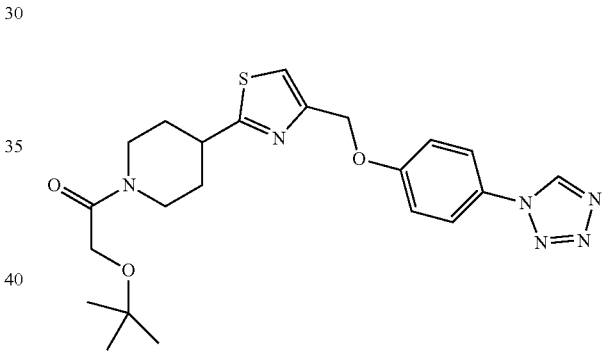

$^1$H NMR (DMSO-d$_6$): δ 9.99 (1H, s), 7.81 (2H, m), 7.26 (2H, m), 5.20 (2H, s), 4.36 (1H, m), 3.97 (3H, m), 3.28 (1H, m), 3.12 (1H, m), 2.71 (1H, m), 2.04 (2H, m), 1.67 (2H, m), 1.46(1H, m), 1.13(9H, s).

Examples 158-205 were synthesized from one of Intermediates 3-13 or Intermediates 15-25 with the corresponding 2-chloropyrimidine, 2-iodopyrimidine, 2-chloropyridine, 2-fluoropyridine, 2-methanesulfonyl-pyrimidine, 2-chloropyrazine, 2-chloropyridazine or other suitable heterocycles in a manner similar to that described in Example 47. One skilled in the art of organic synthesis will appreciate that conditions such as solvent (such as DMF, CH$_3$CN); temperature, base (such as NEt$_3$, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 158

5-Ethyl-2-{4-[4-(3-fluoro-4-tetrazol-1-yl-phenoxymethyl)-thiazol-2-yl]-piperidin-1-yl}-pyrimidine

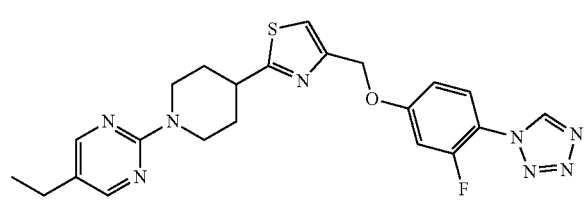 [SMILES: CCc1cnc(N2CCC(c3nc(COc4ccc(-n5cnnn5)c(F)c4)cs3)CC2)nc1]

$^1$H NMR (CDCl$_3$): δ 9.04 (1H, s), 8.19 (2H, s), 7.78 (1H, m), 7.28 (1H, s), 6.70 (2H, m), 5.23 (2H, s), 4.83 (2H, m), 3.31 (1H, m), 3.05 (2H, m), 2.47 (2H, q), 2.21 (2H, m), 1.81 (2H, m), 1.20 (3H, t).

Example 159

2-{4-[4-(2,6-Difluoro-4-tetrazol-1-yl-phenoxymethyl)-thiazol-2-yl]-piperidin-1-yl}-5-ethyl-pyrimidine

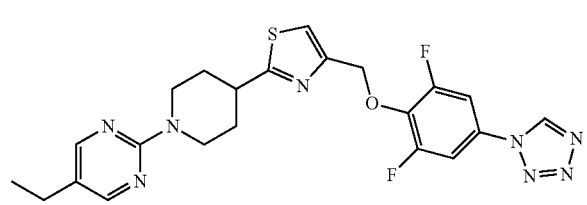 [SMILES: CCc1cnc(N2CCC(c3nc(COc4c(F)cc(-n5cnnn5)cc4F)cs3)CC2)nc1]

$^1$H NMR (CDCl$_3$): δ 8.95 (1H, s), 8.17 (2H, s), 7.34 (2H, m), 7.28 (1H, s), 5.35 (2H, s), 4.76 (2H, m), 3.27 (1H, m), 3.04 (2H, m), 2.46 (2H, q), 2.16 (2H, m), 1.76 (2H, m), 1.19 (3H, t).

Example 160

5-Ethyl-2-{4-[4-(4-pyrrol-1-yl-phenoxymethyl)-thiazol-2-yl]-piperidin-1-yl}-pyrimidine

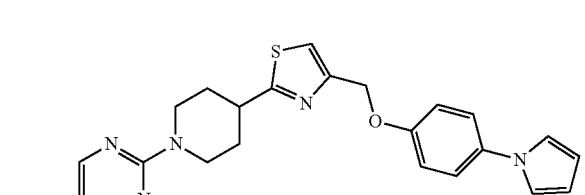

$^1$H NMR (CDCl$_3$): δ 8.18 (2H, s), 7.29 (2H, m), 7.20 (1H, s), 6.99 (4H, m), 6.31 (2H, m), 5.17 (2H, s), 4.84 (2H, m), 3.28 (1H, m), 3.03 (2H, m), 2.46 (2H, q), 2.21 (2H, m), 1.81 (2H, m), 1.19 (3H, t).

Example 161

{2-[1-(5-Ethyl-pyrimidin-2-yl)-piperidin-4-yl]-thiazol-4-ylmethyl}-(4-tetrazol-1-yl-phenyl)-amine

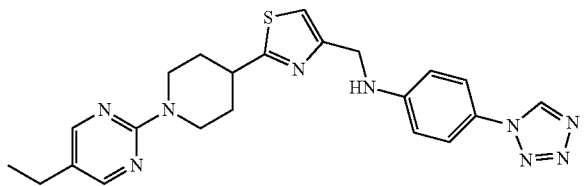 [SMILES: CCc1cnc(N2CCC(c3nc(CNc4ccc(-n5cnnn5)cc4)cs3)CC2)nc1]

$^1$H NMR (CDCl$_3$): δ 8.83 (1H, s), 8.16 (2H, s), 7.41 (2H, m), 7.02 (1H, s), 6.74 (2H, m), 4.82 (1H, s), 4.79 (2H, s), 4.45 (2H, m), 3.25 (1H, m), 3.01 (2H, m), 2.44 (2H, q), 2.17 (2H, m), 1.77 (2H, m), 1.11 (3H, t).

Example 162

2-{4-[4-(2-Fluoro-4-tetrazol-1-yl-phenoxymethyl)-thiazol-2-yl]-piperidin-1-yl}-5-isopropyl-pyrimidine

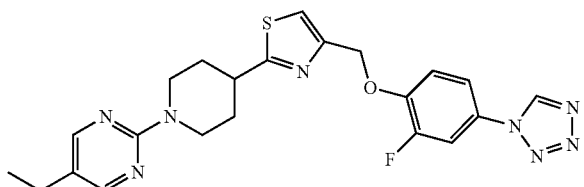

$^1$H NMR (CDCl$_3$): δ 8.92 (1H, s), 8.21 (2H, s), 7.51 (1H, m), 7.40 (1H, m), 7.29 (1H, s), 7.26 (1H, m), 5.30 (2H, s), 4.82 (2H, m), 3.28 (1H, m), 3.04 (2H, m), 2.77 (1H, m), 2.20 (2H, m), 1.80 (2H, m), 1.23 (6H, d).

Example 163

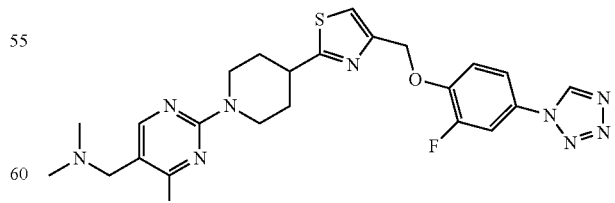

$^1$H NMR (CDCl$_3$): δ 8.97 (1H, s), 7.80 (1H, s), 7.50 (1H, m), 7.40 (1H, m), 7.27 (1H, s), 7.24 (1H, m), 5.27 (2H, s), 4.42 (4H, m), 3.24 (1H, m), 3.04 (9H, m), 2.16 (2H, m), 1.88 (2H, m).

Example 164

5-Ethyl-2-{4-[4-(2-methyl-4-tetrazol-1-yl-phenoxymethyl)-thiazol-2-yl]-piperidin-1-yl}-pyrimidine

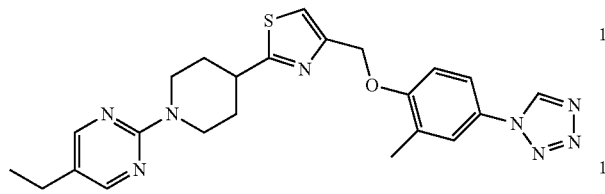

$^1$H NMR (CDCl$_3$): δ 8.88 (1H, s), 8.19 (2H, s), 7.48 (1H, s), 7.44 (1H, m), 7.24 (1H, m), 7.05 (1H, m), 5.26 (2H, s), 4.83 (2H, m), 3.27 (1H, m), 3.05 (2H, m), 2.47 (2H, q), 2.37 (3H, s), 2.22 (2H, m), 1.81 (2H, m), 1.19 (3H, t).

Example 165

5-Chloro-2-{4-[4-(2-chloro-4-tetrazol-1-yl-phenoxymethyl)-thiazol-2-yl]-piperidin-1-yl}-pyrimidine

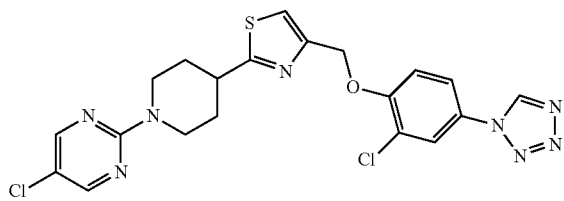 [SMILES: Clc1cnc(N2CCC(c3nc(COc4ccc(-n5cnnn5)cc4Cl)cs3)CC2)nc1]

$^1$H NMR (acetone-d$_6$), δ 9.68 (1H, s), 8.33 (2H, s), 8.01 (1H, s), 7.86 (1H, m), 7.60 (1H, m), 7.59 (1H, s), 5.40 (2H, s), 4.78 (2H, m), 3.40 (1H, m), 3.16 (2H, m), 2.20 (2H, m), 1.77 (2H, m).

Example 166

2-{4-[4-(2-Chloro-4-tetrazol-1-yl-phenoxymethyl)-thiazol-2-yl]-piperidin-1-yl}-5-trifluoromethyl-pyrimidine

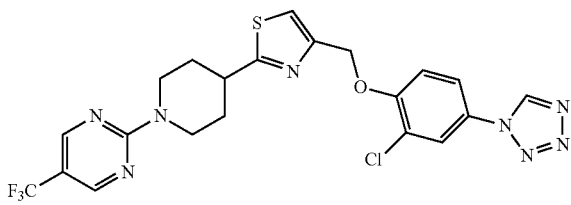 [SMILES: FC(F)(F)c1cnc(N2CCC(c3nc(COc4ccc(-n5cnnn5)cc4Cl)cs3)CC2)nc1]

$^1$H NMR (acetone-d$_6$), δ 9.68 (1H, s), 8.62 (2H, s), 8.01 (1H, s), 7.86 (1H, m), 7.61 (1H, s), 7.60 (1H, m), 5.41 (2H, s), 4.92 (2H, m), 3.46 (1H, m), 3.27 (2H, m), 2.25 (2H, m), 1.80 (2H, m).

Example 167

2-{4-[4-(2-Isopropyl-5-methyl-4-tetrazol-1-yl-phenoxymethyl)-thiazol-2-yl]-piperidin-1-yl}-5-trifluoromethyl-pyrimidine

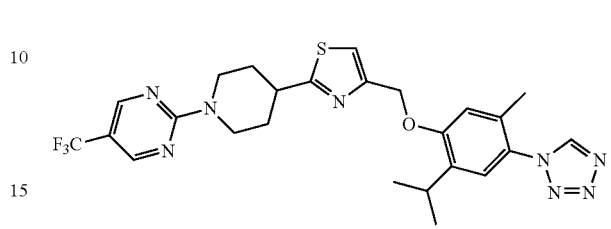

$^1$H NMR (CDCl$_3$): δ 8.73 (1H, s), 8.46 (2H, s), 7.22 (1H, s), 7.10 (1H, s), 6.90 (1H, s), 5.24 (2H, s), 4.93 (2H, m), 3.35 (2H, m), 3.17 (2H, m), 2.23 (2H, m), 2.09 (3H, s), 1.82 (2H, m), 1.20 (6H, d).

Example 168

5-Chloro-2-{4-[4-(2-isopropyl-5-methyl-4-tetrazol-1-yl-phenoxymethyl)-thiazol-2-yl]-piperidin-1-yl}-pyrimidine

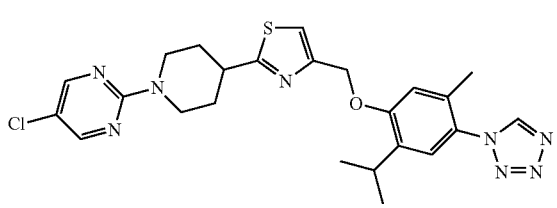 [SMILES: Cc1cc(OCc2csc(C3CCN(c4ncc(Cl)cn4)CC3)n2)c(C(C)C)cc1-n1cnnn1]

$^1$H NMR (CDCl$_3$): δ 8.73 (1H, s), 8.20 (2H, s), 7.21 (1H, s), 7.09 (1H, s), 6.90 (1H, s), 5.24 (2H, s), 4.78 (2H, m), 3.35 (1H, m), 3.28 (1H, m), 3.07 (2H, m), 2.19 (2H, m), 2.09 (3H, s), 1.79 (2H, m), 1.20 (6H, d).

Example 169

5-Ethyl-2-{4-[4-(4-tetrazol-1-yl-phenoxymethyl)-oxazol-2-yl]-piperidin-1-yl}-pyrimidine

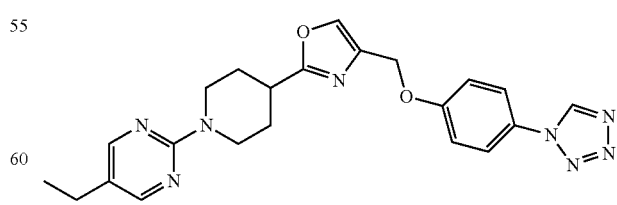

$^1$H NMR (CDCl$_3$): δ 8.91 (1H, s), 8.18 (2H, s), 7.65 (1H, s), 7.60 (2H, m), 7.15 (2H, m), 5.03 (2H, s), 4.69 (2H, m), 3.10 (3H, m), 2.44 (2H, q), 2.14 (2H, m), 1.86 (2H, m), 1.19 (3H, t).

Example 170

5-Ethyl-2-{4-[4-(2-fluoro-4-tetrazol-1-yl-phenoxymethyl)-oxazol-2-yl]-piperidin-1-yl}-pyrimidine

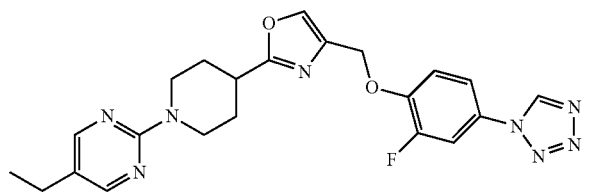 [SMILES: CCc1cnc(N2CCC(c3nc(COc4ccc(-n5cnnn5)cc4F)co3)CC2)nc1]

¹H NMR (CDCl₃): δ 8.93 (1H, s), 8.17 (2H, s), 7.67 (1H, s), 7.50 (1H, m), 7.41 (1H, m), 7.29 (1H, m), 5.11 (2H, s), 4.67 (2H, m), 3.08 (3H, m), 2.45 (2H, q), 2.12 (2H, m), 1.84 (2H, m), 1.18 (3H, t).

Example 171

2-{4-[4-(2-Fluoro-4-tetrazol-1-yl-phenoxymethyl)-thiazol-2-yl]-piperidin-1-yl}-5-trifluoromethyl-pyrimidine

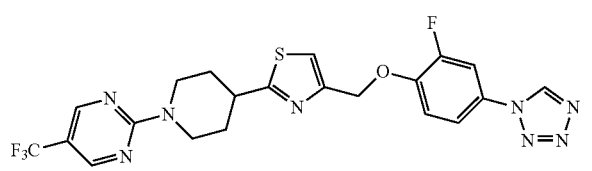 [SMILES: Fc1cc(-n2cnnn2)ccc1OCc1csc(C2CCN(c3ncc(C(F)(F)F)cn3)CC2)n1]

¹H NMR (CDCl₃): δ 8.91 (1H, s), 8.49 (2H, s), 7.52 (1H, d, J=7.6 Hz), 7.41 (1H, d, J=7.6 Hz), 7.32 (1H, s), 7.29 (1H, m), 5.32 (2H, s), 4.95 (2H, m), 3.37 (1H, m), 3.15 (2H, m), 2.24 (2H, m), 1.81 (2H, m).

Example 172

5-Decyl-2-{4-[4-(4-tetrazol-1-yl-phenoxymethyl)-thiazol-2-yl]-piperidin-1-yl}-pyrimidine

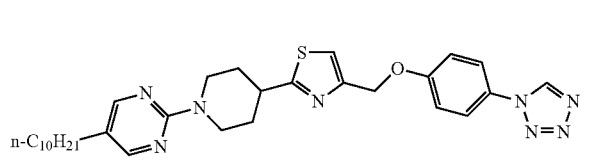

¹H NMR (DMSO-d₆): δ 9.97 (1H, s), 8.21 (2H, s), 7.80 (2H, d, J=8.8 Hz), 7.65 (1H, s), 7.28 (2H, d, J=8.8 Hz), 5.20 (2H, s), 4.66 (2H, m), 3.32 (1H, m), 3.01 (2H, m), 2.37 (2H, m), 2.09 (2H, m), 1.60 (2H, m), 1.45 (2H, m), 1.21 (14H, m), 0.82 (3H, m).

Example 173

6-Methyl-2-{4-[4-(4-tetrazol-1-yl-phenoxymethyl)-thiazol-2-yl]-piperidin-1-yl}-pyrimidine-4-carboxylic acid methyl ester

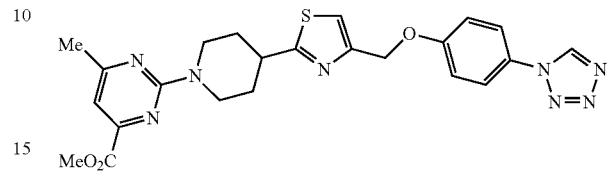

¹H NMR (DMSO-d₆): δ 9.97 (1H, s), 7.80 (2H, d, J=8.8 Hz), 7.66 (1H, s), 7.28 (2H, d, J=8.8 Hz), 7.01 (1H, s), 5.21 (2H, s), 4.76 (2H, m), 3.84 (3H, s), 3.33 (1H, m), 3.06 (2H, m), 2.36 (3H, s), 2.14 (2H, m), 1.61 (2H, m).

Example 174

4-Chloro-2-{4-[4-(4-tetrazol-1-yl-phenoxymethyl)-thiazol-2-yl]-piperidin-1-yl}-pyrimidine

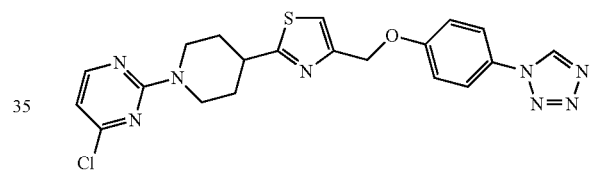

¹H NMR (CDCl₃): δ 8.91 (1H, s), 8.15 (1H, d, J=5.2 Hz), 7.60 (2H, d, J=8.8 Hz), 7.25 (1H, s), 7.16 (2H, d, J=8.8 Hz), 6.49 (1H, d, J=5.2 Hz), 5.22 (2H, s), 4.85 (2H, m), 3.30 (1H, m), 3.07 (2H, m), 2.21 (2H, m), 1.80 (2H, m).

Example 175

2-Chloro-4-{4-[4-(4-tetrazol-1-yl-phenoxymethyl)-thiazol-2-yl]-piperidin-1-yl}-pyrimidine

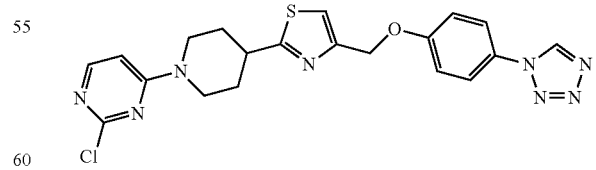

¹H NMR (CDCl₃): δ 8.90 (1H, s), 8.05 (1H, d, J=6.4 Hz), 7.61 (2H, d, J=8.8 Hz), 7.28 (1H, s), 7.17 (2H, d, J=8.8 Hz), 6.46 (1H, d, J=6.4 Hz), 5.23 (2H, s), 4.45 (2H, m), 3.35 (1H, m), 3.15 (2H, m), 2.27 (2H, m), 1.85 (2H, m).

Example 176

6-Methyl-2-{4-[4-(4-tetrazol-1-yl-phenoxymethyl)-thiazol-2-yl]-piperidin-1-yl}-pyrimidine-4-carboxylic acid

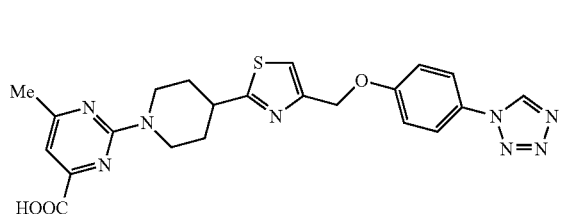 [SMILES: Cc1cc(C(=O)O)nc(N2CCC(c3nc(COc4ccc(-n5cnnn5)cc4)cs3)CC2)n1]

$^1$H NMR (DMSO-d$_6$): δ 13.3 (1H, br), 9.97 (1H, s), 7.80 (2H, d, J=8.8 Hz), 7.66 (1H, s), 7.28 (2H, d, J=8.8 Hz), 6.98 (1H, s), 5.21 (2H, s), 4.79 (2H, m), 3.34 (1H, m), 3.05 (2H, m), 2.35 (3H, s), 2.13 (2H, m), 1.62 (2H, m).

Example 177

5-Chloro-4,6-difluoro-2-{4-[4-(4-tetrazol-1-yl-phenoxymethyl)-thiazol-2-yl]-piperidin-1-yl}-pyrimidine

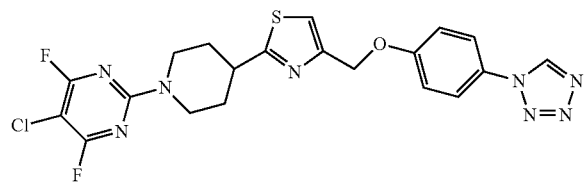 [SMILES: Fc1nc(N2CCC(c3nc(COc4ccc(-n5cnnn5)cc4)cs3)CC2)nc(F)c1Cl]

$^1$H NMR (CDCl$_3$): δ 8.91 (1H, s), 7.61 (2H, d, J=8.8 Hz), 7.27 (1H, s), 7.16 (2H, d, J=8.8 Hz), 5.23 (2H, s), 4.69 (2H, m), 3.32 (1H, m), 3.10 (2H, m), 2.23 (2H, m), 1.80 (2H, m).

Example 178

4-Fluoro-2-{4-[4-(4-tetrazol-1-yl-phenoxymethyl)-thiazol-2-yl]-piperidin-1-yl}-pyrimidine

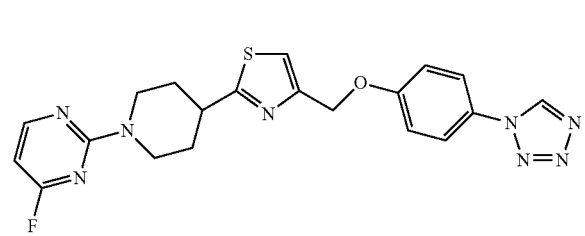 [SMILES: Fc1ccnc(N2CCC(c3nc(COc4ccc(-n5cnnn5)cc4)cs3)CC2)n1]

$^1$H NMR (DMSO-d$_6$): δ 9.97 (1H, s), 8.41 (1H, m), 7.80 (2H, d, J=8.0 Hz), 7.66 (1H, s), 7.28 (2H, d, J=8.0 Hz), 6.34 (1H, m), 5.20 (2H, s), 4.60 (2H, m), 3.32 (1H, m), 3.10 (2H, m), 2.11 (2H, m), 1.61 (2H, m).

Example 179

2-Fluoro-4-{4-[4-(4-tetrazol-1-yl-phenoxymethyl)-thiazol-2-yl]-piperidin-1-yl}-pyrimidine

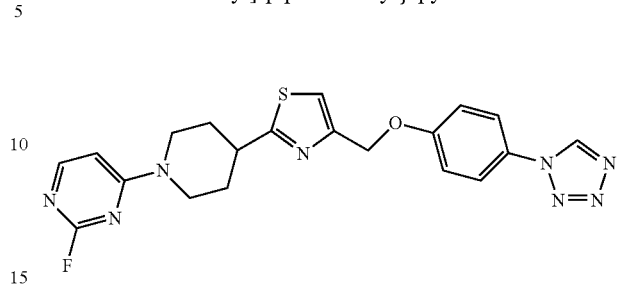

$^1$H NMR (DMSO-d$_6$): δ 9.98 (1H, s), 8.08 (1H, m), 7.80 (2H, d, J=9.2 Hz), 7.67 (1H, s), 7.28 (2H, d, J=9.2 Hz), 6.84 (1H, m), 5.20 (2H, s), 4.40 (2H, m), 3.40 (1H, m), 3.14 (2H, m), 2.13 (2H, m), 1.63 (2H, m).

Example 180

2-{4-[4-(4-Tetrazol-1-yl-phenoxymethyl)-thiazol-2-yl]-piperidin-1-yl}-thiazole-5-carboxylic acid ethyl ester

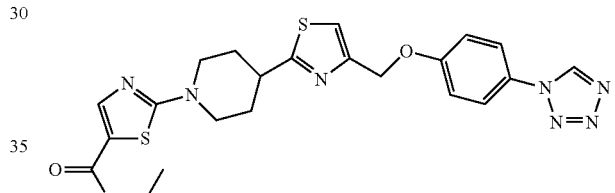

$^1$H NMR (DMSO-d$_6$): δ 9.97 (1H, s), 7.84 (1H, m), 7.80 (2H, d, J=9.0 Hz), 7.68 (1H, s), 7.28 (2H, d, J=9.0 Hz), 5.21 (2H, s), 4.19 (2H, t, J=7.20 Hz), 4.03 (2H, m), 3.35 (3H, m), 2.15 (2H, m), 1.75 (2H, m), 1.23 (3H, t, J=7.20 Hz).

Example 181

4-Imidazol-1-yl-6-{4-[4-(4-tetrazol-1-yl-phenoxymethyl)-thiazol-2-yl]-piperidin-1-yl}-pyrimidine

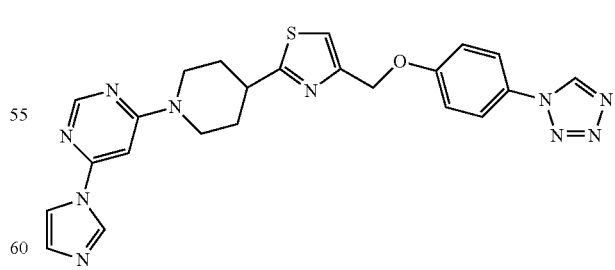

$^1$H NMR (DMSO-d$_6$): δ 9.98 (1H, s), 8.59 (1H, s), 8.43 (1H, s), 8.01 (1H, d, J=1.2 Hz), 7.81 (2H, d, J=8.8 Hz), 7.67 (1H, s), 7.27 (2H, d, J=8.8 Hz), 7.14 (1H, s), 7.10 (1H, d, J=1.2 Hz), 5.20 (2H, s), 4.61 (2H, m), 3.40 (1H, m), 3.15 (2H, m), 2.15 (2H, m), 1.66 (2H, m).

Example 182

5-Ethyl-2-{4-[4-(6-tetrazol-1-yl-pyridin-3-yloxymethyl)-thiazol-2-yl]-piperidin-1-yl}-pyrimidine

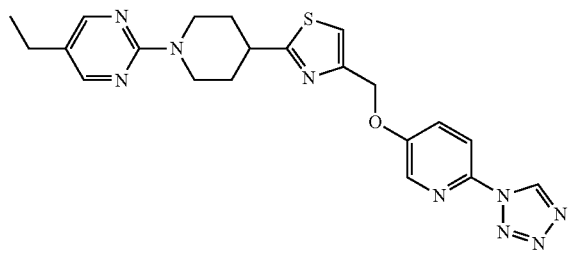 [SMILES: CCc1cnc(N2CCC(c3nc(COc4ccc(-n5cnnn5)nc4)cs3)CC2)nc1]

¹H NMR (CDCl₃): δ 9.44 (1H, s), 8.28 (1H, d, J=3.0 Hz), 8.2 (2H, s), 8.02, (1H, d, J=8.8 Hz), 7.58 (1H, dd, J=8.8 Hz, 3.0 Hz), 7.27 (1H, s), 5.27 (2H, s), 4.82-4.85 (2H, m), 3.22-3.35 (1H, m), 3.0-3.1, (2H, m), 2.47 (2H, q, J=7.2 Hz), 2.2-2.23 (2H, m), 1.76-1.86 (2H, m), 1.19 (3H, t, J=7.2 Hz).

Example 183

5-Methyl-2-{4-[4-(6-tetrazol-1-yl-pyridin-3-yloxymethyl)-thiazol-2-yl]-piperidin-1-yl}-pyrimidine

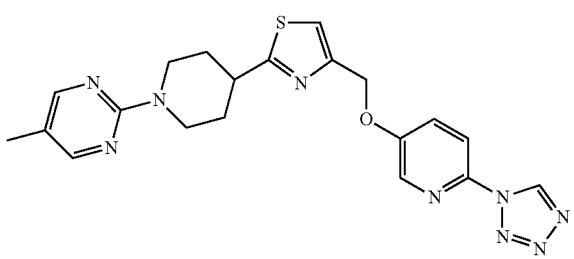 [SMILES: Cc1cnc(N2CCC(c3nc(COc4ccc(-n5cnnn5)nc4)cs3)CC2)nc1]

¹H NMR (DMSO-d₆): δ 10.07 (1H, s), 8.42 (1H, d, J=3.0 Hz), 8.21 (2H, s), 7.99 (1H, d, J=9.2 Hz), 7.86 (1H, dd, J=9.2 Hz, 3.0 Hz), 7.70 (1H, s), 5.30 (2H, s), 4.62 (2H, m), 3.56-3.60 (1H, m), 2.98-3.04 (2H, m), 2.06 (3H, s), 1.72-1.76 (2H, m), 1.59 (2H, m).

Example 184

5-Chloro-2-{4-[4-(6-tetrazol-1-yl-pyridin-3-yloxymethyl)-thiazol-2-yl]-piperidin-1-yl}-pyrimidine

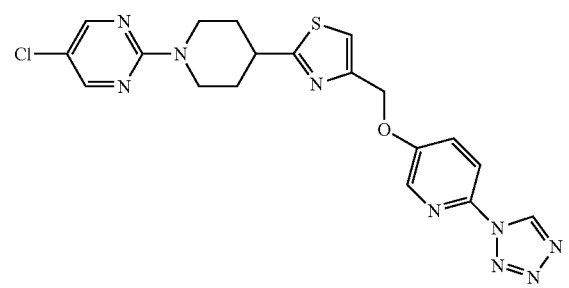 [SMILES: Clc1cnc(N2CCC(c3nc(COc4ccc(-n5cnnn5)nc4)cs3)CC2)nc1]

¹H NMR (CDCl₃) δ 9.44 (1H, s), 8.28 (1H, d, J=3.0 Hz), 8.23 (2H, s), 8.02 (1H, d, J=9.0 Hz), 7.58 (1H, dd, J=9.0 Hz, 3.0 Hz), 7.28 (1H, s), 5.27 (2H, s), 4.8-4.83 (2H, m), 3.22-3.38 (1H, m), 3.04-3.11 (2H, m), 2.20-2.23 (2H, m), 1.80 (2H, m)

Example 185

2-{4-[4-(6-Tetrazol-1-yl-pyridin-3-yloxymethyl)-thiazol-2-yl]-piperidin-1-yl}-5-trifluoromethyl-pyrimidine

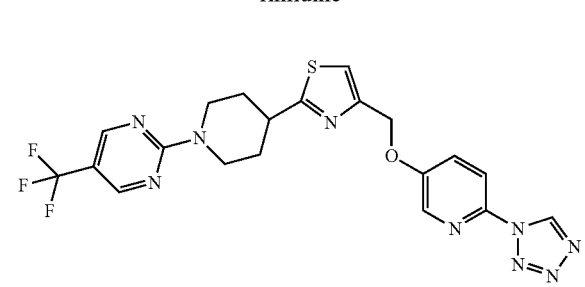

¹H NMR (DMSO-d₆): δ 10.07 (1H, s), 8.68 (2H, s), 8.42 (1H, d, J=3.0 Hz), 7.99 (1H, d, J=9.2 Hz), 7.86 (1H, dd, J=9.2 Hz, 3.0 Hz), 7.72 (1H, s), 5.73 (2H, s), 4.74-4.77 (2H, m), 3.37-3.43 (1H, m), 3.15-3.21 (2H, m), 2.12-2.16 (2H, m), 1.59-1.68 (2H, m).

Example 186

3-Chloro-6-{4-[4-(4-tetrazol-1-yl-phenoxymethyl)-thiazol-2-yl]-piperidin-1-yl}-pyridazine

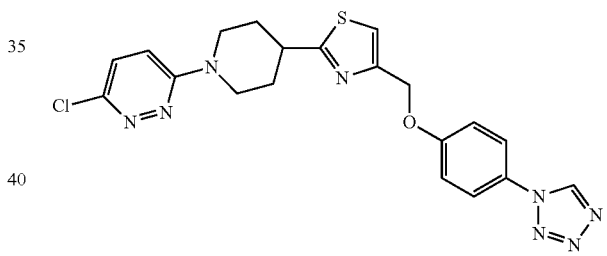

¹H NMR (CDCl₃): δ 8.91 (1H, s), 7.61 (2H, d, J=9.0 Hz), 7.26 (1H, s), 7.22 (1H, d, J=9.6 Hz), 7.17 (2H, d, J=9.0 Hz), 6.95 (1H, d, J=9.6 Hz), 5.23 (2H, s), 4.43-4.47 (2H, m), 3.31-3.37 (1H, m), 3.12-3.19 (2H, m), 2.25-2.28 (2H, m), 1.90 (2H, m).

Example 187

2-Tetrazol-1-yl-5-{4-[4-(4-tetrazol-1-yl-phenoxymethyl)-thiazol-2-yl]-piperidin-1-yl}-pyrazine

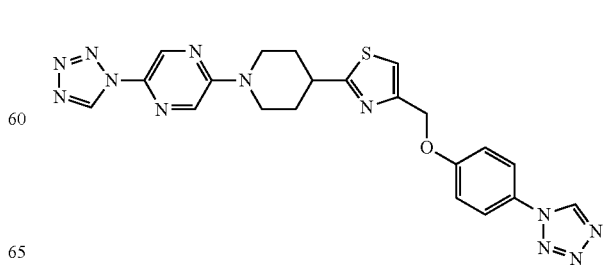

¹H NMR (DMSO-d₆): δ 9.97 (2H, s), 8.67 (1H, s), 8.37 (1H, s), 7.80 (2H, d, J=8.8 Hz), 7.67 (1H, s), 7.28 (2H, d, J=8.8 Hz), 5.21 (2H, s), 4.50-4.53 (2H, m), 3.38-3.44 (1H, m), 3.17-3.23 (2H, m), 2.15-2.18 (2H, m), 1.69-1.77 (2H, m).

Example 188

{2-[1-(5-Ethyl-pyrimidin-2-yl)-piperidin-4-yl]-thiazol-4-ylmethyl}-(6-fluoro-pyridin-3-yl)-amine

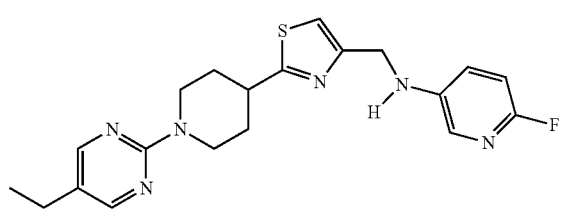 [SMILES: CCc1cnc(N2CCC(c3nc(CNc4ccc(F)nc4)cs3)CC2)nc1]

¹H NMR (CDCl₃): δ 8.19 (2H, s), 7.58-7.62 (1H, m), 7.05-7.10 (1H, m), 7.01 (1H, s), 6.75 (1H, dd, J=8.4 Hz, 2.8 Hz), 4.81-4.85 (2H, m), 4.40 (2H, d, J=5.2 Hz), 4.29 (1H, br s), 3.23-3.29 (1H, m), 3.00-3.06 (2H, m), 2.47 (2H, q, J=7.6 Hz), 2.18-2.20 (2H, m), 1.79 (2H, m), 1.20 (3H, t, J=7.6 Hz).

Example 189

2-{4-[4-(2,6-Difluoro-4-methanesulfonyl-phenoxymethyl)-thiazol-2-yl]-piperidin-1-yl}-5-ethyl-pyrimidine

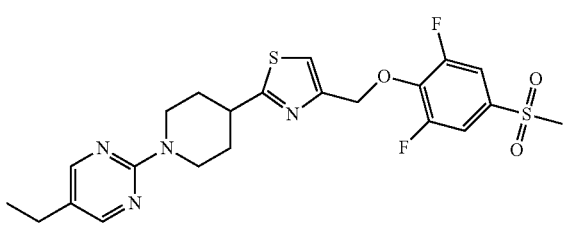 [SMILES: CCc1cnc(N2CCC(c3nc(COc4c(F)cc(S(C)(=O)=O)cc4F)cs3)CC2)nc1]

¹H NMR (CDCl₃): δ 8.19 (2H, s,), 7.51 (2H, d), 7.25 (1H, s), 5.40 (2H, s), 4.82 (2H, m), 3.30 (1H, m), 3.06 (3H, s), 3.03 (2H, m), 2.48 (2H, q), 2.15 (2H, m), 1.74 (2H, m), 1.20 (3H, t).

Example 190

5-Butyl-2-{4-[4-(4-tetrazol-1-yl-phenoxymethyl)-thiazol-2-yl]-piperidin-1-yl}-pyrimidine

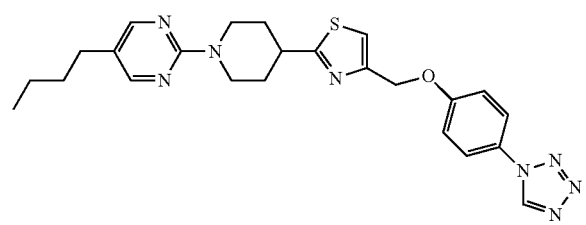 [SMILES: CCCCc1cnc(N2CCC(c3nc(COc4ccc(-n5cnnn5)cc4)cs3)CC2)nc1]

¹H NMR (CDCl₃): δ 8.92 (1H, s), 8.17 (2H, s), 7.62 (2H, m), 7.25 (1H, s), 7.17 (2H, m), 5.24 (2H, s), 4.83 (2H, m), 3.30 (1H, m), 3.04 (2H, m), 2.42 (2H, t), 2.23 (2H, m), 1.84 (2H, m), 1.52 (2H, m), 1.34 (2H, m), 0.92 (3H, m).

Example 191

4-(4-{2-[1-(5-Ethyl-pyrimidin-2-yl)-piperidin-4-yl]-thiazol-4-ylmethoxy}-phenyl)-morpholine

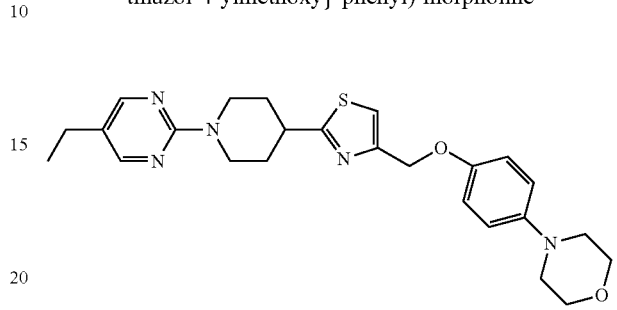

¹H NMR (CDCl₃): δ 8.18 (2H, s), 7.19 (1H, s), 6.92 (4H, m), 5.12 (2H, s), 4.84 (2H, m), 3.86 (4H, br), 3.30 (1H, m), 3.05 (6H, m), 2.46 (2H, q), 2.21 (2H, m), 1.78 (2H, m), 1.19 (3H, t).

Example 192

5-Nitro-2-{4-[4-(4-tetrazol-1-yl-phenoxymethyl)-thiazol-2-yl]-piperidin-1-yl}-pyrimidine

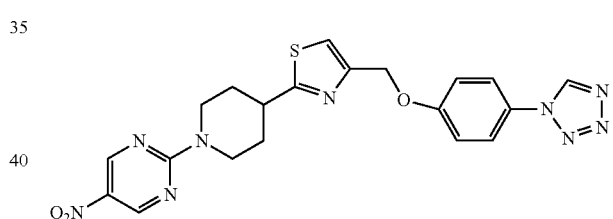

¹H NMR (DMSO-d₆): δ 9.91 (1H, s), 9.11 (2H, s), 7.83 (2H, d, J=8.8 Hz), 7.68 (1H, s), 7.25 (2H, d, J=8.8 Hz), 5.22 (2H, s), 4.81 (2H, m), 3.39 (1H, m), 3.31 (2H, m), 2.23 (2H, s), 1.68 (2H, m).

Example 193

3'-Chloro-4-[4-(4-tetrazol-1-yl-phenoxymethyl)-thiazol-2-yl]-5'-trifluoromethyl-3,4,5,6-tetrahydro-2H-[1,2']bipyridinyl

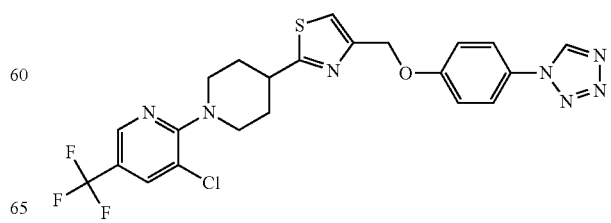

¹H NMR (CDCl₃): δ 8.91 (1H, s), 8.39 (1H, s), 7.76 (1H, s), 7.61 (2H, m), 7.25 (1H, s), 7.18 (2H, m), 5.24 (2H, s), 4.16 (2H, m), 3.26 (1H, m), 3.06 (2H, m), 2.25 (2H, m), 2.01 (2H, m).

Example 194

3'-Chloro-4-[4-(2-fluoro-4-tetrazol-1-yl-phenoxymethyl)-thiazol-2-yl]-5'-trifluoromethyl-3,4,5,6-tetrahydro-2H-[1,2']bipyridinyl

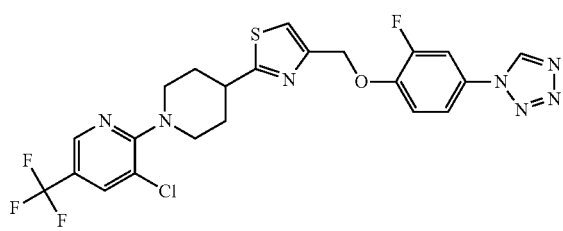 [SMILES: Fc1cc(-n2cnnn2)ccc1OCc1csc(C2CCN(c3ncc(C(F)(F)F)cc3Cl)CC2)n1]

¹H NMR (CDCl₃): δ 8.94 (1H, s), 8.38 (1H, s), 7.75 (1H, s), 7.53 (1H, m), 7.40 (1H, m), 7.31 (1H, s), 7.25 (1H, m), 5.31 (2H, s), 4.15 (2H, d), 3.25 (1H, m), 3.09 (2H, m), 2.23 (2H, d), 1.99 (2H, m).

Example 195

5-Chloro-2-{4-[4-(2-fluoro-4-tetrazol-1-yl-phenoxymethyl)-thiazol-2-yl]-piperidin-1-yl}-pyrimidine

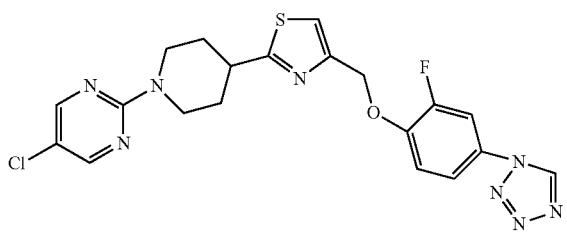 [SMILES: Fc1cc(-n2cnnn2)ccc1OCc1csc(C2CCN(c3ncc(Cl)cn3)CC2)n1]

¹H NMR (CDCl₃): δ 8.96 (1H, s), 8.20 (2H, s), 7.52 (1H, m), 7.40 (1H, m), 7.28 (1H, s), 7.25 (1H, m), 5.28 (2H, s), 4.78 (2H, m), 3.30 (1H, m), 3.07 (2H, m), 2.20 (2H, m), 1.79 (2H, m).

Example 196

3',5'-Dichloro-4-[4-(4-tetrazol-1-yl-phenoxymethyl)-thiazol-2-yl]-3,4,5,6-tetrahydro-2H-[1,2']bipyridinyl

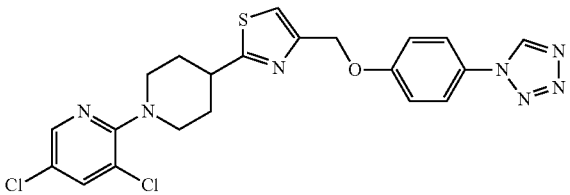 [SMILES: Clc1cnc(N2CCC(c3nc(COc4ccc(-n5cnnn5)cc4)cs3)CC2)c(Cl)c1]

¹H NMR (DMSO-d₆): δ 9.98 (1H, s), 8.26 (1H, s), 8.03 (1H, s), 7.81 (2H, d), 7.67 (1H, s), 7.29 (2H, d), 5.21 (2H, s), 3.79 (2H, m), 3.24 (1H, m), 2.97 (2H, m), 2.14 (2H, m), 1.84 (2H, m).

Example 197

3'-Chloro-4-[4-(4-tetrazol-1-yl-phenoxymethyl)-thiazol-2-yl]-3,4,5,6-tetrahydro-2H-[1,2']bipyridinyl-5'-carboxylic acid ethyl ester

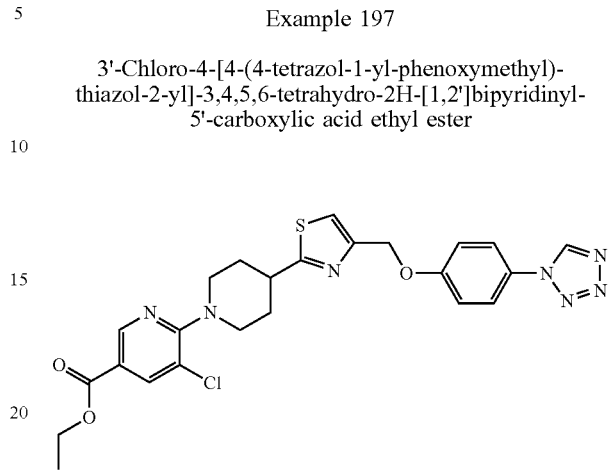

¹H NMR (CDCl₃): δ 8.92 (1H, s), 8.74 (1H, s), 8.11 (1H, s), 7.61 (2H, d), 7.25 (1H, s), 7.17 (2H, d), 5.23 (2H, s), 4.37 (2H, m), 4.22 (2H, m), 3.31 (1H, m), 3.08 (2H, m) 2.26 (2H, m), 1.98 (2H, m), 1.38 (3H, m).

Example 198

5'-Chloro-4-[4-(4-tetrazol-1-yl-phenoxymethyl)-thiazol-2-yl]-3,4,5,6-tetrahydro-2H-[1,2']bipyridinyl-3'-carboxylic acid methyl ester

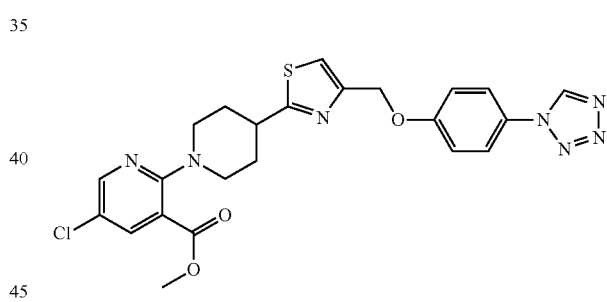

¹H NMR (CDCl₃): δ 8.91 (1H, s), 8.20 (1H, s), 7.99 (1H, s), 7.61 (2H, d), 7.25 (1H, s), 7.16 (2H, d), 5.21 (2H, s), 3.91 (2H, m), 3.88 (3H, s), 3.28 (1H, m), 3.08 (2H, m), 2.20 (2H, m), 1.93 (2H, m).

Example 199

5-Ethyl-2-{3-methyl-4-[4-(4-tetrazol-1-yl-phenoxymethyl)-thiazol-2-yl]-piperidin-1-yl}-pyrimidine

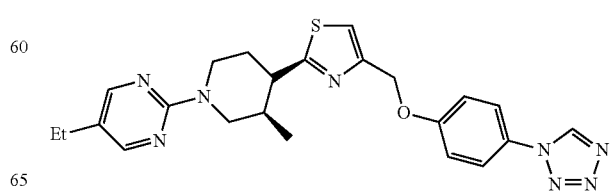

¹H NMR (CDCl₃): δ 8.90 (1H, s), 8.18 (2H), 7.60 (2H, m), 7.25 (1H, s), 7.17 (2H, m), 5.26 (2H), 4.89-4.51 (2H, m), 3.49-3.20 (2H, m), 2.92 (1H, m), 2.65-2.45 (1H, m), 2.45 (2H, m), 2.17-1.81 (2H, m), 1.20 (3H, m), 0.82-0.92 (3H).

Example 200

5-Ethyl-2-{4-[4-(2-fluoro-4-tetrazol-1-yl-phenoxymethyl)-thiazol-2-yl]-3-methyl-piperidin-1-yl}-pyrimidine

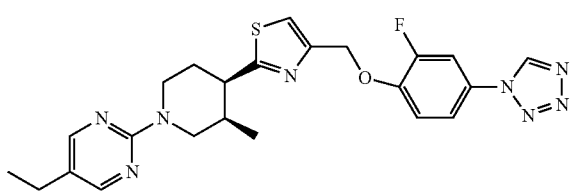 [SMILES: CCc1cnc(N2CC[C@@H](c3nc(COc4ccc(-n5cnnn5)cc4F)cs3)[C@@H](C)C2)nc1]

¹H NMR (CDCl₃): δ 8.93 (1H, s), 8.17 (2H), 7.52-7.25 (4H, m), 5.32 (2H), 4.84-4.46 (2H, m), 3.47-3.22 (2H, m), 2.91 (1H, m), 2.62-2.43 (1H, m), 2.42 (2H, m), 2.07 (2H, m), 1.18 (3H, m), 0.90-0.79 (3H, m).

Example 201

5-Chloro-2-{4-[4-(2-fluoro-4-tetrazol-1-yl-phenoxymethyl)-thiazol-2-yl]-3-methyl-piperidin-1-yl}-pyrimidine

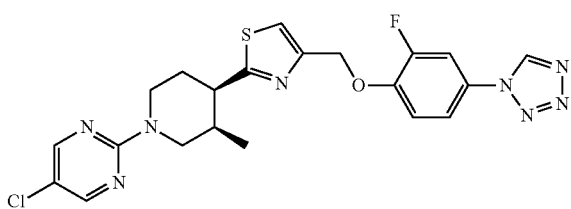 [SMILES: C[C@H]1CN(c2ncc(Cl)cn2)CC[C@H]1c1nc(COc2ccc(-n3cnnn3)cc2F)cs1]

¹H NMR (CDCl₃): δ 8.93 (1H, s), 8.19 (2H), 7.52-7.25 (4H, m), 5.29 (2H), 4.82-4.51 (2H, m), 3.46-3.21 (2H, m), 2.95 (1H, m), 2.64-2.42 (1H, m), 2.02 (2H, m), 0.90-0.78 (3H, m).

Example 202

2-{4-[4-(2-Fluoro-4-tetrazol-1-yl-phenoxymethyl)-thiazol-2-yl]-3-methyl-piperidin-1-yl}-5-trifluoromethyl-pyrimidine

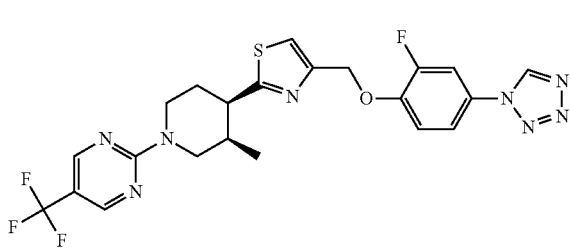 [SMILES: C[C@H]1CN(c2ncc(C(F)(F)F)cn2)CC[C@H]1c1nc(COc2ccc(-n3cnnn3)cc2F)cs1]

¹H NMR (CDCl₃): δ 8.94 (1H, s), 8.47 (2H), 7.53-7.27 (4H, m), 5.34 (2H), 5.02-4.62 (2H, m), 3.52-2.97 (3H, m), 2.73-2.47 (1H, m), 2.17-2.01 (2H, m), 0.94-0.78 (3H, m).

Example 203

5-Ethyl-2-{4-[4-(4-methanesulfonyl-benzyloxymethyl)-thiazol-2-yl]-piperidin-1-yl}-pyrimidine

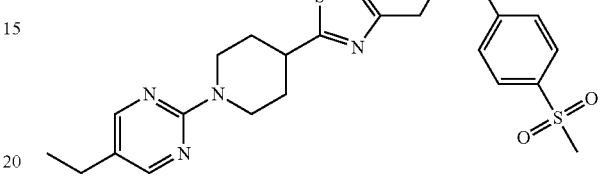

¹H NMR (CDCl₃): δ 8.17 (2H, s), 7.92 (2H, d, J=8.8 Hz), 7.58 (2H, d, J=8.8 Hz), 7.13 (1H, s), 4.83 (2H, m), 4.71 (2H, s), 4.66 (2H, s), 3.27 (1H, m), 3.03 (3H, s), 2.98 (2H, m), 2.46 (2H, m), 2.19 (2H, m), 1.76 (2H, m), 1.19 (3H, m).

Example 204

5-Fluoro-2-{4-[4-(2-fluoro-4-tetrazol-1-yl-phenoxymethyl)-thiazol-2-yl]-piperidin-1-yl}-pyrimidine

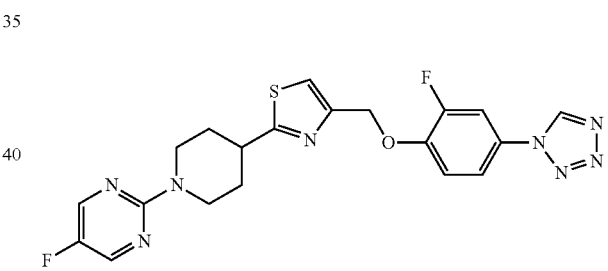

¹H NMR (CDCl₃): δ 8.91 (1H, s), 8.21 (2H, s), 7.52 (1H, m), 7.41 (1H, m), 7.27 (1H, m), 7.25 (1H, s), 5.31 (2H, s), 4.76 (2H, m), 3.28 (1H, m), 3.06 (2H, m), 2.20 (2H, m), 1.81 (2H, m).

Example 205

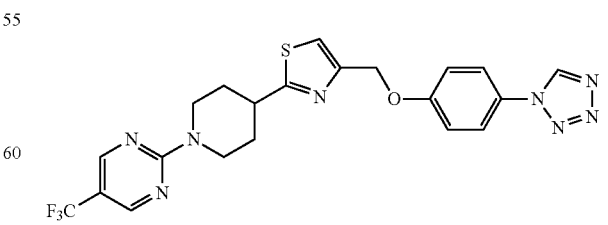

¹H NMR (CDCl₃): δ 8.91 (1H, s), 8.49 (2H, s), 7.61 (2H, d), 7.27 (1H, s), 7.17 (2H, d), 5.24 (2H, s), 4.96 (2H, m), 3.38 (1H, m), 3.14 (2H, m), 2.26 (2H, m), 1.82(2H, m).

Example 206

4-(4-{[(4-Methanesulfonyl-phenyl)-methyl-amino]-methyl}-thiazol-2-yl)-piperidine-1-carboxylic acid tert-butyl ester

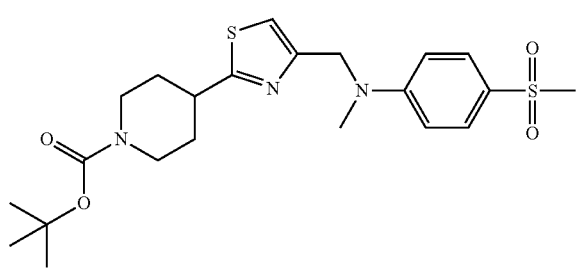 [SMILES: CN(Cc1csc(C2CCN(C(=O)OC(C)(C)C)CC2)n1)c1ccc(S(C)(=O)=O)cc1]

4-{4-[(4-Methanesulfonyl-phenylamino)-methyl]-thiazol-2-yl}-piperidine-1-carboxylic acid tert-butyl ester (Example 138) (0.10 mmol) was dissolved in DMF (2 mL) and NaH (2 eq.) was added in a single portion at room temperature. The reaction was stirred for 30 minutes and methyl iodide (10 eq.) was added. After stirring for 3 hours, the reaction was quenched with water and extracted with EtOAc. The organic layer was washed with brine, dried over sodium sulfate, filtered and concentrated in vacuo. Purification of the residue by silica gel chromatography (Hexanes/EtOAc 1:1) provided the expected product. $^1$H NMR (CDCl$_3$): δ 7.73 (2H, m), 6.78 (2H, m), 6.76 (1H, s), 4.70 (2H, s), 4.20 (2H, br), 3.19 (3H, s), 3.12 (1H, m), 3.01 (3H, s), 2.87 (2H, m), 2.07 (2H, m), 1.80 (2H, m), 1.47 (9H, s).

Example 207

{2-[1-(5-Ethyl-pyrimidin-2-yl)-piperidin-4-yl]-thiazol-4-ylmethyl}-(2-fluoro-4-methanesulfonyl-phenyl)-methyl-amine

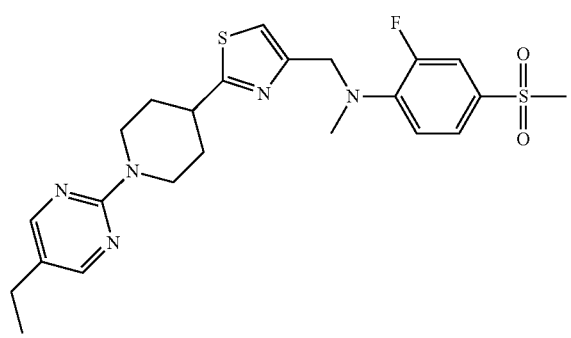 [SMILES: CCc1cnc(N2CCC(c3nc(CN(C)c4ccc(S(C)(=O)=O)cc4F)cs3)CC2)nc1]

Example 207 was synthesized in a manner analogous to Example 206 utilizing {2-[1-(5-Ethyl-pyrimidin-2-yl)-piperidin-4-yl]-thiazol-4-ylmethyl}-(2-fluoro-4-methanesulfonyl-phenyl)-amine (Example 141) as the starting material. $^1$H NMR (CDCl$_3$): δ 8.19 (2H, s), 7.47-7.57 (2H, m), 6.94 (1H, s), 6.91 (1H, m), 4.80 (2H, m), 4.62 (2H, s), 3.24 (1H, m), 3.09 (3H, s), 3.03 (3H, s), 3.00 (2H, m), 2.47 (2H, m), 2.17 (2H, m), 1.74 (2H, m), 1.19 (3H, t).

Example 208

4-[4-(2-Methylsulfanyl-pyrimidin-5-yloxymethyl)-thiazol-2-yl]-piperidine-1-carboxylic acid tert-butyl ester

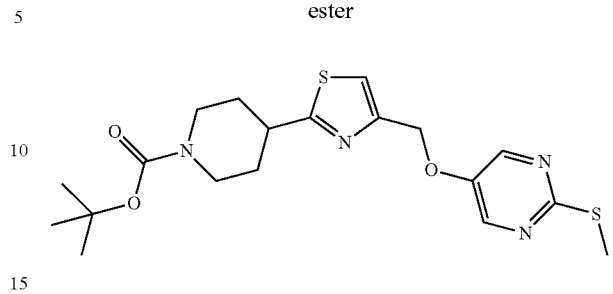

Example 208 was prepared from 4-(4-Chloromethyl-thiazol-2-yl)-piperidine-1-carboxylic acid tert-butyl ester (Intermediate 1) and 2-Methylsulfanyl-pyrimidin-5-ol in a manner similar to that described in Example 1. $^1$H NMR (CDCl$_3$): δ 8.35 (2H, s), 7.23 (1H, s), 5.19 (2H, s), 4.22 (2H, m), 3.16 (1H, m), 2.87 (2H, m), 2.55 (3H, s), 2.10 (2H, m), 1.71 (2H, m), 1.46 (9H, s).

Example 209

4-[4-(4-Tetrazol-1-yl-phenoxymethyl)-thiazol-2-yl]-piperidine-1-carboxylic acid allyl ester

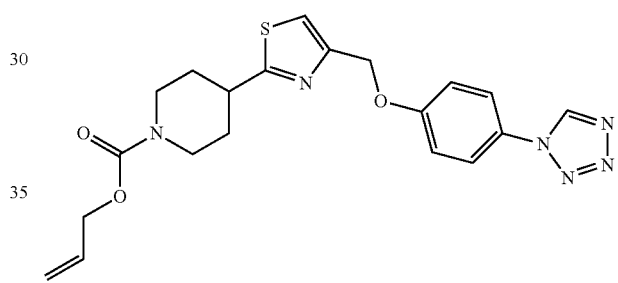

Example 209 was prepared from 4-[4-(4-Tetrazol-1-yl-phenoxymethyl)-thiazol-2-yl]-piperidine (Intermediate 4) and allyl chloroformate in a manner similar to that described in Example 22. $^1$H NMR (CDCl$_3$): δ 8.96 (1H, s), 7.63 (2H, m), 7.20 (1H, s), 7.18 (2H, m), 5.96 (1H, m), 5.31 (1H, m), 5.22 (3H, m), 4.61 (2H, m), 4.29 (2H, m), 3.21 (1H, m), 2.97 (2H, m), 2.15 (2H, m), 1.78 (2H, m).

Example 210

2-{4-[4-Methyl-5-(4-tetrazol-1-yl-phenoxymethyl)-thiazol-2-yl]-piperidin-1-yl}-5-trifluoromethyl-pyrimidine

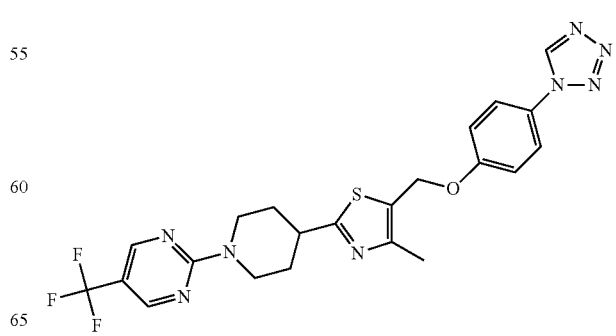

Step 1: 4-[4-Methyl-5-(4-tetrazol-1-yl-phenoxymethyl)-thiazol-2-yl]-piperidine

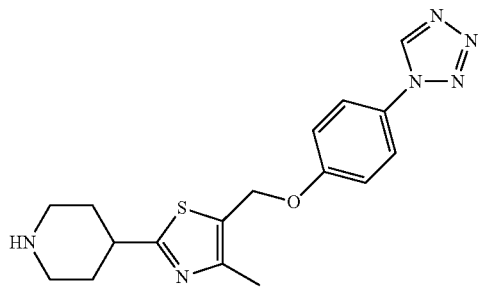 [SMILES: Cc1nc(C2CCNCC2)sc1COc1ccc(-n2cnnn2)cc1]

A solution of 4-[4-Methyl-5-(4-tetrazol-1-yl-phenoxymethyl)-thiazol-2-yl]-piperidine-1-carboxylic acid tert-butyl ester (Example 93) (500 mg, 1.10 mmol) in dichloromethane (5 mL) was treated with 1.5 mL of 4 N HCl in dioxane. The resulting solution was stirred at room temperature for 5 hours and all the solvent were removed in vacuo to afford the desired product as an HCl salt.

Step 2: 2-{4-[4-Methyl-5-(4-tetrazol-1-yl-phenoxymethyl)-thiazol-2-yl]-piperidin-1-yl}-5-trifluoromethyl-pyrimidine

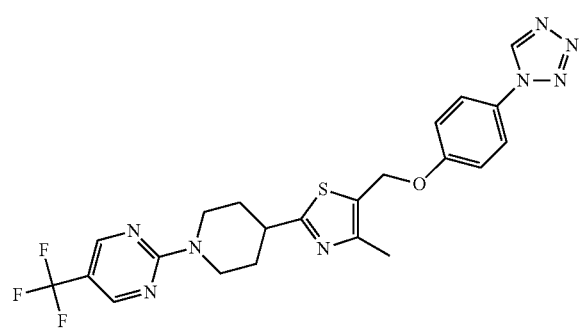 [SMILES: Cc1nc(C2CCN(c3ncc(C(F)(F)F)cn3)CC2)sc1COc1ccc(-n2cnnn2)cc1]

This compound was prepared from 4-[4-Methyl-5-(4-tetrazol-1-yl-phenoxymethyl)-thiazol-2-yl]-piperidine hydrochloride in a similar manner as described in Example 47. $^1$H NMR (CDCl$_3$): δ 8.94 (1H, s), 8.49 (2H, s), 7.64 (2H, m), 7.14 (2H, m), 5.20 (2H, s), 4.95 (2H, m), 3.27 (1H, m), 3.13 (2H, m), 2.46 (3H, s), 2.21 (2H, m), 1.77 (2H, m).

Biological Example 1

A compound of Formula (I) is evaluated in a porcine model of short bowel syndrome (see, e.g., Surgery, 2011 August; 150(2):217-23.). Functional assessment (e.g., changes in body weight and/or nutrient uptake), morphological assessment (e.g., histology), and molecular assessment (e.g., measurement of peptidyl biomarkers) are performed.

Biological Example 2

A composition comprising a compound of Formula (I) and a DPP-IV inhibitor is evaluated in a porcine model of short bowel syndrome, as described in Biological Example 1.

Biological Example 3

A composition comprising a compound of Formula (I), a DPP-IV inhibitor, and metformin is evaluated in a porcine model of short bowel syndrome, as described in Biological Example 1.

Biological Example 4

A compound of Formula (I) is evaluated in a murine model of inflammatory bowel disease (see, e.g., Prog Mol Biol Transl Sci., 2012; 105:263-320). Histologic analysis is performed.

Biological Example 5

A composition comprising a compound of Formula (I) and a DPP-IV inhibitor is evaluated in a murine model of inflammatory bowel disease, as described in Biological Example 4.

Biological Example 6

A composition comprising a compound of Formula (I), a DPP-IV inhibitor, and metformin is evaluated in a murine model of inflammatory bowel disease, as described in Biological Example 4.

Biological Example 7

A compound of Formula (I) is evaluated in a clinical study involving human volunteers with short bowel syndrome. The improvement of intestinal absoprtion is assessed.

Biological Example 8

A composition comprising a compound of Formula (I) and a DPP-IV inhibitor is evaluated in human volunteers with short bowel syndrome, as described in Biological Example 7.

Biological Example 9

A composition comprising a compound of Formula (I), a DPP-IV inhibitor, and metformin is evaluated in human volunteers with short bowel syndrome, as described in Biological Example 7.

Biological Example 10

A compound of Formula (I) is evaluated in a clinical study involving human volunteers with inflammatory bowel disease. Partial or complete response is measured.

Biological Example 11

A composition comprising a compound of Formula (I) and a DPP-IV inhibitor is evaluated in human volunteers with inflammatory bowel disease, as described in Biological Example 10.

Biological Example 12

A composition comprising a compound of Formula (I), a DPP-IV inhibitor, and metformin is evaluated in human volunteers with inflammatory bowel disease, as described in Biological Example 10.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, terths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

Other embodiments are set forth in the following claims.
What is claimed:
1. A method of treating an inflammatory gastrointestinal disease or a gastrointestinal condition involving malabsorption of nutrients and/or fluids in a patient in need thereof, the method comprising administering to the patient a therapeutically effective amount of a compound of Formula (I),

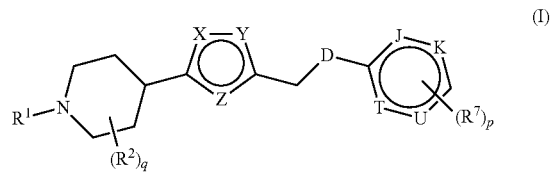

wherein,
D is selected from the group consisting of O, S, and $NR^8$,
X, Y, and Z is

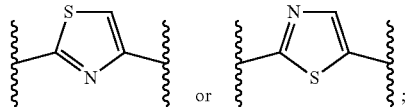 [SMILES: *c1csc(*)n1 ; *c1cnc(*)s1]

J, K, T, and U are each independently selected from the group consisting of CH, and N;
the subscript p is an integer of from 0 to 4;
the subscript q is an integer of from 0 to 4;
$R^1$ is a member selected from the group consisting of H, $C_{1-10}$alkyl, $C_{1-10}$substituted alkyl, $C_{3-7}$cycloalkyl, $C_{2-10}$ alkenyl, $C_{2-10}$ alkynyl, —$X^1$—$COR_a$, —$X^1$—$CO_2R^a$, —$X^1$—$CONR^aR^b$, —$SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1-10}$alkyl, $C_{1-10}$substituted alkyl, $C_{3-7}$cycloalkyl, $C_{2-10}$ alkenyl, $C_{2-10}$ alkynyl, aryl, heteroaryl, —CN, —$NR^aCOR^b$, —$NR^aCONR^aR^b$, —$NO_2$, —$OR^a$, —$NR^aR^b$, —$COR^a$, —$CO_2R^a$, —$CONR^aR^b$, —$S(O)_mR^a$, —$NR^aS(O)_2R^b$, and $SO_2NR^aR^b$, or optionally $R^a$ and $R^b$ are combined to form a 4-, 5- or 6-membered ring, and $X^1$ is selected from the group consisting of a bond, $C_{2-6}$alkene, $C_{2-6}$alkyne, —C(O)—, and —C(O)—$(CH_2)_{1-4}$-, wherein the aliphatic portions of $X^1$ are optionally substituted with one to three members selected from halogen, $C_{1-4}$alkyl, $C_{1-4}$substituted alkyl and $C_{1-4}$haloalkyl;
each $R^2$ is a member independently selected from the group consisting of halogen, $C_{1-5}$ alkyl, $C_{1-5}$substituted alkyl, $C_{3-7}$cycloalkyl, —$COR^a$, —$CO_2R^a$, —$CONR^aR^b$, —$OR^a$, —$NR^aR^b$, —$NR^aCOR^b$, —$SOR^aR^b$, —$SO_2R^a$ and —$SO_2NR^aR^b$, and wherein when the subscript q is 2 and $R^2$ is alkyl or substituted alkyl, the two $R^2$ members can optionally cyclize to form a ring;
each $R^7$ is independently selected from the group consisting of halo, $C_{1-10}$alkyl, $C_{1-10}$ substituted alkyl, $C_{3-7}$cycloalkyl, $C_{2-10}$alkenyl, $C_{2-10}$ alkynyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —S(O)$_m$R$^a$, —NR$^a$SO$_2$R$^b$, and —SO$_2$NR$^a$R$^b$ and wherein the subscript m is an integer of from 0 to 2, or optionally R$^a$ and R$^b$ are combined to form a 4-, 5- or 6-membered ring;

R$^8$ is a member independently selected from the group consisting of hydrogen, $C_{1-4}$alkyl, and $C_{1-4}$haloalkyl;

and each R$^a$ and R$^b$ is independently selected from the group consisting of hydrogen, $C_{1-10}$ alkyl, $C_{1-10}$haloalkyl, $C_{3-10}$ cycloalkyl, heterocyclyl, $C_{2-10}$alkenyl, $C_{2-10}$ alkynyl, aryl, 5- to 6-membered heteroaryl and arylC$_{1-4}$alkyl; and wherein the aliphatic portions of each of said R$^a$ and R$^b$ is optionally substituted with from one to three members selected from the group consisting of halo, —OR″, —OCOR″, —OC(O)N(R″)$_2$, —S(O)R″, —S(O)$_2$R″, —S(O)$_2$N(R″)$_2$, —NR″S(O)$_2$R″, —C(O)N(R″)$_2$, —C(O)R″, —NR″C(O)R″, —NR″C(O)N(R″)$_2$, —CO$_2$R″, —NR″CO$_2$R$^a$, —CN, —NO$_2$, —N(R″)$_2$ and —NR″S(O)$_2$N(R″)$_2$, wherein each R″ is independently hydrogen or an unsubstituted $C_{1-6}$ alkyl;

and wherein the aryl and heteroaryl portions are optionally substituted with from one to three members selected from halogen, —OR′′′, —OC(O)N(R′′′)$_2$, —SR′′′, —S(O)R′′′, —S(O)$_2$R′′′, —S(O)$_2$N(R′′′)$_2$, —NR′′′S(O)$_2$R′′′, —C(O)N(R′′′)$_2$, —C(O)R′′′, —NR′′′C(O)R′′′, —NR′′′C(O)N(R′′′)$_2$, —CO$_2$R′′′, —NR′′′CO$_2$R′′′, —CN, —NO$_2$, —N(R′′′)$_2$ and —NR′′′S(O)$_2$N(R′′′)$_2$, wherein each R′′′ is independently hydrogen or an unsubstituted $C_{1-6}$ alkyl;

or a pharmaceutically acceptable salt or ester thereof; and wherein the molecular weight of said compound is less than 1200;

wherein the inflammatory gastrointestinal disease or the gastrointestinal condition involving malabsorption of nutrients and/or fluids is selected from the group consisting of short bowel syndrome (SBS), inflammatory bowel disease, Crohn's disease, ulcerative colitis, volvulus, and necrotizing enterocolitis.

2. The method of claim 1, wherein said compound of Formula I is selected from the group consisting of

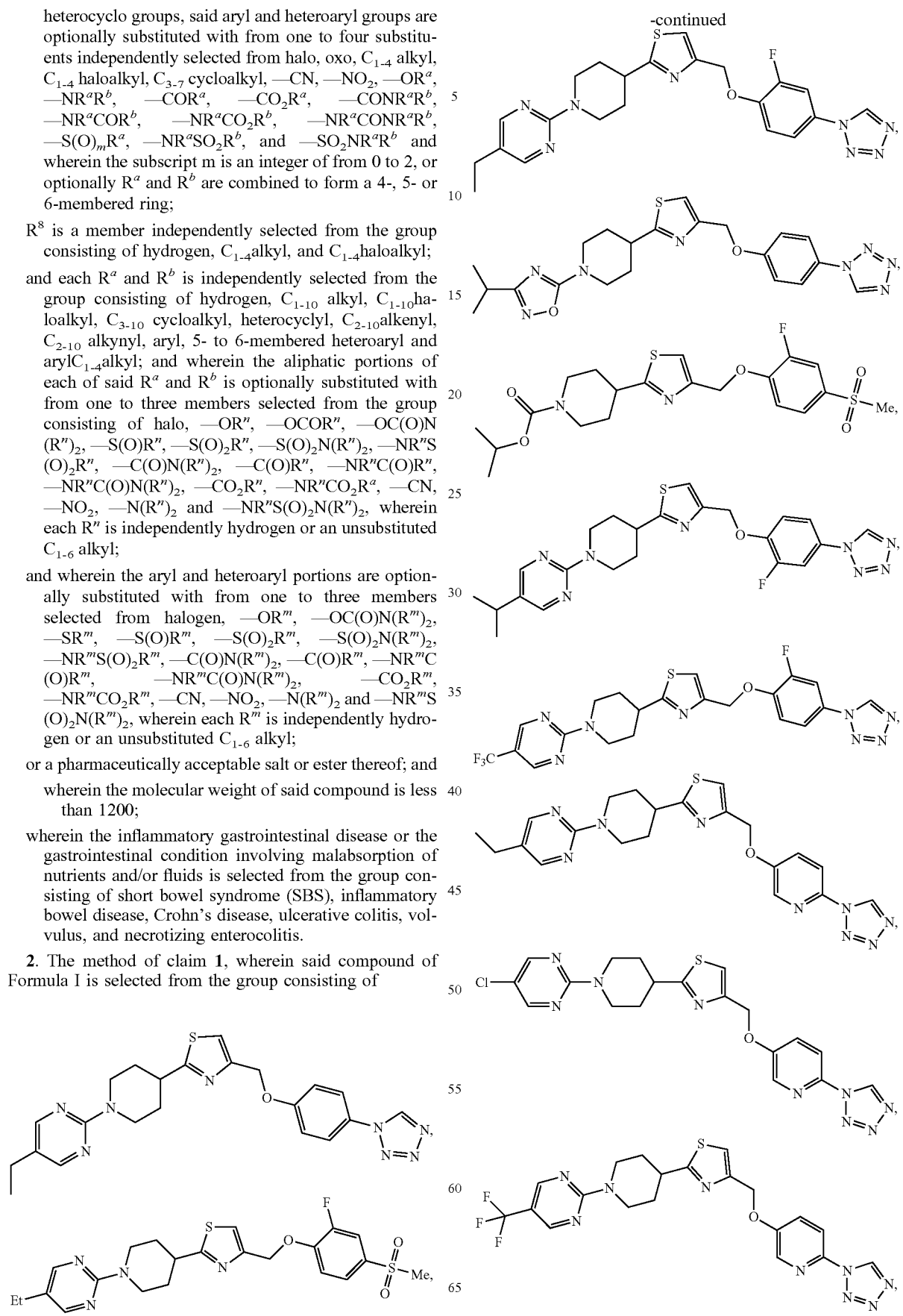

-continued
and

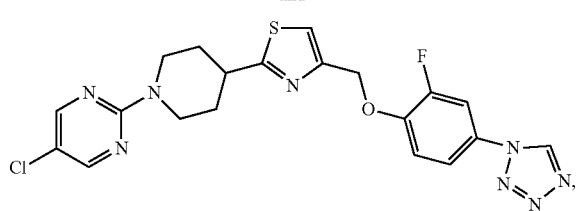

or a pharmaceutically acceptable salt thereof.

3. The method of claim 2, wherein said compound of Formula (I) is

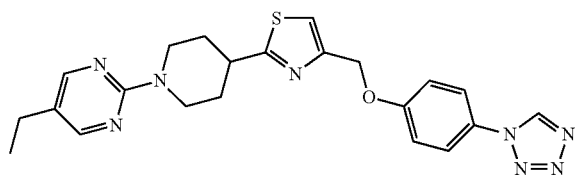 [SMILES: CCc1cnc(N2CCC(c3nc(COc4ccc(-n5cnnn5)cc4)cs3)CC2)nc1]

or a pharmaceutically acceptable salt thereof.

4. The method of claim 1, further comprising concurrently or sequentially administering a DPP-IV inhibitor to the patient.

5. The method of claim 4, wherein said DPP-IV inhibitor is selected from the group consisting of sitagliptin, vildagliptin, denagliptin, saxagliptin, linagliptin, alogliptin, amino-methylpyridine (R1438), isoleucine thiozolidide (P32/98), gemigliptin, anagliptin, teneligliptin, trelagliptin, dutogliptin, and omarigliptin.

6. The method of claim 4, wherein said DPP-IV inhibitor is selected from the group consisting of sitagliptin, vildagliptin, saxagliptin, linagliptin, gemigliptin, anagliptin, teneligliptin, trelagliptin, omarigliptin, and alogliptin.

7. The method of claim 1, further comprising concurrently or sequentially administering metformin to the patient.

8. A method of treating short bowel syndrome in a patient in need thereof, the method comprising administering to the patient a therapeutically effective amount of a compound of Formula (I),

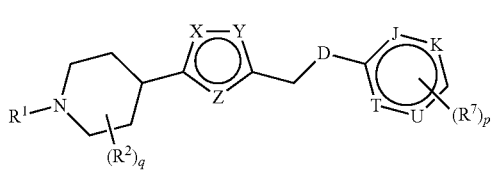

wherein,
D is selected from the group consisting of O, S, and $NR^8$,
X, Y, and Z is

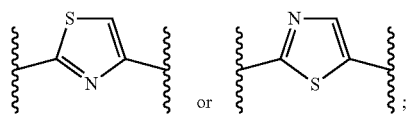 [SMILES: *c1csc(*)n1 ; *c1cnc(*)s1]

J, K, T, and U are each independently selected from the group consisting of C, CH, and N;

the subscript p is an integer of from 0 to 4;
the subscript q is an integer of from 0 to 4;
$R^1$ is a member selected from the group consisting of H, $C_{1\text{-}10}$alkyl, $C_{1\text{-}10}$substituted alkyl, $C_{3\text{-}7}$cycloalkyl, $C_{2\text{-}10}$alkenyl, $C_{2\text{-}10}$ alkynyl, —$X^1$—$COR^a$, —$X^1$—$CO_2R^a$, —$X^1$—$CONR^aR^b$, —$SO_2R^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, $C_{1\text{-}10}$alkyl, $C_{1\text{-}10}$substituted alkyl, $C_{3\text{-}7}$cycloalkyl, $C_{2\text{-}10}$alkenyl, $C_{2\text{-}10}$ alkynyl, aryl, heteroaryl, —CN, —$NR^aCOR^b$, —$NR^aCONR^aR^b$, —$NO_2$, —$OR^a$, —$NR^aR^b$, —$COR^a$, —$CO_2R^a$, —$CONR^aR^b$, —$S(O)_mR^a$, —$NR^aS(O)_2R^b$, and $SO_2NR^aR^b$, or optionally $R^a$ and $R^b$ are combined to form a 4-, 5- or 6-membered ring, and $X^1$ is selected from the group consisting of a bond, $C_{2\text{-}6}$alkene, $C_{2\text{-}6}$alkyne, —C(O)—, and —C(O)—$(CH_2)_{1\text{-}4}$-, wherein the aliphatic portions of $X^1$ are optionally substituted with one to three members selected from halogen, $C_{1\text{-}4}$alkyl, $C_{1\text{-}4}$substituted alkyl and $C_{1\text{-}4}$haloalkyl;
each $R^2$ is a member independently selected from the group consisting of halogen, $C_{1\text{-}5}$ alkyl, $C_{1\text{-}5}$substituted alkyl, $C_{3\text{-}7}$cycloalkyl, —$COR^a$, —$CO_2R^a$, —$CONR^aR^b$, —$OR^a$, —$NR^aR^b$, —$NR^aCOR^b$, —$SOR^aR^b$, —$SO_2R^a$ and —$SO_2NR^aR^b$, and wherein when the subscript q is 2 and $R^2$ is alkyl or substituted alkyl, the two $R^2$ members can optionally cyclize to form a ring;
each $R^7$ is independently selected from the group consisting of halo, $C_{1\text{-}10}$alkyl, $C_{1\text{-}10}$ substituted alkyl, $C_{3\text{-}7}$cycloalkyl, $C_{2\text{-}10}$alkenyl, $C_{2\text{-}10}$ alkynyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1\text{-}4}$ alkyl, $C_{1\text{-}4}$haloalkyl, $C_{3\text{-}7}$ cycloalkyl, —CN, —$NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aCONR^aR^b$, —$S(O)_mR^a$, —$NR^aSO_2R^b$, and —$SO_2NR^aR^b$ and wherein the subscript m is an integer of from 0 to 2, or optionally $R^a$ and $R^b$ are combined to form a 4-, 5- or 6-membered ring;
$R^8$ is a member independently selected from the group consisting of hydrogen, $C_{1\text{-}4}$alkyl, and $C_{1\text{-}4}$haloalkyl;
and each $R^a$ and $R^b$ is independently selected from the group consisting of hydrogen, $C_{1\text{-}10}$ alkyl, $C_{1\text{-}10}$haloalkyl, $C_{3\text{-}10}$ cycloalkyl, heterocyclyl, $C_{2\text{-}10}$ alkenyl, $C_{2\text{-}10}$ alkynyl, aryl, 5- to 6-membered heteroaryl and aryl$C_{1\text{-}4}$alkyl; and wherein the aliphatic portions of each of said $R^a$ and $R^b$ is optionally substituted with from one to three members selected from the group consisting of halo, —$OR''$, —$OCOR''$, —$OC(O)N(R'')_2$, —$SR''$, —$S(O)R''$, —$S(O)_2R''$, —$S(O)_2N(R'')_2$, —$NR''S(O)_2R''$, —$C(O)N(R'')_2$, —$C(O)R''$, —$NR''C(O)R''$, —$NR''C(O)N(R'')_2$, —$CO_2R''$, —$NR''CO_2R''$, —CN, —$NO_2$, —$N(R'')_2$ and —$NR''S(O)_2N(R'')_2$, wherein each $R''$ is independently hydrogen or an unsubstituted $C_{1\text{-}6}$ alkyl;
and wherein the aryl and heteroaryl portions are optionally substituted with from one to three members selected from halogen, —$OR'''$, —$OC(O)N(R''')_2$, —SR'", —S(O)R'", —S(O)₂R'", —S(O)₂N(R'")₂, —NR'"S(O)₂R'", —C(O)N(R'")₂, —C(O)R'", —NR'"C(O)R'", —NR'"C(O)N(R'")₂, —CO₂R'", —NR'"CO₂R'", —CN, —NO₂, —N(R'")₂ and —NR'"S(O)₂N(R'")₂, wherein each R'" is independently hydrogen or an unsubstituted C₁₋₆ alkyl;

or a pharmaceutically acceptable salt or ester thereof; and wherein the molecular weight of said compound is less than 1200.

9. The method of claim 8, wherein said compound of Formula I is selected from the group consisting of

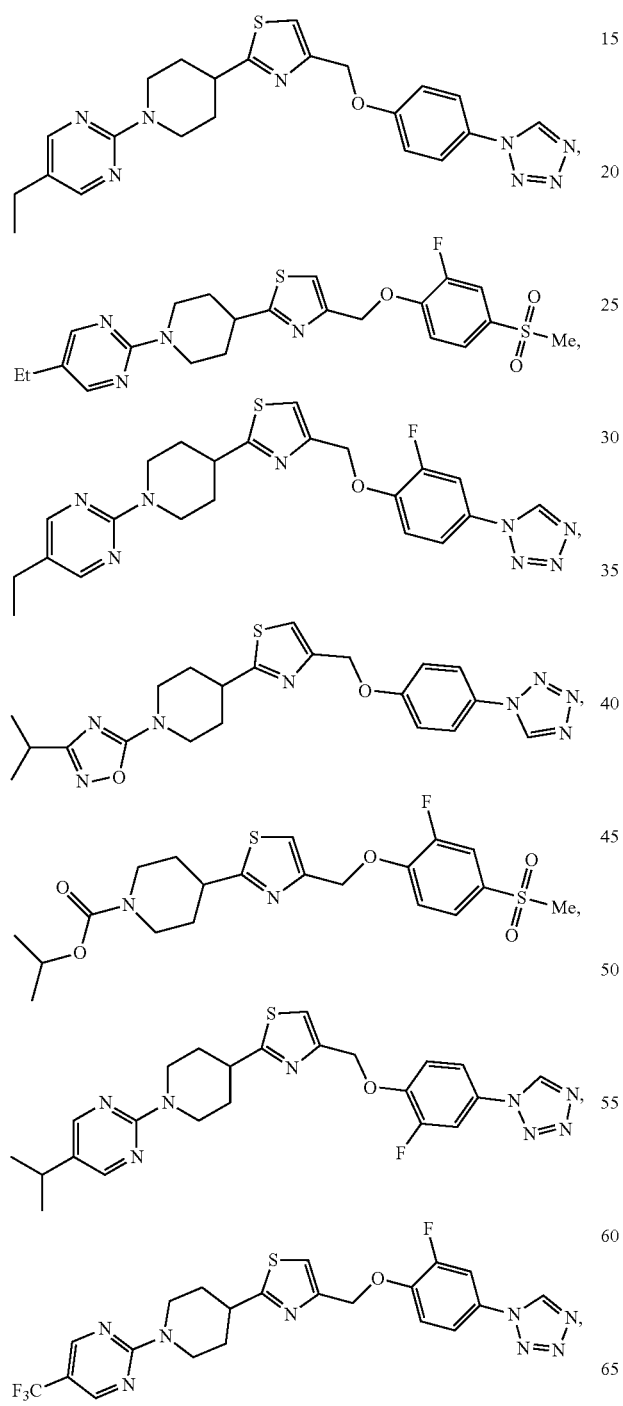

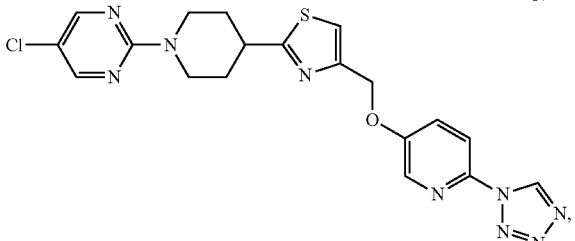

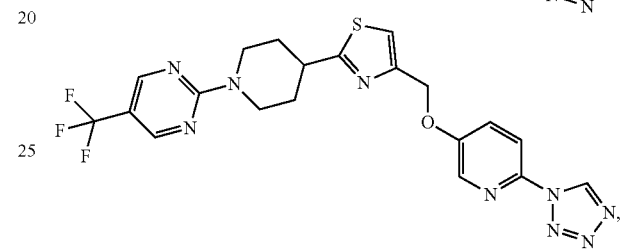

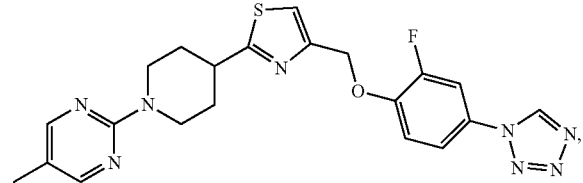

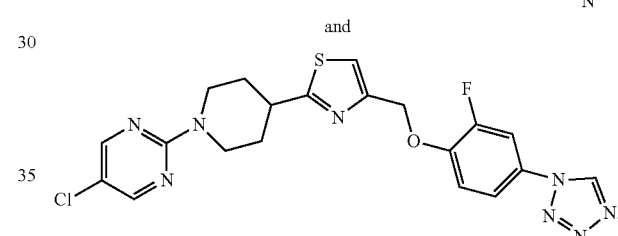

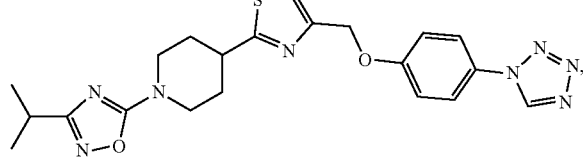

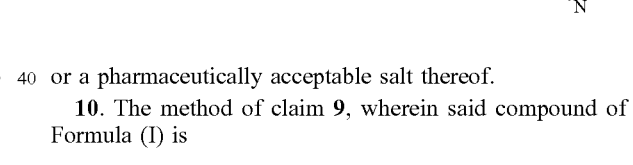

and

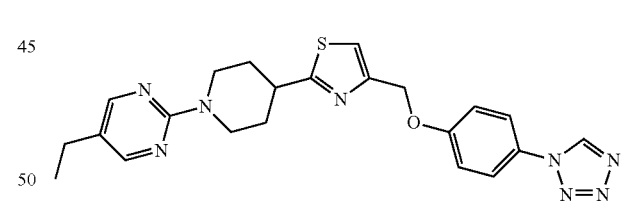

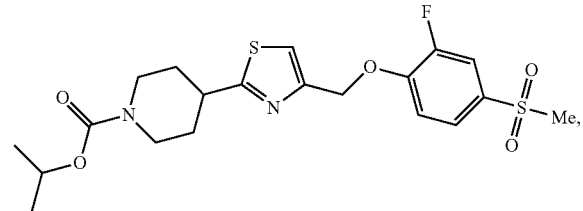

or a pharmaceutically acceptable salt thereof.

10. The method of claim 9, wherein said compound of Formula (I) is

[structure]

or a pharmaceutically acceptable salt thereof.

11. The method of claim 8, further comprising concurrently or sequentially administering a DPP-IV inhibitor to the patient.

12. The method of claim 11, wherein said DPP-IV inhibitor is selected from the group consisting of sitagliptin, vildagliptin, denagliptin, saxagliptin, linagliptin, alogliptin, amino-methylpyridine (R1438), isoleucine thiozolidide (P32/98), gemigliptin, anagliptin, teneligliptin, trelagliptin, dutogliptin, and omarigliptin.

13. The method of claim 11, wherein said DPP-IV inhibitor is selected from the group consisting of sitagliptin, vildagliptin, saxagliptin, linagliptin, gemigliptin, anagliptin, teneligliptin, trelagliptin, omarigliptin, and alogliptin.

14. The method of claim 8, further comprising concurrently or sequentially administering metformin to the patient.

15. A method of treating inflammatory bowel disease in a patient in need thereof, the method comprising administering to the patient a therapeutically effective amount of a compound of Formula (I),

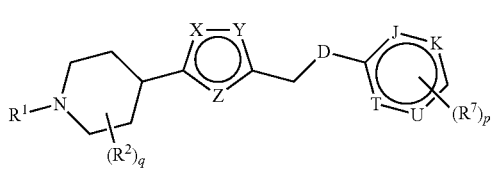

wherein,
D is selected from the group consisting of O, S, and NR$^8$, X, Y, and Z is

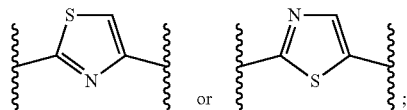 [SMILES: *c1csc(*)n1 ; *c1cnc(*)s1]

J, K, T, and U are each independently selected from the group consisting of CH, and N;
the subscript p is an integer of from 0 to 4;
the subscript q is an integer of from 0 to 4;
R$^1$ is a member selected from the group consisting of H, C$_{1-10}$alkyl, C$_{1-10}$substituted alkyl, C$_{3-7}$cycloalkyl, C$_{2-10}$ alkenyl, C$_{2-10}$ alkynyl, —X$^1$—COR$^a$, —X$^1$—CO$_2$R$^a$, —X$^1$—CONR$^a$R$^b$, —SO$_2$R$^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, C$_{1-10}$alkyl, C$_{1-10}$substituted alkyl, C$_{3-7}$cycloalkyl, C$_{2-10}$ alkenyl, C$_{2-10}$ alkynyl, aryl, heteroaryl, —CN, —NR$^a$COR$^b$, —NR$^a$CONR$^a$R$^b$, —NO$_2$, —OR$^a$, —NR$^a$R$^b$, —COR$^a$, —CO$_2$R$^a$, —CONR$^a$R$^b$, —S(O)$_m$R$^a$, —NR$^a$S(O)$_2$R$^b$, and SO$_2$NR$^a$R$^b$, or optionally R$^a$ and R$^b$ are combined to form a 4-, 5- or 6-membered ring, and X$^1$ is selected from the group consisting of a bond, C$_{2-6}$alkene, C$_{2-6}$alkyne, —C(O)—, and —C(O)—(CH$_2$)$_{1-4}$—, wherein the aliphatic portions of X$^1$ are optionally substituted with one to three members selected from halogen, C$_{1-4}$alkyl, C$_{1-4}$substituted alkyl and C$_{1-4}$haloalkyl;
each R$^2$ is a member independently selected from the group consisting of halogen, C$_{1-5}$ alkyl, C$_{1-5}$substituted alkyl, C$_{3-7}$cycloalkyl, —COR$^a$, —CO$_2$R$^a$, —CONR$^a$R$^b$, —OR$^a$, —NR$^a$R$^b$, —NR$^a$COR$^b$, —SOR$^a$R$^b$, —SO$_2$R$^a$ and —SO$_2$NR$^a$R$^b$, and wherein when the subscript q is 2 and R$^2$ is alkyl or substituted alkyl, the two R$^2$ members can optionally cyclize to form a ring;
each R$^7$ is independently selected from the group consisting of halo, C$_{1-10}$alkyl, C$_{1-10}$ substituted alkyl, C$_{3,7}$cycloalkyl, C$_{2-10}$alkenyl, C$_{2-10}$ alkynyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —S(O)$_m$R$^a$, —NR$^a$S(O)$_m$R$^b$, —SO$_2$NR$^a$R$^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, C$_{1-4}$ alkyl, C$_{1-4}$ haloalkyl, C$_{3-7}$ cycloalkyl, —CN, —NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —S(O)$_m$R$^a$, —NR$^a$SO$_2$R$^b$, and —SO$_2$NR$^a$R$^b$ and wherein the subscript m is an integer of from 0 to 2, or optionally R$^a$ and R$^b$ are combined to form a 4-, 5- or 6-membered ring;
R$^8$ is a member independently selected from the group consisting of hydrogen, C$_{1-4}$alkyl, and C$_{1-4}$haloalkyl;
and each R$^a$ and R$^b$ is independently selected from the group consisting of hydrogen, C$_{1-10}$ alkyl, C$_{1-10}$haloalkyl, C$_{3-10}$ cycloalkyl, heterocyclyl, C$_{2-10}$alkenyl, C$_{2-10}$ alkynyl, aryl, 5- to 6-membered heteroaryl and arylC$_{1-4}$alkyl; and wherein the aliphatic portions of each of said R$^a$ and R$^b$ is optionally substituted with from one to three members selected from the group consisting of halo, —OR$''$, —OCOR$''$, —OC(O)N(R$''$)$_2$, —SR$''$, —S(O)R$''$, —S(O)$_2$R$''$, —S(O)$_2$N(R$''$)$_2$, —NR$''$S(O)$_2$R$''$, —C(O)N(R$''$)$_2$, —C(O)R$''$, —NR$''$C(O)R$''$, —NR$''$C(O)N(R$''$)$_2$, —CO$_2$R$''$, —NR$''$CO$_2$R$''$, —CN, —NO$_2$, —N(R$''$)$_2$ and —NR$''$S(O)$_2$N(R$''$)$_2$, wherein each R$''$ is independently hydrogen or an unsubstituted C$_{1-6}$ alkyl;
and wherein the aryl and heteroaryl portions are optionally substituted with from one to three members selected from halogen, —OR$'''$, —OC(O)N(R$'''$)$_2$, —SR$'''$, —S(O)R$'''$, —S(O)$_2$R$'''$, —S(O)$_2$N(R$'''$)$_2$, —NR$'''$S(O)$_2$R$'''$, —C(O)N(R$'''$)$_2$, —C(O)R$'''$, —NR$'''$C(O)R$'''$, —NR$'''$C(O)N(R$'''$)$_2$, —CO$_2$R$'''$, —NR$'''$CO$_2$R$'''$, —CN, —NO$_2$, —N(R$'''$)$_2$ and —NR$'''$S(O)$_2$N(R$'''$)$_2$, wherein each R$'''$ is independently hydrogen or an unsubstituted C$_{1-6}$ alkyl;
or a pharmaceutically acceptable salt or ester thereof; and wherein the molecular weight of said compound is less than 1200.

16. The method of claim 15, wherein said compound of Formula I is selected from the group consisting of

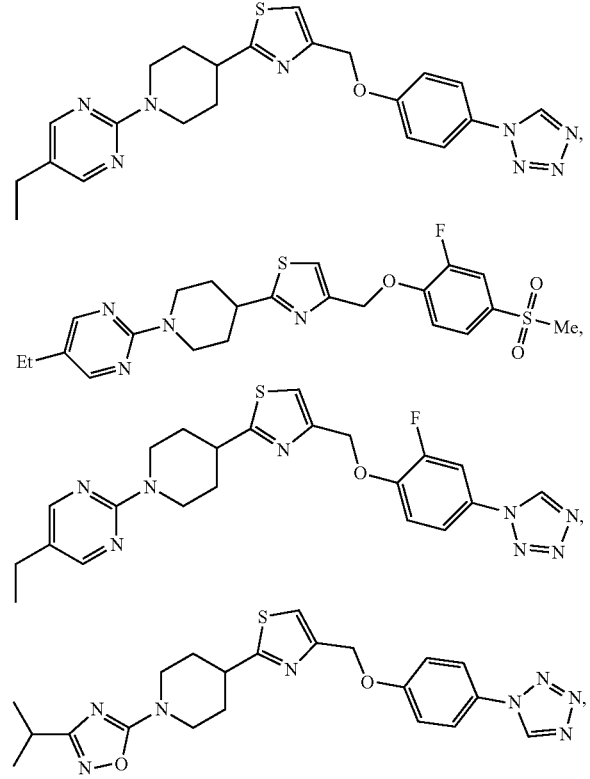

-continued

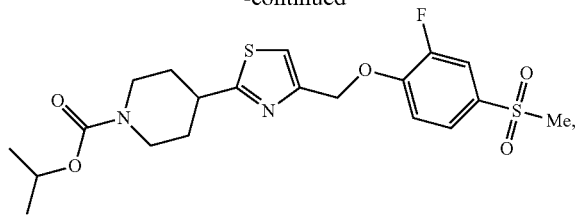

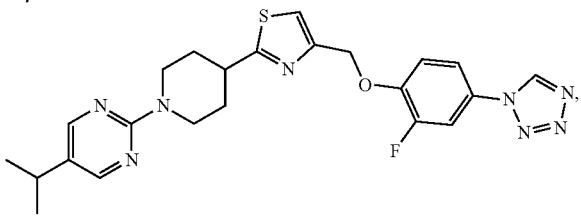

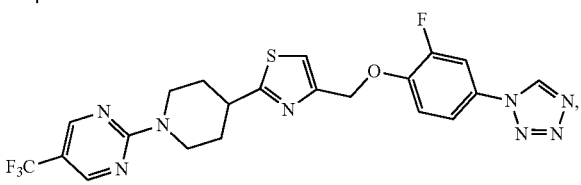

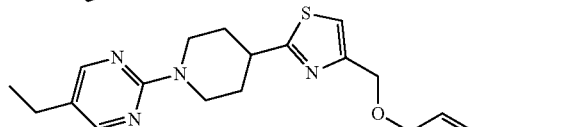

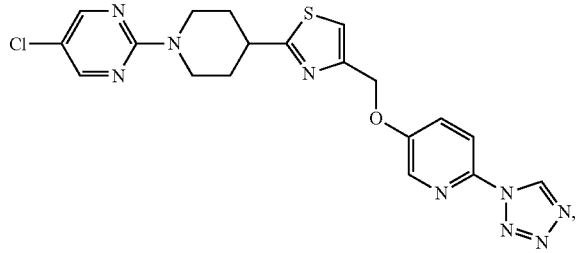

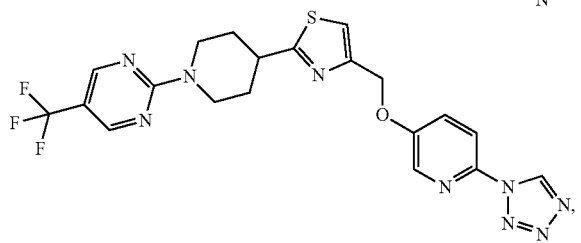

-continued
and

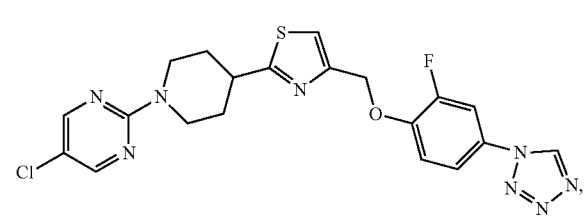

or a pharmaceutically acceptable salt thereof.

17. The method of claim 16, wherein said compound of Formula (I) is

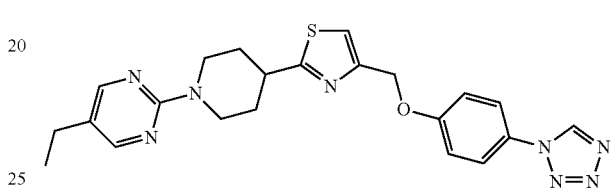

or a pharmaceutically acceptable salt thereof.

18. The method of claim 15, further comprising concurrently or sequentially administering a DPP-IV inhibitor to the patient.

19. The method of claim 18, wherein said DPP-IV inhibitor is selected from the group consisting of sitagliptin, vildagliptin, denagliptin, saxagliptin, linagliptin, alogliptin, amino-methylpyridine (R1438), isoleucine thiozolidide (P32/98), gemigliptin, anagliptin, teneligliptin, trelagliptin, dutogliptin, and omarigliptin.

20. The method of claim 18, wherein said DPP-IV inhibitor is selected from the group consisting of sitagliptin, vildagliptin, saxagliptin, linagliptin, gemigliptin, anagliptin, teneligliptin, trelagliptin, omarigliptin, and alogliptin.

21. The method of claim 15, further comprising concurrently or sequentially administering metformin to the patient.

22. The method of claim 15, wherein the inflammatory bowel disease is Crohn's disease or ulcerative colitis.

* * * * *